(12) United States Patent
Takakura et al.

(10) Patent No.: US 8,343,727 B2
(45) Date of Patent: Jan. 1, 2013

(54) METHOD OF BINDING PROTEINS TO CARRIERS BY MAKING USE OF TAMAVIDINS

(75) Inventors: Yoshimitsu Takakura, Iwata (JP); Masako Ichikawa, Iwata (JP); Satoru Usami, Iwata (JP); Takeshi Yamamoto, Iwata (JP); Hiroshi Tsukamoto, Iwata (JP); Hitomi Kajiwara, Iwata (JP); Naomi Oka, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 126 days.

(21) Appl. No.: 12/675,524

(22) PCT Filed: Aug. 28, 2008

(86) PCT No.: PCT/JP2008/065448
§ 371 (c)(1),
(2), (4) Date: Feb. 26, 2010

(87) PCT Pub. No.: WO2009/028625
PCT Pub. Date: Mar. 5, 2009

(65) Prior Publication Data
US 2010/0311076 A1    Dec. 9, 2010

(30) Foreign Application Priority Data
Aug. 28, 2007  (JP) ................. 2007-220921

(51) Int. Cl.
*G01N 33/53*  (2006.01)
(52) U.S. Cl. ........................... 435/7.1; 436/518
(58) Field of Classification Search .............. None
See application file for complete search history.

(56) References Cited

U.S. PATENT DOCUMENTS

| 2005/0089983 | A1 | 4/2005 | Takakura |
| 2009/0291471 | A1 | 11/2009 | Tsukamoto et al. |

FOREIGN PATENT DOCUMENTS

| EP | 2 112 168 A1 | 10/2009 |
| JP | 4-236353 A | 8/1992 |
| WO | WO-02/072817 A1 | 9/2002 |
| WO | WO-2007/105305 A1 | 9/2007 |
| WO | WO-2008/081938 A1 | 7/2008 |

OTHER PUBLICATIONS

Mackay et al. Genetics 2003, vol. 163, p. 1365-1373 Bowie et al. Science, 1990 vol. 247:1306-1310.*
Kuno et al. J Biol. Chem 1993, vol. 268, p. 13510-13518; Green et al. Pro. Natl. Acad. Sci. 1999 vol. 96, p. 4176-4179.*
Ashmun et al. See Blood 1992, vol. 79, p. 3344-3349; Jane Reece Gillen editor, 4th edition, 1988, p. 342, p. 343, p. 442 and p. 445.*
Erlenbach et al. J. Biol. Chem 2001 vol. 276, p. 29382-29392 Noutoshi et al. Plant Journal 2005 vol. 43, p. 873-888.*
Green, "AVIDIN", Adv Protein Chem, 1975, 29: 85-133.
Green, "Avidin and Streptavidin", Methods in Enzymology, 1990, vol. 184, pp. 51-67.
Airenne et al., "Recombinant avidin and avidin-fusion proteins", Biomolecular Engineering, 1999, 16, 87-92.
Kipriyanov et al., "Single-chain antiboby streptavidin fusions: Tetrameric bifunctional scFv-complexes with biotin binding activity and enhanced affinity to antigen", Hum. Antibod. Hybridomas, 1995, vol. 6, pp. 93-101.
Dübel et al., "Bifunctional and multimeric complexes of streptavidin fused to single chain antibodies (scFv)", Journal of Immunological Methods, 1995, 178, 201-209.
Walsh et al., "An *Escherichia coli* Plasmid Vector System for Production of Streptavidin Fusion Proteins: Expression and Bioselective Adsorption of Streptavidin-β-Galactosidase", Biotechnology and Bioengineering, 1994, vol. 44, pp. 1348-1354.
Hofmann et al., "Iminobiotin affinity columns and their application to retrieval of streptavidin", Proc. Natl. Acad. Sci. USA, Aug. 1980, vol. 77, No. 8, pp. 4666-4668.
Iba et al., "Expression vectors for the introduction of highly diverged sequences into the six complementarity-determining regions of an antibody", Gene, 1997, 194, 35-46.
Ideno et al., "Expression of foreign proteins in *Escherichia coli* by fusing with an archaeal FK506 binding protein", App Microbiol Biotechnol., 2004, 64, 99-105.
Kada et al., "Accurate measurement of avidin and streptavidin in crude biofluids with a new, optimized biotin-fluorescein conjugate", Biochimica et Biophysica Acta, 1999, 1427, 33-43.
Kawahashi et al., "In vitro protein microarrays for detecting protein-protein interactions: Application of a new method for fluorescence labeling of proteins", Proteomics, 2003, 3, 1236-1243.
Huang et al., "Simultaneous isolation and immobilization of streptavidin-β-galactosidase: Some kinetic characteristics of the immobilized enzyme and regeneration of bioreactors", Enzyme and Microbial Technology, 1996, 19, 378-383.

* cited by examiner

*Primary Examiner* — Jacob Cheu
(74) *Attorney, Agent, or Firm* — Birch, Stewart, Kolasch & Birch, LLP

(57) ABSTRACT

The present invention provides a method of binding a protein to a carrier in such a way that the protein is not impaired in its function but can be allowed to act more efficiently than when it is bound directly.
The method of the present invention for binding a protein to a carrier comprises:
  preparing a biotin-bound carrier;
  preparing a fusion protein having the protein bound to a tamavidin; and
  binding the protein to the carrier via tamavidin-biotin bonds.

8 Claims, 10 Drawing Sheets

SEQUENCE LISTING

```
<160> NUMBER OF SEQ ID NOS: 85

<210> SEQ ID NO 1
<211> LENGTH: 432
<212> TYPE: DNA
<213> ORGANISM: Pleurotus cornucopiae
<220> FEATURE:
<221> NAME/KEY: CDS
<222> LOCATION: (1)..(432)

<400> SEQUENCE: 1 atg aaa gac gtc caa tct ctc ctc acc gga acc tgg tac aat gaa ctc      48
Met Lys Asp Val Gln Ser Leu Leu Thr Gly Thr Trp Tyr Asn Glu Leu
1               5                   10                  15 ggc tca aca atg aat ttg act gca aat aaa gac ggt tcg ctc acc gga      96
Gly Ser Thr Met Asn Leu Thr Ala Asn Lys Asp Gly Ser Leu Thr Gly
                20                  25                  30 acg tac cac tcc aac gtc ggc gag gtt ccc cca act tat cac ctt tct     144
Thr Tyr His Ser Asn Val Gly Glu Val Pro Pro Thr Tyr His Leu Ser
            35                  40                  45 ggc cgg tac aac ctc cag ccc ccc tcg ggt caa ggc gtt act ctg gga     192
Gly Arg Tyr Asn Leu Gln Pro Pro Ser Gly Gln Gly Val Thr Leu Gly
        50                  55                  60 tgg gcg gtg tct ttc gaa aac act agt gcg aat gtt cat tct gtc tca     240
Trp Ala Val Ser Phe Glu Asn Thr Ser Ala Asn Val His Ser Val Ser
65                  70                  75                  80 aca tgg agc ggg cag tac ttc tct gaa ccc gcc gag gtg atc ctc acc     288
Thr Trp Ser Gly Gln Tyr Phe Ser Glu Pro Ala Glu Val Ile Leu Thr
                85                  90                  95 cag tgg ctg ttg tca agg agc tct gag cgc gaa gat ttg tgg cag tcc     336
Gln Trp Leu Leu Ser Arg Ser Ser Glu Arg Glu Asp Leu Trp Gln Ser
            100                 105                 110 acc cat gtg ggg cat gat gag ttc agc aag aca aag cca acc aag gag     384
Thr His Val Gly His Asp Glu Phe Ser Lys Thr Lys Pro Thr Lys Glu
        115                 120                 125
```

```
aag att gcc cag gct caa ctc ctt cgt cgc ggg ttg aag ttc gag tga         432
Lys Ile Ala Gln Ala Gln Leu Leu Arg Arg Gly Leu Lys Phe Glu
    130                 135                 140
```

<210> SEQ ID NO 2
<211> LENGTH: 143
<212> TYPE: PRT
<213> ORGANISM: Pleurotus cornucopiae

<400> SEQUENCE: 2

```
Met Lys Asp Val Gln Ser Leu Leu Thr Gly Thr Trp Tyr Asn Glu Leu
1               5                   10                  15

Gly Ser Thr Met Asn Leu Thr Ala Asn Lys Asp Gly Ser Leu Thr Gly
            20                  25                  30

Thr Tyr His Ser Asn Val Gly Glu Val Pro Pro Thr Tyr His Leu Ser
        35                  40                  45

Gly Arg Tyr Asn Leu Gln Pro Pro Ser Gly Gln Gly Val Thr Leu Gly
    50                  55                  60

Trp Ala Val Ser Phe Glu Asn Thr Ser Ala Asn Val His Ser Val Ser
65                  70                  75                  80

Thr Trp Ser Gly Gln Tyr Phe Ser Glu Pro Ala Glu Val Ile Leu Thr
                85                  90                  95

Gln Trp Leu Leu Ser Arg Ser Ser Glu Arg Glu Asp Leu Trp Gln Ser
            100                 105                 110

Thr His Val Gly His Asp Glu Phe Ser Lys Thr Lys Pro Thr Lys Glu
        115                 120                 125

Lys Ile Ala Gln Ala Gln Leu Leu Arg Arg Gly Leu Lys Phe Glu
    130                 135                 140
```

<210> SEQ ID NO 3
<211> LENGTH: 426
<212> TYPE: DNA
<213> ORGANISM: Pleurotus cornucopiae
<220> FEATURE:
<221> NAME/KEY: CDS
<222> LOCATION: (1)..(426)

<400> SEQUENCE: 3

```
atg tca gac gtt caa tct tca ctc acc gga acc tgg tac aat gaa ctc          48
Met Ser Asp Val Gln Ser Ser Leu Thr Gly Thr Trp Tyr Asn Glu Leu
1               5                   10                  15 aac tcc aag atg gaa ttg act gca aac aaa gac ggt act ctc act gga          96
Asn Ser Lys Met Glu Leu Thr Ala Asn Lys Asp Gly Thr Leu Thr Gly
            20                  25                  30 aag tac ctc tcc aaa gtt ggg gat gtc tac gtg ccc tac cca ctc tct         144
Lys Tyr Leu Ser Lys Val Gly Asp Val Tyr Val Pro Tyr Pro Leu Ser
        35                  40                  45 ggt cgc tat aac ctc caa ccc ccc gcg gga caa ggc gtc gct ctt ggg         192
Gly Arg Tyr Asn Leu Gln Pro Pro Ala Gly Gln Gly Val Ala Leu Gly
    50                  55                  60 tgg gcg gta tcc tgg gag aac agt aaa att cat tcc gct acg aca tgg         240
Trp Ala Val Ser Trp Glu Asn Ser Lys Ile His Ser Ala Thr Thr Trp
65                  70                  75                  80 agc gga cag ttc ttc tct gag tcg tct cca gtg att ctt act cag tgg         288
Ser Gly Gln Phe Phe Ser Glu Ser Ser Pro Val Ile Leu Thr Gln Trp
                85                  90                  95 ttg ttg tca tcg agc act gcg cgt ggg gac gta tgg gaa tcc aca ctt         336
Leu Leu Ser Ser Ser Thr Ala Arg Gly Asp Val Trp Glu Ser Thr Leu
            100                 105                 110
```

```
gtg ggg aat gat tcg ttt aca aag acg gcg ccg act gag cag cag atc      384
Val Gly Asn Asp Ser Phe Thr Lys Thr Ala Pro Thr Glu Gln Gln Ile
        115                 120                 125 gct cat gct caa ctc cat tgt cgc gca ccg agg ttg aag taa              426
Ala His Ala Gln Leu His Cys Arg Ala Pro Arg Leu Lys
130                 135                 140

<210> SEQ ID NO 4
<211> LENGTH: 141
<212> TYPE: PRT
<213> ORGANISM: Pleurotus cornucopiae

<400> SEQUENCE: 4

Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65                  70                  75                  80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
        115                 120                 125

Ala His Ala Gln Leu His Cys Arg Ala Pro Arg Leu Lys
    130                 135                 140

<210> SEQ ID NO 5
<211> LENGTH: 1935
<212> TYPE: DNA
<213> ORGANISM: Artificial sequence
<220> FEATURE:
<223> OTHER INFORMATION: Synthetic construct: ISH224-alpha2,6ST-linkTM2
<220> FEATURE:
<221> NAME/KEY: CDS
<222> LOCATION: 1..1494
<223> OTHER INFORMATION: nucleotides 1-1494 encodes ISH224-alpha2,6
      sialic acid transferase
<220> FEATURE:
<221> NAME/KEY: CDS
<222> LOCATION: 1513..1935
<223> OTHER INFORMATION: nucleotides 1513-1935 encodes tamavidin 2

<400> SEQUENCE: 5 atg tca gaa gaa aat aca caa tct att att aaa aat gat att aat aaa     48
Met Ser Glu Glu Asn Thr Gln Ser Ile Ile Lys Asn Asp Ile Asn Lys
1               5                   10                  15 act att att gat gag gag tat gtt aat tta gag cca att aat caa tca     96
Thr Ile Ile Asp Glu Glu Tyr Val Asn Leu Glu Pro Ile Asn Gln Ser
            20                  25                  30 aac atc tct ttt aca aaa cac tct tgg gta caa act tgt ggt acg caa    144
Asn Ile Ser Phe Thr Lys His Ser Trp Val Gln Thr Cys Gly Thr Gln
        35                  40                  45 caa cta tta aca gaa caa aat aaa gag tca ata tca tta tct gta gtg    192
Gln Leu Leu Thr Glu Gln Asn Lys Glu Ser Ile Ser Leu Ser Val Val
    50                  55                  60 gcg cca cga tta gat gac gat gaa aag tac tgc ttt gat ttt aat ggt    240
Ala Pro Arg Leu Asp Asp Asp Glu Lys Tyr Cys Phe Asp Phe Asn Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 65  |     |     |     | 70  |     |     |     | 75  |     |     |     | 80  |     |      |
| gtt | agt | aat | aaa | ggt | gaa | aaa | tat | ata | aca | aaa | gta | aca | tta | aac | gta | 288  |
| Val | Ser | Asn | Lys | Gly | Glu | Lys | Tyr | Ile | Thr | Lys | Val | Thr | Leu | Asn | Val |      |
|     |     |     |     | 85  |     |     |     |     | 90  |     |     |     |     | 95  |     |      |
| gtg | gct | cca | tct | tta | gag | gtt | tat | gtt | gat | cat | gca | tct | ctt | cca | act | 336  |
| Val | Ala | Pro | Ser | Leu | Glu | Val | Tyr | Val | Asp | His | Ala | Ser | Leu | Pro | Thr |      |
|     |     |     | 100 |     |     |     |     | 105 |     |     |     |     | 110 |     |     |      |
| ctt | cag | cag | cta | atg | gat | att | att | aaa | tcg | gaa | gaa | gaa | aat | cct | aca | 384  |
| Leu | Gln | Gln | Leu | Met | Asp | Ile | Ile | Lys | Ser | Glu | Glu | Glu | Asn | Pro | Thr |      |
|     |     |     |     | 115 |     |     |     |     | 120 |     |     |     |     | 125 |     |      |
| gca | caa | aga | tat | ata | gct | tgg | ggg | aga | ata | gtt | ccg | act | gat | gag | caa | 432  |
| Ala | Gln | Arg | Tyr | Ile | Ala | Trp | Gly | Arg | Ile | Val | Pro | Thr | Asp | Glu | Gln |      |
|     |     | 130 |     |     |     |     | 135 |     |     |     |     | 140 |     |     |     |      |
| atg | aaa | gag | tta | aat | att | aca | tcg | ttt | gca | ttg | ata | aat | aac | cat | aca | 480  |
| Met | Lys | Glu | Leu | Asn | Ile | Thr | Ser | Phe | Ala | Leu | Ile | Asn | Asn | His | Thr |      |
| 145 |     |     |     |     | 150 |     |     |     |     | 155 |     |     |     |     | 160 |      |
| cca | gct | gac | tta | gta | caa | gaa | att | gtt | aag | caa | gca | caa | aca | aag | cat | 528  |
| Pro | Ala | Asp | Leu | Val | Gln | Glu | Ile | Val | Lys | Gln | Ala | Gln | Thr | Lys | His |      |
|     |     |     |     | 165 |     |     |     |     | 170 |     |     |     |     | 175 |     |      |
| aga | ttg | aat | gtt | aaa | ctt | agc | tct | aac | act | gct | cat | tca | ttt | gat | aat | 576  |
| Arg | Leu | Asn | Val | Lys | Leu | Ser | Ser | Asn | Thr | Ala | His | Ser | Phe | Asp | Asn |      |
|     |     |     | 180 |     |     |     |     | 185 |     |     |     |     | 190 |     |     |      |
| tta | gtg | cca | ata | cta | aaa | gaa | tta | aat | tcg | ttt | aat | aac | gtt | acg | gta | 624  |
| Leu | Val | Pro | Ile | Leu | Lys | Glu | Leu | Asn | Ser | Phe | Asn | Asn | Val | Thr | Val |      |
|     |     |     |     | 195 |     |     |     |     | 200 |     |     |     |     | 205 |     |      |
| aca | aat | ata | gat | tta | tat | gat | gat | ggt | tca | gca | gaa | tat | gta | aat | tta | 672  |
| Thr | Asn | Ile | Asp | Leu | Tyr | Asp | Asp | Gly | Ser | Ala | Glu | Tyr | Val | Asn | Leu |      |
|     |     | 210 |     |     |     |     | 215 |     |     |     |     | 220 |     |     |     |      |
| tat | aac | tgg | aga | gat | aca | tta | aat | aaa | aca | gat | aat | tta | aaa | att | ggt | 720  |
| Tyr | Asn | Trp | Arg | Asp | Thr | Leu | Asn | Lys | Thr | Asp | Asn | Leu | Lys | Ile | Gly |      |
| 225 |     |     |     |     | 230 |     |     |     |     | 235 |     |     |     |     | 240 |      |
| aaa | gat | tat | ctt | gag | gat | gtc | att | aat | ggt | atc | aat | gaa | gac | act | tca | 768  |
| Lys | Asp | Tyr | Leu | Glu | Asp | Val | Ile | Asn | Gly | Ile | Asn | Glu | Asp | Thr | Ser |      |
|     |     |     |     | 245 |     |     |     |     | 250 |     |     |     |     | 255 |     |      |
| aat | aca | gga | aca | tca | tct | gtt | tat | aac | tgg | caa | aaa | cta | tat | cca | gct | 816  |
| Asn | Thr | Gly | Thr | Ser | Ser | Val | Tyr | Asn | Trp | Gln | Lys | Leu | Tyr | Pro | Ala |      |
|     |     |     | 260 |     |     |     |     | 265 |     |     |     |     | 270 |     |     |      |
| aac | tac | cat | ttt | tta | aga | aaa | gat | tat | tta | act | tta | gaa | cca | tca | tta | 864  |
| Asn | Tyr | His | Phe | Leu | Arg | Lys | Asp | Tyr | Leu | Thr | Leu | Glu | Pro | Ser | Leu |      |
|     |     + 275 |     |     |     |     | 280 |     |     |     |     | 285 |     |     |     |      |
| cat | gag | tta | cga | gac | tat | att | ggt | gat | agt | tta | aag | caa | atg | caa | tgg | 912  |
| His | Glu | Leu | Arg | Asp | Tyr | Ile | Gly | Asp | Ser | Leu | Lys | Gln | Met | Gln | Trp |      |
|     | 290 |     |     |     |     | 295 |     |     |     |     | 300 |     |     |     |     |      |
| gat | ggt | ttc | aaa | aaa | ttc | aat | agc | aaa | caa | caa | gaa | tta | ttc | tta | tcg | 960  |
| Asp | Gly | Phe | Lys | Lys | Phe | Asn | Ser | Lys | Gln | Gln | Glu | Leu | Phe | Leu | Ser |      |
| 305 |     |     |     |     | 310 |     |     |     |     | 315 |     |     |     |     | 320 |      |
| att | gtt | aat | ttt | gac | aaa | caa | aaa | tta | caa | aat | gaa | tat | aat | tca | tct | 1008 |
| Ile | Val | Asn | Phe | Asp | Lys | Gln | Lys | Leu | Gln | Asn | Glu | Tyr | Asn | Ser | Ser |      |
|     |     |     |     | 325 |     |     |     |     | 330 |     |     |     |     | 335 |     |      |
| aat | tta | cca | aac | ttt | gtg | ttt | aca | ggt | acg | act | gta | tgg | gct | ggt | aac | 1056 |
| Asn | Leu | Pro | Asn | Phe | Val | Phe | Thr | Gly | Thr | Thr | Val | Trp | Ala | Gly | Asn |      |
|     |     |     | 340 |     |     |     |     | 345 |     |     |     |     | 350 |     |     |      |
| cat | gaa | aga | gag | tat | tat | gcg | aaa | caa | caa | att | aat | gtc | att | aat | aat | 1104 |
| His | Glu | Arg | Glu | Tyr | Tyr | Ala | Lys | Gln | Gln | Ile | Asn | Val | Ile | Asn | Asn |      |
|     |     | 355 |     |     |     |     | 360 |     |     |     |     | 365 |     |     |     |      |
| gca | att | aat | gaa | tcg | agc | cca | cat | tat | tta | ggc | aat | agt | tat | gat | ttg | 1152 |
| Ala | Ile | Asn | Glu | Ser | Ser | Pro | His | Tyr | Leu | Gly | Asn | Ser | Tyr | Asp | Leu |      |
| 370 |     |     |     |     | 375 |     |     |     |     | 380 |     |     |     |     |     |      |
| ttc | ttc | aaa | ggt | cac | cct | ggt | ggc | ggt | atc | att | aat | aca | tta | ata | atg | 1200 |
| Phe | Phe | Lys | Gly | His | Pro | Gly | Gly | Gly | Ile | Ile | Asn | Thr | Leu | Ile | Met |      |

-continued

| | | | | |
|---|---|---|---|---|
| | 385 | 390 | 395 | 400 |
| caa aac tat cct tca atg gtt gat att cca tca aaa ata tca ttt gaa<br>Gln Asn Tyr Pro Ser Met Val Asp Ile Pro Ser Lys Ile Ser Phe Glu<br>                            405                            410                            415 | | | | 1248 |

```
                 385                 390                 395                 400 caa aac tat cct tca atg gtt gat att cca tca aaa ata tca ttt gaa       1248
Gln Asn Tyr Pro Ser Met Val Asp Ile Pro Ser Lys Ile Ser Phe Glu
                405                 410                 415 gtt ttg atg atg aca gat atg ctt cct gat gca gtt gct ggt ata gcg       1296
Val Leu Met Met Thr Asp Met Leu Pro Asp Ala Val Ala Gly Ile Ala
            420                 425                 430 agc tct tta tat ttc acg ata cca gct gaa aaa att aaa ttt ata gtt       1344
Ser Ser Leu Tyr Phe Thr Ile Pro Ala Glu Lys Ile Lys Phe Ile Val
        435                 440                 445 ttt aca tcg aca gaa act ata act gat cgt gaa act gct ttg aga agt       1392
Phe Thr Ser Thr Glu Thr Ile Thr Asp Arg Glu Thr Ala Leu Arg Ser
    450                 455                 460 cct tta gtt caa gta atg ata aaa cta ggt att gta aaa gaa gag aat       1440
Pro Leu Val Gln Val Met Ile Lys Leu Gly Ile Val Lys Glu Glu Asn
465                 470                 475                 480 gta ctt ttt tgg gct gat ctg cca aat tgt gaa aca ggt gtt tgt att       1488
Val Leu Phe Trp Ala Asp Leu Pro Asn Cys Glu Thr Gly Val Cys Ile
                485                 490                 495 gca gtc ggt ggc ggt ggc agc ggt tca gac gtt caa tct tca ctc acc       1536
Ala Val Gly Gly Gly Gly Ser Gly Ser Asp Val Gln Ser Ser Leu Thr
            500                 505                 510 gga acc tgg tac aat gaa ctc aac tcc aag atg gaa ttg act gca aac       1584
Gly Thr Trp Tyr Asn Glu Leu Asn Ser Lys Met Glu Leu Thr Ala Asn
        515                 520                 525 aaa gac ggt act ctc act gga aag tac ctc tcc aaa gtt ggg gat gtc       1632
Lys Asp Gly Thr Leu Thr Gly Lys Tyr Leu Ser Lys Val Gly Asp Val
    530                 535                 540 tac gtg ccc tac cca ctc tct ggt cgc tat aac ctc caa ccc ccc gcg       1680
Tyr Val Pro Tyr Pro Leu Ser Gly Arg Tyr Asn Leu Gln Pro Pro Ala
545                 550                 555                 560 gga caa ggc gtc gct ctt ggg tgg gcg gta tcc tgg gag aac agt aaa       1728
Gly Gln Gly Val Ala Leu Gly Trp Ala Val Ser Trp Glu Asn Ser Lys
                565                 570                 575 att cat tcc gct acg aca tgg agc gga cag ttc ttc tct gag tcg tct       1776
Ile His Ser Ala Thr Thr Trp Ser Gly Gln Phe Phe Ser Glu Ser Ser
            580                 585                 590 cca gtg att ctt act cag tgg ttg ttg tca tcg agc act gcg cgt ggg       1824
Pro Val Ile Leu Thr Gln Trp Leu Leu Ser Ser Ser Thr Ala Arg Gly
        595                 600                 605 gac gta tgg gaa tcc aca ctt gtg ggg aat gat tcg ttt aca aag acg       1872
Asp Val Trp Glu Ser Thr Leu Val Gly Asn Asp Ser Phe Thr Lys Thr
    610                 615                 620 gcg ccg act gag cag cag atc gct cat gct caa ctc cat tgt cgc gca       1920
Ala Pro Thr Glu Gln Gln Ile Ala His Ala Gln Leu His Cys Arg Ala
625                 630                 635                 640 ccg agg ttg aag taa                                                    1935
Pro Arg Leu Lys <210> SEQ ID NO 6
<211> LENGTH: 873
<212> TYPE: DNA
<213> ORGANISM: Artificial sequence
<220> FEATURE:
<223> OTHER INFORMATION: Synthetic construct: PelB-AntiHELscFv-myc
<220> FEATURE:
<221> NAME/KEY: CDS
<222> LOCATION: 1..66
<223> OTHER INFORMATION: nucleotides 1-66 encodes PelB leader peptide
<220> FEATURE:
<221> NAME/KEY: CDS
<222> LOCATION: 67..840
<223> OTHER INFORMATION: nucleotides 67-840 encodes Fv fragment of Hen
```

```
        egg lysozyme (HEL) D1.3 antibody
<220> FEATURE:
<221> NAME/KEY: CDS
<222> LOCATION: 859..870
<223> OTHER INFORMATION: nucleotides 859-870 encodes myc tag

<400> SEQUENCE: 6 atg aaa tac cta ttg cct acg gca gcc gct ggc ttg ctg ctg ctg gca        48
Met Lys Tyr Leu Leu Pro Thr Ala Ala Ala Gly Leu Leu Leu Leu Ala
1               5                   10                  15 gct cag ccg gcc atg gcg cag gtg cag ctg cag gag tca gga cct ggc        96
Ala Gln Pro Ala Met Ala Gln Val Gln Leu Gln Glu Ser Gly Pro Gly
                20                  25                  30 ctg gtg gcg ccc tca cag agc ctg tcc atc aca tgc acc gtc tca ggg       144
Leu Val Ala Pro Ser Gln Ser Leu Ser Ile Thr Cys Thr Val Ser Gly
        35                  40                  45 ttc tca tta acc ggc tat ggt gta aac tgg gtt cgc cag cct cca gga       192
Phe Ser Leu Thr Gly Tyr Gly Val Asn Trp Val Arg Gln Pro Pro Gly
    50                  55                  60 aag ggt ctg gag tgg ctg gga atg att tgg ggt gat gga aac aca gac       240
Lys Gly Leu Glu Trp Leu Gly Met Ile Trp Gly Asp Gly Asn Thr Asp
65                  70                  75                  80 tat aat tca gct ctc aaa tcc aga ctg agc atc agc aag gac aac tcc       288
Tyr Asn Ser Ala Leu Lys Ser Arg Leu Ser Ile Ser Lys Asp Asn Ser
                85                  90                  95 aag agc caa gtt ttc tta aaa atg aac agt ctg cac act gat gac aca       336
Lys Ser Gln Val Phe Leu Lys Met Asn Ser Leu His Thr Asp Asp Thr
            100                 105                 110 gcc agg tac tac tgt gcc aga gag aga gat tat agg ctt gac tac tgg       384
Ala Arg Tyr Tyr Cys Ala Arg Glu Arg Asp Tyr Arg Leu Asp Tyr Trp
        115                 120                 125 ggc caa ggg acc acg gtc acc gtc tcc tca ggc ggt ggc gga tca ggt       432
Gly Gln Gly Thr Thr Val Thr Val Ser Ser Gly Gly Gly Gly Ser Gly
    130                 135                 140 ggc ggt gga agt ggc ggt ggt ggg tct gac atc gag ctc acc cag tct       480
Gly Gly Gly Ser Gly Gly Gly Gly Ser Asp Ile Glu Leu Thr Gln Ser
145                 150                 155                 160 cca gcc tcc ctt tct gcg tct gtg gga gaa act gtc acc atc aca tgt       528
Pro Ala Ser Leu Ser Ala Ser Val Gly Glu Thr Val Thr Ile Thr Cys
                165                 170                 175 cga gca agt ggg aat att cac aat tat tta gca tgg tat cag cag aaa       576
Arg Ala Ser Gly Asn Ile His Asn Tyr Leu Ala Trp Tyr Gln Gln Lys
            180                 185                 190 cag gga aaa tct cct cag ctc ctg gtc tat tat aca aca acc tta gca       624
Gln Gly Lys Ser Pro Gln Leu Leu Val Tyr Tyr Thr Thr Thr Leu Ala
        195                 200                 205 gat ggt gtg cca tca agg ttc agt ggc agt gga tca gga aca caa tat       672
Asp Gly Val Pro Ser Arg Phe Ser Gly Ser Gly Ser Gly Thr Gln Tyr
    210                 215                 220 tct ctc aag atc aac agc ctg caa cct gaa gat ttt ggg agt tat tac       720
Ser Leu Lys Ile Asn Ser Leu Gln Pro Glu Asp Phe Gly Ser Tyr Tyr
225                 230                 235                 240 tgt caa cat ttt tgg agt act cct cgg acg ttc ggt gga ggg acc aag       768
Cys Gln His Phe Trp Ser Thr Pro Arg Thr Phe Gly Gly Gly Thr Lys
                245                 250                 255 ctg gag ctc gag gga atc cat atg act agt aga tcc tct aga gtc gac       816
Leu Glu Leu Glu Gly Ile His Met Thr Ser Arg Ser Ser Arg Val Asp
            260                 265                 270 ctg cag gca tgc aag ctt tcc cta gaa caa aag ctg atc tca gaa gaa       864
Leu Gln Ala Cys Lys Leu Ser Leu Glu Gln Lys Leu Ile Ser Glu Glu
        275                 280                 285
```

-continued

```
gat cta taa                                              873
Asp Leu
    290

<210> SEQ ID NO 7
<211> LENGTH: 1281
<212> TYPE: DNA
<213> ORGANISM: Artificial sequence
<220> FEATURE:
<223> OTHER INFORMATION: Synthetic construct: PelB-antiHELscFv-TM2
<220> FEATURE:
<221> NAME/KEY: CDS
<222> LOCATION: 1..66
<223> OTHER INFORMATION: nucleotides 1-66 encodes PelB leader peptide
<220> FEATURE:
<221> NAME/KEY: CDS
<222> LOCATION: 67..840
<223> OTHER INFORMATION: nucleotides 67-840 encodes Fv fragment of Hen
      egg lysozyme (HEL) D1.3 antibody
<220> FEATURE:
<221> NAME/KEY: CDS
<222> LOCATION: 859..1281
<223> OTHER INFORMATION: nucleotides 859-1281 encodes tamavidin 2

<400> SEQUENCE: 7 atg aaa tac cta ttg cct acg gca gcc gct ggc ttg ctg ctg ctg gca      48
Met Lys Tyr Leu Leu Pro Thr Ala Ala Ala Gly Leu Leu Leu Leu Ala
1               5                   10                  15 gct cag ccg gcc atg gcg cag gtg cag ctg cag gag tca gga cct ggc      96
Ala Gln Pro Ala Met Ala Gln Val Gln Leu Gln Glu Ser Gly Pro Gly
            20                  25                  30 ctg gtg gcg ccc tca cag agc ctg tcc atc aca tgc acc gtc tca ggg     144
Leu Val Ala Pro Ser Gln Ser Leu Ser Ile Thr Cys Thr Val Ser Gly
        35                  40                  45 ttc tca tta acc ggc tat ggt gta aac tgg gtt cgc cag cct cca gga     192
Phe Ser Leu Thr Gly Tyr Gly Val Asn Trp Val Arg Gln Pro Pro Gly
    50                  55                  60 aag ggt ctg gag tgg ctg gga atg att tgg ggt gat gga aac aca gac     240
Lys Gly Leu Glu Trp Leu Gly Met Ile Trp Gly Asp Gly Asn Thr Asp
65                  70                  75                  80 tat aat tca gct ctc aaa tcc aga ctg agc atc agc aag gac aac tcc     288
Tyr Asn Ser Ala Leu Lys Ser Arg Leu Ser Ile Ser Lys Asp Asn Ser
                85                  90                  95 aag agc caa gtt ttc tta aaa atg aac agt ctg cac act gat gac aca     336
Lys Ser Gln Val Phe Leu Lys Met Asn Ser Leu His Thr Asp Asp Thr
            100                 105                 110 gcc agg tac tac tgt gcc aga gag aga gat tat agg ctt gac tac tgg     384
Ala Arg Tyr Tyr Cys Ala Arg Glu Arg Asp Tyr Arg Leu Asp Tyr Trp
        115                 120                 125 ggc caa ggg acc acg gtc acc gtc tcc tca ggc ggt ggc gga tca ggt     432
Gly Gln Gly Thr Thr Val Thr Val Ser Ser Gly Gly Gly Gly Ser Gly
    130                 135                 140 ggc ggt gga agt ggc ggt ggt ggg tct gac atc gag ctc acc cag tct     480
Gly Gly Gly Ser Gly Gly Gly Gly Ser Asp Ile Glu Leu Thr Gln Ser
145                 150                 155                 160 cca gcc tcc ctt tct gcg tct gtg gga gaa act gtc acc atc aca tgt     528
Pro Ala Ser Leu Ser Ala Ser Val Gly Glu Thr Val Thr Ile Thr Cys
                165                 170                 175 cga gca agt ggg aat att cac aat tat tta gca tgg tat cag cag aaa     576
Arg Ala Ser Gly Asn Ile His Asn Tyr Leu Ala Trp Tyr Gln Gln Lys
            180                 185                 190 cag gga aaa tct cct cag ctc ctg gtc tat tat aca aca acc tta gca     624
Gln Gly Lys Ser Pro Gln Leu Leu Val Tyr Tyr Thr Thr Thr Leu Ala
        195                 200                 205 gat ggt gtg cca tca agg ttc agt ggc agt gga tca gga aca caa tat     672
Asp Gly Val Pro Ser Arg Phe Ser Gly Ser Gly Ser Gly Thr Gln Tyr
```

```
                Asp Gly Val Pro Ser Arg Phe Ser Gly Ser Gly Ser Gly Thr Gln Tyr
                    210             215                 220 tct ctc aag atc aac agc ctg caa cct gaa gat ttt ggg agt tat tac       720
Ser Leu Lys Ile Asn Ser Leu Gln Pro Glu Asp Phe Gly Ser Tyr Tyr
225                 230                 235                 240 tgt caa cat ttt tgg agt act cct cgg acg ttc ggt gga ggg acc aag       768
Cys Gln His Phe Trp Ser Thr Pro Arg Thr Phe Gly Gly Gly Thr Lys
                245                 250                 255 ctg gag ctc gag gga atc cat atg act agt aga tcc tct aga gtc gac       816
Leu Glu Leu Glu Gly Ile His Met Thr Ser Arg Ser Ser Arg Val Asp
                260                 265                 270 ctg cag gca tgc aag ctt tcc cta ggt ggc ggt ggc agc ggt tca gac       864
Leu Gln Ala Cys Lys Leu Ser Leu Gly Gly Gly Gly Ser Gly Ser Asp
            275                 280                 285 gtt caa tct tca ctc acc gga acc tgg tac aat gaa ctc aac tcc aag       912
Val Gln Ser Ser Leu Thr Gly Thr Trp Tyr Asn Glu Leu Asn Ser Lys
        290                 295                 300 atg gaa ttg act gca aac aaa gac ggt act ctc act gga aag tac ctc       960
Met Glu Leu Thr Ala Asn Lys Asp Gly Thr Leu Thr Gly Lys Tyr Leu
305                 310                 315                 320 tcc aaa gtt ggg gat gtc tac gtg ccc tac cca ctc tct ggt cgc tat      1008
Ser Lys Val Gly Asp Val Tyr Val Pro Tyr Pro Leu Ser Gly Arg Tyr
                325                 330                 335 aac ctc caa ccc ccc gcg gga caa ggc gtc gct ctt ggg tgg gcg gta      1056
Asn Leu Gln Pro Pro Ala Gly Gln Gly Val Ala Leu Gly Trp Ala Val
                340                 345                 350 tcc tgg gag aac agt aaa att cat tcc gct acg aca tgg agc gga cag      1104
Ser Trp Glu Asn Ser Lys Ile His Ser Ala Thr Thr Trp Ser Gly Gln
            355                 360                 365 ttc ttc tct gag tcg tct cca gtg att ctt act cag tgg ttg ttg tca      1152
Phe Phe Ser Glu Ser Ser Pro Val Ile Leu Thr Gln Trp Leu Leu Ser
370                 375                 380 tcg agc act gcg cgt ggg gac gta tgg gaa tcc aca ctt gtg ggg aat      1200
Ser Ser Thr Ala Arg Gly Asp Val Trp Glu Ser Thr Leu Val Gly Asn
385                 390                 395                 400 gat tcg ttt aca aag acg gcg ccg act gag cag cag atc gct cat gct      1248
Asp Ser Phe Thr Lys Thr Ala Pro Thr Glu Gln Gln Ile Ala His Ala
                405                 410                 415 caa ctc cat tgt cgc gca ccg agg ttg aag taa                          1281
Gln Leu His Cys Arg Ala Pro Arg Leu Lys
                420                 425

<210> SEQ ID NO 8
<211> LENGTH: 644
<212> TYPE: PRT
<213> ORGANISM: Artificial sequence
<220> FEATURE:
<223> OTHER INFORMATION: Synthetic construct: 224-alpha2,6ST-TM2
<220> FEATURE:
<221> NAME/KEY: misc_feature
<222> LOCATION: 1..498
<223> OTHER INFORMATION: amino acids 1-498 corresponds to
      ISH224-alpha2,6 sialic acid transferase
<220> FEATURE:
<221> NAME/KEY: misc_feature
<222> LOCATION: 506..644
<223> OTHER INFORMATION: amino acid 505-644 corresponds to tamavidin 2

<400> SEQUENCE: 8

Met Ser Glu Glu Asn Thr Gln Ser Ile Ile Lys Asn Asp Ile Asn Lys
1               5                   10                  15

Thr Ile Ile Asp Glu Gly Tyr Val Asn Leu Glu Pro Ile Asn Gln Ser
                20                  25                  30
```

```
Asn Ile Ser Phe Thr Lys His Ser Trp Val Gln Thr Cys Gly Thr Gln
     35                  40                  45
Gln Leu Leu Thr Glu Gln Asn Lys Glu Ser Ile Ser Leu Ser Val Val
 50                  55                  60
Ala Pro Arg Leu Asp Asp Glu Lys Tyr Cys Phe Asp Phe Asn Gly
 65                  70                  75                  80
Val Ser Asn Lys Gly Glu Lys Tyr Ile Thr Lys Val Thr Leu Asn Val
                 85                  90                  95
Val Ala Pro Ser Leu Glu Val Tyr Val Asp His Ala Ser Leu Pro Thr
             100                 105                 110
Leu Gln Gln Leu Met Asp Ile Ile Lys Ser Glu Glu Asn Pro Thr
         115                 120                 125
Ala Gln Arg Tyr Ile Ala Trp Gly Arg Ile Val Pro Thr Asp Glu Gln
     130                 135                 140
Met Lys Glu Leu Asn Ile Thr Ser Phe Ala Leu Ile Asn Asn His Thr
145                 150                 155                 160
Pro Ala Asp Leu Val Gln Glu Ile Val Lys Gln Ala Gln Thr Lys His
                 165                 170                 175
Arg Leu Asn Val Lys Leu Ser Ser Asn Thr Ala His Ser Phe Asp Asn
             180                 185                 190
Leu Val Pro Ile Leu Lys Glu Leu Asn Ser Phe Asn Asn Val Thr Val
         195                 200                 205
Thr Asn Ile Asp Leu Tyr Asp Asp Gly Ser Ala Glu Tyr Val Asn Leu
210                 215                 220
Tyr Asn Trp Arg Asp Thr Leu Asn Lys Thr Asp Asn Leu Lys Ile Gly
225                 230                 235                 240
Lys Asp Tyr Leu Glu Asp Val Ile Asn Gly Ile Asn Glu Asp Thr Ser
                 245                 250                 255
Asn Thr Gly Thr Ser Ser Val Tyr Asn Trp Gln Lys Leu Tyr Pro Ala
             260                 265                 270
Asn Tyr His Phe Leu Arg Lys Asp Tyr Leu Thr Leu Glu Pro Ser Leu
         275                 280                 285
His Glu Leu Arg Asp Tyr Ile Gly Asp Ser Leu Lys Gln Met Gln Trp
     290                 295                 300
Asp Gly Phe Lys Lys Phe Asn Ser Lys Gln Gln Glu Leu Phe Leu Ser
305                 310                 315                 320
Ile Val Asn Phe Asp Lys Gln Lys Leu Gln Asn Glu Tyr Asn Ser Ser
                 325                 330                 335
Asn Leu Pro Asn Phe Val Phe Thr Gly Thr Thr Val Trp Ala Gly Asn
             340                 345                 350
His Glu Arg Glu Tyr Tyr Ala Lys Gln Gln Ile Asn Val Ile Asn Asn
         355                 360                 365
Ala Ile Asn Glu Ser Ser Pro His Tyr Leu Gly Asn Ser Tyr Asp Leu
     370                 375                 380
Phe Phe Lys Gly His Pro Gly Gly Gly Ile Ile Asn Thr Leu Ile Met
385                 390                 395                 400
Gln Asn Tyr Pro Ser Met Val Asp Ile Pro Ser Lys Ile Ser Phe Glu
                 405                 410                 415
Val Leu Met Met Thr Asp Met Leu Pro Asp Ala Val Ala Gly Ile Ala
             420                 425                 430
Ser Ser Leu Tyr Phe Thr Ile Pro Ala Glu Lys Ile Lys Phe Ile Val
         435                 440                 445
Phe Thr Ser Thr Glu Thr Ile Thr Asp Arg Glu Thr Ala Leu Arg Ser
     450                 455                 460
```

Pro Leu Val Gln Val Met Ile Lys Leu Gly Ile Val Lys Glu Glu Asn
465                 470                 475                 480

Val Leu Phe Trp Ala Asp Leu Pro Asn Cys Glu Thr Gly Val Cys Ile
                485                 490                 495

Ala Val Gly Gly Gly Ser Gly Ser Asp Val Gln Ser Leu Thr
            500                 505                 510

Gly Thr Trp Tyr Asn Glu Leu Asn Ser Lys Met Glu Leu Thr Ala Asn
            515                 520                 525

Lys Asp Gly Thr Leu Thr Gly Lys Tyr Leu Ser Lys Val Gly Asp Val
            530                 535                 540

Tyr Val Pro Tyr Pro Leu Ser Gly Arg Tyr Asn Leu Gln Pro Pro Ala
545                 550                 555                 560

Gly Gln Gly Val Ala Leu Gly Trp Ala Val Ser Trp Glu Asn Ser Lys
                565                 570                 575

Ile His Ser Ala Thr Thr Trp Ser Gly Gln Phe Phe Ser Glu Ser Ser
            580                 585                 590

Pro Val Ile Leu Thr Gln Trp Leu Leu Ser Ser Ser Thr Ala Arg Gly
            595                 600                 605

Asp Val Trp Glu Ser Thr Leu Val Gly Asn Asp Ser Phe Thr Lys Thr
            610                 615                 620

Ala Pro Thr Glu Gln Gln Ile Ala His Ala Gln Leu His Cys Arg Ala
625                 630                 635                 640

Pro Arg Leu Lys

<210> SEQ ID NO 9
<211> LENGTH: 290
<212> TYPE: PRT
<213> ORGANISM: Artificial sequence
<220> FEATURE:
<223> OTHER INFORMATION: Synthetic construct: PelB::AntiHELscFv::myc
<220> FEATURE:
<221> NAME/KEY: misc_feature
<222> LOCATION: 1..22
<223> OTHER INFORMATION: amino acids 1-22 corresponds to PelB leader
      peptide
<220> FEATURE:
<221> NAME/KEY: misc_feature
<222> LOCATION: 23..280
<223> OTHER INFORMATION: amino acids 23-280 corresponds to Fv fragment
      of Hen egg lysozyme (HEL) D1.3 antibody
<220> FEATURE:
<221> NAME/KEY: misc_feature
<222> LOCATION: 281..290
<223> OTHER INFORMATION: amino acids 281-290 corresponds to c-myc tag

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Pro Gly
            20                  25                  30

Leu Val Ala Pro Ser Gln Ser Leu Ser Ile Thr Cys Thr Val Ser Gly
        35                  40                  45

Phe Ser Leu Thr Gly Tyr Gly Val Asn Trp Val Arg Gln Pro Pro Gly
    50                  55                  60

Lys Gly Leu Glu Trp Leu Gly Met Ile Trp Gly Asp Gly Asn Thr Asp
65                  70                  75                  80

Tyr Asn Ser Ala Leu Lys Ser Arg Leu Ser Ile Ser Lys Asp Asn Ser
                85                  90                  95

Lys Ser Gln Val Phe Leu Lys Met Asn Ser Leu His Thr Asp Asp Thr
            100                 105                 110

```
Ala Arg Tyr Tyr Cys Ala Arg Glu Arg Asp Tyr Arg Leu Asp Tyr Trp
        115                 120                 125

Gly Gln Gly Thr Thr Val Thr Val Ser Ser Gly Gly Gly Ser Gly
    130                 135                 140

Gly Gly Gly Ser Gly Gly Gly Ser Asp Ile Glu Leu Thr Gln Ser
145                 150                 155                 160

Pro Ala Ser Leu Ser Ala Ser Val Gly Glu Thr Val Thr Ile Thr Cys
                165                 170                 175

Arg Ala Ser Gly Asn Ile His Asn Tyr Leu Ala Trp Tyr Gln Gln Lys
            180                 185                 190

Gln Gly Lys Ser Pro Gln Leu Leu Val Tyr Tyr Thr Thr Thr Leu Ala
        195                 200                 205

Asp Gly Val Pro Ser Arg Phe Ser Gly Ser Gly Ser Gly Thr Gln Tyr
    210                 215                 220

Ser Leu Lys Ile Asn Ser Leu Gln Pro Glu Asp Phe Gly Ser Tyr Tyr
225                 230                 235                 240

Cys Gln His Phe Trp Ser Thr Pro Arg Thr Phe Gly Gly Gly Thr Lys
                245                 250                 255

Leu Glu Leu Glu Gly Ile His Met Thr Ser Arg Ser Ser Arg Val Asp
            260                 265                 270

Leu Gln Ala Cys Lys Leu Ser Leu Glu Gln Lys Leu Ile Ser Glu Glu
        275                 280                 285

Asp Leu
    290

<210> SEQ ID NO 10
<211> LENGTH: 426
<212> TYPE: PRT
<213> ORGANISM: Artificial sequence
<220> FEATURE:
<223> OTHER INFORMATION: Synthetic construct: PelB::antiHELscFv-TM2
<220> FEATURE:
<221> NAME/KEY: misc_feature
<222> LOCATION: 1..22
<223> OTHER INFORMATION: amino acids 1-22 corresdponds to PelB leader
      peptide
<220> FEATURE:
<221> NAME/KEY: misc_feature
<222> LOCATION: 23..280
<223> OTHER INFORMATION: amino acid 23-280 corresponds to Fv fragment of
      Hen egg lysozyme (HEL) D1.3 antibody
<220> FEATURE:
<221> NAME/KEY: misc_feature
<222> LOCATION: 287..426
<223> OTHER INFORMATION: amino acid 287-426 corresponds to tamavidin 2

<400> SEQUENCE: 10

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Pro Gly
            20                  25                  30

Leu Val Ala Pro Ser Gln Ser Leu Ser Ile Thr Cys Thr Val Ser Gly
        35                  40                  45

Phe Ser Leu Thr Gly Tyr Gly Val Asn Trp Val Arg Gln Pro Pro Gly
    50                  55                  60

Lys Gly Leu Glu Trp Leu Gly Met Ile Trp Gly Asp Gly Asn Thr Asp
65                  70                  75                  80

Tyr Asn Ser Ala Leu Lys Ser Arg Leu Ser Ile Ser Lys Asp Asn Ser
                85                  90                  95

Lys Ser Gln Val Phe Leu Lys Met Asn Ser Leu His Thr Asp Asp Thr
```

```
            100                 105                 110
Ala Arg Tyr Tyr Cys Ala Arg Glu Arg Asp Tyr Arg Leu Asp Tyr Trp
            115                 120                 125

Gly Gln Gly Thr Thr Val Thr Val Ser Ser Gly Gly Gly Ser Gly
        130                 135                 140

Gly Gly Gly Ser Gly Gly Gly Ser Asp Ile Glu Leu Thr Gln Ser
145                 150                 155                 160

Pro Ala Ser Leu Ser Ala Ser Val Gly Glu Thr Val Thr Ile Thr Cys
                165                 170                 175

Arg Ala Ser Gly Asn Ile His Asn Tyr Leu Ala Trp Tyr Gln Gln Lys
                180                 185                 190

Gln Gly Lys Ser Pro Gln Leu Leu Val Tyr Tyr Thr Thr Thr Leu Ala
            195                 200                 205

Asp Gly Val Pro Ser Arg Phe Ser Gly Ser Gly Ser Gly Thr Gln Tyr
            210                 215                 220

Ser Leu Lys Ile Asn Ser Leu Gln Pro Glu Asp Phe Gly Ser Tyr Tyr
225                 230                 235                 240

Cys Gln His Phe Trp Ser Thr Pro Arg Thr Phe Gly Gly Gly Thr Lys
                245                 250                 255

Leu Glu Leu Glu Gly Ile His Met Thr Ser Arg Ser Ser Arg Val Asp
            260                 265                 270

Leu Gln Ala Cys Lys Leu Ser Leu Gly Gly Gly Gly Ser Gly Ser Asp
            275                 280                 285

Val Gln Ser Ser Leu Thr Gly Thr Trp Tyr Asn Glu Leu Asn Ser Lys
        290                 295                 300

Met Glu Leu Thr Ala Asn Lys Asp Gly Thr Leu Thr Gly Lys Tyr Leu
305                 310                 315                 320

Ser Lys Val Gly Asp Val Tyr Val Pro Tyr Pro Leu Ser Gly Arg Tyr
                325                 330                 335

Asn Leu Gln Pro Pro Ala Gly Gln Gly Val Ala Leu Gly Trp Ala Val
                340                 345                 350

Ser Trp Glu Asn Ser Lys Ile His Ser Ala Thr Thr Trp Ser Gly Gln
            355                 360                 365

Phe Phe Ser Glu Ser Ser Pro Val Ile Leu Thr Gln Trp Leu Leu Ser
370                 375                 380

Ser Ser Thr Ala Arg Gly Asp Val Trp Glu Ser Thr Leu Val Gly Asn
385                 390                 395                 400

Asp Ser Phe Thr Lys Thr Ala Pro Thr Glu Gln Gln Ile Ala His Ala
                405                 410                 415

Gln Leu His Cys Arg Ala Pro Arg Leu Lys
            420                 425

<210> SEQ ID NO 11
<211> LENGTH: 92
<212> TYPE: DNA
<213> ORGANISM: Artificial Sequence
<220> FEATURE:
<223> OTHER INFORMATION: Designed and synthesized DNA as a PCR primer

<400> SEQUENCE: 11
aaatcatgaa atacctattg cctacggcag ccgctggctt gctgctgctg gcagctcagc      60
cggccatggc gcaggtgcag ctgcaggagt ca                                   92

<210> SEQ ID NO 12
<211> LENGTH: 62
<212> TYPE: DNA
```

-continued

<213> ORGANISM: Artificial Sequence
<220> FEATURE:
<223> OTHER INFORMATION: Designed and synthesized DNA as a PCR primer

<400> SEQUENCE: 12
tttggatcct tatagatctt cttctgagat cagcttttgt tctagggaaa gcttgcatgc    60
ct                                                                   62

<210> SEQ ID NO 13
<211> LENGTH: 37
<212> TYPE: DNA
<213> ORGANISM: Artificial Sequence
<220> FEATURE:
<223> OTHER INFORMATION: Designed and synthesized DNA as a PCR primer

<400> SEQUENCE: 13
accgctgcca ccgccaccta gggaaagctt gcatgcc                              37

<210> SEQ ID NO 14
<211> LENGTH: 58
<212> TYPE: DNA
<213> ORGANISM: Artificial Sequence
<220> FEATURE:
<223> OTHER INFORMATION: Designed and synthesized DNA as a PCR primer

<400> SEQUENCE: 14
ggcatgcaag ctttccctag gtggcggtgg cagcggttca gacgttcaat cttcactc      58

<210> SEQ ID NO 15
<211> LENGTH: 31
<212> TYPE: DNA
<213> ORGANISM: Artificial Sequence
<220> FEATURE:
<223> OTHER INFORMATION: Designed and synthesized DNA as a PCR primer

<400> SEQUENCE: 15 tttttttggat ccttacttca acctcggtgc g                                  31

<210> SEQ ID NO 16
<211> LENGTH: 31
<212> TYPE: DNA
<213> ORGANISM: Artificial Sequence
<220> FEATURE:
<223> OTHER INFORMATION: Designed and synthesized DNA as a PCR primer

<400> SEQUENCE: 16
cttgtaacat gtcagaagaa aatacacaat c                                   31

<210> SEQ ID NO 17
<211> LENGTH: 59
<212> TYPE: DNA
<213> ORGANISM: Artificial Sequence
<220> FEATURE:
<223> OTHER INFORMATION: Designed and synthesized DNA as a PCR primer

<400> SEQUENCE: 17
caggtgtttg tattgcagtc ggtggcggtg gcagcggttc agacgttcaa tcttcactc     59

<210> SEQ ID NO 18
<211> LENGTH: 38
<212> TYPE: DNA
<213> ORGANISM: Artificial Sequence
<220> FEATURE:
<223> OTHER INFORMATION: Designed and synthesized DNA as a PCR primer

<400> SEQUENCE: 18
accgctgcca ccgccaccga ctgcaataca aacacctg     38

<210> SEQ ID NO 19
<211> LENGTH: 1992
<212> TYPE: DNA
<213> ORGANISM: Artificial sequence
<220> FEATURE:
<223> OTHER INFORMATION: Synthetic construct: ISH224-alpha2,6ST-
      5XlinkTM2
<220> FEATURE:
<221> NAME/KEY: CDS
<222> LOCATION: 1..1494
<223> OTHER INFORMATION: nucleotides 1-1494 encodes ISH224-alpha2,6
      sialic acid transferase
<220> FEATURE:
<221> NAME/KEY: CDS
<222> LOCATION: 1570..1992
<223> OTHER INFORMATION: nucleotides 1570-1992 encodes tamavidin 2

<400> SEQUENCE: 19

| | | | | | | | | | | | | | | | | |
|---|---|---|---|---|---|---|---|---|---|---|---|---|---|---|---|---|
| atg | tca | gaa | gaa | aat | aca | caa | tct | att | att | aaa | aat | gat | att | aat | aaa | 48 |
| Met | Ser | Glu | Glu | Asn | Thr | Gln | Ser | Ile | Ile | Lys | Asn | Asp | Ile | Asn | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| act | att | att | gat | gag | gag | tat | gtt | aat | tta | gag | cca | att | aat | caa | tca | 96 |
| Thr | Ile | Ile | Asp | Glu | Glu | Tyr | Val | Asn | Leu | Glu | Pro | Ile | Asn | Gln | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | atc | tct | ttt | aca | aaa | cac | tct | tgg | gta | caa | act | tgt | ggt | acg | caa | 144 |
| Asn | Ile | Ser | Phe | Thr | Lys | His | Ser | Trp | Val | Gln | Thr | Cys | Gly | Thr | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| caa | cta | tta | aca | gaa | caa | aat | aaa | gag | tca | ata | tca | tta | tct | gta | gtg | 192 |
| Gln | Leu | Leu | Thr | Glu | Gln | Asn | Lys | Glu | Ser | Ile | Ser | Leu | Ser | Val | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| gcg | cca | cga | tta | gat | gac | gat | gaa | aag | tac | tgc | ttt | gat | ttt | aat | ggt | 240 |
| Ala | Pro | Arg | Leu | Asp | Asp | Asp | Glu | Lys | Tyr | Cys | Phe | Asp | Phe | Asn | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtt | agt | aat | aaa | ggt | gaa | aaa | tat | ata | aca | aaa | gta | aca | tta | aac | gta | 288 |
| Val | Ser | Asn | Lys | Gly | Glu | Lys | Tyr | Ile | Thr | Lys | Val | Thr | Leu | Asn | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| gtg | gct | cca | tct | tta | gag | gtt | tat | gtt | gat | cat | gca | tct | ctt | cca | act | 336 |
| Val | Ala | Pro | Ser | Leu | Glu | Val | Tyr | Val | Asp | His | Ala | Ser | Leu | Pro | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| ctt | cag | cag | cta | atg | gat | att | att | aaa | tcg | gaa | gaa | gaa | aat | cct | aca | 384 |
| Leu | Gln | Gln | Leu | Met | Asp | Ile | Ile | Lys | Ser | Glu | Glu | Glu | Asn | Pro | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| gca | caa | aga | tat | ata | gct | tgg | ggg | aga | ata | gtt | ccg | act | gat | gag | caa | 432 |
| Ala | Gln | Arg | Tyr | Ile | Ala | Trp | Gly | Arg | Ile | Val | Pro | Thr | Asp | Glu | Gln | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | aaa | gag | tta | aat | att | aca | tcg | ttt | gca | ttg | ata | aat | aac | cat | aca | 480 |
| Met | Lys | Glu | Leu | Asn | Ile | Thr | Ser | Phe | Ala | Leu | Ile | Asn | Asn | His | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cca | gct | gac | tta | gta | caa | gaa | att | gtt | aag | caa | gca | caa | aca | aag | cat | 528 |
| Pro | Ala | Asp | Leu | Val | Gln | Glu | Ile | Val | Lys | Gln | Ala | Gln | Thr | Lys | His | |
| | | | | 165 | | | | | 170 | | | | | 175 | | |

| | | | | | | | | | | | | | | | | |
|---|---|---|---|---|---|---|---|---|---|---|---|---|---|---|---|---|
| aga | ttg | aat | gtt | aaa | ctt | agc | tct | aac | act | gct | cat | tca | ttt | gat | aat | 576 |
| Arg | Leu | Asn | Val | Lys | Leu | Ser | Ser | Asn | Thr | Ala | His | Ser | Phe | Asp | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| tta | gtg | cca | ata | cta | aaa | gaa | tta | aat | tcg | ttt | aat | aac | gtt | acg | gta | 624 |
| Leu | Val | Pro | Ile | Leu | Lys | Glu | Leu | Asn | Ser | Phe | Asn | Asn | Val | Thr | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| aca | aat | ata | gat | tta | tat | gat | gat | ggt | tca | gca | gaa | tat | gta | aat | tta | 672 |
| Thr | Asn | Ile | Asp | Leu | Tyr | Asp | Asp | Gly | Ser | Ala | Glu | Tyr | Val | Asn | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | aac | tgg | aga | gat | aca | tta | aat | aaa | aca | gat | aat | tta | aaa | att | ggt | 720 |
| Tyr | Asn | Trp | Arg | Asp | Thr | Leu | Asn | Lys | Thr | Asp | Asn | Leu | Lys | Ile | Gly | |

```
             225                 230                 235                 240
aaa gat tat ctt gag gat gtc att aat ggt atc aat gaa gac act tca       768
Lys Asp Tyr Leu Glu Asp Val Ile Asn Gly Ile Asn Glu Asp Thr Ser
                245                 250                 255 aat aca gga aca tca tct gtt tat aac tgg caa aaa cta tat cca gct       816
Asn Thr Gly Thr Ser Ser Val Tyr Asn Trp Gln Lys Leu Tyr Pro Ala
                260                 265                 270 aac tac cat ttt tta aga aaa gat tat tta act tta gaa cca tca tta       864
Asn Tyr His Phe Leu Arg Lys Asp Tyr Leu Thr Leu Glu Pro Ser Leu
                275                 280                 285 cat gag tta cga gac tat att ggt gat agt tta aag caa atg caa tgg       912
His Glu Leu Arg Asp Tyr Ile Gly Asp Ser Leu Lys Gln Met Gln Trp
                290                 295                 300 gat ggt ttc aaa aaa ttc aat agc aaa caa caa gaa tta ttc tta tcg       960
Asp Gly Phe Lys Lys Phe Asn Ser Lys Gln Gln Glu Leu Phe Leu Ser
305                 310                 315                 320 att gtt aat ttt gac aaa caa aaa tta caa aat gaa tat aat tca tct      1008
Ile Val Asn Phe Asp Lys Gln Lys Leu Gln Asn Glu Tyr Asn Ser Ser
                325                 330                 335 aat tta cca aac ttt gtg ttt aca ggt acg act gta tgg gct ggt aac      1056
Asn Leu Pro Asn Phe Val Phe Thr Gly Thr Thr Val Trp Ala Gly Asn
                340                 345                 350 cat gaa aga gag tat tat gcg aaa caa caa att aat gtc att aat aat      1104
His Glu Arg Glu Tyr Tyr Ala Lys Gln Gln Ile Asn Val Ile Asn Asn
                355                 360                 365 gca att aat gaa tcg agc cca cat tat tta ggc aat agt tat gat ttg      1152
Ala Ile Asn Glu Ser Ser Pro His Tyr Leu Gly Asn Ser Tyr Asp Leu
                370                 375                 380 ttc ttc aaa ggt cac cct ggt ggc ggt atc att aat aca tta ata atg      1200
Phe Phe Lys Gly His Pro Gly Gly Gly Ile Ile Asn Thr Leu Ile Met
385                 390                 395                 400 caa aac tat cct tca atg gtt gat att cca tca aaa ata tca ttt gaa      1248
Gln Asn Tyr Pro Ser Met Val Asp Ile Pro Ser Lys Ile Ser Phe Glu
                405                 410                 415 gtt ttg atg atg aca gat atg ctt cct gat gca gtt gct ggt ata gcg      1296
Val Leu Met Met Thr Asp Met Leu Pro Asp Ala Val Ala Gly Ile Ala
                420                 425                 430 agc tct tta tat ttc acg ata cca gct gaa aaa att aaa ttt ata gtt      1344
Ser Ser Leu Tyr Phe Thr Ile Pro Ala Glu Lys Ile Lys Phe Ile Val
                435                 440                 445 ttt aca tcg aca gaa act ata act gat cgt gaa act gct ttg aga agt      1392
Phe Thr Ser Thr Glu Thr Ile Thr Asp Arg Glu Thr Ala Leu Arg Ser
450                 455                 460 cct tta gtt caa gta atg ata aaa cta ggt att gta aaa gaa gag aat      1440
Pro Leu Val Gln Val Met Ile Lys Leu Gly Ile Val Lys Glu Glu Asn
465                 470                 475                 480 gta ctt ttt tgg gct gat ctg cca aat tgt gaa aca ggt gtt tgt att      1488
Val Leu Phe Trp Ala Asp Leu Pro Asn Cys Glu Thr Gly Val Cys Ile
                485                 490                 495 gca gtc ggt ggc ggt ggc agc ggt ggc ggt ggc agc ggt ggc ggt ggc      1536
Ala Val Gly Gly Gly Gly Ser Gly Gly Gly Gly Ser Gly Gly Gly Gly
                500                 505                 510 agc ggt ggc ggt ggc agc ggt ggc ggt ggc agc tca gac gtt caa tct      1584
Ser Gly Gly Gly Gly Ser Gly Gly Gly Gly Ser Ser Asp Val Gln Ser
                515                 520                 525 tca ctc acc gga acc tgg tac aat gaa ctc aac tcc aag atg gaa ttg      1632
Ser Leu Thr Gly Thr Trp Tyr Asn Glu Leu Asn Ser Lys Met Glu Leu
                530                 535                 540 act gca aac aaa gac ggt act ctc act gga aag tac ctc tcc aaa gtt      1680
Thr Ala Asn Lys Asp Gly Thr Leu Thr Gly Lys Tyr Leu Ser Lys Val
```

```
                   545                 550                 555                 560
ggg gat gtc tac gtg ccc tac cca ctc tct ggt cgc tat aac ctc caa    1728
Gly Asp Val Tyr Val Pro Tyr Pro Leu Ser Gly Arg Tyr Asn Leu Gln
                565                 570                 575 ccc ccc gcg gga caa ggc gtc gct ctt ggg tgg gcg gta tcc tgg gag    1776
Pro Pro Ala Gly Gln Gly Val Ala Leu Gly Trp Ala Val Ser Trp Glu
            580                 585                 590 aac agt aaa att cat tcc gct acg aca tgg agc gga cag ttc ttc tct    1824
Asn Ser Lys Ile His Ser Ala Thr Thr Trp Ser Gly Gln Phe Phe Ser
        595                 600                 605 gag tcg tct cca gtg att ctt act cag tgg ttg ttg tca tcg agc act    1872
Glu Ser Ser Pro Val Ile Leu Thr Gln Trp Leu Leu Ser Ser Ser Thr
    610                 615                 620 gcg cgt ggg gac gta tgg gaa tcc aca ctt gtg ggg aat gat tcg ttt    1920
Ala Arg Gly Asp Val Trp Glu Ser Thr Leu Val Gly Asn Asp Ser Phe
625                 630                 635                 640 aca aag acg gcg ccg act gag cag cag atc gct cat gct caa ctc cat    1968
Thr Lys Thr Ala Pro Thr Glu Gln Gln Ile Ala His Ala Gln Leu His
                645                 650                 655 tgt cgc gca ccg agg ttg aag taa                                    1992
Cys Arg Ala Pro Arg Leu Lys
            660

<210> SEQ ID NO 20
<211> LENGTH: 663
<212> TYPE: PRT
<213> ORGANISM: Artificial sequence
<220> FEATURE:
<223> OTHER INFORMATION: Synthetic construct: ISH224-alpha2,6ST-
      5XlinkTM2
<220> FEATURE:
<221> NAME/KEY: misc_feature
<222> LOCATION: 1..498
<223> OTHER INFORMATION: amino acids 1-498 corresponds to ISH224-
      alpha2,6 sialic acid transferase
<220> FEATURE:
<221> NAME/KEY: misc_feature
<222> LOCATION: 524..663
<223> OTHER INFORMATION: amino acid 524-663 corresponds to tamavidin 2

<400> SEQUENCE: 20

Met Ser Glu Glu Asn Thr Gln Ser Ile Ile Lys Asn Asp Ile Asn Lys
1               5                   10                  15

Thr Ile Ile Asp Glu Glu Tyr Val Asn Leu Glu Pro Ile Asn Gln Ser
            20                  25                  30

Asn Ile Ser Phe Thr Lys His Ser Trp Val Gln Thr Cys Gly Thr Gln
        35                  40                  45

Gln Leu Leu Thr Glu Gln Asn Lys Glu Ser Ile Ser Leu Ser Val Val
    50                  55                  60

Ala Pro Arg Leu Asp Asp Asp Glu Lys Tyr Cys Phe Asp Phe Asn Gly
65                  70                  75                  80

Val Ser Asn Lys Gly Glu Lys Tyr Ile Thr Lys Val Thr Leu Asn Val
                85                  90                  95

Val Ala Pro Ser Leu Glu Val Tyr Val Asp His Ala Ser Leu Pro Thr
            100                 105                 110

Leu Gln Gln Leu Met Asp Ile Ile Lys Ser Glu Glu Glu Asn Pro Thr
        115                 120                 125

Ala Gln Arg Tyr Ile Ala Trp Gly Arg Ile Val Pro Thr Asp Glu Gln
    130                 135                 140

Met Lys Glu Leu Asn Ile Thr Ser Phe Ala Leu Ile Asn Asn His Thr
145                 150                 155                 160
```

-continued

```
Pro Ala Asp Leu Val Gln Glu Ile Val Lys Gln Ala Gln Thr Lys His
                165                 170                 175

Arg Leu Asn Val Lys Leu Ser Ser Asn Thr Ala His Ser Phe Asp Asn
            180                 185                 190

Leu Val Pro Ile Leu Lys Glu Leu Asn Ser Phe Asn Asn Val Thr Val
        195                 200                 205

Thr Asn Ile Asp Leu Tyr Asp Asp Gly Ser Ala Glu Tyr Val Asn Leu
    210                 215                 220

Tyr Asn Trp Arg Asp Thr Leu Asn Lys Thr Asp Asn Leu Lys Ile Gly
225                 230                 235                 240

Lys Asp Tyr Leu Glu Asp Val Ile Asn Gly Ile Asn Glu Asp Thr Ser
            245                 250                 255

Asn Thr Gly Thr Ser Ser Val Tyr Asn Trp Gln Lys Leu Tyr Pro Ala
            260                 265                 270

Asn Tyr His Phe Leu Arg Lys Asp Tyr Leu Thr Leu Glu Pro Ser Leu
        275                 280                 285

His Glu Leu Arg Asp Tyr Ile Gly Asp Ser Leu Lys Gln Met Gln Trp
    290                 295                 300

Asp Gly Phe Lys Lys Phe Asn Ser Lys Gln Gln Glu Leu Phe Leu Ser
305                 310                 315                 320

Ile Val Asn Phe Asp Lys Gln Lys Leu Gln Asn Glu Tyr Asn Ser Ser
            325                 330                 335

Asn Leu Pro Asn Phe Val Phe Thr Gly Thr Thr Val Trp Ala Gly Asn
            340                 345                 350

His Glu Arg Glu Tyr Tyr Ala Lys Gln Gln Ile Asn Val Ile Asn Asn
        355                 360                 365

Ala Ile Asn Glu Ser Ser Pro His Tyr Leu Gly Asn Ser Tyr Asp Leu
    370                 375                 380

Phe Phe Lys Gly His Pro Gly Gly Ile Ile Asn Thr Leu Ile Met
385                 390                 395                 400

Gln Asn Tyr Pro Ser Met Val Asp Ile Pro Ser Lys Ile Ser Phe Glu
            405                 410                 415

Val Leu Met Met Thr Asp Met Leu Pro Asp Ala Val Ala Gly Ile Ala
            420                 425                 430

Ser Ser Leu Tyr Phe Thr Ile Pro Ala Glu Lys Ile Lys Phe Ile Val
        435                 440                 445

Phe Thr Ser Thr Glu Thr Ile Thr Asp Arg Glu Thr Ala Leu Arg Ser
    450                 455                 460

Pro Leu Val Gln Val Met Ile Lys Leu Gly Ile Val Lys Glu Glu Asn
465                 470                 475                 480

Val Leu Phe Trp Ala Asp Leu Pro Asn Cys Glu Thr Gly Val Cys Ile
            485                 490                 495

Ala Val Gly Gly Gly Ser Gly Gly Gly Ser Gly Gly Gly
            500                 505                 510

Ser Gly Gly Gly Ser Gly Gly Gly Ser Ser Asp Val Gln Ser
        515                 520                 525

Ser Leu Thr Gly Thr Trp Tyr Asn Glu Leu Asn Ser Lys Met Glu Leu
    530                 535                 540

Thr Ala Asn Lys Asp Gly Thr Leu Thr Gly Lys Tyr Leu Ser Lys Val
545                 550                 555                 560

Gly Asp Val Tyr Val Pro Tyr Pro Leu Ser Gly Arg Tyr Asn Leu Gln
            565                 570                 575

Pro Pro Ala Gly Gln Gly Val Ala Leu Gly Trp Ala Val Ser Trp Glu
            580                 585                 590
```

```
Asn Ser Lys Ile His Ser Ala Thr Thr Trp Ser Gly Gln Phe Phe Ser
            595                 600                 605

Glu Ser Ser Pro Val Ile Leu Thr Gln Trp Leu Leu Ser Ser Ser Thr
        610                 615                 620

Ala Arg Gly Asp Val Trp Glu Ser Thr Leu Val Gly Asn Asp Ser Phe
625                 630                 635                 640

Thr Lys Thr Ala Pro Thr Glu Gln Gln Ile Ala His Ala Gln Leu His
            645                 650                 655

Cys Arg Ala Pro Arg Leu Lys
            660

<210> SEQ ID NO 21
<211> LENGTH: 116
<212> TYPE: DNA
<213> ORGANISM: Artificial Sequence
<220> FEATURE:
<223> OTHER INFORMATION: Designed and synthesized DNA as a PCR primer

<400> SEQUENCE: 21
caggtgtttg tattgcagtc ggtggcggtg gcagcggtgg cggtggcagc ggtggcggtg      60
gcagcggtgg cggtggcagc ggtggcggtg gcagctcaga cgttcaatct tcactc        116

<210> SEQ ID NO 22
<211> LENGTH: 31
<212> TYPE: DNA
<213> ORGANISM: Artificial Sequence
<220> FEATURE:
<223> OTHER INFORMATION: Designed and synthesized DNA as a PCR primer

<400> SEQUENCE: 22 tttttttggat ccttacttca acctcggtgc g                                    31

<210> SEQ ID NO 23
<211> LENGTH: 81
<212> TYPE: DNA
<213> ORGANISM: Artificial Sequence
<220> FEATURE:
<223> OTHER INFORMATION: Designed and synthesized DNA as a PCR primer
      224-26ST-3XlinkTM2FW

<400> SEQUENCE: 23
ggtgtttgta ttgcagtcgg tggcggtggc agcggtggcg gtggcagcgg tggcggtggc      60
agctcagacg ttcaatcttc a                                               81

<210> SEQ ID NO 24
<211> LENGTH: 1962
<212> TYPE: DNA
<213> ORGANISM: Artificial sequence
<220> FEATURE:
<223> OTHER INFORMATION: Synthetic construct: ISH224-alpha2,6ST-
      3XlinkTM2
<220> FEATURE:
<221> NAME/KEY: CDS
<222> LOCATION: 1..1494
<223> OTHER INFORMATION: nucleotides 1-1494 encodes ISH224-alpha2,6
      sialic acid transferase
<220> FEATURE:
<221> NAME/KEY: CDS
<222> LOCATION: 1540..1962
<223> OTHER INFORMATION: nucleotides 1540-1962 encodes tamavidin 2

<400> SEQUENCE: 24 atg tca gaa gaa aat aca caa tct att att aaa aat gat att aat aaa        48
Met Ser Glu Glu Asn Thr Gln Ser Ile Ile Lys Asn Asp Ile Asn Lys
1               5                   10                  15
```

|     |     |     |     |     |     |     |     |     |     |     |     |     |     |     |     |     |
|---|---|---|---|---|---|---|---|---|---|---|---|---|---|---|---|---|
| act | att | att | gat | gag | gag | tat | gtt | aat | tta | gag | cca | att | aat | caa | tca | 96 |
| Thr | Ile | Ile | Asp | Glu | Glu | Tyr | Val | Asn | Leu | Glu | Pro | Ile | Asn | Gln | Ser | |
| | | | 20 | | | | | 25 | | | | | 30 | | | |
| aac | atc | tct | ttt | aca | aaa | cac | tct | tgg | gta | caa | act | tgt | ggt | acg | caa | 144 |
| Asn | Ile | Ser | Phe | Thr | Lys | His | Ser | Trp | Val | Gln | Thr | Cys | Gly | Thr | Gln | |
| | | 35 | | | | | 40 | | | | | 45 | | | | |
| caa | cta | tta | aca | gaa | caa | aat | aaa | gag | tca | ata | tca | tta | tct | gta | gtg | 192 |
| Gln | Leu | Leu | Thr | Glu | Gln | Asn | Lys | Glu | Ser | Ile | Ser | Leu | Ser | Val | Val | |
| 50 | | | | | 55 | | | | | 60 | | | | | | |
| gcg | cca | cga | tta | gat | gac | gat | gaa | aag | tac | tgc | ttt | gat | ttt | aat | ggt | 240 |
| Ala | Pro | Arg | Leu | Asp | Asp | Asp | Glu | Lys | Tyr | Cys | Phe | Asp | Phe | Asn | Gly | |
| 65 | | | | 70 | | | | | 75 | | | | | 80 | | |
| gtt | agt | aat | aaa | ggt | gaa | aaa | tat | ata | aca | aaa | gta | aca | tta | aac | gta | 288 |
| Val | Ser | Asn | Lys | Gly | Glu | Lys | Tyr | Ile | Thr | Lys | Val | Thr | Leu | Asn | Val | |
| | | | | 85 | | | | | 90 | | | | | 95 | | |
| gtg | gct | cca | tct | tta | gag | gtt | tat | gtt | gat | cat | gca | tct | ctt | cca | act | 336 |
| Val | Ala | Pro | Ser | Leu | Glu | Val | Tyr | Val | Asp | His | Ala | Ser | Leu | Pro | Thr | |
| | | | 100 | | | | | 105 | | | | | 110 | | | |
| ctt | cag | cag | cta | atg | gat | att | att | aaa | tcg | gaa | gaa | gaa | aat | cct | aca | 384 |
| Leu | Gln | Gln | Leu | Met | Asp | Ile | Ile | Lys | Ser | Glu | Glu | Glu | Asn | Pro | Thr | |
| | | 115 | | | | | 120 | | | | | 125 | | | | |
| gca | caa | aga | tat | ata | gct | tgg | ggg | aga | ata | gtt | ccg | act | gat | gag | caa | 432 |
| Ala | Gln | Arg | Tyr | Ile | Ala | Trp | Gly | Arg | Ile | Val | Pro | Thr | Asp | Glu | Gln | |
| 130 | | | | | 135 | | | | | 140 | | | | | | |
| atg | aaa | gag | tta | aat | att | aca | tcg | ttt | gca | ttg | ata | aat | aac | cat | aca | 480 |
| Met | Lys | Glu | Leu | Asn | Ile | Thr | Ser | Phe | Ala | Leu | Ile | Asn | Asn | His | Thr | |
| 145 | | | | 150 | | | | | 155 | | | | | 160 | | |
| cca | gct | gac | tta | gta | caa | gaa | att | gtt | aag | caa | gca | caa | aca | aag | cat | 528 |
| Pro | Ala | Asp | Leu | Val | Gln | Glu | Ile | Val | Lys | Gln | Ala | Gln | Thr | Lys | His | |
| | | | | 165 | | | | | 170 | | | | | 175 | | |
| aga | ttg | aat | gtt | aaa | ctt | agc | tct | aac | act | gct | cat | tca | ttt | gat | aat | 576 |
| Arg | Leu | Asn | Val | Lys | Leu | Ser | Ser | Asn | Thr | Ala | His | Ser | Phe | Asp | Asn | |
| | | | 180 | | | | | 185 | | | | | 190 | | | |
| tta | gtg | cca | ata | cta | aaa | gaa | tta | aat | tcg | ttt | aat | aac | gtt | acg | gta | 624 |
| Leu | Val | Pro | Ile | Leu | Lys | Glu | Leu | Asn | Ser | Phe | Asn | Asn | Val | Thr | Val | |
| | | 195 | | | | | 200 | | | | | 205 | | | | |
| aca | aat | ata | gat | tta | tat | gat | gat | ggt | tca | gca | gaa | tat | gta | aat | tta | 672 |
| Thr | Asn | Ile | Asp | Leu | Tyr | Asp | Asp | Gly | Ser | Ala | Glu | Tyr | Val | Asn | Leu | |
| | 210 | | | | | 215 | | | | | 220 | | | | | |
| tat | aac | tgg | aga | gat | aca | tta | aat | aaa | aca | gat | aat | tta | aaa | att | ggt | 720 |
| Tyr | Asn | Trp | Arg | Asp | Thr | Leu | Asn | Lys | Thr | Asp | Asn | Leu | Lys | Ile | Gly | |
| 225 | | | | | 230 | | | | | 235 | | | | | 240 | |
| aaa | gat | tat | ctt | gag | gat | gtc | att | aat | ggt | atc | aat | gaa | gac | act | tca | 768 |
| Lys | Asp | Tyr | Leu | Glu | Asp | Val | Ile | Asn | Gly | Ile | Asn | Glu | Asp | Thr | Ser | |
| | | | | 245 | | | | | 250 | | | | | 255 | | |
| aat | aca | gga | aca | tca | tct | gtt | tat | aac | tgg | caa | aaa | cta | tat | cca | gct | 816 |
| Asn | Thr | Gly | Thr | Ser | Ser | Val | Tyr | Asn | Trp | Gln | Lys | Leu | Tyr | Pro | Ala | |
| | | | 260 | | | | | 265 | | | | | 270 | | | |
| aac | tac | cat | ttt | tta | aga | aaa | gat | tat | tta | act | tta | gaa | cca | tca | tta | 864 |
| Asn | Tyr | His | Phe | Leu | Arg | Lys | Asp | Tyr | Leu | Thr | Leu | Glu | Pro | Ser | Leu | |
| | | 275 | | | | | 280 | | | | | 285 | | | | |
| cat | gag | tta | cga | gac | tat | att | ggt | gat | agt | tta | aag | caa | atg | caa | tgg | 912 |
| His | Glu | Leu | Arg | Asp | Tyr | Ile | Gly | Asp | Ser | Leu | Lys | Gln | Met | Gln | Trp | |
| 290 | | | | | 295 | | | | | 300 | | | | | | |
| gat | ggt | ttc | aaa | aaa | ttc | aat | agc | aaa | caa | caa | gaa | tta | ttc | tta | tcg | 960 |
| Asp | Gly | Phe | Lys | Lys | Phe | Asn | Ser | Lys | Gln | Gln | Glu | Leu | Phe | Leu | Ser | |
| 305 | | | | 310 | | | | | 315 | | | | | 320 | | |
| att | gtt | aat | ttt | gac | aaa | caa | aaa | tta | caa | aat | gaa | tat | aat | tca | tct | 1008 |
| Ile | Val | Asn | Phe | Asp | Lys | Gln | Lys | Leu | Gln | Asn | Glu | Tyr | Asn | Ser | Ser | |
| | | | 325 | | | | | 330 | | | | | 335 | | | |

```
aat tta cca aac ttt gtg ttt aca ggt acg act gta tgg gct ggt aac       1056
Asn Leu Pro Asn Phe Val Phe Thr Gly Thr Thr Val Trp Ala Gly Asn
            340                 345                 350 cat gaa aga gag tat tat gcg aaa caa caa att aat gtc att aat aat       1104
His Glu Arg Glu Tyr Tyr Ala Lys Gln Gln Ile Asn Val Ile Asn Asn
        355                 360                 365 gca att aat gaa tcg agc cca cat tat tta ggc aat agt tat gat ttg       1152
Ala Ile Asn Glu Ser Ser Pro His Tyr Leu Gly Asn Ser Tyr Asp Leu
370                 375                 380 ttc ttc aaa ggt cac cct ggt ggc ggt atc att aat aca tta ata atg       1200
Phe Phe Lys Gly His Pro Gly Gly Gly Ile Ile Asn Thr Leu Ile Met
385                 390                 395                 400 caa aac tat cct tca atg gtt gat att cca tca aaa ata tca ttt gaa       1248
Gln Asn Tyr Pro Ser Met Val Asp Ile Pro Ser Lys Ile Ser Phe Glu
            405                 410                 415 gtt ttg atg atg aca gat atg ctt cct gat gca gtt gct ggt ata gcg       1296
Val Leu Met Met Thr Asp Met Leu Pro Asp Ala Val Ala Gly Ile Ala
        420                 425                 430 agc tct tta tat ttc acg ata cca gct gaa aaa att aaa ttt ata gtt       1344
Ser Ser Leu Tyr Phe Thr Ile Pro Ala Glu Lys Ile Lys Phe Ile Val
            435                 440                 445 ttt aca tcg aca gaa act ata act gat cgt gaa act gct ttg aga agt       1392
Phe Thr Ser Thr Glu Thr Ile Thr Asp Arg Glu Thr Ala Leu Arg Ser
450                 455                 460 cct tta gtt caa gta atg ata aaa cta ggt att gta aaa gaa gag aat       1440
Pro Leu Val Gln Val Met Ile Lys Leu Gly Ile Val Lys Glu Glu Asn
465                 470                 475                 480 gta ctt ttt tgg gct gat ctg cca aat tgt gaa aca ggt gtt tgt att       1488
Val Leu Phe Trp Ala Asp Leu Pro Asn Cys Glu Thr Gly Val Cys Ile
            485                 490                 495 gca gtc ggt ggc ggt ggc agc ggt ggc ggt ggc agc ggt ggc ggt ggc       1536
Ala Val Gly Gly Gly Gly Ser Gly Gly Gly Gly Ser Gly Gly Gly Gly
        500                 505                 510 agc tca gac gtt caa tct tca ctc acc gga acc tgg tac aat gaa ctc       1584
Ser Ser Asp Val Gln Ser Ser Leu Thr Gly Thr Trp Tyr Asn Glu Leu
            515                 520                 525 aac tcc aag atg gaa ttg act gca aac aaa gac ggt act ctc act gga       1632
Asn Ser Lys Met Glu Leu Thr Ala Asn Lys Asp Gly Thr Leu Thr Gly
530                 535                 540 aag tac ctc tcc aaa gtt ggg gat gtc tac gtg ccc tac cca ctc tct       1680
Lys Tyr Leu Ser Lys Val Gly Asp Val Tyr Val Pro Tyr Pro Leu Ser
545                 550                 555                 560 ggt cgc tat aac ctc caa ccc ccc gcg gga caa ggc gtc gct ctt ggg       1728
Gly Arg Tyr Asn Leu Gln Pro Pro Ala Gly Gln Gly Val Ala Leu Gly
            565                 570                 575 tgg gcg gta tcc tgg gag aac agt aaa att cat tcc gct acg aca tgg       1776
Trp Ala Val Ser Trp Glu Asn Ser Lys Ile His Ser Ala Thr Thr Trp
        580                 585                 590 agc gga cag ttc ttc tct gag tcg tct cca gtg att ctt act cag tgg       1824
Ser Gly Gln Phe Phe Ser Glu Ser Ser Pro Val Ile Leu Thr Gln Trp
            595                 600                 605 ttg ttg tca tcg agc act gcg cgt ggg gac gta tgg gaa tcc aca ctt       1872
Leu Leu Ser Ser Ser Thr Ala Arg Gly Asp Val Trp Glu Ser Thr Leu
610                 615                 620 gtg ggg aat gat tcg ttt aca aag acg gcg ccg act gag cag cag atc       1920
Val Gly Asn Asp Ser Phe Thr Lys Thr Ala Pro Thr Glu Gln Gln Ile
625                 630                 635                 640 gct cat gct caa ctc cat tgt cgc gca ccg agg ttg aag taa               1962
Ala His Ala Gln Leu His Cys Arg Ala Pro Arg Leu Lys
                645                 650
```

<210> SEQ ID NO 25
<211> LENGTH: 653
<212> TYPE: PRT
<213> ORGANISM: Artificial sequence
<220> FEATURE:
<223> OTHER INFORMATION: Synthetic construct: ISH224-alpha2,6ST-3XlinkTM2
<220> FEATURE:
<221> NAME/KEY: misc_feature
<222> LOCATION: 1..498
<223> OTHER INFORMATION: amino acids 1-498 corresponds to ISH224-alpha2,6 sialic acid transferase
<220> FEATURE:
<221> NAME/KEY: misc_feature
<222> LOCATION: 514..653
<223> OTHER INFORMATION: amino acid 514-653 corresponds to tamavidin 2

<400> SEQUENCE: 25

```
Met Ser Glu Glu Asn Thr Gln Ser Ile Ile Lys Asn Asp Ile Asn Lys
1               5                   10                  15

Thr Ile Ile Asp Glu Glu Tyr Val Asn Leu Glu Pro Ile Asn Gln Ser
            20                  25                  30

Asn Ile Ser Phe Thr Lys His Ser Trp Val Gln Thr Cys Gly Thr Gln
        35                  40                  45

Gln Leu Leu Thr Glu Gln Asn Lys Glu Ser Ile Ser Leu Ser Val Val
    50                  55                  60

Ala Pro Arg Leu Asp Asp Glu Lys Tyr Cys Phe Asp Phe Asn Gly
65                  70                  75                  80

Val Ser Asn Lys Gly Lys Tyr Ile Thr Lys Val Thr Leu Asn Val
                85                  90                  95

Val Ala Pro Ser Leu Glu Val Tyr Val Asp His Ala Ser Leu Pro Thr
            100                 105                 110

Leu Gln Gln Leu Met Asp Ile Ile Lys Ser Glu Glu Asn Pro Thr
        115                 120                 125

Ala Gln Arg Tyr Ile Ala Trp Gly Arg Ile Val Pro Thr Asp Glu Gln
    130                 135                 140

Met Lys Glu Leu Asn Ile Thr Ser Phe Ala Leu Ile Asn Asn His Thr
145                 150                 155                 160

Pro Ala Asp Leu Val Gln Glu Ile Val Lys Gln Ala Gln Thr Lys His
                165                 170                 175

Arg Leu Asn Val Lys Leu Ser Ser Asn Thr Ala His Ser Phe Asp Asn
            180                 185                 190

Leu Val Pro Ile Leu Lys Glu Leu Asn Ser Phe Asn Asn Val Thr Val
        195                 200                 205

Thr Asn Ile Asp Leu Tyr Asp Asp Gly Ser Ala Glu Tyr Val Asn Leu
    210                 215                 220

Tyr Asn Trp Arg Asp Thr Leu Asn Lys Thr Asn Leu Lys Ile Gly
225                 230                 235                 240

Lys Asp Tyr Leu Glu Asp Val Ile Asn Gly Ile Asn Glu Asp Thr Ser
                245                 250                 255

Asn Thr Gly Thr Ser Ser Val Tyr Asn Trp Gln Lys Leu Tyr Pro Ala
            260                 265                 270

Asn Tyr His Phe Leu Arg Lys Asp Tyr Leu Thr Leu Glu Pro Ser Leu
        275                 280                 285

His Glu Leu Arg Asp Tyr Ile Gly Asp Ser Leu Lys Gln Met Gln Trp
    290                 295                 300

Asp Gly Phe Lys Lys Phe Asn Ser Lys Gln Gln Glu Leu Phe Leu Ser
305                 310                 315                 320
```

```
Ile Val Asn Phe Asp Lys Gln Lys Leu Gln Asn Glu Tyr Asn Ser Ser
                325                 330                 335

Asn Leu Pro Asn Phe Val Phe Thr Gly Thr Thr Val Trp Ala Gly Asn
                340                 345                 350

His Glu Arg Glu Tyr Tyr Ala Lys Gln Gln Ile Asn Val Ile Asn Asn
                355                 360                 365

Ala Ile Asn Glu Ser Ser Pro His Tyr Leu Gly Asn Ser Tyr Asp Leu
        370                 375                 380

Phe Phe Lys Gly His Pro Gly Gly Ile Ile Asn Thr Leu Ile Met
385                 390                 395                 400

Gln Asn Tyr Pro Ser Met Val Asp Ile Pro Ser Lys Ile Ser Phe Glu
                405                 410                 415

Val Leu Met Met Thr Asp Met Leu Pro Asp Ala Val Ala Gly Ile Ala
                420                 425                 430

Ser Ser Leu Tyr Phe Thr Ile Pro Ala Glu Lys Ile Lys Phe Ile Val
                435                 440                 445

Phe Thr Ser Thr Glu Thr Ile Thr Asp Arg Glu Thr Ala Leu Arg Ser
                450                 455                 460

Pro Leu Val Gln Val Met Ile Lys Leu Gly Ile Val Lys Glu Glu Asn
465                 470                 475                 480

Val Leu Phe Trp Ala Asp Leu Pro Asn Cys Glu Thr Gly Val Cys Ile
                485                 490                 495

Ala Val Gly Gly Gly Ser Gly Gly Gly Ser Gly Gly Gly
                500                 505                 510

Ser Ser Asp Val Gln Ser Ser Leu Thr Gly Thr Trp Tyr Asn Glu Leu
                515                 520                 525

Asn Ser Lys Met Glu Leu Thr Ala Asn Lys Asp Gly Thr Leu Thr Gly
                530                 535                 540

Lys Tyr Leu Ser Lys Val Gly Asp Val Tyr Val Pro Tyr Pro Leu Ser
545                 550                 555                 560

Gly Arg Tyr Asn Leu Gln Pro Pro Ala Gly Gln Gly Val Ala Leu Gly
                565                 570                 575

Trp Ala Val Ser Trp Glu Asn Ser Lys Ile His Ser Ala Thr Thr Trp
                580                 585                 590

Ser Gly Gln Phe Phe Ser Glu Ser Ser Pro Val Ile Leu Thr Gln Trp
                595                 600                 605

Leu Leu Ser Ser Ser Thr Ala Arg Gly Asp Val Trp Glu Ser Thr Leu
        610                 615                 620

Val Gly Asn Asp Ser Phe Thr Lys Thr Ala Pro Thr Glu Gln Gln Ile
625                 630                 635                 640

Ala His Ala Gln Leu His Cys Arg Ala Pro Arg Leu Lys
                645                 650

<210> SEQ ID NO 26
<211> LENGTH: 32
<212> TYPE: DNA
<213> ORGANISM: Artificial Sequence
<220> FEATURE:
<223> OTHER INFORMATION: Designed and synthesized DNA as a PCR primer
      SBA5-XbaI

<400> SEQUENCE: 26
aaatctagaa tggctacttc aaagttgaaa ac                           32

<210> SEQ ID NO 27
<211> LENGTH: 54
```

-continued

```
<212> TYPE: DNA
<213> ORGANISM: Artificial Sequence
<220> FEATURE:
<223> OTHER INFORMATION: Designed and synthesized DNA as a PCR primer
      SBA-link-TM2-RV

<400> SEQUENCE: 27
tgaagattga acgtctgaac cgctgccacc gccaccgatg gcctcatgca acac          54

<210> SEQ ID NO 28
<211> LENGTH: 54
<212> TYPE: DNA
<213> ORGANISM: Artificial Sequence
<220> FEATURE:
<223> OTHER INFORMATION: Designed and synthesized DNA as a PCR primer
      SBA-link-TM2-FW

<400> SEQUENCE: 28
gtgttgcatg aggccatcgg tggcggtggc agcggttcag acgttcaatc ttca          54

<210> SEQ ID NO 29
<211> LENGTH: 28
<212> TYPE: DNA
<213> ORGANISM: Artificial Sequence
<220> FEATURE:
<223> OTHER INFORMATION: Designed and synthesized DNA as a PCR primer
      TM2CtermSac

<400> SEQUENCE: 29
aaagagctct tacttcaacc tcggtgcg                                       28

<210> SEQ ID NO 30
<211> LENGTH: 29
<212> TYPE: DNA
<213> ORGANISM: Artificial Sequence
<220> FEATURE:
<223> OTHER INFORMATION: Designed and synthesized DNA as a PCR primer
      WGA-A5'XbaI

<400> SEQUENCE: 30
aaatctagaa tgaagatgat gagcaccag                                      29

<210> SEQ ID NO 31
<211> LENGTH: 111
<212> TYPE: DNA
<213> ORGANISM: Artificial Sequence
<220> FEATURE:
<223> OTHER INFORMATION: Designed and synthesized DNA as a PCR primer
      WGA-A-5xlink-TM2-R

<400> SEQUENCE: 31
tgaagattga acgtctgagc tgccaccgcc accgctgcca ccgccaccgc tgccaccgcc    60
accgctgcca ccgccaccgc tgccaccgcc accttcttgg agaagagtgg a            111

<210> SEQ ID NO 32
<211> LENGTH: 111
<212> TYPE: DNA
<213> ORGANISM: Artificial Sequence
<220> FEATURE:
<223> OTHER INFORMATION: Designed and synthesized DNA as a PCR primer
      WGA-A-5xlink-TM2-F

<400> SEQUENCE: 32
tccactcttc tccaagaagg tggcggtggc agcggtggcg gtggcagcgg tggcggtggc    60
agcggtggcg gtggcagcgg tggcggtggc agctcagacg ttcaatcttc a            111
```

```
<210> SEQ ID NO 33
<211> LENGTH: 29
<212> TYPE: DNA
<213> ORGANISM: Artificial Sequence
<220> FEATURE:
<223> OTHER INFORMATION: Designed and synthesized DNA as a PCR primer
      WGA-D5'XbaI

<400> SEQUENCE: 33
aaatctagaa tgagaaagat gatgagcac                                       29

<210> SEQ ID NO 34
<211> LENGTH: 111
<212> TYPE: DNA
<213> ORGANISM: Artificial Sequence
<220> FEATURE:
<223> OTHER INFORMATION: Designed and synthesized DNA as a PCR primer
      WGA-D-5xlink-TM2-R

<400> SEQUENCE: 34
tgaagattga acgtctgagc tgccaccgcc accgctgcca ccgccaccgc tgccaccgcc      60
accgctgcca ccgccaccgc tgccaccgcc accttctgcg agaagagtgg a             111

<210> SEQ ID NO 35
<211> LENGTH: 111
<212> TYPE: DNA
<213> ORGANISM: Artificial Sequence
<220> FEATURE:
<223> OTHER INFORMATION: Designed and synthesized DNA as a PCR primer
      WGA-D-5xlink-TM2-F

<400> SEQUENCE: 35
tccactcttc tcgcagaagg tggcggtggc agcggtggcg gtggcagcgg tggcggtggc      60
agcggtggcg gtggcagcgg tggcggtggc agctcagacg ttcaatcttc a             111

<210> SEQ ID NO 36
<211> LENGTH: 32
<212> TYPE: DNA
<213> ORGANISM: Artificial Sequence
<220> FEATURE:
<223> OTHER INFORMATION: Designed and synthesized DNA as a PCR primer
      sp-spa 5' NcoI-F

<400> SEQUENCE: 36
aaaccatggc catgaaaaag aaaaacattt at                                   32

<210> SEQ ID NO 37
<211> LENGTH: 54
<212> TYPE: DNA
<213> ORGANISM: Artificial Sequence
<220> FEATURE:
<223> OTHER INFORMATION: Designed and synthesized DNA as a PCR primer:
      spa(SA)deltaC-1xlink-TM2-R

<400> SEQUENCE: 37
tgaagattga acgtctgaac cgctgccacc gccacctttt ggtgcttgtg catc            54

<210> SEQ ID NO 38
<211> LENGTH: 111
<212> TYPE: DNA
<213> ORGANISM: Artificial Sequence
<220> FEATURE:
<223> OTHER INFORMATION: Designed and synthesized DNA as a PCR primer:
      spa(SA)deltaC-5xlink-TM2-R

<400> SEQUENCE: 38
tgaagattga acgtctgagc tgccaccgcc accgctgcca ccgccaccgc tgccaccgcc      60
```

```
accgctgcca ccgccaccgc tgccaccgcc acctttggt gcttgtgcat c          111
```

<210> SEQ ID NO 39
<211> LENGTH: 54
<212> TYPE: DNA
<213> ORGANISM: Artificial Sequence
<220> FEATURE:
<223> OTHER INFORMATION: Designed and synthesized DNA as a PCR primer:
      spa(SA)deltaC-1xlink-TM2-F

<400> SEQUENCE: 39

```
gatgcacaag caccaaaagg tggcggtggc agcggttcag acgttcaatc ttca       54
```

<210> SEQ ID NO 40
<211> LENGTH: 111
<212> TYPE: DNA
<213> ORGANISM: Artificial Sequence
<220> FEATURE:
<223> OTHER INFORMATION: Designed and synthesized DNA as a PCR primer:
      spa(SA)deltaC-5xlink-TM2-F

<400> SEQUENCE: 40

```
gatgcacaag caccaaaagg tggcggtggc agcggtggcg gtggcagcgg tggcggtggc   60
agcggtggcg gtggcagcgg tggcggtggc agctcagacg ttcaatcttc a           111
```

<210> SEQ ID NO 41
<211> LENGTH: 28
<212> TYPE: DNA
<213> ORGANISM: Artificial Sequence
<220> FEATURE:
<223> OTHER INFORMATION: Designed and synthesized DNA as a PCR primer
      TM2CtermBam

<400> SEQUENCE: 41

```
tttggatcct tacttcaacc tcggtgcg                                    28
```

<210> SEQ ID NO 42
<211> LENGTH: 29
<212> TYPE: DNA
<213> ORGANISM: Artificial Sequence
<220> FEATURE:
<223> OTHER INFORMATION: Designed and synthesized DNA as a PCR primer
      TM2NtermNotI-F

<400> SEQUENCE: 42

```
aaaccatggg ctcagacgtt caatcttca                                   29
```

<210> SEQ ID NO 43
<211> LENGTH: 133
<212> TYPE: DNA
<213> ORGANISM: Artificial Sequence
<220> FEATURE:
<223> OTHER INFORMATION: Designed and synthesized DNA as a PCR primer:
      TM2-1xlink-EK-MCS-His-R

<400> SEQUENCE: 43

```
gtttaagctt tcatcagccg tggtgatggt gatggtggcc cgcggccgct cgaggatccc   60
gggtaccgag ctcgaattcc ggcttatcgt catcgtcacc gctgccaccg ccacccttca  120
acctcggtgc gcg                                                    133
```

<210> SEQ ID NO 44
<211> LENGTH: 160
<212> TYPE: DNA
<213> ORGANISM: Artificial Sequence
<220> FEATURE:

<223> OTHER INFORMATION: Designed and synthesized DNA as a PCR primer:
      TM2-3xlink-EK-MCS-His-R

<400> SEQUENCE: 44
gtttaagctt tcatcagcca tggtgatggt gatggtggcc cgcggccgct cgaggatccc    60
gggtaccgag ctcgaattcc ggcttatcgt catcgtcgct gccaccgcca ccgctgccac   120
cgccaccgct gccaccgcca cccttcaacc tcggtgcgcg                         160

<210> SEQ ID NO 45
<211> LENGTH: 110
<212> TYPE: DNA
<213> ORGANISM: Artificial Sequence
<220> FEATURE:
<223> OTHER INFORMATION: Designed and synthesized DNA as a PCR primer:
      TM2-5xlink-EK-MCS-His-R1

<400> SEQUENCE: 45
ggcttatcgt catcgtcgct gccaccgcca ccgctgccac cgccaccgct gccaccgcca    60
ccgctgccac cgccaccgct gccaccgcca cccttcaacc tcggtgcgcg              110

<210> SEQ ID NO 46
<211> LENGTH: 110
<212> TYPE: DNA
<213> ORGANISM: Artificial Sequence
<220> FEATURE:
<223> OTHER INFORMATION: Designed and synthesized DNA as a PCR primer:
      TM2-5xlink-EK-MCS-His-R2

<400> SEQUENCE: 46
gtttaagctt tcatcagcca tggtgatggt gatggtggcc cgcggccgct cgaggatccc    60
gggtaccgag ctcgaattcc ggcttatcgt catcgtcgct gccaccgcca              110

<210> SEQ ID NO 47
<211> LENGTH: 123
<212> TYPE: DNA
<213> ORGANISM: Artificial Sequence
<220> FEATURE:
<223> OTHER INFORMATION: Designed and synthesized DNA as a PCR primer:
      His-MCS-EK-1xlink-TM2-F

<400> SEQUENCE: 47
caaaccatgg cccaccatca ccatcaccat gcgaattcga gctcggtacc cgggatcctc    60
gagcggccgc gggacgatga cgataagggt ggcggtggca gcggttcaga cgttcaatct   120
tca                                                                 123

<210> SEQ ID NO 48
<211> LENGTH: 150
<212> TYPE: DNA
<213> ORGANISM: Artificial Sequence
<220> FEATURE:
<223> OTHER INFORMATION: Designed and synthesized DNA as a PCR primer:
      His-MCS-EK-3xlink-TM2-F

<400> SEQUENCE: 48
caaaccatgg cccaccatca ccatcaccat gcgaattcga gctcggtacc cgggatcctc    60
gagcggccgc gggacgatga cgataagggt ggcggtggca gcggtggcgg tggcagcggt   120
ggcggtggca gctcagacgt tcaatcttca                                    150

<210> SEQ ID NO 49
<211> LENGTH: 110
<212> TYPE: DNA
<213> ORGANISM: Artificial Sequence

```
<220> FEATURE:
<223> OTHER INFORMATION: Designed and synthesized DNA as a PCR primer:
      His-MCS-EK-5xlink-TM2-F1

<400> SEQUENCE: 49
gggacgatga cgataagggt ggcggtggca gcggtggcgg tggcagcggt ggcggtggca        60
gcggtggcgg tggcagcggt ggcggtggca gctcagacgt tcaatcttca                  110

<210> SEQ ID NO 50
<211> LENGTH: 110
<212> TYPE: DNA
<213> ORGANISM: Artificial Sequence
<220> FEATURE:
<223> OTHER INFORMATION: Designed and synthesized DNA as a PCR primer:
      His-MCS-EK-5xlink-TM2-F2

<400> SEQUENCE: 50
caaaccatgg cccaccatca ccatcaccat gcgaattcga gctcggtacc cgggatcctc        60
gagcggccgc gggacgatga cgataagggt ggcggtggca gcggtggcgg                   110

<210> SEQ ID NO 51
<211> LENGTH: 31
<212> TYPE: DNA
<213> ORGANISM: Artificial Sequence
<220> FEATURE:
<223> OTHER INFORMATION: Designed and synthesized DNA as a PCR primer:
      TM2CtermHindIII-R

<400> SEQUENCE: 51
gtttaagctt ttacttcaac ctcggtgcgc g                                       31

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide linker

<400> SEQUENCE: 52

Gly Gly Gly Gly Ser
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic peptide linker

<400> SEQUENCE: 53

Gly Gly Ser Gly Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic peptide linker

<400> SEQUENCE: 54

Gly Ala Ser Ala Gly
1               5

<210> SEQ ID NO 55
<211> LENGTH: 5
```

```
<212> TYPE: PRT
<213> ORGANISM: Artificial Sequence
<220> FEATURE:
<223> OTHER INFORMATION: Synthetic peptide linker

<400> SEQUENCE: 55

Gly Ser Gly Ala Ala
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic peptide linker

<400> SEQUENCE: 56

Gly Ser Gly Ser Ala
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide linker

<400> SEQUENCE: 57

Gly Gly Gly Gly Ser Gly
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide linker

<400> SEQUENCE: 58

Gly Gly Gly Ser Gly Gly Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide linker

<400> SEQUENCE: 59

Gly Gly Ser Gly Gly Gly Gly Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide linker

<400> SEQUENCE: 60

Ala Ala Ala Ala Gly Ser Gly Ala Ala
1               5

<210> SEQ ID NO 61
<211> LENGTH: 15
<212> TYPE: PRT
<213> ORGANISM: Artificial Sequence
```

-continued

```
<220> FEATURE:
<223> OTHER INFORMATION: Synthetic peptide linker

<400> SEQUENCE: 61

Gly Gly Gly Gly Ser Gly Gly Gly Gly Ser Gly Gly Gly Gly Ser
1               5                   10                  15

<210> SEQ ID NO 62
<211> LENGTH: 25
<212> TYPE: PRT
<213> ORGANISM: Artificial Sequence
<220> FEATURE:
<223> OTHER INFORMATION: Synthetic peptide linker

<400> SEQUENCE: 62

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 63
<211> LENGTH: 1296
<212> TYPE: DNA
<213> ORGANISM: Artificial sequence
<220> FEATURE:
<223> OTHER INFORMATION: Synthetic construct: SBA-1xlink-TM2
<220> FEATURE:
<221> NAME/KEY: CDS
<222> LOCATION: 1..1293

<400> SEQUENCE: 63 atg gct act tca aag ttg aaa acc cag aat gtg gtt gta tct ctc tcc      48
Met Ala Thr Ser Lys Leu Lys Thr Gln Asn Val Val Val Ser Leu Ser
1               5                   10                  15 cta acc tta acc ttg gta ctg gtg cta ctg acc agc aag gca aac tca      96
Leu Thr Leu Thr Leu Val Leu Val Leu Leu Thr Ser Lys Ala Asn Ser
            20                  25                  30 gcg gaa act gtt tct ttc agc tgg aac aag ttc gtg ccg aag caa cca     144
Ala Glu Thr Val Ser Phe Ser Trp Asn Lys Phe Val Pro Lys Gln Pro
        35                  40                  45 aac atg atc ctc caa gga gac gct att gtg acc tcc tcg gga aag tta     192
Asn Met Ile Leu Gln Gly Asp Ala Ile Val Thr Ser Ser Gly Lys Leu
    50                  55                  60 caa ctc aat aag gtt gac gaa aac ggc acc cca aaa ccc tcg tct ctt     240
Gln Leu Asn Lys Val Asp Glu Asn Gly Thr Pro Lys Pro Ser Ser Leu
65                  70                  75                  80 ggt cgc gcc ctc tac tcc acc ccc atc cac att tgg gac aaa gaa acc     288
Gly Arg Ala Leu Tyr Ser Thr Pro Ile His Ile Trp Asp Lys Glu Thr
                85                  90                  95 ggt agc gtt gcc agc ttc gcc gct tcc ttc aac ttc acc ttc tat gcc     336
Gly Ser Val Ala Ser Phe Ala Ala Ser Phe Asn Phe Thr Phe Tyr Ala
            100                 105                 110 cct gac aca aaa agg ctt gca gat ggg ctt gcc ttc ttt ctc gca cca     384
Pro Asp Thr Lys Arg Leu Ala Asp Gly Leu Ala Phe Phe Leu Ala Pro
        115                 120                 125 att gac act aag cca caa aca cat gca ggt tat ctt ggt ctt ttc aac     432
Ile Asp Thr Lys Pro Gln Thr His Ala Gly Tyr Leu Gly Leu Phe Asn
    130                 135                 140 gaa aac gag tct ggt gat caa gtc gtc gct gtt gag ttt gac act ttc     480
Glu Asn Glu Ser Gly Asp Gln Val Val Ala Val Glu Phe Asp Thr Phe
145                 150                 155                 160 cgg aac tct tgg gat cca cca aat cca cac atc gga att aac gtc aat     528
Arg Asn Ser Trp Asp Pro Pro Asn Pro His Ile Gly Ile Asn Val Asn
                165                 170                 175
```

```
tct atc aga tcc atc aaa acg acg tct tgg gat ttg gcc aac aat aaa      576
Ser Ile Arg Ser Ile Lys Thr Thr Ser Trp Asp Leu Ala Asn Asn Lys
            180                 185                 190 gta gcc aag gtt ctc att acc tat gat gcc tcc acc agc ctc ttg gtt      624
Val Ala Lys Val Leu Ile Thr Tyr Asp Ala Ser Thr Ser Leu Leu Val
        195                 200                 205 gct tct ttg gtc tac cct tca cag aga acc agc aat atc ctc tcc gat      672
Ala Ser Leu Val Tyr Pro Ser Gln Arg Thr Ser Asn Ile Leu Ser Asp
    210                 215                 220 gtg gtc gat ttg aag act tct ctt ccc gag tgg gtg agg ata ggg ttc      720
Val Val Asp Leu Lys Thr Ser Leu Pro Glu Trp Val Arg Ile Gly Phe
225                 230                 235                 240 tct gct gcc acg gga ctc gac ata cct ggg gaa tcg cat gac gtg ctt      768
Ser Ala Ala Thr Gly Leu Asp Ile Pro Gly Glu Ser His Asp Val Leu
                245                 250                 255 tct tgg tct ttt gct tcc aat ttg cca cac gct agc agt aac att gat      816
Ser Trp Ser Phe Ala Ser Asn Leu Pro His Ala Ser Ser Asn Ile Asp
            260                 265                 270 cct ttg gat ctt aca agc ttt gtg ttg cat gag gcc atc ggt ggc ggt      864
Pro Leu Asp Leu Thr Ser Phe Val Leu His Glu Ala Ile Gly Gly Gly
        275                 280                 285 ggc agc ggt tca gac gtt caa tct tca ctc acc gga acc tgg tac aat      912
Gly Ser Gly Ser Asp Val Gln Ser Ser Leu Thr Gly Thr Trp Tyr Asn
    290                 295                 300 gaa ctc aac tcc aag atg gaa ttg act gca aac aaa gac ggt act ctc      960
Glu Leu Asn Ser Lys Met Glu Leu Thr Ala Asn Lys Asp Gly Thr Leu
305                 310                 315                 320 act gga aag tac ctc tcc aaa gtt ggg gat gtc tac gtg ccc tac cca     1008
Thr Gly Lys Tyr Leu Ser Lys Val Gly Asp Val Tyr Val Pro Tyr Pro
                325                 330                 335 ctc tct ggt cgc tat aac ctc caa ccc ccg gcg gga caa ggc gtc gct     1056
Leu Ser Gly Arg Tyr Asn Leu Gln Pro Pro Ala Gly Gln Gly Val Ala
            340                 345                 350 ctt ggg tgg gcg gta tcc tgg gag aac agt aaa att cat tcc gct acg     1104
Leu Gly Trp Ala Val Ser Trp Glu Asn Ser Lys Ile His Ser Ala Thr
        355                 360                 365 aca tgg agc gga cag ttc ttc tct gag tcg tct cca gtg att ctt act     1152
Thr Trp Ser Gly Gln Phe Phe Ser Glu Ser Ser Pro Val Ile Leu Thr
    370                 375                 380 cag tgg ttg ttg tca tcg agc act gcg cgt ggg gac gta tgg gaa tcc     1200
Gln Trp Leu Leu Ser Ser Ser Thr Ala Arg Gly Asp Val Trp Glu Ser
385                 390                 395                 400 aca ctt gtg ggg aat gat tcg ttt aca aag acg gcg ccg act gag cag     1248
Thr Leu Val Gly Asn Asp Ser Phe Thr Lys Thr Ala Pro Thr Glu Gln
                405                 410                 415 cag atc gct cat gct caa ctc cat tgt cgc gca ccg agg ttg aag taa     1296
Gln Ile Ala His Ala Gln Leu His Cys Arg Ala Pro Arg Leu Lys
            420                 425                 430
```

<210> SEQ ID NO 64
<211> LENGTH: 431
<212> TYPE: PRT
<213> ORGANISM: Artificial sequence
<220> FEATURE:
<223> OTHER INFORMATION: Synthetic construct: SBA-1xlink-TM2

<400> SEQUENCE: 64

```
Met Ala Thr Ser Lys Leu Lys Thr Gln Asn Val Val Ser Leu Ser
1               5                   10                  15

Leu Thr Leu Thr Leu Val Leu Val Leu Leu Thr Ser Lys Ala Asn Ser
                20                  25                  30
```

Ala Glu Thr Val Ser Phe Ser Trp Asn Lys Phe Val Pro Lys Gln Pro
         35                  40                  45

Asn Met Ile Leu Gln Gly Asp Ala Ile Val Thr Ser Ser Gly Lys Leu
 50                  55                  60

Gln Leu Asn Lys Val Asp Glu Asn Gly Thr Pro Lys Pro Ser Ser Leu
 65                  70                  75                  80

Gly Arg Ala Leu Tyr Ser Thr Pro Ile His Ile Trp Asp Lys Glu Thr
                 85                  90                  95

Gly Ser Val Ala Ser Phe Ala Ala Ser Phe Asn Phe Thr Phe Tyr Ala
                100                 105                 110

Pro Asp Thr Lys Arg Leu Ala Asp Gly Leu Ala Phe Phe Leu Ala Pro
                115                 120                 125

Ile Asp Thr Lys Pro Gln Thr His Ala Gly Tyr Leu Gly Leu Phe Asn
        130                 135                 140

Glu Asn Glu Ser Gly Asp Gln Val Val Ala Val Glu Phe Asp Thr Phe
145                 150                 155                 160

Arg Asn Ser Trp Asp Pro Pro Asn Pro His Ile Gly Ile Asn Val Asn
                165                 170                 175

Ser Ile Arg Ser Ile Lys Thr Thr Ser Trp Asp Leu Ala Asn Asn Lys
                180                 185                 190

Val Ala Lys Val Leu Ile Thr Tyr Asp Ala Ser Thr Ser Leu Leu Val
                195                 200                 205

Ala Ser Leu Val Tyr Pro Ser Gln Arg Thr Ser Asn Ile Leu Ser Asp
        210                 215                 220

Val Val Asp Leu Lys Thr Ser Leu Pro Glu Trp Val Arg Ile Gly Phe
225                 230                 235                 240

Ser Ala Ala Thr Gly Leu Asp Ile Pro Gly Glu Ser His Asp Val Leu
                245                 250                 255

Ser Trp Ser Phe Ala Ser Asn Leu Pro His Ala Ser Asn Ile Asp
                260                 265                 270

Pro Leu Asp Leu Thr Ser Phe Val Leu His Glu Ala Ile Gly Gly Gly
        275                 280                 285

Gly Ser Gly Ser Asp Val Gln Ser Ser Leu Thr Gly Thr Trp Tyr Asn
        290                 295                 300

Glu Leu Asn Ser Lys Met Glu Leu Thr Ala Asn Lys Asp Gly Thr Leu
305                 310                 315                 320

Thr Gly Lys Tyr Leu Ser Lys Val Gly Asp Val Tyr Val Pro Tyr Pro
                325                 330                 335

Leu Ser Gly Arg Tyr Asn Leu Gln Pro Pro Ala Gly Gln Gly Val Ala
                340                 345                 350

Leu Gly Trp Ala Val Ser Trp Glu Asn Ser Lys Ile His Ser Ala Thr
                355                 360                 365

Thr Trp Ser Gly Gln Phe Phe Ser Glu Ser Pro Val Ile Leu Thr
        370                 375                 380

Gln Trp Leu Leu Ser Ser Ser Thr Ala Arg Gly Asp Val Trp Glu Ser
385                 390                 395                 400

Thr Leu Val Gly Asn Asp Ser Phe Thr Lys Thr Ala Pro Thr Glu Gln
                405                 410                 415

Gln Ile Ala His Ala Gln Leu His Cys Arg Ala Pro Arg Leu Lys
                420                 425                 430

<210> SEQ ID NO 65
<211> LENGTH: 1134
<212> TYPE: DNA

<213> ORGANISM: Artificial sequence
<220> FEATURE:
<223> OTHER INFORMATION: Synthetic construct: WGA-A-5xlink-TM2
<220> FEATURE:
<221> NAME/KEY: CDS
<222> LOCATION: 1..1131

<400> SEQUENCE: 65

```
atg aag atg atg agc acc agg gcc ctc gcg ctc ggc gcg gct gcc gtc      48
Met Lys Met Met Ser Thr Arg Ala Leu Ala Leu Gly Ala Ala Ala Val
1               5                   10                  15 ctc gcc ttc gcc gcg gcg acc gct cag gcc cag agg tgc ggc gag caa      96
Leu Ala Phe Ala Ala Ala Thr Ala Gln Ala Gln Arg Cys Gly Glu Gln
                20                  25                  30 ggc agc aac atg gag tgc ccc aac aac ctc tgc tgc agc cag tac ggc     144
Gly Ser Asn Met Glu Cys Pro Asn Asn Leu Cys Cys Ser Gln Tyr Gly
            35                  40                  45 tac tgc ggg atg ggc ggc gac tac tgc ggc aag ggc tgc cag aac ggc     192
Tyr Cys Gly Met Gly Gly Asp Tyr Cys Gly Lys Gly Cys Gln Asn Gly
        50                  55                  60 gcc tgc tgg acc agc aag cgc tgc ggc agc cag gcc ggc ggc gcg acg     240
Ala Cys Trp Thr Ser Lys Arg Cys Gly Ser Gln Ala Gly Gly Ala Thr
65                  70                  75                  80 tgc acc aac aac cag tgc tgc agc cag tac ggg tac tgc ggc ttc ggc     288
Cys Thr Asn Asn Gln Cys Cys Ser Gln Tyr Gly Tyr Cys Gly Phe Gly
                85                  90                  95 gcc gag tac tgc ggc gcc ggc tgc cag ggc ggc ccc tgc cgc gcc gac     336
Ala Glu Tyr Cys Gly Ala Gly Cys Gln Gly Gly Pro Cys Arg Ala Asp
                100                 105                 110 atc aag tgc ggc agc cag gcc ggc ggc aag ctg tgc ccg aac aac ctc     384
Ile Lys Cys Gly Ser Gln Ala Gly Gly Lys Leu Cys Pro Asn Asn Leu
            115                 120                 125 tgc tgc agc cag tgg gga ttc tgc ggc ctc ggt tcc gag ttc tgc ggc     432
Cys Cys Ser Gln Trp Gly Phe Cys Gly Leu Gly Ser Glu Phe Cys Gly
        130                 135                 140 ggc ggc tgc cag agc ggt gct tgc agc acc gac aaa ccg tgc ggc aag     480
Gly Gly Cys Gln Ser Gly Ala Cys Ser Thr Asp Lys Pro Cys Gly Lys
145                 150                 155                 160 gac gcc ggc ggc aga gtt tgc act aac aac tac tgt tgt agc aag tgg     528
Asp Ala Gly Gly Arg Val Cys Thr Asn Asn Tyr Cys Cys Ser Lys Trp
                165                 170                 175 gga tcc tgt ggc atc ggc ccg ggc tat tgc ggt gca ggc tgc cag agt     576
Gly Ser Cys Gly Ile Gly Pro Gly Tyr Cys Gly Ala Gly Cys Gln Ser
                180                 185                 190 ggc ggc tgc gat ggt gtc ttc gcc gag gcc atc acc gcc aac tcc act     624
Gly Gly Cys Asp Gly Val Phe Ala Glu Ala Ile Thr Ala Asn Ser Thr
            195                 200                 205 ctt ctc caa gaa ggt ggt ggc agc ggt ggt ggc agc ggt ggc             672
Leu Leu Gln Glu Gly Gly Gly Ser Gly Gly Gly Ser Gly Gly
        210                 215                 220 ggt ggc agc ggt ggc ggt ggc agc ggt ggc ggt ggc agc tca gac gtt     720
Gly Gly Ser Gly Gly Gly Gly Ser Gly Gly Gly Ser Ser Asp Val
225                 230                 235                 240 caa tct tca ctc acc gga acc tgg tac aat gaa ctc aac tcc aag atg     768
Gln Ser Ser Leu Thr Gly Thr Trp Tyr Asn Glu Leu Asn Ser Lys Met
                245                 250                 255 gaa ttg act gca aac aaa gac ggt act ctc act gga aag tac ctc tcc     816
Glu Leu Thr Ala Asn Lys Asp Gly Thr Leu Thr Gly Lys Tyr Leu Ser
                260                 265                 270 aaa gtt ggg gat gtc tac gtg ccc tac cca ctc tct ggt cgc tat aac     864
Lys Val Gly Asp Val Tyr Val Pro Tyr Pro Leu Ser Gly Arg Tyr Asn
            275                 280                 285
```

-continued

| | | |
|---|---|---|
| ctc caa ccc ccc gcg gga caa ggc gtc gct ctt ggg tgg gcg gta tcc<br>Leu Gln Pro Pro Ala Gly Gln Gly Val Ala Leu Gly Trp Ala Val Ser<br>290                        295                        300 | | 912 |
| tgg gag aac agt aaa att cat tcc gct acg aca tgg agc gga cag ttc<br>Trp Glu Asn Ser Lys Ile His Ser Ala Thr Thr Trp Ser Gly Gln Phe<br>305                        310                        315                        320 | | 960 |
| ttc tct gag tcg tct cca gtg att ctt act cag tgg ttg ttg tca tcg<br>Phe Ser Glu Ser Ser Pro Val Ile Leu Thr Gln Trp Leu Leu Ser Ser<br>                        325                        330                        335 | | 1008 |
| agc act gcg cgt ggg gac gta tgg gaa tcc aca ctt gtg ggg aat gat<br>Ser Thr Ala Arg Gly Asp Val Trp Glu Ser Thr Leu Val Gly Asn Asp<br>                        340                        345                        350 | | 1056 |
| tcg ttt aca aag acg gcg ccg act gag cag cag atc gct cat gct caa<br>Ser Phe Thr Lys Thr Ala Pro Thr Glu Gln Gln Ile Ala His Ala Gln<br>                        355                        360                        365 | | 1104 |
| ctc cat tgt cgc gca ccg agg ttg aag taa<br>Leu His Cys Arg Ala Pro Arg Leu Lys<br>                        370                        375 | | 1134 |

<210> SEQ ID NO 66
<211> LENGTH: 377
<212> TYPE: PRT
<213> ORGANISM: Artificial sequence
<220> FEATURE:
<223> OTHER INFORMATION: Synthetic construct: WGA-A-5xlink-TM2

<400> SEQUENCE: 66

Met Lys Met Met Ser Thr Arg Ala Leu Ala Leu Gly Ala Ala Ala Val
1               5                   10                  15

Leu Ala Phe Ala Ala Ala Thr Ala Gln Ala Gln Arg Cys Gly Glu Gln
                20                  25                  30

Gly Ser Asn Met Glu Cys Pro Asn Asn Leu Cys Cys Ser Gln Tyr Gly
            35                  40                  45

Tyr Cys Gly Met Gly Gly Asp Tyr Cys Gly Lys Gly Cys Gln Asn Gly
        50                  55                  60

Ala Cys Trp Thr Ser Lys Arg Cys Gly Ser Gln Ala Gly Gly Ala Thr
65                  70                  75                  80

Cys Thr Asn Asn Gln Cys Cys Ser Gln Tyr Gly Tyr Cys Gly Phe Gly
                85                  90                  95

Ala Glu Tyr Cys Gly Ala Gly Cys Gln Gly Gly Pro Cys Arg Ala Asp
            100                 105                 110

Ile Lys Cys Gly Ser Gln Ala Gly Gly Lys Leu Cys Pro Asn Asn Leu
        115                 120                 125

Cys Cys Ser Gln Trp Gly Phe Cys Gly Leu Gly Ser Glu Phe Cys Gly
    130                 135                 140

Gly Gly Cys Gln Ser Gly Ala Cys Ser Thr Asp Lys Pro Cys Gly Lys
145                 150                 155                 160

Asp Ala Gly Gly Arg Val Cys Thr Asn Asn Tyr Cys Cys Ser Lys Trp
                165                 170                 175

Gly Ser Cys Gly Ile Gly Pro Gly Tyr Cys Gly Ala Gly Cys Gln Ser
            180                 185                 190

Gly Gly Cys Asp Gly Val Phe Ala Glu Ala Ile Thr Ala Asn Ser Thr
        195                 200                 205

Leu Leu Gln Glu Gly Gly Gly Ser Gly Gly Ser Gly Gly
        210                 215                 220

Gly Gly Ser Gly Gly Gly Gly Ser Gly Gly Gly Ser Ser Asp Val
225                 230                 235                 240

```
Gln Ser Ser Leu Thr Gly Thr Trp Tyr Asn Glu Leu Asn Ser Lys Met
            245                 250                 255

Glu Leu Thr Ala Asn Lys Asp Gly Thr Leu Thr Gly Lys Tyr Leu Ser
            260                 265                 270

Lys Val Gly Asp Val Tyr Val Pro Tyr Pro Leu Ser Gly Arg Tyr Asn
            275                 280                 285

Leu Gln Pro Pro Ala Gly Gln Gly Val Ala Leu Gly Trp Ala Val Ser
            290                 295                 300

Trp Glu Asn Ser Lys Ile His Ser Ala Thr Thr Trp Ser Gly Gln Phe
305                 310                 315                 320

Phe Ser Glu Ser Ser Pro Val Ile Leu Thr Gln Trp Leu Leu Ser Ser
                    325                 330                 335

Ser Thr Ala Arg Gly Asp Val Trp Glu Ser Thr Leu Val Gly Asn Asp
            340                 345                 350

Ser Phe Thr Lys Thr Ala Pro Thr Glu Gln Gln Ile Ala His Ala Gln
            355                 360                 365

Leu His Cys Arg Ala Pro Arg Leu Lys
            370                 375

<210> SEQ ID NO 67
<211> LENGTH: 1137
<212> TYPE: DNA
<213> ORGANISM: Artificial sequence
<220> FEATURE:
<223> OTHER INFORMATION: Synthetic construct: WGA-D-5xlink-TM2
<220> FEATURE:
<221> NAME/KEY: CDS
<222> LOCATION: 1..1134

<400> SEQUENCE: 67 atg aga aag atg atg agc acc atg gcc ctt acg ctc ggc gcg gct gtc      48
Met Arg Lys Met Met Ser Thr Met Ala Leu Thr Leu Gly Ala Ala Val
1               5                   10                  15 ttc ctc gcc ttc gcc gcg gcg acc gcg cag gcc cag agg tgt ggc gag      96
Phe Leu Ala Phe Ala Ala Ala Thr Ala Gln Ala Gln Arg Cys Gly Glu
            20                  25                  30 cag ggc agc aac atg gag tgc ccc aac aac ctc tgc tgc agc cag tac     144
Gln Gly Ser Asn Met Glu Cys Pro Asn Asn Leu Cys Cys Ser Gln Tyr
        35                  40                  45 ggg tac tgc ggc atg ggc ggc gac tac tgc ggc aag ggc tgc cag aac     192
Gly Tyr Cys Gly Met Gly Gly Asp Tyr Cys Gly Lys Gly Cys Gln Asn
    50                  55                  60 ggc gcc tgc tgg acc agc aag cgc tgc ggc agc cag gcc ggg gcg         240
Gly Ala Cys Trp Thr Ser Lys Arg Cys Gly Ser Gln Ala Gly Gly Ala
65                  70                  75                  80 acg tgt ccc aac aac cac tgc tgc agc cag tac ggg cac tgc ggc ttc     288
Thr Cys Pro Asn Asn His Cys Cys Ser Gln Tyr Gly His Cys Gly Phe
                85                  90                  95 gga gcc gag tac tgc ggc gcc ggc tgc cag ggc ggc ccc tgc cgc gcc     336
Gly Ala Glu Tyr Cys Gly Ala Gly Cys Gln Gly Gly Pro Cys Arg Ala
            100                 105                 110 gac atc aag tgc ggc agc cag tcc ggc ggc aag cta tgc ccg aac aac     384
Asp Ile Lys Cys Gly Ser Gln Ser Gly Gly Lys Leu Cys Pro Asn Asn
        115                 120                 125 ctc tgc tgc agc cag tgg gga ttc tgc ggc cta ggt tcc gag ttc tgc     432
Leu Cys Cys Ser Gln Trp Gly Phe Cys Gly Leu Gly Ser Glu Phe Cys
    130                 135                 140 ggc ggt ggc tgc cag agc ggt gct tgc agc acc gac aag ccg tgc ggc     480
Gly Gly Gly Cys Gln Ser Gly Ala Cys Ser Thr Asp Lys Pro Cys Gly
145                 150                 155                 160
```

```
aag gac gcc ggc ggc agg gtt tgc act aac aac tac tgt tgt agc aag     528
Lys Asp Ala Gly Gly Arg Val Cys Thr Asn Asn Tyr Cys Cys Ser Lys
            165                 170                 175 tgg gga tcc tgt ggc atc ggc ccg ggc tat tgc ggt gca ggc tgc cag     576
Trp Gly Ser Cys Gly Ile Gly Pro Gly Tyr Cys Gly Ala Gly Cys Gln
            180                 185                 190 agc ggc ggc tgt gac gct gtc ttt gcc ggc gcc atc acc gcc aac tcc     624
Ser Gly Gly Cys Asp Ala Val Phe Ala Gly Ala Ile Thr Ala Asn Ser
            195                 200                 205 act ctt ctc gca gaa ggt ggc ggt ggc agc ggt ggc ggt ggc agc ggt     672
Thr Leu Leu Ala Glu Gly Gly Gly Gly Ser Gly Gly Gly Gly Ser Gly
            210                 215                 220 ggc ggt ggc agc ggt ggc ggt ggc agc ggt ggc ggt ggc agc tca gac     720
Gly Gly Gly Ser Gly Gly Gly Gly Ser Gly Gly Gly Gly Ser Ser Asp
225                 230                 235                 240 gtt caa tct tca ctc acc gga acc tgg tac aat gaa ctc aac tcc aag     768
Val Gln Ser Ser Leu Thr Gly Thr Trp Tyr Asn Glu Leu Asn Ser Lys
                245                 250                 255 atg gaa ttg act gca aac aaa gac ggt act ctc act gga aag tac ctc     816
Met Glu Leu Thr Ala Asn Lys Asp Gly Thr Leu Thr Gly Lys Tyr Leu
            260                 265                 270 tcc aaa gtt ggg gat gtc tac gtg ccc tac cca ctc tct ggt cgc tat     864
Ser Lys Val Gly Asp Val Tyr Val Pro Tyr Pro Leu Ser Gly Arg Tyr
            275                 280                 285 aac ctc caa ccc ccg gcg gga caa ggc gtc gct ctt ggg tgg gcg gta     912
Asn Leu Gln Pro Pro Ala Gly Gln Gly Val Ala Leu Gly Trp Ala Val
            290                 295                 300 tcc tgg gag aac agt aaa att cat tcc gct acg aca tgg agc gga cag     960
Ser Trp Glu Asn Ser Lys Ile His Ser Ala Thr Thr Trp Ser Gly Gln
305                 310                 315                 320 ttc ttc tct gag tcg tct cca gtg att ctt act cag tgg ttg ttg tca    1008
Phe Phe Ser Glu Ser Ser Pro Val Ile Leu Thr Gln Trp Leu Leu Ser
                325                 330                 335 tcg agc act gcg cgt ggg gac gta tgg gaa tcc aca ctt gtg ggg aat    1056
Ser Ser Thr Ala Arg Gly Asp Val Trp Glu Ser Thr Leu Val Gly Asn
            340                 345                 350 gat tcg ttt aca aag acg gcg ccg act gag cag cag atc gct cat gct    1104
Asp Ser Phe Thr Lys Thr Ala Pro Thr Glu Gln Gln Ile Ala His Ala
            355                 360                 365 caa ctc cat tgt cgc gca ccg agg ttg aag taa                        1137
Gln Leu His Cys Arg Ala Pro Arg Leu Lys
            370                 375

<210> SEQ ID NO 68
<211> LENGTH: 378
<212> TYPE: PRT
<213> ORGANISM: Artificial sequence
<220> FEATURE:
<223> OTHER INFORMATION: Synthetic construct: WGA-D-5xlink-TM2

<400> SEQUENCE: 68

Met Arg Lys Met Met Ser Thr Met Ala Leu Thr Leu Gly Ala Ala Val
1               5                   10                  15

Phe Leu Ala Phe Ala Ala Ala Thr Ala Gln Ala Gln Arg Cys Gly Glu
            20                  25                  30

Gln Gly Ser Asn Met Glu Cys Pro Asn Asn Leu Cys Cys Ser Gln Tyr
        35                  40                  45

Gly Tyr Cys Gly Met Gly Gly Asp Tyr Cys Gly Lys Gly Cys Gln Asn
    50                  55                  60

Gly Ala Cys Trp Thr Ser Lys Arg Cys Gly Ser Gln Ala Gly Gly Ala
65                  70                  75                  80
```

Thr Cys Pro Asn Asn His Cys Cys Ser Gln Tyr Gly His Cys Gly Phe
                85                  90                  95

Gly Ala Glu Tyr Cys Gly Ala Gly Cys Gln Gly Gly Pro Cys Arg Ala
            100                 105                 110

Asp Ile Lys Cys Gly Ser Gln Ser Gly Gly Lys Leu Cys Pro Asn Asn
        115                 120                 125

Leu Cys Cys Ser Gln Trp Gly Phe Cys Gly Leu Gly Ser Glu Phe Cys
130                 135                 140

Gly Gly Gly Cys Gln Ser Gly Ala Cys Ser Thr Asp Lys Pro Cys Gly
145                 150                 155                 160

Lys Asp Ala Gly Gly Arg Val Cys Thr Asn Asn Tyr Cys Cys Ser Lys
                165                 170                 175

Trp Gly Ser Cys Gly Ile Gly Pro Gly Tyr Cys Gly Ala Gly Cys Gln
            180                 185                 190

Ser Gly Gly Cys Asp Ala Val Phe Ala Gly Ala Ile Thr Ala Asn Ser
        195                 200                 205

Thr Leu Leu Ala Glu Gly Gly Gly Ser Gly Gly Gly Ser Gly
210                 215                 220

Gly Gly Gly Ser Gly Gly Gly Ser Gly Gly Gly Ser Ser Asp
225                 230                 235                 240

Val Gln Ser Ser Leu Thr Gly Thr Trp Tyr Asn Glu Leu Asn Ser Lys
                245                 250                 255

Met Glu Leu Thr Ala Asn Lys Asp Gly Thr Leu Thr Gly Lys Tyr Leu
            260                 265                 270

Ser Lys Val Gly Asp Val Tyr Val Pro Tyr Pro Leu Ser Gly Arg Tyr
        275                 280                 285

Asn Leu Gln Pro Pro Ala Gly Gln Gly Val Ala Leu Gly Trp Ala Val
        290                 295                 300

Ser Trp Glu Asn Ser Lys Ile His Ser Ala Thr Thr Trp Ser Gly Gln
305                 310                 315                 320

Phe Phe Ser Glu Ser Ser Pro Val Ile Leu Thr Gln Trp Leu Leu Ser
                325                 330                 335

Ser Ser Thr Ala Arg Gly Asp Val Trp Glu Ser Thr Leu Val Gly Asn
            340                 345                 350

Asp Ser Phe Thr Lys Thr Ala Pro Thr Glu Gln Gln Ile Ala His Ala
        355                 360                 365

Gln Leu His Cys Arg Ala Pro Arg Leu Lys
    370                 375

<210> SEQ ID NO 69
<211> LENGTH: 1254
<212> TYPE: DNA
<213> ORGANISM: Artificial sequence
<220> FEATURE:
<223> OTHER INFORMATION: Synthetic construct: spa(SA)deltaC-1xlink-TM2
<220> FEATURE:
<221> NAME/KEY: CDS
<222> LOCATION: 1..1251

<400> SEQUENCE: 69 atg gcc atg aaa aag aaa aac att tat tca att cgt aaa cta ggt gta     48
Met Ala Met Lys Lys Lys Asn Ile Tyr Ser Ile Arg Lys Leu Gly Val
1               5                   10                  15 ggt att gca tct gta act tta ggt aca tta ctt ata tct ggt ggc gta     96
Gly Ile Ala Ser Val Thr Leu Gly Thr Leu Leu Ile Ser Gly Gly Val
            20                  25                  30 aca cct gct gca aat gct gcg caa cac gat gaa gct caa caa aat gct    144

```
      Thr Pro Ala Ala Asn Ala Ala Gln His Asp Glu Ala Gln Gln Asn Ala
              35                  40                  45 ttt tat caa gtg tta aat atg cct aac tta aac gct gat caa cgt aat         192
Phe Tyr Gln Val Leu Asn Met Pro Asn Leu Asn Ala Asp Gln Arg Asn
     50                  55                  60 ggt ttt atc caa agc ctt aaa gat gat cca agc caa agt gct aac gtt         240
Gly Phe Ile Gln Ser Leu Lys Asp Asp Pro Ser Gln Ser Ala Asn Val
 65                  70                  75                  80 tta ggt gaa gct caa aaa ctt aat gac tct caa gct cca aaa gct gat         288
Leu Gly Glu Ala Gln Lys Leu Asn Asp Ser Gln Ala Pro Lys Ala Asp
                 85                  90                  95 gcg caa caa aat aac ttc aac aaa gat caa caa agc gcc ttc tat gaa         336
Ala Gln Gln Asn Asn Phe Asn Lys Asp Gln Gln Ser Ala Phe Tyr Glu
            100                 105                 110 atc ttg aac atg cct aac tta aac gaa gcg caa cgt aac ggc ttc att         384
Ile Leu Asn Met Pro Asn Leu Asn Glu Ala Gln Arg Asn Gly Phe Ile
        115                 120                 125 caa agt ctt aaa gac gac cca agc caa agc act aat gtt tta ggt gaa         432
Gln Ser Leu Lys Asp Asp Pro Ser Gln Ser Thr Asn Val Leu Gly Glu
    130                 135                 140 gct aaa aaa tta aac gaa tct caa gca ccg aaa gct gat aac aat ttc         480
Ala Lys Lys Leu Asn Glu Ser Gln Ala Pro Lys Ala Asp Asn Asn Phe
145                 150                 155                 160 aac aaa gaa caa caa aat gct ttc tat gaa atc ttg aat atg cct aac         528
Asn Lys Glu Gln Gln Asn Ala Phe Tyr Glu Ile Leu Asn Met Pro Asn
                165                 170                 175 tta aac gaa gaa caa cgc aat ggt ttc atc caa agc tta aaa gat gac         576
Leu Asn Glu Glu Gln Arg Asn Gly Phe Ile Gln Ser Leu Lys Asp Asp
            180                 185                 190 cca agc caa agt gct aac cta ttg tca gaa gct aaa aag tta aat gaa         624
Pro Ser Gln Ser Ala Asn Leu Leu Ser Glu Ala Lys Lys Leu Asn Glu
        195                 200                 205 tct caa gca ccg aaa gcg gat aac aaa ttc aac aaa gaa caa caa aat         672
Ser Gln Ala Pro Lys Ala Asp Asn Lys Phe Asn Lys Glu Gln Gln Asn
    210                 215                 220 gct ttc tat gaa atc tta cat tta cct aac tta aac gaa gaa caa cgt         720
Ala Phe Tyr Glu Ile Leu His Leu Pro Asn Leu Asn Glu Glu Gln Arg
225                 230                 235                 240 aac ggc ttc atc caa agc ctt aaa gac gat cct tca gtg agc aaa gaa         768
Asn Gly Phe Ile Gln Ser Leu Lys Asp Asp Pro Ser Val Ser Lys Glu
                245                 250                 255 att tta gca gaa gct aaa aag cta aac gat gct caa gca cca aaa ggt         816
Ile Leu Ala Glu Ala Lys Lys Leu Asn Asp Ala Gln Ala Pro Lys Gly
            260                 265                 270 ggc ggt ggc agc ggt tca gac gtt caa tct tca ctc acc gga acc tgg         864
Gly Gly Gly Ser Gly Ser Asp Val Gln Ser Ser Leu Thr Gly Thr Trp
        275                 280                 285 tac aat gaa ctc aac tcc aag atg gaa ttg act gca aac aaa gac ggt         912
Tyr Asn Glu Leu Asn Ser Lys Met Glu Leu Thr Ala Asn Lys Asp Gly
    290                 295                 300 act ctc act gga aag tac ctc tcc aaa gtt ggg gat gtc tac gtg ccc         960
Thr Leu Thr Gly Lys Tyr Leu Ser Lys Val Gly Asp Val Tyr Val Pro
305                 310                 315                 320 tac cca ctc tct ggt cgc tat aac ctc caa ccc ccg gcg gga caa ggc        1008
Tyr Pro Leu Ser Gly Arg Tyr Asn Leu Gln Pro Pro Ala Gly Gln Gly
                325                 330                 335 gtc gct ctt ggg tgg gcg gta tcc tgg gag aac agt aaa att cat tcc        1056
Val Ala Leu Gly Trp Ala Val Ser Trp Glu Asn Ser Lys Ile His Ser
            340                 345                 350 gct acg aca tgg agc gga cag ttc ttc tct gag tcg tct cca gtg att        1104
```

```
Ala Thr Thr Trp Ser Gly Gln Phe Phe Ser Glu Ser Ser Pro Val Ile
        355                 360                 365 ctt act cag tgg ttg ttg tca tcg agc act gcg cgt ggg gac gta tgg      1152
Leu Thr Gln Trp Leu Leu Ser Ser Ser Thr Ala Arg Gly Asp Val Trp
    370                 375                 380 gaa tcc aca ctt gtg ggg aat gat tcg ttt aca aag acg gcg ccg act      1200
Glu Ser Thr Leu Val Gly Asn Asp Ser Phe Thr Lys Thr Ala Pro Thr
385                 390                 395                 400 gag cag cag atc gct cat gct caa ctc cat tgt cgc gca ccg agg ttg      1248
Glu Gln Gln Ile Ala His Ala Gln Leu His Cys Arg Ala Pro Arg Leu
                405                 410                 415 aag taa                                                              1254
Lys

<210> SEQ ID NO 70
<211> LENGTH: 417
<212> TYPE: PRT
<213> ORGANISM: Artificial sequence
<220> FEATURE:
<223> OTHER INFORMATION: Synthetic construct: spa(SA)deltaC-1xlink-TM2

<400> SEQUENCE: 70

Met Ala Met Lys Lys Asn Ile Tyr Ser Ile Arg Lys Leu Gly Val
1               5                   10                  15

Gly Ile Ala Ser Val Thr Leu Gly Thr Leu Leu Ile Ser Gly Gly Val
            20                  25                  30

Thr Pro Ala Ala Asn Ala Ala Gln His Asp Glu Ala Gln Gln Asn Ala
        35                  40                  45

Phe Tyr Gln Val Leu Asn Met Pro Asn Leu Asn Ala Asp Gln Arg Asn
    50                  55                  60

Gly Phe Ile Gln Ser Leu Lys Asp Asp Pro Ser Gln Ser Ala Asn Val
65                  70                  75                  80

Leu Gly Glu Ala Gln Lys Leu Asn Asp Ser Gln Ala Pro Lys Ala Asp
                85                  90                  95

Ala Gln Gln Asn Asn Phe Asn Lys Asp Gln Gln Ser Ala Phe Tyr Glu
            100                 105                 110

Ile Leu Asn Met Pro Asn Leu Asn Glu Ala Gln Arg Asn Gly Phe Ile
        115                 120                 125

Gln Ser Leu Lys Asp Asp Pro Ser Gln Ser Thr Asn Val Leu Gly Glu
    130                 135                 140

Ala Lys Lys Leu Asn Glu Ser Gln Ala Pro Lys Ala Asp Asn Asn Phe
145                 150                 155                 160

Asn Lys Glu Gln Gln Asn Ala Phe Tyr Glu Ile Leu Asn Met Pro Asn
                165                 170                 175

Leu Asn Glu Glu Gln Arg Asn Gly Phe Ile Gln Ser Leu Lys Asp Asp
            180                 185                 190

Pro Ser Gln Ser Ala Asn Leu Leu Ser Glu Ala Lys Lys Leu Asn Glu
        195                 200                 205

Ser Gln Ala Pro Lys Ala Asp Asn Lys Phe Asn Lys Glu Gln Gln Asn
    210                 215                 220

Ala Phe Tyr Glu Ile Leu His Leu Pro Asn Leu Asn Glu Glu Gln Arg
225                 230                 235                 240

Asn Gly Phe Ile Gln Ser Leu Lys Asp Asp Pro Ser Val Ser Lys Glu
                245                 250                 255

Ile Leu Ala Glu Ala Lys Lys Leu Asn Asp Ala Gln Ala Pro Lys Gly
            260                 265                 270

Gly Gly Gly Ser Gly Ser Asp Val Gln Ser Ser Leu Thr Gly Thr Trp
```

```
                    275                 280                 285
Tyr Asn Glu Leu Asn Ser Lys Met Glu Leu Thr Ala Asn Lys Asp Gly
                290                 295                 300

Thr Leu Thr Gly Lys Tyr Leu Ser Lys Val Gly Asp Val Tyr Val Pro
305                 310                 315                 320

Tyr Pro Leu Ser Gly Arg Tyr Asn Leu Gln Pro Ala Gly Gln Gly
                325                 330                 335

Val Ala Leu Gly Trp Ala Val Ser Trp Glu Asn Ser Lys Ile His Ser
                340                 345                 350

Ala Thr Thr Trp Ser Gly Gln Phe Phe Ser Glu Ser Pro Val Ile
                355                 360                 365

Leu Thr Gln Trp Leu Leu Ser Ser Ser Thr Ala Arg Gly Asp Val Trp
370                 375                 380

Glu Ser Thr Leu Val Gly Asn Asp Ser Phe Thr Lys Thr Ala Pro Thr
385                 390                 395                 400

Glu Gln Gln Ile Ala His Ala Gln Leu His Cys Arg Ala Pro Arg Leu
                405                 410                 415
Lys

<210> SEQ ID NO 71
<211> LENGTH: 1254
<212> TYPE: DNA
<213> ORGANISM: Artificial sequence
<220> FEATURE:
<223> OTHER INFORMATION: Synthetic construct: spa(MW)deltaC-1xlink-TM2
<220> FEATURE:
<221> NAME/KEY: CDS
<222> LOCATION: 1..1251

<400> SEQUENCE: 71 atg gcc atg aaa aag aaa aac att tat tca att cgt aaa cta ggt gta      48
Met Ala Met Lys Lys Lys Asn Ile Tyr Ser Ile Arg Lys Leu Gly Val
1               5                   10                  15 ggt att gca tct gta act tta ggt aca tta ctt ata tct ggt ggc gta      96
Gly Ile Ala Ser Val Thr Leu Gly Thr Leu Leu Ile Ser Gly Gly Val
                20                  25                  30 aca cct gct gca aat gct gcg caa cac gat gaa gct caa caa aat gct    144
Thr Pro Ala Ala Asn Ala Ala Gln His Asp Glu Ala Gln Gln Asn Ala
            35                  40                  45 ttt tat caa gtg tta aat atg cct aac tta aac gct gat caa cgt aat    192
Phe Tyr Gln Val Leu Asn Met Pro Asn Leu Asn Ala Asp Gln Arg Asn
        50                  55                  60 ggt ttt atc caa agc ctt aaa gat gat cca agc caa agt gct aac gtt    240
Gly Phe Ile Gln Ser Leu Lys Asp Asp Pro Ser Gln Ser Ala Asn Val
65                  70                  75                  80 tta ggt gaa gct caa aaa ctt aat gac tct caa gct cca aaa gct gat    288
Leu Gly Glu Ala Gln Lys Leu Asn Asp Ser Gln Ala Pro Lys Ala Asp
                85                  90                  95 gcg caa caa aat aac ttc aac aaa gat caa caa agc gcc ttc tat gaa    336
Ala Gln Gln Asn Asn Phe Asn Lys Asp Gln Gln Ser Ala Phe Tyr Glu
            100                 105                 110 atc ttg aac atg cct aac tta aac gaa gcg caa cgc aat ggt ttc att    384
Ile Leu Asn Met Pro Asn Leu Asn Glu Ala Gln Arg Asn Gly Phe Ile
        115                 120                 125 caa agt ctt aaa gac gat cca agc caa agc act aac gtt tta ggt gaa    432
Gln Ser Leu Lys Asp Asp Pro Ser Gln Ser Thr Asn Val Leu Gly Glu
    130                 135                 140 gct aaa aaa tta aac gaa tct caa gca ccg aaa gct gac aac aat ttc    480
Ala Lys Lys Leu Asn Glu Ser Gln Ala Pro Lys Ala Asp Asn Asn Phe
145                 150                 155                 160
```

```
aac aaa gaa caa caa aat gct ttc tat gaa atc ttg aac atg cct aac    528
Asn Lys Glu Gln Gln Asn Ala Phe Tyr Glu Ile Leu Asn Met Pro Asn
            165                 170                 175 ttg aac gaa gaa caa cgc aat ggt ttc atc caa agc tta aaa gat gac    576
Leu Asn Glu Glu Gln Arg Asn Gly Phe Ile Gln Ser Leu Lys Asp Asp
        180                 185                 190 cca agt caa agt gct aac cta ttg tca gaa gct aaa aag tta aat gaa    624
Pro Ser Gln Ser Ala Asn Leu Leu Ser Glu Ala Lys Lys Leu Asn Glu
        195                 200                 205 tct caa gca ccg aaa gcg gat aac aaa ttc aac aaa gaa caa caa aat    672
Ser Gln Ala Pro Lys Ala Asp Asn Lys Phe Asn Lys Glu Gln Gln Asn
    210                 215                 220 gct ttc tat gaa atc tta cat tta cct aac tta aac gaa gaa caa cgc    720
Ala Phe Tyr Glu Ile Leu His Leu Pro Asn Leu Asn Glu Glu Gln Arg
225                 230                 235                 240 aat ggt ttc atc caa agc tta aaa gat gac cca agc caa agc gct aac    768
Asn Gly Phe Ile Gln Ser Leu Lys Asp Asp Pro Ser Gln Ser Ala Asn
                245                 250                 255 ctt tta gca gaa gct aaa aag cta aat gat gca caa gca cca aaa ggt    816
Leu Leu Ala Glu Ala Lys Lys Leu Asn Asp Ala Gln Ala Pro Lys Gly
            260                 265                 270 ggc ggt ggc agc ggt tca gac gtt caa tct tca ctc acc gga acc tgg    864
Gly Gly Gly Ser Gly Ser Asp Val Gln Ser Ser Leu Thr Gly Thr Trp
        275                 280                 285 tac aat gaa ctc aac tcc aag atg gaa ttg act gca aac aaa gac ggt    912
Tyr Asn Glu Leu Asn Ser Lys Met Glu Leu Thr Ala Asn Lys Asp Gly
        290                 295                 300 act ctc act gga aag tac ctc tcc aaa gtt ggg gat gtc tac gtg ccc    960
Thr Leu Thr Gly Lys Tyr Leu Ser Lys Val Gly Asp Val Tyr Val Pro
305                 310                 315                 320 tac cca ctc tct ggt cgc tat aac ctc caa ccc ccc gcg gga caa ggc   1008
Tyr Pro Leu Ser Gly Arg Tyr Asn Leu Gln Pro Pro Ala Gly Gln Gly
                325                 330                 335 gtc gct ctt ggg tgg gcg gta tcc tgg gag aac agt aaa att cat tcc   1056
Val Ala Leu Gly Trp Ala Val Ser Trp Glu Asn Ser Lys Ile His Ser
            340                 345                 350 gct acg aca tgg agc gga cag ttc ttc tct gag tcg tct cca gtg att   1104
Ala Thr Thr Trp Ser Gly Gln Phe Phe Ser Glu Ser Ser Pro Val Ile
        355                 360                 365 ctt act cag tgg ttg ttg tca tcg agc act gcg cgt ggg gac gta tgg   1152
Leu Thr Gln Trp Leu Leu Ser Ser Ser Thr Ala Arg Gly Asp Val Trp
        370                 375                 380 gaa tcc aca ctt gtg ggg aat gat tcg ttt aca aag acg gcg ccg act   1200
Glu Ser Thr Leu Val Gly Asn Asp Ser Phe Thr Lys Thr Ala Pro Thr
385                 390                 395                 400 gag cag cag atc gct cat gct caa ctc cat tgt cgc gca ccg agg ttg   1248
Glu Gln Gln Ile Ala His Ala Gln Leu His Cys Arg Ala Pro Arg Leu
                405                 410                 415 aag taa                                                           1254
Lys

<210> SEQ ID NO 72
<211> LENGTH: 417
<212> TYPE: PRT
<213> ORGANISM: Artificial sequence
<220> FEATURE:
<223> OTHER INFORMATION: Synthetic construct: spa(MW)deltaC-1xlink-TM2

<400> SEQUENCE: 72

Met Ala Met Lys Lys Lys Asn Ile Tyr Ser Ile Arg Lys Leu Gly Val
1               5                   10                  15
```

-continued

Gly Ile Ala Ser Val Thr Leu Gly Thr Leu Leu Ile Ser Gly Gly Val
             20                  25                  30

Thr Pro Ala Ala Asn Ala Ala Gln His Asp Glu Ala Gln Gln Asn Ala
             35                  40                  45

Phe Tyr Gln Val Leu Asn Met Pro Asn Leu Asn Ala Asp Gln Arg Asn
 50                      55                  60

Gly Phe Ile Gln Ser Leu Lys Asp Asp Pro Ser Gln Ser Ala Asn Val
 65                  70                  75                  80

Leu Gly Glu Ala Gln Lys Leu Asn Asp Ser Gln Ala Pro Lys Ala Asp
                 85                  90                  95

Ala Gln Gln Asn Asn Phe Asn Lys Asp Gln Gln Ser Ala Phe Tyr Glu
                100                 105                 110

Ile Leu Asn Met Pro Asn Leu Asn Glu Ala Gln Arg Asn Gly Phe Ile
                115                 120                 125

Gln Ser Leu Lys Asp Asp Pro Ser Gln Ser Thr Asn Val Leu Gly Glu
    130                 135                 140

Ala Lys Lys Leu Asn Glu Ser Gln Ala Pro Lys Ala Asp Asn Asn Phe
145                 150                 155                 160

Asn Lys Glu Gln Gln Asn Ala Phe Tyr Glu Ile Leu Asn Met Pro Asn
                165                 170                 175

Leu Asn Glu Glu Gln Arg Asn Gly Phe Ile Gln Ser Leu Lys Asp Asp
            180                 185                 190

Pro Ser Gln Ser Ala Asn Leu Leu Ser Glu Ala Lys Lys Leu Asn Glu
        195                 200                 205

Ser Gln Ala Pro Lys Ala Asp Asn Lys Phe Asn Lys Glu Gln Gln Asn
    210                 215                 220

Ala Phe Tyr Glu Ile Leu His Leu Pro Asn Leu Asn Glu Glu Gln Arg
225                 230                 235                 240

Asn Gly Phe Ile Gln Ser Leu Lys Asp Asp Pro Ser Gln Ser Ala Asn
                245                 250                 255

Leu Leu Ala Glu Ala Lys Lys Leu Asn Asp Ala Gln Ala Pro Lys Gly
            260                 265                 270

Gly Gly Gly Ser Gly Ser Asp Val Gln Ser Ser Leu Thr Gly Thr Trp
        275                 280                 285

Tyr Asn Glu Leu Asn Ser Lys Met Glu Leu Thr Ala Asn Lys Asp Gly
    290                 295                 300

Thr Leu Thr Gly Lys Tyr Leu Ser Lys Val Gly Asp Val Tyr Val Pro
305                 310                 315                 320

Tyr Pro Leu Ser Gly Arg Tyr Asn Leu Gln Pro Ala Gly Gln Gly
                325                 330                 335

Val Ala Leu Gly Trp Ala Val Ser Trp Glu Asn Ser Lys Ile His Ser
            340                 345                 350

Ala Thr Thr Trp Ser Gly Gln Phe Phe Ser Glu Ser Ser Pro Val Ile
        355                 360                 365

Leu Thr Gln Trp Leu Leu Ser Ser Ser Thr Ala Arg Gly Asp Val Trp
    370                 375                 380

Glu Ser Thr Leu Val Gly Asn Asp Ser Phe Thr Lys Thr Ala Pro Thr
385                 390                 395                 400

Glu Gln Gln Ile Ala His Ala Gln Leu His Cys Arg Ala Pro Arg Leu
                405                 410                 415

Lys

<210> SEQ ID NO 73

<211> LENGTH: 1311
<212> TYPE: DNA
<213> ORGANISM: Artificial sequence
<220> FEATURE:
<223> OTHER INFORMATION: Synthetic construct: spa(SA)deltaC-5xlink-TM2
<220> FEATURE:
<221> NAME/KEY: CDS
<222> LOCATION: 1..1308

<400> SEQUENCE: 73

```
atg gcc atg aaa aag aaa aac att tat tca att cgt aaa cta ggt gta      48
Met Ala Met Lys Lys Lys Asn Ile Tyr Ser Ile Arg Lys Leu Gly Val
1               5                   10                  15 ggt att gca tct gta act tta ggt aca tta ctt ata tct ggt ggc gta      96
Gly Ile Ala Ser Val Thr Leu Gly Thr Leu Leu Ile Ser Gly Gly Val
                20                  25                  30 aca cct gct gca aat gct gcg caa cac gat gaa gct caa caa aat gct     144
Thr Pro Ala Ala Asn Ala Ala Gln His Asp Glu Ala Gln Gln Asn Ala
            35                  40                  45 ttt tat caa gtg tta aat atg cct aac tta aac gct gat caa cgt aat     192
Phe Tyr Gln Val Leu Asn Met Pro Asn Leu Asn Ala Asp Gln Arg Asn
        50                  55                  60 ggt ttt atc caa agc ctt aaa gat gat cca agc caa agt gct aac gtt     240
Gly Phe Ile Gln Ser Leu Lys Asp Asp Pro Ser Gln Ser Ala Asn Val
65                  70                  75                  80 tta ggt gaa gct caa aaa ctt aat gac tct caa gct cca aaa gct gat     288
Leu Gly Glu Ala Gln Lys Leu Asn Asp Ser Gln Ala Pro Lys Ala Asp
                85                  90                  95 gcg caa caa aat aac ttc aac aaa gat caa caa agc gcc ttc tat gaa     336
Ala Gln Gln Asn Asn Phe Asn Lys Asp Gln Gln Ser Ala Phe Tyr Glu
            100                 105                 110 atc ttg aac atg cct aac tta aac gaa gcg caa cgt aac ggc ttc att     384
Ile Leu Asn Met Pro Asn Leu Asn Glu Ala Gln Arg Asn Gly Phe Ile
        115                 120                 125 caa agt ctt aaa gac gac cca agc caa agc act aat gtt tta ggt gaa     432
Gln Ser Leu Lys Asp Asp Pro Ser Gln Ser Thr Asn Val Leu Gly Glu
    130                 135                 140 gct aaa aaa tta aac gaa tct caa gca ccg aaa gct gat aac aat ttc     480
Ala Lys Lys Leu Asn Glu Ser Gln Ala Pro Lys Ala Asp Asn Asn Phe
145                 150                 155                 160 aac aaa gaa caa caa aat gct ttc tat gaa atc ttg aat atg cct aac     528
Asn Lys Glu Gln Gln Asn Ala Phe Tyr Glu Ile Leu Asn Met Pro Asn
                165                 170                 175 tta aac gaa gaa caa cgc aat ggt ttc atc caa agc tta aaa gat gac     576
Leu Asn Glu Glu Gln Arg Asn Gly Phe Ile Gln Ser Leu Lys Asp Asp
            180                 185                 190 cca agc caa agt gct aac cta ttg tca gaa gct aaa aag tta aat gaa     624
Pro Ser Gln Ser Ala Asn Leu Leu Ser Glu Ala Lys Lys Leu Asn Glu
        195                 200                 205 tct caa gca ccg aaa gcg gat aac aaa ttc aac aaa gaa caa caa aat     672
Ser Gln Ala Pro Lys Ala Asp Asn Lys Phe Asn Lys Glu Gln Gln Asn
    210                 215                 220 gct ttc tat gaa atc tta cat tta cct aac tta aac gaa gaa caa cgt     720
Ala Phe Tyr Glu Ile Leu His Leu Pro Asn Leu Asn Glu Glu Gln Arg
225                 230                 235                 240 aac ggc ttc atc caa agc ctt aaa gac gat cct tca gtg agc aaa gaa     768
Asn Gly Phe Ile Gln Ser Leu Lys Asp Asp Pro Ser Val Ser Lys Glu
                245                 250                 255 att tta gca gaa gct aaa aag cta aac gat gct caa gca cca aaa ggt     816
Ile Leu Ala Glu Ala Lys Lys Leu Asn Asp Ala Gln Ala Pro Lys Gly
            260                 265                 270 ggc ggt ggc agc ggt ggc ggt ggc agc ggt ggc ggt ggc agc ggt ggc     864
```

```
                Gly Gly Gly Ser Gly Gly Gly Ser Gly Gly Gly Ser Gly Gly
                            275                 280                 285 ggt ggc agc ggt ggc ggt ggc agc tca gac gtt caa tct tca ctc acc        912
Gly Gly Ser Gly Gly Gly Gly Ser Ser Asp Val Gln Ser Ser Leu Thr
            290                 295                 300 gga acc tgg tac aat gaa ctc aac tcc aag atg gaa ttg act gca aac        960
Gly Thr Trp Tyr Asn Glu Leu Asn Ser Lys Met Glu Leu Thr Ala Asn
305                 310                 315                 320 aaa gac ggt act ctc act gga aag tac ctc tcc aaa gtt ggg gat gtc       1008
Lys Asp Gly Thr Leu Thr Gly Lys Tyr Leu Ser Lys Val Gly Asp Val
                325                 330                 335 tac gtg ccc tac cca ctc tct ggt cgc tat aac ctc caa ccc ccc gcg       1056
Tyr Val Pro Tyr Pro Leu Ser Gly Arg Tyr Asn Leu Gln Pro Pro Ala
            340                 345                 350 gga caa ggc gtc gct ctt ggg tgg gcg gta tcc tgg gag aac agt aaa       1104
Gly Gln Gly Val Ala Leu Gly Trp Ala Val Ser Trp Glu Asn Ser Lys
        355                 360                 365 att cat tcc gct acg aca tgg agc gga cag ttc ttc tct gag tcg tct       1152
Ile His Ser Ala Thr Thr Trp Ser Gly Gln Phe Phe Ser Glu Ser Ser
370                 375                 380 cca gtg att ctt act cag tgg ttg ttg tca tcg agc act gcg cgt ggg       1200
Pro Val Ile Leu Thr Gln Trp Leu Leu Ser Ser Ser Thr Ala Arg Gly
385                 390                 395                 400 gac gta tgg gaa tcc aca ctt gtg ggg aat gat tcg ttt aca aag acg       1248
Asp Val Trp Glu Ser Thr Leu Val Gly Asn Asp Ser Phe Thr Lys Thr
                405                 410                 415 gcg ccg act gag cag cag atc gct cat gct caa ctc cat tgt cgc gca       1296
Ala Pro Thr Glu Gln Gln Ile Ala His Ala Gln Leu His Cys Arg Ala
            420                 425                 430 ccg agg ttg aag taa                                                    1311
Pro Arg Leu Lys
        435

<210> SEQ ID NO 74
<211> LENGTH: 436
<212> TYPE: PRT
<213> ORGANISM: Artificial sequence
<220> FEATURE:
<223> OTHER INFORMATION: Synthetic construct: spa(SA)deltaC-5xlink-TM2

<400> SEQUENCE: 74

Met Ala Met Lys Lys Asn Ile Tyr Ser Ile Arg Lys Leu Gly Val
1               5                   10                  15

Gly Ile Ala Ser Val Thr Leu Gly Thr Leu Leu Ile Ser Gly Gly Val
            20                  25                  30

Thr Pro Ala Ala Asn Ala Ala Gln His Asp Glu Ala Gln Gln Asn Ala
        35                  40                  45

Phe Tyr Gln Val Leu Asn Met Pro Asn Leu Asn Ala Asp Gln Arg Asn
    50                  55                  60

Gly Phe Ile Gln Ser Leu Lys Asp Asp Pro Ser Gln Ser Ala Asn Val
65                  70                  75                  80

Leu Gly Glu Ala Gln Lys Leu Asn Asp Ser Gln Ala Pro Lys Ala Asp
                85                  90                  95

Ala Gln Gln Asn Asn Phe Asn Lys Asp Gln Gln Ser Ala Phe Tyr Glu
            100                 105                 110

Ile Leu Asn Met Pro Asn Leu Asn Glu Ala Gln Arg Asn Gly Phe Ile
        115                 120                 125

Gln Ser Leu Lys Asp Asp Pro Ser Gln Ser Thr Asn Val Leu Gly Glu
    130                 135                 140
```

```
Ala Lys Lys Leu Asn Glu Ser Gln Ala Pro Lys Ala Asp Asn Asn Phe
145                 150                 155                 160

Asn Lys Glu Gln Gln Asn Ala Phe Tyr Glu Ile Leu Asn Met Pro Asn
            165                 170                 175

Leu Asn Glu Glu Gln Arg Asn Gly Phe Ile Gln Ser Leu Lys Asp Asp
        180                 185                 190

Pro Ser Gln Ser Ala Asn Leu Leu Ser Glu Ala Lys Lys Leu Asn Glu
            195                 200                 205

Ser Gln Ala Pro Lys Ala Asp Asn Lys Phe Asn Lys Glu Gln Gln Asn
    210                 215                 220

Ala Phe Tyr Glu Ile Leu His Leu Pro Asn Leu Asn Glu Glu Gln Arg
225                 230                 235                 240

Asn Gly Phe Ile Gln Ser Leu Lys Asp Asp Pro Ser Val Ser Lys Glu
            245                 250                 255

Ile Leu Ala Glu Ala Lys Lys Leu Asn Asp Ala Gln Ala Pro Lys Gly
        260                 265                 270

Gly Gly Gly Ser Gly Gly Gly Ser Gly Gly Gly Ser Gly Gly
            275                 280                 285

Gly Gly Ser Gly Gly Gly Ser Ser Asp Val Gln Ser Ser Leu Thr
290                 295                 300

Gly Thr Trp Tyr Asn Glu Leu Asn Ser Lys Met Glu Leu Thr Ala Asn
305                 310                 315                 320

Lys Asp Gly Thr Leu Thr Gly Lys Tyr Leu Ser Lys Val Gly Asp Val
            325                 330                 335

Tyr Val Pro Tyr Pro Leu Ser Gly Arg Tyr Asn Leu Gln Pro Pro Ala
        340                 345                 350

Gly Gln Gly Val Ala Leu Gly Trp Ala Val Ser Trp Glu Asn Ser Lys
    355                 360                 365

Ile His Ser Ala Thr Thr Trp Ser Gly Gln Phe Phe Ser Glu Ser Ser
370                 375                 380

Pro Val Ile Leu Thr Gln Trp Leu Leu Ser Ser Ser Thr Ala Arg Gly
385                 390                 395                 400

Asp Val Trp Glu Ser Thr Leu Val Gly Asn Asp Ser Phe Thr Lys Thr
            405                 410                 415

Ala Pro Thr Glu Gln Gln Ile Ala His Ala Gln Leu His Cys Arg Ala
        420                 425                 430

Pro Arg Leu Lys
        435

<210> SEQ ID NO 75
<211> LENGTH: 1311
<212> TYPE: DNA
<213> ORGANISM: Artificial sequence
<220> FEATURE:
<223> OTHER INFORMATION: Synthetic construct: spa(MW)deltaC-5xlink-TM2
<220> FEATURE:
<221> NAME/KEY: CDS
<222> LOCATION: 1..1308

<400> SEQUENCE: 75 atg gcc atg aaa aag aaa aac att tat tca att cgt aaa cta ggt gta        48
Met Ala Met Lys Lys Lys Asn Ile Tyr Ser Ile Arg Lys Leu Gly Val
1               5                   10                  15 ggt att gca tct gta act tta ggt aca tta ctt ata tct ggt ggc gta        96
Gly Ile Ala Ser Val Thr Leu Gly Thr Leu Leu Ile Ser Gly Gly Val
            20                  25                  30 aca cct gct gca aat gct gcg caa cac gat gaa gct caa caa aat gct      144
Thr Pro Ala Ala Asn Ala Ala Gln His Asp Glu Ala Gln Gln Asn Ala
```

-continued

```
                 35                  40                  45 ttt tat caa gtg tta aat atg cct aac tta aac gct gat caa cgt aat     192
Phe Tyr Gln Val Leu Asn Met Pro Asn Leu Asn Ala Asp Gln Arg Asn
 50                  55                  60 ggt ttt atc caa agc ctt aaa gat gat cca agc caa agt gct aac gtt     240
Gly Phe Ile Gln Ser Leu Lys Asp Asp Pro Ser Gln Ser Ala Asn Val
 65                  70                  75                  80 tta ggt gaa gct caa aaa ctt aat gac tct caa gct cca aaa gct gat     288
Leu Gly Glu Ala Gln Lys Leu Asn Asp Ser Gln Ala Pro Lys Ala Asp
                 85                  90                  95 gcg caa caa aat aac ttc aac aaa gat caa caa agc gcc ttc tat gaa     336
Ala Gln Gln Asn Asn Phe Asn Lys Asp Gln Gln Ser Ala Phe Tyr Glu
            100                 105                 110 atc ttg aac atg cct aac tta aac gaa gcg caa cgc aat ggt ttc att     384
Ile Leu Asn Met Pro Asn Leu Asn Glu Ala Gln Arg Asn Gly Phe Ile
            115                 120                 125 caa agt ctt aaa gac gat cca agc caa agc act aac gtt tta ggt gaa     432
Gln Ser Leu Lys Asp Asp Pro Ser Gln Ser Thr Asn Val Leu Gly Glu
130                 135                 140 gct aaa aaa tta aac gaa tct caa gca ccg aaa gct gac aac aat ttc     480
Ala Lys Lys Leu Asn Glu Ser Gln Ala Pro Lys Ala Asp Asn Asn Phe
145                 150                 155                 160 aac aaa gaa caa caa aat gct ttc tat gaa atc ttg aac atg cct aac     528
Asn Lys Glu Gln Gln Asn Ala Phe Tyr Glu Ile Leu Asn Met Pro Asn
                165                 170                 175 ttg aac gaa gaa caa cgc aat ggt ttc atc caa agc tta aaa gat gac     576
Leu Asn Glu Glu Gln Arg Asn Gly Phe Ile Gln Ser Leu Lys Asp Asp
            180                 185                 190 cca agt caa agt gct aac cta ttg tca gaa gct aaa aag tta aat gaa     624
Pro Ser Gln Ser Ala Asn Leu Leu Ser Glu Ala Lys Lys Leu Asn Glu
            195                 200                 205 tct caa gca ccg aaa gcg gat aac aaa ttc aac aaa gaa caa caa aat     672
Ser Gln Ala Pro Lys Ala Asp Asn Lys Phe Asn Lys Glu Gln Gln Asn
210                 215                 220 gct ttc tat gaa atc tta cat tta cct aac tta aac gaa gaa caa cgc     720
Ala Phe Tyr Glu Ile Leu His Leu Pro Asn Leu Asn Glu Glu Gln Arg
225                 230                 235                 240 aat ggt ttc atc caa agc tta aaa gat gac cca agc caa agc gct aac     768
Asn Gly Phe Ile Gln Ser Leu Lys Asp Asp Pro Ser Gln Ser Ala Asn
                245                 250                 255 ctt tta gca gaa gct aaa aag cta aat gat gca caa gca cca aaa ggt     816
Leu Leu Ala Glu Ala Lys Lys Leu Asn Asp Ala Gln Ala Pro Lys Gly
            260                 265                 270 ggc ggt ggc agc ggt ggc ggt ggc agc ggt ggc ggt ggc agc ggt ggc     864
Gly Gly Gly Ser Gly Gly Gly Gly Ser Gly Gly Gly Gly Ser Gly Gly
            275                 280                 285 ggt ggc agc ggt ggc ggt ggc agc tca gac gtt caa tct tca ctc acc     912
Gly Gly Ser Gly Gly Gly Gly Ser Ser Asp Val Gln Ser Ser Leu Thr
            290                 295                 300 gga acc tgg tac aat gaa ctc aac tcc aag atg gaa ttg act gca aac     960
Gly Thr Trp Tyr Asn Glu Leu Asn Ser Lys Met Glu Leu Thr Ala Asn
305                 310                 315                 320 aaa gac ggt act ctc act gga aag tac ctc tcc aaa gtt ggg gat gtc    1008
Lys Asp Gly Thr Leu Thr Gly Lys Tyr Leu Ser Lys Val Gly Asp Val
                325                 330                 335 tac gtg ccc tac cca ctc tct ggt cgc tat aac ctc caa ccc ccc gcg    1056
Tyr Val Pro Tyr Pro Leu Ser Gly Arg Tyr Asn Leu Gln Pro Pro Ala
            340                 345                 350 gga caa ggc gtc gct ctt ggg tgg gcg gta tcc tgg gag aac agt aaa    1104
Gly Gln Gly Val Ala Leu Gly Trp Ala Val Ser Trp Glu Asn Ser Lys
```

```
                        355                 360                 365
att cat tcc gct acg aca tgg agc gga cag ttc ttc tct gag tcg tct       1152
Ile His Ser Ala Thr Thr Trp Ser Gly Gln Phe Phe Ser Glu Ser Ser
    370                 375                 380 cca gtg att ctt act cag tgg ttg ttg tca tcg agc act gcg cgt ggg       1200
Pro Val Ile Leu Thr Gln Trp Leu Leu Ser Ser Ser Thr Ala Arg Gly
385                 390                 395                 400 gac gta tgg gaa tcc aca ctt gtg ggg aat gat tcg ttt aca aag acg       1248
Asp Val Trp Glu Ser Thr Leu Val Gly Asn Asp Ser Phe Thr Lys Thr
                405                 410                 415 gcg ccg act gag cag cag atc gct cat gct caa ctc cat tgt cgc gca       1296
Ala Pro Thr Glu Gln Gln Ile Ala His Ala Gln Leu His Cys Arg Ala
                420                 425                 430 ccg agg ttg aag taa                                                    1311
Pro Arg Leu Lys
        435

<210> SEQ ID NO 76
<211> LENGTH: 436
<212> TYPE: PRT
<213> ORGANISM: Artificial sequence
<220> FEATURE:
<223> OTHER INFORMATION: Synthetic construct: spa(MW)deltaC-5xlink-TM2

<400> SEQUENCE: 76

Met Ala Met Lys Lys Asn Ile Tyr Ser Ile Arg Lys Leu Gly Val
1               5                   10                  15

Gly Ile Ala Ser Val Thr Leu Gly Thr Leu Leu Ile Ser Gly Gly Val
                20                  25                  30

Thr Pro Ala Ala Asn Ala Ala Gln His Asp Glu Ala Gln Gln Asn Ala
            35                  40                  45

Phe Tyr Gln Val Leu Asn Met Pro Asn Leu Asn Ala Asp Gln Arg Asn
        50                  55                  60

Gly Phe Ile Gln Ser Leu Lys Asp Asp Pro Ser Gln Ser Ala Asn Val
65                  70                  75                  80

Leu Gly Glu Ala Gln Lys Leu Asn Asp Ser Gln Ala Pro Lys Ala Asp
                85                  90                  95

Ala Gln Gln Asn Asn Phe Asn Lys Asp Gln Gln Ser Ala Phe Tyr Glu
            100                 105                 110

Ile Leu Asn Met Pro Asn Leu Asn Glu Ala Gln Arg Asn Gly Phe Ile
        115                 120                 125

Gln Ser Leu Lys Asp Asp Pro Ser Gln Ser Thr Asn Val Leu Gly Glu
    130                 135                 140

Ala Lys Lys Leu Asn Glu Ser Gln Ala Pro Lys Ala Asp Asn Asn Phe
145                 150                 155                 160

Asn Lys Glu Gln Gln Asn Ala Phe Tyr Glu Ile Leu Asn Met Pro Asn
                165                 170                 175

Leu Asn Glu Glu Gln Arg Asn Gly Phe Ile Gln Ser Leu Lys Asp Asp
            180                 185                 190

Pro Ser Gln Ser Ala Asn Leu Leu Ser Glu Ala Lys Lys Leu Asn Glu
        195                 200                 205

Ser Gln Ala Pro Lys Ala Asp Asn Lys Phe Asn Lys Glu Gln Gln Asn
    210                 215                 220

Ala Phe Tyr Glu Ile Leu His Leu Pro Asn Leu Asn Glu Glu Gln Arg
225                 230                 235                 240

Asn Gly Phe Ile Gln Ser Leu Lys Asp Asp Pro Ser Gln Ser Ala Asn
                245                 250                 255
```

```
Leu Leu Ala Glu Ala Lys Lys Leu Asn Asp Ala Gln Ala Pro Lys Gly
        260                 265                 270

Gly Gly Gly Ser Gly Gly Gly Gly Ser Gly Gly Gly Gly Ser Gly Gly
            275                 280                 285

Gly Gly Ser Gly Gly Gly Gly Ser Ser Asp Val Gln Ser Ser Leu Thr
        290                 295                 300

Gly Thr Trp Tyr Asn Glu Leu Asn Ser Lys Met Glu Leu Thr Ala Asn
305                 310                 315                 320

Lys Asp Gly Thr Leu Thr Gly Lys Tyr Leu Ser Lys Val Gly Asp Val
                325                 330                 335

Tyr Val Pro Tyr Pro Leu Ser Gly Arg Tyr Asn Leu Gln Pro Pro Ala
            340                 345                 350

Gly Gln Gly Val Ala Leu Gly Trp Ala Val Ser Trp Glu Asn Ser Lys
        355                 360                 365

Ile His Ser Ala Thr Thr Trp Ser Gly Gln Phe Phe Ser Glu Ser Ser
    370                 375                 380

Pro Val Ile Leu Thr Gln Trp Leu Leu Ser Ser Thr Ala Arg Gly
385                 390                 395                 400

Asp Val Trp Glu Ser Thr Leu Val Gly Asn Asp Ser Phe Thr Lys Thr
                405                 410                 415

Ala Pro Thr Glu Gln Gln Ile Ala His Ala Gln Leu His Cys Arg Ala
            420                 425                 430

Pro Arg Leu Lys
        435

<210> SEQ ID NO 77
<211> LENGTH: 4653
<212> TYPE: DNA
<213> ORGANISM: Artificial sequence
<220> FEATURE:
<223> OTHER INFORMATION: Synthetic construct: TM2-1xlink-EK-MCS-His
<220> FEATURE:
<221> NAME/KEY: CDS
<222> LOCATION: 267..791

<400> SEQUENCE: 77
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc       120
gcactcccgt tctggataat gttttttgcg ccgacatcat aacggttctg gcaaatattc       180
tgaaatgagc tgttgacaat taatcatccg gctcgtataa tgtgtggaat tgtgagcgga       240
taacaatttc acacaggaaa cagacc atg ggc tca gac gtt caa tct tca ctc       293
                              Met Gly Ser Asp Val Gln Ser Ser Leu
                                1               5 acc gga acc tgg tac aat gaa ctc aac tcc aag atg gaa ttg act gca       341
Thr Gly Thr Trp Tyr Asn Glu Leu Asn Ser Lys Met Glu Leu Thr Ala
 10              15                  20                  25 aac aaa gac ggt act ctc act gga aag tac ctc tcc aaa gtt ggg gat       389
Asn Lys Asp Gly Thr Leu Thr Gly Lys Tyr Leu Ser Lys Val Gly Asp
             30                  35                  40 gtc tac gtg ccc tac cca ctc tct ggt cgc tat aac ctc caa ccc ccc       437
Val Tyr Val Pro Tyr Pro Leu Ser Gly Arg Tyr Asn Leu Gln Pro Pro
         45                  50                  55 gcg gga caa ggc gtc gct ctt ggg tgg gcg gta tcc tgg gag aac agt       485
Ala Gly Gln Gly Val Ala Leu Gly Trp Ala Val Ser Trp Glu Asn Ser
     60                  65                  70 aaa att cat tcc gct acg aca tgg agc gga cag ttc ttc tct gag tcg       533
Lys Ile His Ser Ala Thr Thr Trp Ser Gly Gln Phe Phe Ser Glu Ser
 75                  80                  85
```

```
tct cca gtg att ctt act cag tgg ttg ttg tca tcg agc act gcg cgt    581
Ser Pro Val Ile Leu Thr Gln Trp Leu Leu Ser Ser Ser Thr Ala Arg
 90              95                 100                 105 ggg gac gta tgg gaa tcc aca ctt gtg ggg aat gat tcg ttt aca aag    629
Gly Asp Val Trp Glu Ser Thr Leu Val Gly Asn Asp Ser Phe Thr Lys
                110                 115                 120 acg gcg ccg act gag cag cag atc gct cat gct caa ctc cat tgt cgc    677
Thr Ala Pro Thr Glu Gln Gln Ile Ala His Ala Gln Leu His Cys Arg
            125                 130                 135 gca ccg agg ttg aag ggt ggc ggt ggc agc ggt gac gat gac gat aag    725
Ala Pro Arg Leu Lys Gly Gly Gly Gly Ser Gly Asp Asp Asp Asp Lys
        140                 145                 150 ccg gaa ttc gag ctc ggt acc cgg gat cct cga gcg gcc gcg ggc cac    773
Pro Glu Phe Glu Leu Gly Thr Arg Asp Pro Arg Ala Ala Ala Gly His
    155                 160                 165 cat cac cat cac cac ggc tga tga aagcttggct gttttggcgg atgagaaag    827
His His His His His Gly
170             175 attttcagcc tgatacagat taaatcagaa cgcagaagcg gtctgataaa acagaatttg    887
cctggcggca gtagcgcggt ggtcccacct gaccccatgc cgaactcaga agtgaaacgc    947
cgtagcgccg atggtagtgt ggggtctccc catgcgagag tagggaactg ccaggcatca   1007
aataaaacga aaggctcagt cgaaagactg ggcctttcgt tttatctgtt gtttgtcggt   1067
gaacgctctc ctgagtagga caaatccgcc gggagcggat ttgaacgttg cgaagcaacg   1127
gcccggaggg tggcgggcag gacgcccgcc ataaactgcc aggcatcaaa ttaagcagaa   1187
ggccatcctg acggatggcc ttttttgcgtt tctacaaact cttttttgttt attttttctaa   1247
atacattcaa atatgtatcc gctcatgaga caataaccct gataaatgct tcaataatat   1307
tgaaaaagga agagtatgag tattcaacat ttccgtgtcg cccttattcc cttttttgcg   1367
gcatttttgcc ttcctgtttt tgctcaccca gaaacgctgg tgaaagtaaa agatgctgaa   1427
gatcagttgg gtgcacgagt gggttacatc gaactggatc tcaacagcgg taagatcctt   1487
gagagttttc gccccgaaga acgttttcca atgatgagca cttttaaagt tctgctatgt   1547
ggcgcggtat tatcccgtgt tgacgccggg caagagcaac tcggtcgccg catacactat   1607
tctcagaatg acttggttga gtactcacca gtcacagaaa agcatcttac ggatggcatg   1667
acagtaagag aattatgcag tgctgccata accatgagtg ataacactgc ggccaactta   1727
cttctgacaa cgatcggagg accgaaggag ctaaccgctt ttttgcacaa catgggggat   1787
catgtaactc gccttgatcg ttgggaaccg gagctgaatg aagccatacc aaacgacgag   1847
cgtgacacca cgatgcctac agcaatggca acaacgttgc gcaaactatt aactggcgaa   1907
ctacttactc tagcttcccg gcaacaatta atagactgga tggaggcgga taaagttgca   1967
ggaccacttc tgcgctcggc ccttccggct ggctggttta ttgctgataa atctggagcc   2027
ggtgagcgtg ggtctcgcgg tatcattgca gcactggggc cagatggtaa gccctcccgt   2087
atcgtagtta tctacacgac ggggagtcag gcaactatgg atgaacgaaa tagacagatc   2147
gctgagatag gtgcctcact gattaagcat tggtaactgt cagaccaagt ttactcatat   2207
atactttaga ttgatttaaa acttcatttt taatttaaaa ggatctaggt gaagatcctt   2267
tttgataatc tcatgaccaa aatcccttaa cgtgagtttt cgttccactg agcgtcagac   2327
cccgtagaaa agatcaaagg atcttcttga gatcctttttt ttctgcgcgt aatctgctgc   2387
ttgcaaacaa aaaaaccacc gctaccagcg gtggtttgtt tgccggatca agagctacca   2447
actcttttttc cgaaggtaac tggcttcagc agagcgcaga taccaaatac tgtccttcta   2507
```

```
gtgtagccgt agttaggcca ccacttcaag aactctgtag caccgcctac atacctcgct    2567
ctgctaatcc tgttaccagt ggctgctgcc agtggcgata agtcgtgtct taccggggttg   2627 gactcaagac gatagttacc ggataaggcg cagcggtcgg gctgaacggg gggttcgtgc    2687
acacagccca gcttggagcg aacgacctac accgaactga gatacctaca gcgtgagcta   2747
tgagaaagcg ccacgcttcc cgaagggaga aaggcggaca ggtatccggt aagcggcagg   2807
gtcggaacag gagagcgcac gagggagctt ccaggggaa acgcctggta tctttatagt   2867
cctgtcgggt ttcgccacct ctgacttgag cgtcgatttt tgtgatgctc gtcaggggg    2927 cggagcctat ggaaaaacgc cagcaacgcg gcctttttac ggttcctggc cttttgctgg   2987
ccttttgctc acatgttctt tcctgcgtta tcccctgatt ctgtggataa ccgtattacc   3047
gcctttgagt gagctgatac cgctcgccgc agccgaacga ccgagcgcag cgagtcagtg   3107
agcgaggaag cggaagagcg cctgatgcgg tatttctcc ttacgcatct gtgcggtatt   3167
tcacaccgca tatggtgcac tctcagtaca atctgctctg atgccgcata gttaagccag   3227
tatacactcc gctatcgcta cgtgactggg tcatggctgc gccccgacac cgccaacac    3287 ccgctgacgc gccctgacgg gcttgtctgc tcccggcatc cgcttacaga caagctgtga   3347
ccgtctccgg gagctgcatg tgtcagaggt tttcaccgtc atcaccgaaa cgcgcgaggc   3407
agcagatcaa ttcgcgcgcg aaggcgaagc ggcatgcatt tacgttgaca ccatcgaatg   3467
gtgcaaaacc tttcgcggta tggcatgata gcgcccggaa gagagtcaat tcagggtggt   3527
gaatgtgaaa ccagtaacgt tatacgatgt cgcagagtat gccggtgtct cttatcagac   3587
cgtttcccgc gtggtgaacc aggccagcca cgtttctgcg aaaacgcggg aaaaagtgga   3647
agcggcgatg gcggagctga attacattcc caaccgcgtg gcacaacaac tggcgggcaa   3707
acagtcgttg ctgattggcg ttgccacctc cagtctggcc ctgcacgcgc cgtcgcaaat   3767
tgtcgcggcg attaaatctc gcgccgatca actgggtgcc agcgtggtgg tgtcgatggt   3827
agaacgaagc ggcgtcgaag cctgtaaagc ggcggtgcac aatcttctcg cgcaacgcgt   3887
cagtgggctg atcattaact atccgctgga tgaccaggat gccattgctg tggaagctgc   3947
ctgcactaat gttccggcgt tatttcttga tgtctctgac cagacaccca tcaacagtat   4007
tattttctcc catgaagacg gtacgcgact gggcgtggag catctggtcg cattgggtca   4067
ccagcaaatc gcgctgttag cgggcccatt aagttctgtc tcggcgcgtc tgcgtctggc   4127
tggctggcat aaatatctca ctcgcaatca aattcagccg atagcggaac gggaaggcga   4187
ctggagtgcc atgtccggtt ttcaacaaac catgcaaatg ctgaatgagg gcatcgttcc   4247
cactgcgatg ctggttgcca acgatcagat ggcgctgggc gcaatgcgcg ccattaccga   4307
gtccgggctg cgcgttggtg cggatatctc ggtagtggga tacgacgata ccgaagacag   4367
ctcatgttat atcccgccgt caaccaccat caaacaggat tttcgcctgc tggggcaaac   4427
cagcgtggac cgcttgctgc aactctctca gggccaggc gtgaagggca atcagctgtt   4487
gcccgtctca ctggtgaaaa gaaaaaccac cctggcgccc aatacgcaaa ccgcctctcc   4547
ccgcgcgttg gccgattcat taatgcagct ggcacgacag gtttcccgac tggaaagcgg   4607
gcagtgagcg caacgcaatt aatgtgagtt agcgcgaatt gatctg                  4653
```

<210> SEQ ID NO 78
<211> LENGTH: 4680
<212> TYPE: DNA
<213> ORGANISM: Artificial sequence
<220> FEATURE:
<223> OTHER INFORMATION: Synthetic construct: TM2-3xlink-EK-MCS-His

```
<220> FEATURE:
<221> NAME/KEY: CDS
<222> LOCATION: 267..818

<400> SEQUENCE: 78
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagacc atg ggc tca gac gtt caa tct tca ctc      293
                              Met Gly Ser Asp Val Gln Ser Ser Leu
                                1               5 acc gga acc tgg tac aat gaa ctc aac tcc aag atg gaa ttg act gca        341
Thr Gly Thr Trp Tyr Asn Glu Leu Asn Ser Lys Met Glu Leu Thr Ala
 10              15                  20                  25 aac aaa gac ggt act ctc act gga aag tac ctc tcc aaa gtt ggg gat        389
Asn Lys Asp Gly Thr Leu Thr Gly Lys Tyr Leu Ser Lys Val Gly Asp
                 30                  35                  40 gtc tac gtg ccc tac cca ctc tct ggt cgc tat aac ctc caa ccc ccc        437
Val Tyr Val Pro Tyr Pro Leu Ser Gly Arg Tyr Asn Leu Gln Pro Pro
                45                  50                  55 gcg gga caa ggc gtc gct ctt ggg tgg gcg gta tcc tgg gag aac agt        485
Ala Gly Gln Gly Val Ala Leu Gly Trp Ala Val Ser Trp Glu Asn Ser
     60                  65                  70 aaa att cat tcc gct acg aca tgg agc gga cag ttc ttc tct gag tcg        533
Lys Ile His Ser Ala Thr Thr Trp Ser Gly Gln Phe Phe Ser Glu Ser
 75                  80                  85 tct cca gtg att ctt act cag tgg ttg ttg tca tcg agc act gcg cgt        581
Ser Pro Val Ile Leu Thr Gln Trp Leu Leu Ser Ser Ser Thr Ala Arg
 90                  95                 100                 105 ggg gac gta tgg gaa tcc aca ctt gtg ggg aat gat tcg ttt aca aag        629
Gly Asp Val Trp Glu Ser Thr Leu Val Gly Asn Asp Ser Phe Thr Lys
                110                 115                 120 acg gcg ccg act gag cag cag atc gct cat gct caa ctc cat tgt cgc        677
Thr Ala Pro Thr Glu Gln Gln Ile Ala His Ala Gln Leu His Cys Arg
                125                 130                 135 gca ccg agg ttg aag ggt ggt ggt ggc agc ggt ggc ggt ggc agc ggt        725
Ala Pro Arg Leu Lys Gly Gly Gly Gly Ser Gly Gly Gly Gly Ser Gly
    140                 145                 150 ggc ggt ggc agc gac gat gac gat aag ccg gaa ttc gag ctc ggt acc        773
Gly Gly Gly Ser Asp Asp Asp Asp Lys Pro Glu Phe Glu Leu Gly Thr
155                 160                 165 cgg gat cct cga gcg gcc gcg ggc cac cat cac cat cac cac ggc tga        821
Arg Asp Pro Arg Ala Ala Ala Gly His His His His His His Gly
170                 175                 180 tga aagcttggct gttttggcgg atgagagaag attttcagcc tgatacagat taaatc       880 agaacgcaga agcggtctga taaaacagaa tttgcctggc ggcagtagcg cggtggtccc      940
acctgacccc atgccgaact cagaagtgaa acgccgtagc gccgatggta gtgtggggtc     1000
tccccatgcg agagtaggga actgccaggc atcaaataaa acgaaaggct cagtcgaaag     1060
actgggcctt tcgttttatc tgttgtttgt cggtgaacgc tctcctgagt aggacaaatc     1120
cgccgggagc ggatttgaac gttgcgaagc aacggcccgg agggtggcgg gcaggacgcc     1180
cgccataaac tgccaggcat caaattaagc agaaggccat cctgacggat ggcctttttg     1240
cgtttctaca aactcttttt gtttattttt ctaaatacat tcaaatatgt atccgctcat     1300
gagacaataa ccctgataaa tgcttcaata atattgaaaa aggaagagta tgagtattca     1360
```

-continued

```
acatttccgt gtcgcccttc ttcccttttt tgcggcattt tgccttcctg tttttgctca   1420
cccagaaacg ctggtgaaag taaaagatgc tgaagatcag ttgggtgcac gagtgggtta   1480
catcgaactg gatctcaaca gcggtaagat ccttgagagt tttcgccccg aagaacgttt   1540
tccaatgatg agcactttta aagttctgct atgtggcgcg gtattatccc gtgttgacgc   1600
cgggcaagag caactcggtc gccgcataca ctattctcag aatgacttgg ttgagtactc   1660
accagtcaca gaaaagcatc ttacggatgg catgacagta agagaattat gcagtgctgc   1720
cataaccatg agtgataaca ctgcggccaa cttacttctg acaacgatcg gaggaccgaa   1780
ggagctaacc gcttttttgc acaacatggg ggatcatgta actcgccttg atcgttggga   1840
accggagctg aatgaagcca taccaaacga cgagcgtgac accacgatgc ctacagcaat   1900
ggcaacaacg ttgcgcaaac tattaactgg cgaactactt actctagctt cccggcaaca   1960
attaatagac tggatggagg cggataaagt tgcaggacca cttctgcgct cggcccttcc   2020
ggctggctgg tttattgctg ataaatctgg agccggtgag cgtgggtctc gcggtatcat   2080
tgcagcactg gggccagatg gtaagccctc ccgtatcgta gttatctaca cgacggggag   2140
tcaggcaact atggatgaac gaaatagaca gatcgctgag ataggtgcct cactgattaa   2200
gcattggtaa ctgtcagacc aagtttactc atatatactt tagattgatt taaaacttca   2260
tttttaattt aaaaggatct aggtgaagat cctttttgat aatctcatga ccaaaatccc   2320
ttaacgtgag ttttcgttcc actgagcgtc agaccccgta gaaaagatca aaggatcttc   2380
ttgagatcct ttttttctgc gcgtaatctg ctgcttgcaa acaaaaaaac caccgctacc   2440
agcggtggtt tgtttgccgg atcaagagct accaactctt tttccgaagg taactggctt   2500
cagcagagcg cagataccaa atactgtcct tctagtgtag ccgtagttag gccaccactt   2560
caagaactct gtagcaccgc ctacatacct cgctctgcta atcctgttac cagtggctgc   2620
tgccagtggc gataagtcgt gtcttaccgg gttggactca agacgatagt taccggataa   2680
ggcgcagcgg tcgggctgaa cggggggttc gtgcacacag cccagcttgg agcgaacgac   2740
ctacaccgaa ctgagatacc tacagcgtga gctatgagaa agcgccacgc ttcccgaagg   2800
gagaaaggcg gacaggtatc cggtaagcgg cagggtcgga acaggagagc gcacgaggga   2860
gcttccaggg ggaaacgcct ggtatcttta tagtcctgtc gggtttcgcc acctctgact   2920
tgagcgtcga tttttgtgat gctcgtcagg gggcggagc ctatggaaaa acgccagcaa   2980
cgcggccttt ttacggttcc tggccttttg ctggccttt gctcacatgt tctttcctgc   3040
gttatcccct gattctgtgg ataaccgtat taccgccttt gagtgagctg ataccgctcg   3100
ccgcagccga acgaccgagc gcagcgagtc agtgagcgag gaagcggaag agcgcctgat   3160
gcggtatttt ctccttacgc atctgtgcgg tatttcacac cgcatatggt gcactctcag   3220
tacaatctgc tctgatgccg catagttaag ccagtataca ctccgctatc gctacgtgac   3280
tgggtcatgg ctgcgccccg acacccgcca acacccgctg acgcgccctg acgggcttgt   3340
ctgctcccgg catccgctta cagacaagct gtgaccgtct ccgggagctg catgtgtcag   3400
aggttttcac cgtcatcacc gaaacgcgcg aggcagcaga tcaattcgcg cgcgaaggcg   3460
aagcggcatg catttacgtt gacaccatcg aatggtgcaa aacctttcgc ggtatggcat   3520
gatagcgccc ggaagagagt caattcaggg tggtgaatgt gaaaccagta acgttatacg   3580
atgtcgcaga gtatgccggt gtctcttatc agaccgtttc ccgcgtggtg aaccaggcca   3640
gccacgtttc tgcgaaaacg cgggaaaaag tggaagcggc gatggcggag ctgaattaca   3700
ttcccaaccg cgtggcacaa caactggcgg gcaaacagtc gttgctgatt ggcgttgcca   3760
```

-continued

```
cctccagtct ggccctgcac gcgccgtcgc aaattgtcgc ggcgattaaa tctcgcgccg      3820
atcaactggg tgccagcgtg gtggtgtcga tggtagaacg aagcggcgtc gaagcctgta      3880
aagcggcggt gcacaatctt ctcgcgcaac gcgtcagtgg gctgatcatt aactatccgc      3940
tggatgacca ggatgccatt gctgtggaag ctgcctgcac taatgttccg gcgttatttc      4000
ttgatgtctc tgaccagaca cccatcaaca gtattatttt ctcccatgaa gacggtacgc      4060
gactgggcgt ggagcatctg gtcgcattgg gtcaccagca aatcgcgctg ttagcgggcc      4120
cattaagttc tgtctcggcg cgtctgcgtc tggctggctg gcataaatat ctcactcgca      4180
atcaaattca gccgatagcg gaacgggaag gcgactggag tgccatgtcc ggttttcaac      4240
aaaccatgca aatgctgaat gagggcatcg ttcccactgc gatgctggtt gccaacgatc      4300
agatggcgct gggcgcaatg cgcgccatta ccgagtccgg gctgcgcgtt ggtgcggata      4360
tctcggtagt gggatacgac gataccgaag acagctcatg ttatatcccg ccgtcaacca      4420
ccatcaaaca ggattttcgc ctgctggggc aaaccagcgt ggaccgcttg ctgcaactct      4480
ctcagggcca ggcggtgaag ggcaatcagc tgttgcccgt ctcactggtg aaaagaaaaa      4540
ccaccctggc gcccaatacg caaaccgcct ctccccgcgc gttggccgat tcattaatgc      4600
agctggcacg acaggtttcc cgactggaaa gcgggcagtg agcgcaacgc aattaatgtg      4660
agttagcgcg aattgatctg                                                 4680
```

<210> SEQ ID NO 79
<211> LENGTH: 4710
<212> TYPE: DNA
<213> ORGANISM: Artificial sequence
<220> FEATURE:
<223> OTHER INFORMATION: Synthetic construct: TM2-5xlink-EK-MCS-His
<220> FEATURE:
<221> NAME/KEY: CDS
<222> LOCATION: 267..848

<400> SEQUENCE: 79

```
gtttgacagc ttatcatcga ctgcacggtg caccaatgct tctggcgtca ggcagccatc       60
ggaagctgtg gtatggctgt gcaggtcgta aatcactgca taattcgtgt cgctcaaggc      120
gcactcccgt tctggataat gttttttgcg ccgacatcat aacggttctg gcaaatattc      180
tgaaatgagc tgttgacaat taatcatccg gctcgtataa tgtgtggaat tgtgagcgga      240
taacaatttc acacaggaaa cagacc atg ggc tca gac gtt caa tct tca ctc       293
                               Met Gly Ser Asp Val Gln Ser Ser Leu
                                 1               5 acc gga acc tgg tac aat gaa ctc aac tcc aag atg gaa ttg act gca       341
Thr Gly Thr Trp Tyr Asn Glu Leu Asn Ser Lys Met Glu Leu Thr Ala
 10              15                  20                  25 aac aaa gac ggt act ctc act gga aag tac ctc tcc aaa gtt ggg gat       389
Asn Lys Asp Gly Thr Leu Thr Gly Lys Tyr Leu Ser Lys Val Gly Asp
                 30                  35                  40 gtc tac gtg ccc tac cca ctc tct ggt cgc tat aac ctc caa ccc ccc       437
Val Tyr Val Pro Tyr Pro Leu Ser Gly Arg Tyr Asn Leu Gln Pro Pro
             45                  50                  55 gcg gga caa ggc gtc gct ctt ggg tgg gcg gta tcc tgg gag aac agt       485
Ala Gly Gln Gly Val Ala Leu Gly Trp Ala Val Ser Trp Glu Asn Ser
         60                  65                  70 aaa att cat tcc gct acg aca tgg agc gga cag ttc ttc tct gag tcg       533
Lys Ile His Ser Ala Thr Thr Trp Ser Gly Gln Phe Phe Ser Glu Ser
 75                  80                  85 tct cca gtg att ctt act cag tgg ttg ttg tca tcg agc act gcg cgt       581
Ser Pro Val Ile Leu Thr Gln Trp Leu Leu Ser Ser Ser Thr Ala Arg
 90                  95                 100                 105
```

```
ggg gac gta tgg gaa tcc aca ctt gtg ggg aat gat tcg ttt aca aag      629
Gly Asp Val Trp Glu Ser Thr Leu Val Gly Asn Asp Ser Phe Thr Lys
            110                 115                 120 acg gcg ccg act gag cag cag atc gct cat gct caa ctc cat tgt cgc      677
Thr Ala Pro Thr Glu Gln Gln Ile Ala His Ala Gln Leu His Cys Arg
        125                 130                 135 gca ccg agg ttg aag ggt ggc ggt ggc agc ggt ggc ggt ggc agc ggt      725
Ala Pro Arg Leu Lys Gly Gly Gly Gly Ser Gly Gly Gly Gly Ser Gly
    140                 145                 150 ggc ggt ggc agc ggt ggc ggt ggc agc ggt ggc ggt ggc agc gac gat      773
Gly Gly Gly Ser Gly Gly Gly Gly Ser Gly Gly Gly Gly Ser Asp Asp
        155                 160                 165 gac gat aag ccg gaa ttc gag ctc ggt acc cgg gat cct cga gcg gcc      821
Asp Asp Lys Pro Glu Phe Glu Leu Gly Thr Arg Asp Pro Arg Ala Ala
170             175                 180                 185 gcg ggc cac cat cac cat cac cac ggc tga tga aagcttggct gttttggcgg    874
Ala Gly His His His His His His Gly
                190 atgagagaag attttcagcc tgatacagat taaatcagaa cgcagaagcg gtctgataaa    934
acagaatttg cctggcggca gtagcgcggt ggtcccacct gacccatgc cgaactcaga     994
agtgaaacgc cgtagcgccg atggtagtgt ggggtctccc catgcgagag tagggaactg    1054
ccaggcatca aataaaacga aaggctcagt cgaaagactg ggcctttcgt tttatctgtt    1114
gtttgtcggt gaacgctctc ctgagtagga caaatccgcc gggagcggat ttgaacgttg    1174
cgaagcaacg gcccggaggg tggcgggcag gacgcccgcc ataaactgcc aggcatcaaa    1234
ttaagcagaa ggccatcctg acggatggcc tttttgcgtt tctacaaact cttttgttt    1294
attttctaa atacattcaa atatgtatcc gctcatgaga caataaccct gataaatgct     1354
tcaataatat tgaaaaagga agagtatgag tattcaacat ttccgtgtcg cccttattcc    1414
cttttttgcg gcattttgcc ttcctgtttt tgctcaccca gaaacgctgg tgaaagtaaa    1474
agatgctgaa gatcagttgg gtgcacgagt gggttacatc gaactggatc tcaacagcgg    1534
taagatcctt gagagttttc gccccgaaga acgttttcca atgatgagca cttttaaagt    1594
tctgctatgt ggcgcggtat tatcccgtgt tgacgccggg caagagcaac tcggtcgccg    1654
catacactat tctcagaatg acttggttga gtactcacca gtcacagaaa agcatcttac    1714
ggatggcatg acagtaagag aattatgcag tgctgccata accatgagtg ataacactgc    1774
ggccaactta cttctgacaa cgatcggagg accgaaggag ctaaccgctt ttttgcacaa    1834
catggggat catgtaactc gccttgatcg ttgggaaccg gagctgaatg aagccatacc     1894
aaacgacgag cgtgacacca cgatgcctac agcaatggca acaacgttgc gcaaactatt    1954
aactggcgaa ctacttactc tagcttcccg gcaacaatta atagactgga tggaggcgga    2014
taaagttgca ggaccacttc tgcgctcggc ccttccggct ggctggttta ttgctgataa    2074
atctggagcc ggtgagcgtg gtctcgcgg tatcattgca gcactgggc cagatggtaa      2134
gccctcccgt atcgtagtta tctacacgac ggggagtcag gcaactatgg atgaacgaaa    2194
tagacagatc gctgagatag gtgcctcact gattaagcat tggtaactgt cagaccaagt    2254
ttactcatat atactttaga ttgatttaaa acttcatttt taatttaaaa ggatctaggt    2314
gaagatcctt tttgataatc tcatgaccaa atcccttaa cgtgagtttt cgttccactg     2374
agcgtcagac cccgtagaaa agatcaaagg atcttcttga gatcctttt ttctgcgcgt     2434
aatctgctgc ttgcaaacaa aaaaaccacc gctaccagcg gtggtttgtt tgccggatca    2494
agagctacca actctttttc cgaaggtaac tggcttcagc agagcgcaga taccaaatac    2554
```

```
tgtccttcta gtgtagccgt agttaggcca ccacttcaag aactctgtag caccgcctac    2614
atacctcgct ctgctaatcc tgttaccagt ggctgctgcc agtggcgata agtcgtgtct    2674 taccggggttg gactcaagac gatagttacc ggataaggcg cagcggtcgg gctgaacggg    2734
gggttcgtgc acacagccca gcttggagcg aacgacctac accgaactga gatacctaca    2794
gcgtgagcta tgagaaagcg ccacgcttcc cgaagggaga aaggcggaca ggtatccggt    2854
aagcggcagg gtcggaacag gagagcgcac gagggagctt ccaggggggaa acgcctggta    2914 tctttatagt cctgtcgggt ttcgccacct ctgacttgag cgtcgatttt tgtgatgctc    2974
gtcagggggg cggagcctat ggaaaaacgc cagcaacgcg gcctttttac ggttcctggc    3034
cttttgctgg cctttttgctc acatgttctt cctgcgttta tcccctgatt ctgtggataa    3094
ccgtattacc gcctttgagt gagctgatac cgctcgccgc agccgaacga ccgagcgcag    3154
cgagtcagtg agcgaggaag cggaagagcg cctgatgcgg tatttctcc ttacgcatct    3214 gtgcggtatt tcacaccgca tatggtgcac tctcagtaca atctgctctg atgccgcata    3274
gttaagccag tatacactcc gctatcgcta cgtgactggg tcatggctgc gccccgacac    3334
ccgccaacac ccgctgacgc gccctgacgg gcttgtctgc tcccggcatc cgcttacaga    3394
caagctgtga ccgtctccgg gagctgcatg tgtcagaggt tttcaccgtc atcaccgaaa    3454
cgcgcgaggc agcagatcaa ttcgcgcgcg aaggcgaagc ggcatgcatt tacgttgaca    3514
ccatcgaatg gtgcaaaacc tttcgcggta tggcatgata gcgcccggaa gagagtcaat    3574
tcagggtggt gaatgtgaaa ccagtaacgt tatacgatgt cgcagagtat gccggtgtct    3634
cttatcagac cgtttcccgc gtggtgaacc aggccagcca cgtttctgcg aaaacgcggg    3694
aaaaagtgga agcggcgatg gcggagctga attacattcc caaccgcgtg cacaacaac    3754 tggcgggcaa acagtcgttg ctgattggcg ttgccacctc cagtctggcc ctgcacgcgc    3814
cgtcgcaaat tgtcgcggcg attaaatctc gcgccgatca actgggtgcc agcgtggtgg    3874
tgtcgatggt agaacgaagc ggcgtcgaag cctgtaaagc ggcggtgcac aatcttctcg    3934
cgcaacgcgt cagtgggctg atcattaact atccgctgga tgaccaggat gccattgctg    3994
tggaagctgc ctgcactaat gttccggcgt tatttcttga tgtctctgac cagacaccca    4054
tcaacagtat tatttctcc catgaagacg gtacgcgact gggcgtggag catctggtcg    4114
cattgggtca ccagcaaatc gcgctgttag cgggcccatt aagttctgtc tcggcgcgtc    4174
tgcgtctggc tggctggcat aaatatctca ctcgcaatca aattcagccg atagcggaac    4234
gggaaggcga ctggagtgcc atgtccggtt ttcaacaaac catgcaaatg ctgaatgagg    4294
gcatcgttcc cactgcgatg ctggttgcca acgatcagat ggcgctgggc gcaatgcgcg    4354
ccattaccga gtccgggctg cgcgttggtg cggatatctc ggtagtggga tacgacgata    4414
ccgaagacag ctcatgttat atcccgccgt caaccaccat caaacaggat tttcgcctgc    4474
tggggcaaac cagcgtggac cgcttgctgc aactctctca gggccaggcg gtgaagggca    4534
atcagctgtt gcccgtctca ctggtgaaaa gaaaaaccac cctggcgccc aatacgcaaa    4594
ccgcctctcc ccgcgcgttg gccgattcat taatgcagct ggcacgacag gtttcccgac    4654
tggaaagcgg gcagtgagcg caacgcaatt aatgtgagtt agcgcgaatt gatctg        4710
```

<210> SEQ ID NO 80
<211> LENGTH: 4644
<212> TYPE: DNA
<213> ORGANISM: Artificial sequence
<220> FEATURE:
<223> OTHER INFORMATION: Synthetic construct: His-MCS-EK-1xlink-TM2

```
<220> FEATURE:
<221> NAME/KEY: CDS
<222> LOCATION: 267..785

<400> SEQUENCE: 80
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat aatcatccg gctcgtataa tgtgtggaat tgtgagcgga     240
taacaatttc acacaggaaa cagacc atg gcc cac cat cac cat cac cat gcg     293
                                Met Ala His His His His His His Ala
                                  1               5 aat tcg agc tcg gta ccc ggg atc ctc gag cgg ccg cgg gac gat gac     341
Asn Ser Ser Ser Val Pro Gly Ile Leu Glu Arg Pro Arg Asp Asp Asp
 10              15                  20                  25 gat aag ggt ggc ggt ggc agc ggt tca gac gtt caa tct tca ctc acc     389
Asp Lys Gly Gly Gly Gly Ser Gly Ser Asp Val Gln Ser Ser Leu Thr
                 30                  35                  40 gga acc tgg tac aat gaa ctc aac tcc aag atg gaa ttg act gca aac     437
Gly Thr Trp Tyr Asn Glu Leu Asn Ser Lys Met Glu Leu Thr Ala Asn
             45                  50                  55 aaa gac ggt act ctc act gga aag tac ctc tcc aaa gtt ggg gat gtc     485
Lys Asp Gly Thr Leu Thr Gly Lys Tyr Leu Ser Lys Val Gly Asp Val
 60                  65                  70 tac gtg ccc tac cca ctc tct ggt cgc tat aac ctc caa ccc ccc gcg     533
Tyr Val Pro Tyr Pro Leu Ser Gly Arg Tyr Asn Leu Gln Pro Pro Ala
     75                  80                  85 gga caa ggc gtc gct ctt ggg tgg gcg gta tcc tgg gag aac agt aaa     581
Gly Gln Gly Val Ala Leu Gly Trp Ala Val Ser Trp Glu Asn Ser Lys
 90                  95                 100                 105 att cat tcc gct acg aca tgg agc gga cag ttc ttc tct gag tcg tct     629
Ile His Ser Ala Thr Thr Trp Ser Gly Gln Phe Phe Ser Glu Ser Ser
                110                 115                 120 cca gtg att ctt act cag tgg ttg ttg tca tcg agc act gcg cgt ggg     677
Pro Val Ile Leu Thr Gln Trp Leu Leu Ser Ser Ser Thr Ala Arg Gly
            125                 130                 135 gac gta tgg gaa tcc aca ctt gtg ggg aat gat tcg ttt aca aag acg     725
Asp Val Trp Glu Ser Thr Leu Val Gly Asn Asp Ser Phe Thr Lys Thr
        140                 145                 150 gcg ccg act gag cag cag atc gct cat gct caa ctc cat tgt cgc gca     773
Ala Pro Thr Glu Gln Gln Ile Ala His Ala Gln Leu His Cys Arg Ala
    155                 160                 165 ccg agg ttg aag taa aagcttggct gttttggcgg atgagagaag attttcagcc t   829
Pro Arg Leu Lys
170 gatacagatt aaatcagaac gcagaagcgg tctgataaaa cagaatttgc ctggcggcag    889 tagcgcggtg gtcccacctg acccatgcc gaactcagaa gtgaaacgcc gtagcgccga    949 tggtagtgtg gggtctcccc atgcgagagt agggaactgc caggcatcaa ataaaacgaa   1009 aggctcagtc gaaagactgg cctttcgtt ttatctgttg tttgtcggtg aacgctctcc    1069 tgagtaggac aaatccgccg ggagcggatt tgaacgttgc gaagcaacgg cccggagggt    1129 ggcgggcagg acgcccgcca taaactgcca ggcatcaaat taagcagaag gccatcctga    1189 cggatggcct ttttgcgttt ctacaaactc ttttttgttta ttttttctaaa tacattcaaa   1249 tatgtatccg ctcatgagac aataaccctg ataaatgctt caataatatt gaaaaggaa    1309 gagtatgagt attcaacatt tccgtgtcgc ccttattccc ttttttgcgg cattttgcct    1369
```

```
tcctgttttt gctcacccag aaacgctggt gaaagtaaaa gatgctgaag atcagttggg    1429
tgcacgagtg ggttacatcg aactggatct caacagcggt aagatccttg agagttttcg    1489
ccccgaagaa cgttttccaa tgatgagcac ttttaaagtt ctgctatgtg gcgcggtatt    1549
atcccgtgtt gacgccgggc aagagcaact cggtcgccgc atacactatt ctcagaatga    1609
cttggttgag tactcaccag tcacagaaaa gcatcttacg gatggcatga cagtaagaga    1669
attatgcagt gctgccataa ccatgagtga taacactgcg ccaacttac ttctgacaac     1729
gatcggagga ccgaaggagc taaccgcttt tttgcacaac atgggggatc atgtaactcg    1789
ccttgatcgt tgggaaccgg agctgaatga agccatacca aacgacgagc gtgacaccac    1849
gatgcctaca gcaatggcaa caacgttgcg caaactatta actggcgaac tacttactct    1909
agcttcccgg caacaattaa tagactggat ggaggcggat aaagttgcag gaccacttct    1969
gcgctcggcc cttccggctg gctggtttat tgctgataaa tctggagccg gtgagcgtgg    2029
gtctcgcggt atcattgcag cactggggcc agatggtaag ccctcccgta tcgtagttat    2089
ctacacgacg gggagtcagg caactatgga tgaacgaaat agacagatcg ctgagatagg    2149
tgcctcactg attaagcatt ggtaactgtc agaccaagtt tactcatata ctttagat     2209
tgatttaaaa cttcattttt aatttaaaag gatctaggtg aagatccttt ttgataatct    2269
catgaccaaa atcccttaac gtgagttttc gttccactga gcgtcagacc ccgtagaaaa    2329
gatcaaagga tcttcttgag atcctttttt tctgcgcgta atctgctgct tgcaaacaaa    2389
aaaaccaccg ctaccagcgg tggtttgttt gccggatcaa gagctaccaa ctctttttcc    2449
gaaggtaact ggcttcagca gagcgcagat accaaatact gtccttctag tgtagccgta    2509
gttaggccac cacttcaaga actctgtagc accgcctaca tacctcgctc tgctaatcct    2569
gttaccagtg gctgctgcca gtggcgataa gtcgtgtctt accgggttgg actcaagacg    2629
atagttaccg gataaggcgc agcggtcggg ctgaacgggg ggttcgtgca cacagcccag    2689
cttggagcga acgacctaca ccgaactgag atacctacag cgtgagctat gagaaagcgc    2749
cacgcttccc gaagggagaa aggcggacag gtatccggta agcggcaggg tcggaacagg    2809
agagcgcacg agggagcttc caggggggaaa cgcctggtat ctttatagtc ctgtcgggtt    2869
tcgccacctc tgacttgagc gtcgattttt gtgatgctcg tcagggggggc ggagcctatg    2929
gaaaaacgcc agcaacgcgg ccttttttacg gttcctggcc ttttgctggc cttttgctca    2989
catgttcttt cctgcgttat cccctgattc tgtggataac cgtattaccg cctttgagtg    3049
agctgatacc gctcgccgca gccgaacgac cgagcgcagc gagtcagtga gcgaggaagc    3109
ggaagagcgc ctgatgcggt attttctcct tacgcatctg tgcggtattt cacaccgcat    3169
atggtgcact ctcagtacaa tctgctctga tgccgcatag ttaagccagt atacactccg    3229
ctatcgctac gtgactgggt catggctgcg ccccgacacc cgccaacacc cgctgacgcg    3289
ccctgacggg cttgtctgct cccggcatcc gcttacagac aagctgtgac cgtctccggg    3349
agctgcatgt gtcagaggtt ttcaccgtca tcaccgaaac gcgcgaggca gcagatcaat    3409
tcgcgcgcga aggcgaagcg gcatgcattt acgttgacac catcgaatgg tgcaaaacct    3469
ttcgcggtat ggcatgatag cgcccggaag agagtcaatt cagggtggtg aatgtgaaac    3529
cagtaacgtt atacgatgtc gcagagtatg ccggtgtctc ttatcagacc gtttcccgcg    3589
tggtgaacca ggccagccac gtttctgcga aaacgcggga aaaagtggaa gcggcgatgg    3649
cggagctgaa ttacattccc aaccgcgtgg cacaacaact ggcgggcaaa cagtcgttgc    3709
tgattggcgt tgccacctcc agtctggccc tgcacgcgcc gtcgcaaatt gtcgcggcga    3769
```

```
ttaaatctcg cgccgatcaa ctgggtgcca gcgtggtggt gtcgatggta gaacgaagcg    3829
gcgtcgaagc ctgtaaagcg gcggtgcaca atcttctcgc gcaacgcgtc agtgggctga    3889
tcattaacta tccgctggat gaccaggatg ccattgctgt ggaagctgcc tgcactaatg    3949
ttccggcgtt atttcttgat gtctctgacc agacacccat caacagtatt attttctccc    4009
atgaagacgg tacgcgactg ggcgtggagc atctggtcgc attgggtcac cagcaaatcg    4069
cgctgttagc gggcccatta agttctgtct cggcgcgtct cgtctggct ggctggcata    4129 aatatctcac tcgcaatcaa attcagccga tagcggaacg ggaaggcgac tggagtgcca    4189
tgtccggttt tcaacaaacc atgcaaatgc tgaatgaggg catcgttccc actgcgatgc    4249
tggttgccaa cgatcagatg gcgctgggcg caatgcgcgc cattaccgag tccgggctgc    4309
gcgttggtgc ggatatctcg gtagtgggat acgacgatac cgaagacagc tcatgttata    4369
tcccgccgtc aaccaccatc aaacaggatt ttcgcctgct ggggcaaacc agcgtggacc    4429
gcttgctgca actctctcag gccaggcgg tgaaggcaa tcagctgttg cccgtctcac    4489
tggtgaaaag aaaaaccacc ctggcgccca atacgcaaac cgcctctccc cgcgcgttgg    4549
ccgattcatt aatgcagctg gcacgacagg tttcccgact ggaaagcggg cagtgagcgc    4609
aacgcaatta atgtgagtta gcgcgaattg atctg                             4644
```

<210> SEQ ID NO 81
<211> LENGTH: 4671
<212> TYPE: DNA
<213> ORGANISM: Artificial sequence
<220> FEATURE:
<223> OTHER INFORMATION: Synthetic construct: His-MCS-EK-3xlink-TM2
<220> FEATURE:
<221> NAME/KEY: CDS
<222> LOCATION: 267..812

<400> SEQUENCE: 81

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagacc atg gcc cac cat cac cat cac cat gcg      293
                              Met Ala His His His His His His Ala
                                1               5 aat tcg agc tcg gta ccc ggg atc ctc gag cgg ccg cgg gac gat gac       341
Asn Ser Ser Ser Val Pro Gly Ile Leu Glu Arg Pro Arg Asp Asp Asp
 10              15                  20                  25 gat aag ggt ggc ggt ggc agc ggt ggc ggt ggc agc ggt ggc ggt ggc       389
Asp Lys Gly Gly Gly Gly Ser Gly Gly Gly Gly Ser Gly Gly Gly Gly
                 30                  35                  40 agc tca gac gtt caa tct tca ctc acc gga acc tgg tac aat gaa ctc       437
Ser Ser Asp Val Gln Ser Ser Leu Thr Gly Thr Trp Tyr Asn Glu Leu
             45                  50                  55 aac tcc aag atg gaa ttg act gca aac aaa gac ggt act ctc act gga       485
Asn Ser Lys Met Glu Leu Thr Ala Asn Lys Asp Gly Thr Leu Thr Gly
         60                  65                  70 aag tac ctc tcc aaa gtt ggg gat gtc tac gtg ccc tac cca ctc tct       533
Lys Tyr Leu Ser Lys Val Gly Asp Val Tyr Val Pro Tyr Pro Leu Ser
     75                  80                  85 ggt cgc tat aac ctc caa ccc ccg gcg gga caa ggc gtc gct ctt ggg       581
Gly Arg Tyr Asn Leu Gln Pro Pro Ala Gly Gln Gly Val Ala Leu Gly
 90                  95                 100                 105 tgg gcg gta tcc tgg gag aac agt aaa att cat tcc gct acg aca tgg       629
Trp Ala Val Ser Trp Glu Asn Ser Lys Ile His Ser Ala Thr Thr Trp
```

```
                Trp Ala Val Ser Trp Glu Asn Ser Lys Ile His Ser Ala Thr Thr Trp
                            110                 115                 120 agc gga cag ttc ttc tct gag tcg tct cca gtg att ctt act cag tgg       677
Ser Gly Gln Phe Phe Ser Glu Ser Ser Pro Val Ile Leu Thr Gln Trp
            125                 130                 135 ttg ttg tca tcg agc act gcg cgt ggg gac gta tgg gaa tcc aca ctt       725
Leu Leu Ser Ser Ser Thr Ala Arg Gly Asp Val Trp Glu Ser Thr Leu
            140                 145                 150 gtg ggg aat gat tcg ttt aca aag acg gcg ccg act gag cag cag atc       773
Val Gly Asn Asp Ser Phe Thr Lys Thr Ala Pro Thr Glu Gln Gln Ile
            155                 160                 165 gct cat gct caa ctc cat tgt cgc gca ccg agg ttg aag taa aagcttggc     824
Ala His Ala Gln Leu His Cys Arg Ala Pro Arg Leu Lys
170                 175                 180 tgttttggcg gatgagagaa gattttcagc ctgatacaga ttaaatcaga acgcagaagc     884
ggtctgataa aacagaattt gcctggcggc agtagcgcgg tggtcccacc tgacccatg      944
ccgaactcag aagtgaaacg ccgtagcgcc gatggtagtg tggggtctcc ccatgcgaga    1004
gtagggaact gccaggcatc aaataaaacg aaaggctcag tcgaaagact gggcctttcg    1064
ttttatctgt tgtttgtcgg tgaacgctct cctgagtagg acaaatccgc cgggagcgga    1124
tttgaacgtt gcgaagcaac ggcccggagg gtggcgggca ggacgcccgc cataaactgc    1184
caggcatcaa attaagcaga aggccatcct gacggatggc cttttgcgt ttctacaaac     1244
tcttttttgtt tattttttcta aatacattca aatatgtatc cgctcatgag acaataaccc  1304
tgataaatgc ttcaataata ttgaaaaagg aagagtatga gtattcaaca tttccgtgtc    1364
gcccttattc ccttttttgc ggcattttgc cttcctgttt ttgctcaccc agaaacgctg    1424
gtgaaagtaa aagatgctga agatcagttg ggtgcacgag tgggttacat cgaactggat    1484
ctcaacagcg gtaagatcct tgagagtttt cgccccgaag aacgttttcc aatgatgagc    1544
acttttaaag ttctgctatg tggcgcggta ttatcccgtg ttgacgccgg caagagcaa     1604
ctcggtcgcc gcatacacta ttctcagaat gacttggttg agtactcacc agtcacagaa    1664
aagcatctta cggatggcat gacagtaaga gaattatgca gtgctgccat aaccatgagt    1724
gataacactg cggccaactt acttctgaca acgatcggag gaccgaagga gctaaccgct    1784
tttttgcaca acatggggga tcatgtaact cgccttgatc gttgggaacc ggagctgaat    1844
gaagccatac caaacgacga gcgtgacacc acgatgccta gcaatggc aacaacgttg      1904
cgcaaactat taactggcga actacttact ctagcttccc ggcaacaatt aatagactgg    1964
atggaggcgg ataaagttgc aggaccactt ctgcgctcgg cccttccggc tggctggttt    2024
attgctgata atctggagc cggtgagcgt gggtctcgcg gtatcattgc agcactgggg     2084
ccagatggta agccctcccg tatcgtagtt atctacacga cggggagtca ggcaactatg    2144
gatgaacgaa atagacagat cgctgagata ggtgcctcac tgattaagca ttggtaactg    2204
tcagaccaag tttactcata tatactttag attgatttaa aacttcattt ttaatttaaa    2264
aggatctagg tgaagatcct ttttgataat ctcatgacca aaatccctta acgtgagttt    2324
tcgttccact gagcgtcaga ccccgtagaa aagatcaaag gatcttcttg agatcctttt    2384
tttctgcgcg taatctgctg cttgcaaaca aaaaaaccac cgctaccagc ggtggtttgt    2444
ttgccggatc aagagctacc aactcttttt ccgaaggtaa ctggcttcag cagagcgcag    2504
ataccaaata ctgtccttct agtgtagccg tagttaggcc accacttcaa gaactctgta    2564
gcaccgccta catacctcgc tctgctaatc ctgttaccag tggctgctgc cagtggcgat    2624
aagtcgtgtc ttaccgggtt ggactcaaga cgatagttac cggataaggc gcagcggtcg    2684
```

-continued

```
ggctgaacgg ggggttcgtg cacacagccc agcttggagc gaacgaccta caccgaactg    2744
agatacctac agcgtgagct atgagaaagc gccacgcttc ccgaagggag aaaggcggac    2804
aggtatccgg taagcggcag ggtcggaaca ggagagcgca cgagggagct tccaggggga    2864
aacgcctggt atctttatag tcctgtcggg tttcgccacc tctgacttga gcgtcgattt    2924
ttgtgatgct cgtcagggggg gcggagccta tggaaaaacg ccagcaacgc ggcctttttta   2984 cggttcctgg ccttttgctg gccttttgct cacatgttct ttcctgcgtt atccctgat    3044 tctgtggata accgtattac cgcctttgag tgagctgata ccgctcgccg cagccgaacg    3104
accgagcgca gcgagtcagt gagcgaggaa gcggaagagc gcctgatgcg gtattttctc    3164
cttacgcatc tgtgcggtat ttcacaccgc atatggtgca ctctcagtac aatctgctct    3224
gatgccgcat agttaagcca gtatacactc cgctatcgct acgtgactgg gtcatggctg    3284
cgccccgaca cccgccaaca cccgctgacg cgccctgacg ggcttgtctg ctcccggcat    3344
ccgcttacag acaagctgtg accgtctccg ggagctgcat gtgtcagagg ttttcaccgt    3404
catcaccgaa acgcgcgagg cagcagatca attcgcgcgc gaaggcgaag cggcatgcat    3464
ttacgttgac accatcgaat ggtgcaaaac ctttcgcggt atggcatgat agcgcccgga    3524
agagagtcaa ttcagggtgg tgaatgtgaa accagtaacg ttatacgatg tcgcagagta    3584
tgccggtgtc tcttatcaga ccgtttcccg cgtggtgaac caggccagcc acgtttctgc    3644
gaaaacgcgg gaaaaagtgg aagcggcgat ggcggagctg aattacattc ccaaccgcgt    3704
ggcacaacaa ctggcgggca acagtcgtt gctgattggc gttgccacct ccagtctggc    3764
cctgcacgcg ccgtcgcaaa ttgtcgcggc gattaaatct cgcgccgatc aactgggtgc    3824
cagcgtggtg gtgtcgatgg tagaacgaag cggcgtcgaa gcctgtaaag cggcggtgca    3884
caatcttctc gcgcaacgcg tcagtgggct gatcattaac tatccgctgg atgaccagga    3944
tgccattgct gtggaagctg cctgcactaa tgttccggcg ttatttcttg atgtctctga    4004
ccagacaccc atcaacagta ttattttctc ccatgaagac ggtacgcgac tgggcgtgga    4064
gcatctggtc gcattgggtc accagcaaat cgcgctgtta gcgggcccat taagttctgt    4124
ctcggcgcgt ctgcgtctgg ctggctggca taaatatctc actcgcaatc aaattcagcc    4184
gatagcggaa cggaaggcg actggagtgc catgtccggt tttcaacaaa ccatgcaaat    4244
gctgaatgag ggcatcgttc ccactgcgat gctggttgcc aacgatcaga tggcgctggg    4304
cgcaatgcgc gccattaccg agtccgggct gcgcgttggt gcggatatct cggtagtggg    4364
atacgacgat accgaagaca gctcatgtta tcccgccg tcaaccacca tcaaacagga    4424
ttttcgcctg ctggggcaaa ccagcgtgga ccgcttgctg caactctctc agggccaggc    4484
ggtgaagggc aatcagctgt tgcccgtctc actggtgaaa agaaaaacca ccctggcgcc    4544
caatacgcaa accgcctctc cccgcgcgtt ggccgattca ttaatgcagc tggcacgaca    4604
ggtttcccga ctggaaagcg gcagtgagc gcaacgcaat taatgtgagt tagcgcgaat    4664
tgatctg                                                             4671
```

<210> SEQ ID NO 82
<211> LENGTH: 4701
<212> TYPE: DNA
<213> ORGANISM: Artificial sequence
<220> FEATURE:
<223> OTHER INFORMATION: Synthetic construct: His-MCS-EK-5xlink-TM2
<220> FEATURE:
<221> NAME/KEY: CDS
<222> LOCATION: 267..842

<400> SEQUENCE: 82

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagacc atg gcc cac cat cac cat cac cat gcg      293
                              Met Ala His His His His His His Ala
                               1               5 aat tcg agc tcg gta ccc ggg atc ctc gag cgg ccg cgg gac gat gac       341
Asn Ser Ser Ser Val Pro Gly Ile Leu Glu Arg Pro Arg Asp Asp Asp
 10              15                  20                  25 gat aag ggt ggc ggt ggc agc ggt ggc ggt ggc agc ggt ggc ggt ggc       389
Asp Lys Gly Gly Gly Gly Ser Gly Gly Gly Gly Ser Gly Gly Gly Gly
                 30                  35                  40 agc ggt ggc ggt ggc agc ggt ggc ggt ggc agc tca gac gtt caa tct       437
Ser Gly Gly Gly Gly Ser Gly Gly Gly Gly Ser Ser Asp Val Gln Ser
             45                  50                  55 tca ctc acc gga acc tgg tac aat gaa ctc aac tcc aag atg gaa ttg       485
Ser Leu Thr Gly Thr Trp Tyr Asn Glu Leu Asn Ser Lys Met Glu Leu
         60                  65                  70 act gca aac aaa gac ggt act ctc act gga aag tac ctc tcc aaa gtt       533
Thr Ala Asn Lys Asp Gly Thr Leu Thr Gly Lys Tyr Leu Ser Lys Val
     75                  80                  85 ggg gat gtc tac gtg ccc tac cca ctc tct ggt cgc tat aac ctc caa       581
Gly Asp Val Tyr Val Pro Tyr Pro Leu Ser Gly Arg Tyr Asn Leu Gln
 90                  95                 100                 105 ccc ccc gcg gga caa ggc gtc gct ctt ggg tgg gcg gta tcc tgg gag       629
Pro Pro Ala Gly Gln Gly Val Ala Leu Gly Trp Ala Val Ser Trp Glu
                110                 115                 120 aac agt aaa att cat tcc gct acg aca tgg agc gga cag ttc ttc tct       677
Asn Ser Lys Ile His Ser Ala Thr Thr Trp Ser Gly Gln Phe Phe Ser
            125                 130                 135 gag tcg tct cca gtg att ctt act cag tgg ttg ttg tca tcg agc act       725
Glu Ser Ser Pro Val Ile Leu Thr Gln Trp Leu Leu Ser Ser Ser Thr
        140                 145                 150 gcg cgt ggg gac gta tgg gaa tcc aca ctt gtg ggg aat gat tcg ttt       773
Ala Arg Gly Asp Val Trp Glu Ser Thr Leu Val Gly Asn Asp Ser Phe
    155                 160                 165 aca aag acg gcg ccg act gag cag cag atc gct cat gct caa ctc cat       821
Thr Lys Thr Ala Pro Thr Glu Gln Gln Ile Ala His Ala Gln Leu His
170                 175                 180                 185 tgt cgc gca ccg agg ttg aag taa aagcttggct gttttggcgg atgagagaag      875
Cys Arg Ala Pro Arg Leu Lys
                190 attttcagcc tgatacagat taaatcagaa cgcagaagcg gtctgataaa acagaatttg     935 cctggcggca gtagcgcggt ggtcccacct gaccccatgc cgaactcaga agtgaaacgc     995 cgtagcgccg atggtagtgt ggggtctccc catgcgagag tagggaactg ccaggcatca    1055 aataaaacga aaggctcagt cgaaagactg ggcctttcgt tttatctgtt gtttgtcggt    1115 gaacgctctc ctgagtagga caaatccgcc gggagcggat ttgaacgttg cgaagcaacg    1175 gcccggaggg tggcgggcag gacgcccgcc ataaactgcc aggcatcaaa ttaagcagaa    1235 ggccatcctg acggatggcc tttttgcgtt tctacaaact cttttgtttt atttttctaa    1295 atacattcaa atatgtatcc gctcatgaga caataaccct gataaatgct tcaataatat    1355 tgaaaaagga agagtatgag tattcaacat ttccgtgtcg cccttattcc cttttttgcg    1415
```

```
gcattttgcc ttcctgtttt tgctcaccca gaaacgctgg tgaaagtaaa agatgctgaa    1475
gatcagttgg gtgcacgagt gggttacatc gaactggatc tcaacagcgg taagatcctt    1535
gagagttttc gccccgaaga acgttttcca atgatgagca cttttaaagt tctgctatgt    1595
ggcgcggtat tatcccgtgt tgacgccggg caagagcaac tcggtcgccg catacactat    1655
tctcagaatg acttggttga gtactcacca gtcacagaaa agcatcttac ggatggcatg    1715
acagtaagag aattatgcag tgctgccata accatgagtg ataacactgc ggccaactta    1775
cttctgacaa cgatcggagg accgaaggag ctaaccgctt ttttgcacaa catggggat    1835 catgtaactc gccttgatcg ttgggaaccg gagctgaatg aagccatacc aaacgacgag    1895
cgtgacacca cgatgcctac agcaatggca acaacgttgc gcaaactatt aactggcgaa    1955
ctacttactc tagcttcccg gcaacaatta atagactgga tggaggcgga taaagttgca    2015
ggaccacttc tgcgctcggc ccttccggct ggctggttta ttgctgataa atctggagcc    2075
ggtgagcgtg ggtctcgcgg tatcattgca gcactgggc cagatggtaa gccctcccgt    2135
atcgtagtta tctacacgac ggggagtcag gcaactatgg atgaacgaaa tagacagatc    2195
gctgagatag gtgcctcact gattaagcat tggtaactgt cagaccaagt ttactctat    2255 atactttaga ttgatttaaa acttcatttt taatttaaaa ggatctaggt gaagatcctt    2315
tttgataatc tcatgaccaa aatcccttaa cgtgagtttt cgttccactg agcgtcagac    2375
cccgtagaaa agatcaaagg atcttcttga gatcctttt ttctgcgcgt aatctgctgc    2435
ttgcaaacaa aaaaaccacc gctaccagcg gtggtttgtt tgccggatca agagctacca    2495 actcttttc gaaggtaac tggcttcagc agagcgcaga taccaaatac tgtccttcta    2555
gtgtagccgt agttaggcca ccacttcaag aactctgtag caccgcctac atacctcgct    2615
ctgctaatcc tgttaccagt ggctgctgcc agtggcgata agtcgtgtct taccgggttg    2675
gactcaagac gatagttacc ggataaggcg cagcggtcgg gctgaacggg gggttcgtgc    2735
acacagccca gcttggagcg aacgacctac accgaactga gatacctaca gcgtgagcta    2795
tgagaaagcg ccacgcttcc cgaagggaga aaggcggaca ggtatccggt aagcggcagg    2855
gtcggaacag gagagcgcac gagggagctt ccaggggaa acgcctggta tctttatagt    2915
cctgtcgggt ttcgccacct ctgacttgag cgtcgatttt tgtgatgctc gtcagggggg    2975
cggagcctat ggaaaaacgc cagcaacgcg gccttttac ggttcctggc ctttgctgg    3035 ccttttgctc acatgttctt tcctgcgtta tcccctgatt ctgtggataa ccgtattacc    3095
gcctttgagt gagctgatac cgctcgccgc agccgaacga ccgagcgcag cgagtcagtg    3155
agcgaggaag cggaagagcg cctgatgcgg tattttctcc ttacgcatct gtgcggtatt    3215
tcacaccgca tatggtgcac tctcagtaca atctgctctg atgccgcata gttaagccag    3275
tatacactcc gctatcgcta cgtgactggg tcatggctgc gccccgacac ccgccaacac    3335
ccgctgacgc gccctgacgg gcttgtctgc tcccggcatc cgcttacaga caagctgtga    3395
ccgtctccgg gagctgcatg tgtcagaggt tttcaccgtc atcaccgaaa cgcgcgaggc    3455
agcagatcaa ttcgcgcgcg aaggcgaagc ggcatgcatt tacgttgaca ccatcgaatg    3515
gtgcaaaacc tttcgcggta tggcatgata gcgcccggaa gagagtcaat tcagggtggt    3575
gaatgtgaaa ccagtaacgt tatacgatgt cgcagagtat gccggtgtct cttatcagac    3635
cgtttcccgc gtggtgaacc aggccagcca cgtttctgcg aaaacgcggg aaaaagtgga    3695
agcggcgatg gcggagctga attacattcc caaccgcgtg gcacaacaac tggcgggcaa    3755
```

```
acagtcgttg ctgattggcg ttgccacctc cagtctggcc ctgcacgcgc cgtcgcaaat    3815
tgtcgcggcg attaaatctc gcgccgatca actgggtgcc agcgtggtgg tgtcgatggt    3875
agaacgaagc ggcgtcgaag cctgtaaagc ggcggtgcac aatcttctcg cgcaacgcgt    3935
cagtgggctg atcattaact atccgctgga tgaccaggat gccattgctg tggaagctgc    3995
ctgcactaat gttccggcgt tatttcttga tgtctctgac cagacaccca tcaacagtat    4055
tattttctcc catgaagacg gtacgcgact gggcgtggag catctggtcg cattgggtca    4115
ccagcaaatc gcgctgttag cgggcccatt aagttctgtc tcggcgcgtc tgcgtctggc    4175
tggctggcat aaatatctca ctcgcaatca aattcagccg atagcggaac gggaaggcga    4235
ctggagtgcc atgtccggtt ttcaacaaac catgcaaatg ctgaatgagg catcgttcc    4295 cactgcgatg ctggttgcca acgatcagat ggcgctgggc gcaatgcgcg ccattaccga    4355
gtccgggctg cgcgttggtg cggatatctc ggtagtggga tacgacgata ccgaagacag    4415
ctcatgttat atcccgccgt caaccaccat caaacaggat tttcgcctgc tggggcaaac    4475
cagcgtggac cgcttgctgc aactctctca gggccaggcg gtgaagggca atcagctgtt    4535
gcccgtctca ctggtgaaaa gaaaaaccac cctggcgccc aatacgcaaa ccgcctctcc    4595
ccgcgcgttg gccgattcat taatgcagct ggcacgacag gtttcccgac tggaaagcgg    4655
gcagtgagcg caacgcaatt aatgtgagtt agcgcgaatt gatctg                  4701
```

<210> SEQ ID NO 83
<211> LENGTH: 10
<212> TYPE: PRT
<213> ORGANISM: Artificial Sequence
<220> FEATURE:
<223> OTHER INFORMATION: Synthetic peptide

<400> SEQUENCE: 83

Glu Gln Lys Leu Ile Ser Glu Glu Asp Leu
1               5                   10

<210> SEQ ID NO 84
<211> LENGTH: 33
<212> TYPE: DNA
<213> ORGANISM: Artificial Sequence
<220> FEATURE:
<223> OTHER INFORMATION: Synthetic primer

<400> SEQUENCE: 84 tttttttggat ccctagactg caatacaaac acc                                33

<210> SEQ ID NO 85
<211> LENGTH: 22
<212> TYPE: DNA
<213> ORGANISM: Artificial Sequence
<220> FEATURE:
<223> OTHER INFORMATION: Synthetic primer

<400> SEQUENCE: 85
gcccatacag tcgtacctgt aa                                             22

METHOD OF BINDING PROTEINS TO CARRIERS BY MAKING USE OF TAMAVIDINS

TECHNICAL FIELD

This application claims priority based on the Japanese Patent Application No. 2007-220921 filed on Aug. 28, 2007.

The present invention relates to a method of binding proteins to carriers by making use of tamavidins.

BACKGROUND ART

Heretofore known common methods for causing proteins to bind to carriers such as microplates, microbeads or sensor chips include hydrophobic bonding, covalent bonding, and the like. Hydrophobic bonding depends on the interaction between a hydrophobic surface of the carrier and a hydrophobic portion of the protein and it is convenient in that it requires no special reagent; on the other hand, it generally presents a weak binding force and if it is used in ELISA (enzyme-linked immunosorbent assay) or the like, washing and other operations that are performed after the binding often cause the protein to come off the carrier. It is also known that when proteins and carriers are bound together by hydrophobic bonding, most of the proteins lose their functions either completely or partially. In contrast, covalent bonding presents a strong binding force because it depends on the interaction between functional groups (e.g. amino groups) in the protein and functional groups (e.g. carboxyl groups) provided on the carrier's surface. However, when proteins and carriers are bound together by covalent bonding, most of the proteins have their functions lost either completely or partially as in the case of hydrophobic bonding.

In addition to hydrophobic bonding and covalent bonding, a method is known in which a plurality of histidines are fused to a terminal end of protein and the fused protein having such histidine tags is bound to a substrate such as a protein chip that has nickel provided on its surface. However, the interaction between the histidine tag and the nickel ion is not very strong and, what is more, the nickel ion which is known to bind nonspecifically to various biomolecules is not necessarily an all-purpose tool.

Avidin is a glycoprotein derived from egg white and it binds to biotin (vitamin H) extremely strongly. The interaction between avidin and biotin is one of the strongest modes of non-covalent bonding (Green (1975) Adv Protein Chem 29: 85-133). Streptavidin is an avidin-like protein derived from actinomycetes and it also strongly binds to biotin. So far, the (strept)avidin-biotin interaction, because of its strong force, has been extensively used in the fields of molecular biology and biochemistry for such purposes as the detection of antigens and antibodies (Green (1990) Methods Enzymol 184: 51-67).

Methods have been devised that bind proteins to carriers by making use of the above-described biotin binding ability of avidin or streptavidin. One example is a method in which (strept)avidin is fixed to a substrate such as a microplate by covalent or hydrophobic bonding and a biotinylated protein is then immobilized by binding to the (strept)avidin. In this method, however, the activity of avidin per se is lost partially and, what is more, the specific activity of the protein bound via biotin decreases, resulting in an action efficiency that is by no means satisfactory.

In contrast, a technique has been reported in which an avidin protein is first bound to a biotin-bound substrate by forming avidin-biotin bonds, to which a desired biotinylated protein is bound to ensure that avidin is bound to additional biotin pockets, whereby biotin, avidin, biotin, and the desired protein are fixed in that order to the substrate (JP 4-236353 A1). However, this method involves the step of biotinylating the desired protein, which results in the need for extra labor; another problem is the need to take the efficiency of biotin labeling into consideration.

Heretofore, with a view to using them as a protein labelling, a diagnosis marker, or a cell-specific targeting factor, fused proteins using avidin or streptavidin have been prepared (Airenne et al. (1999) Biomol Eng 16:87-92). In particular, the fused proteins prepared by fusing avidin or streptavidin to antibodies such as scFV or Fab fragments and IgG have been studied for their potential application in the specific targeting of drugs to cancer cells and the like. In addition, the idea has been described of a column that uses a streptavidin-scFv fused protein to fix scFv via avidin-biotin bonds (Kiprivanov et al. (1995) Hum Antib Hybrid 6: 93-101 and Dubel et al. (1995) J Immunol Methods 178: 201-209). However, avidin and streptavidin are difficult to express in *E. coli* as a soluble form in high yield; what is more, there has been no report in which an avidin-fused protein or a streptavidin-fused protein is immobilized by being bound to a biotinylated carrier so as to improve the activity of the proteins in comparison with the conventional binding methods. On the contrary, it has been reported that when a fusion protein of streptavidin and β-galactosidase was bound to biotinylated beads, the specific activity of β-galactosidase decreased to about 50% (Huang et al. (1996) Enzyme and Microbial technology.)

Patent Document 1: JP 4-236353 A1
Patent Document 2: WO02/072817
Patent Document 3: PCT/JP2006/326260
Patent Document 4: PCT/JP2006/304993
Non-patent Document 1: Green (1975) Adv Protein Chem 29: 85-133
Non-patent Document 2: Green (1990) Methods Enzymol 184: 51-67
Non-patent Document 3: Airenne et al. (1999) Biomol Eng 16: 87-92
Non-patent Document 4: Kiprivanov et al. (1995) Hum Antib Hybrid 6: 93-101
Non-patent Document 5: Dubel et al. (1995) J Immunol Methods 178: 201-209
Non-patent Document 6: Huang et al. (1996) Enzyme and Microbial technology
Non-patent Document 7: Hofmann et al. (1980) Proc Natl Acad Sci USA 77: 4666-4668
Non-patent Document 8: Iba et al. (1997) Gene 194: 35-46
Non-patent Document 9: Ideno et al. (2004) Appl Microbiol Biotechnol 64: 99-105
Non-patent Document 10: Kada et al. (1999) Biochim. Biophys. Acta., 1427: 33-43

DISCLOSURE OF THE INVENTION

Problems to be Solved by the Invention

The present invention has as its object providing a method of binding a protein to a carrier in such a way that the protein will act more efficiently than when it is bound directly. The conventional methods that involve direct binding of proteins to carriers have had the problem of lowered activity of the bound protein. The present invention aims at solving this problem with the conventional methods of protein immobilization.

Means for Solving the Problems

As a result of their intensive research efforts to solve the problem, the present inventors prepared a protein having tamavidin fused to a desired protein and found that by binding the fused protein to a carrier having biotin immobilized on its surface, the desired protein was not impaired in its function but it could also be allowed to act far more efficiently than when it was fixed to the carrier by the conventional methods.

To be more specific, the present inventors used fusion proteins of an enzyme and tamavidin to get them to be bound to biotinylated magnetic beads by forming tamavidin-biotin bonds and found that the enzyme activity improved greatly by a factor 10 and more compared to the case where the enzyme protein was bound to the magnetic heads by covalent bonding. The inventors also found that when fusion proteins of an antibody fragment and tamavidin were bound to a biotinylated microplate, the antigen binding activity was higher than in the case where the antibody fragment of interest was bound to the microplate by hydrophobic bonding. The inventors further found that when fusion proteins of protein A and tamavidin were bound to a biotinylated micro-plate and antibodies were then bound to the micro-plate, the detection sensitivity improved by a factor of about 2 to 4, compared to the case where the antibodies were directly bound to the microplate by hydrophobic bonding.

On the basis of these findings, the present invention provides a novel method of binding proteins to carriers without impairing the activities of those proteins.

Modes for Carrying Out the Present Invention

The present invention preferably includes the following modes.

Mode (1)

A method of binding a protein to a carrier, which comprises:
preparing a biotin-bound carrier;
preparing a fusion protein having the protein bound to a tamavidin; and
binding the protein to the carrier via tamavidin-biotin bonds.

Mode (2)

The method according to mode 1, wherein the tamavidin is selected from:

(a) a protein consisting of an amino acid sequence with deletion, substitution or addition of one or more amino acids in SEQ ID NO: 2 or SEQ ID NO: 4 and having biotin-binding activity; or (b) a protein consisting of an amino acid sequence sharing an identity of 60% or more with SEQ ID NO: 2 or SEQ ID NO: 4 and having biotin-binding activity; or (c) a protein consisting of the amino acid sequence of SEQ ID NO: 2 or SEQ ID NO: 4; or (d) a protein consisting of an amino acid sequence encoded by a nucleic acid hybridizable under stringent conditions with a strand complementary to the base sequence of SEQ ID NO: 1 or SEQ ID NO: 3 and having biotin-binding activity.

Mode (3)

The method according to any one of modes 1 and 2, wherein the protein is selected from the group consisting of antibodies or fragments thereof, antigenic proteins, enzymes, lectins, peptides, protein A, protein G, and protein L.

Mode (4)

The method according to any one of modes 1 to 3, wherein the carrier is selected from the group consisting of beads, magnetic beads, thin films, microtubes, filters, plates, microplates, carbon nanotubes, and sensor chips.

Mode (5)

The method according to any one of modes 1 to 4, wherein the tamavidin and the protein are bound via a linker to constitute the fusion protein.

Mode (6)

The mode according to any one of modes 1 to 4, wherein the tamavidin and the protein are bound via a linker consisting of six or more amino acids to constitute the fusion protein.

Mode (7)

The method according to any one of modes 1 to 6, wherein the fusion protein further has a leader sequence bound thereto.

Mode (8)

The method according to any one of modes 1 to 7, wherein biotin and the carrier are bound via a linker greater than 13.5 Å in length.

Mode (9)

A tamavidin fused protein-hound carrier in which a fusion protein having a protein bound to a tamavidin is bound to a biotin-bound carrier via tamavidin-biotin bonds.

Mode (10)

An expression vector for expressing a tamavidin fused protein which comprises a nucleic acid coding for a fusion protein having a tamavidin bound to a protein via a linker On the following pages, preferred modes for carrying out the present invention are described.

Tamavidins

Tamavidins are novel biotin-binding proteins that were discovered from an edible mushroom, *Pleurotus cornucopiae* (WO 02/072817). This document shows:

that tamavidin 1 and tamavidin 2 have an amino acid homology of 65.5% with each other and bind strongly to biotin;

that tamavidin 2 is highly expressed in *E. coli* in soluble fractions; and that when tamavidin 2 was expressed in *E. coli,* 4.5-hr culture gave a purified recombinant protein of high purity in an amount of about 1 mg per 50 ml of culture; this is a very high value, even greater than those for avidin and streptavidin which are known as biotin-binding proteins.

The present inventors made further studies on tamavidins and found the following:

tamavidin 1 is also highly expressed in *E. coli* in soluble fractions; and when tamavidin 1 was expressed in *E. coli,* 4.5-hr culture also gave a purified recombinant protein of high purity in an amount of about 1 mg per 50 ml of culture.

Carriers that had proteins such as enzymes or antibodies bound thereto by the binding method of the present invention which used the tamavidin fused protein successfully exhibited a marked increase in their activities as compared with the conventional carriers to which they were bound by hydrophobic or covalent bonding. Briefly, by expressing a desired protein as a fusion protein with a tamavidin and binding the fusion protein to a biotin-bound carrier, the activity of the desired protein could be markedly improved over the case where it was bound by other methods. Although not wishing to he hound by theory, it is speculated that the reason would be due to the effect of protein orientation. In addition, when binding was effected by this method, protein purification and binding to the carrier could be performed simultaneously, so that the production process could be simplified enough to realize a marked reduction in both manpower and cost. What is more, if lectin is chosen as the desired protein, it can be immobilized by the present method without interfering with its activity although lectins have heretofore been considered to be difficult to fix to carriers. Thus, even proteins that are difficult to fix to carriers can be immobilized by the present method without any problems. Further, it is believed that a bound carrier using a tamavidin as a biotin-binding protein has a smaller extent of nonspecific binding than in the conventional case where avidin is used and that it is more heat-resistant than when streptavidin is used. Further in addition, when tamavidins are used, they are unlike avidin and streptavidin in that they themselves are highly expressed as a soluble form in *E. coli*, so if the desired protein to he fused to tamavidins is expressed as a soluble form in *E. coli*, the fusion protein is also believed to be expressed as a soluble form in *E. coli*; hence, the manpower and cost needed to prepare this tamavidin-fused protein and the carrier having this protein bonded thereto can be markedly reduced.

The force of binding between tamavidin and biotin is stronger than that of other bindings such as the aforementioned binding between histidine tags and nickel, so after the fused protein is bound to the desired biotinylated carrier, strong washing can be done using, for example, a surfactant or a high concentration of salt, with the result that the extent of nonspecific binding in which biomaterials other than the fused protein bind to the carrier can be minimized Furthermore, compared to nickel, biotin causes an almost negligible amount of nonspecific binding with biomaterials. These contribute to noise reduction in the ELISA plate, magnetic beads or sensor chips to be finally prepared and to higher detection sensitivity.

The "tamavidins" as used herein means tamavidin 1, tamavidin 2, or variants thereof. Specifically, the tamavidins of the present invention may typically be a protein comprising the amino acid sequence of SEQ ID NO: 2 or SEQ ID NO: 4, or a protein encoded by a nucleic acid comprising the base sequence of SEQ ID NO: 1 or SEQ ID NO: 3. Alternatively they may be variants of the protein comprising the amino acid sequence of SEQ ID NO: 2 or SEQ ID NO: 4 or the protein encoded by a nucleic acid comprising the base sequence of SEQ ID NO: 1 or SEQ ID NO: 3, provided that they are proteins having the same biotin-binding activity as tamavidin 1 or 2 has. Hereinafter, tamavidin 1, tamavidin 2 and their variants are sometimes collectively referred to simply as tamavidins.

Variants of tamavidin 1 or 2 may be proteins that comprise an amino acid sequence with deletion, substitution, insertion and/or addition of one or more amino acids in the amino acid sequence of SEQ ID NO: 2 or SEQ ID NO: 4 and which have the biotin-binding activity as tamavidin 1 or 2 has. Substitution may be conservative substitution, which means the replacement of a certain amino acid residue by another residue having similar physical and chemical characteristics. Non-limiting examples of conservative substitution include substitution of one aliphatic-group containing amino acid residue (e.g., Ile, Val, Leu or Ala) for another, and substitution of one polar residue for another, as between Lys and Arg, or Glu and Asp, or Gln and Asn.

The variants due to amino acid deletions, substitutions, insertions and/or additions can be prepared from the native protein encoding DNA by applying a well-known technique, say, site-specific mutagenesis (see, for example, Nucleic Acid Research, Vol. 10, No. 20, p. 6487-6500, 1982, which is incorporated herein by reference in its entirety). As used herein, the expression "one or more amino acids" means a feasible number of amino acids that can be deleted, substituted, inserted and/or added by site-specific mutagenesis. It should also be noted that the expression "one or more amino acids" as used herein may sometimes mean one or several amino acids.

Site-specific mutagenesis may be performed as follows using synthetic oligonucleotide primers that are complementary to the single-stranded phage DNA to be mutated, except for a specific mismatch that corresponds to the desirable mutation. To be more specific, the above-mentioned synthetic oligonucleotides are used as primers to synthesize a strand complementary to the phage and a host cell is transformed with the resulting double-stranded DNA. A culture of the transformed cell is plated on agar and plaques are formed from the phage-containing single cells. Then, theoretically, 50% of the new colonies contain phages having a mutation in a single strand and the remaining 50% have the original sequence. The obtained plaques are hybridized with a synthetic probe, as labeled by kinase treatment, at a temperature that allows for hybridization with those colonies that exhibit complete match with DNA having the above-mentioned desirable mutation but that does not allow for hybridization with those colonies having the original strand. Subsequently, plaques that hybridize with that probe are picked and cultured for DNA recovery.

Note that the methods of introducing deletion, substitution, insertion and/or addition of one or more amino acids in the amino acid sequence of a biologically active peptide while retaining its activity include not only the above-described site-specific mutagenesis but also a method that involves treating the gene with a mutagen, as well as a method that comprises cleaving the gene selectively, then removing, substituting, inserting or adding the chosen nucleotide, and finally linking the cleaved fragments. More preferably, the tamavidins as used in the present invention are proteins that consist of an amino acid sequence with deletion, substitution, insertion or addition of one to ten amino acids in the amino acid sequence of SEQ ID NO:2 or SEQ ID NO: 4 and which have biotin-binding activity.

The variant of tamavidin 1 or 2 may also be a protein that comprises an amino acid sequence having at least 60% identical, preferably at least 65% identical, at least 70% identical, at least 75% identical, at least 80% identical, at least 85% identical, at least 90% identical, at least 95% identical, at least 96% identical, at least 97% identical, at least 98% identical, or at least 99% identical, and more preferably at least 99.3% identical, to the amino acid sequence of SEQ ID NO:2 or SEQ ID NO: 4 and which has the similar biotin-binding activity as tamavidin 1 or 2 has.

Percent identity between two amino acid sequences may be determined by visual inspection and mathematical calculation. Alternatively, the percent identity of two protein sequences can be determined by comparing sequence information using the GAP computer program that is based on the algorithm of Needleman, S. B. and Wunsch, C. D. (J. Mol. Biol., 48: 443-453, 1970) and which is available from the University of Wisconsin Genetics Computer Group (UWGCG). The preferred default parameters for the GAP program include: (1) a scoring matrix, blosum 62, as described by Henikoff, S. and Henikoff, J. G. (Proc. Natl. Acad. Sci. USA 89: 10915-10919, 1992); (2) a gap weight of 12; (3) a gap length weight of 4; and (4) no penalty for end gaps.

Other programs used by skilled artisans for sequence comparison may also be used. Percent identity can be determined by comparison with sequence information using the BLAST program descried in, for example, Altschul et al. (Nucl. Acids. Res., 25, p. 3389-3402, 1997). This program can be accessed from the Internet at the website of the National Center for Biotechnology Information (NCBI) or the DNA Data Bank of Japan (DDBJ). Various conditions (parameters) for identity search by the BLAST program are detailed at those websites and part of the settings can be varied as appropriate, although search is typically performed using the default values. Alternatively, percent identity between two amino acid sequences may be determined by a program such as the genetic information processing software GENETYX Ver. 7 (Genetyx) or the FASTA algorithm. In this alternative case, search may be performed using the default values.

The percent identity of two nucleic acid sequences may be determined by visual inspection and mathematical calculation, or more preferably by comparing sequence information using a computer program. A typical, preferred computer program is the Wisconsin package, the program GAP of version 10.0, of Genetics Computer Group (GCG; Madison, State of Wisconsin) (Devereux et al., Nucl. Acids Res. 12: 387, 1984). Using this program GAP, one can perform comparison not only between two nucleic acid sequences but also between two amino acid sequences and between a nucleic acid sequence and an amino acid sequence. Here, the preferred default parameters for the program GAP include: (1) GCG implementation of a unary comparison matrix (containing a value of 1 for identities and 0 for non-identities) for nucleotides, and the weighted amino acid comparison matrix of Gribskov and Burgess, Nucl. Acids Res. 14: 6745, 1986, as described by Schwartz and Dayhoff, eds., Atlas of Polypeptide Sequence and Structure, National Biomedical Research Foundation, pp. 353-358, 1979, or other applicable comparison matrices; (2) a penalty of 30 fnr each amino acid gap and an additional 1 penalty for each symbol in each gap, or a penalty of 50 for each gap in a nucleotide sequence and an additional 3 penalty for each symbol in each gap; (3) no penalty for end gaps; and (4) no maximum penalty for long gaps. Other sequence comparison programs that are used by skilled artisans and which may be used in the present invention include the BLAST program, version 2.2.7, that can be downloaded from the website of the US National Library of Medicine (http://www.ncbi.nlm.nih.gov/blast/bl2seq/bls.html), or the UW-BLAST 2.0 algorithm. Settings of standard default parameters for UW-BLAST 2.0 are described at the following website: http://blast.wustl.edu. In addition, the BLAST algorithm uses the amino acid scoring matrix BLOSUM 62 and the selection parameters that can be used are as follows: (A) inclusion of a filter for masking segments of query sequence having low compositional complexity (as determined by the SEG program of Wootton and Federhen (Computers and Chemistry, 1993); see also Wootton and Federhen, "Analysis of compositionally biased regions in sequence databases" in Methods Enzymol., 266: 544-71, 1996,) or for masking segments comprising internal repeats of short periodicity (as determined by the XNU program of Claverie and States (Computers and Chemistry, 1993)); and (B) expected probabilities of a match that is to be found merely by chance in accordance with a statistic model of thresholds, or E-scores (Karlin and Altschul, 1990), of statistically significant differences for reporting a match with database sequences (if a statistically significant difference due to a certain match is greater than an E-score threshold, the match is not reported); the numerical value of a preferred E-score threshold is either 0.5 or, in increasing order of preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The tamavidin variants are required not to cause any negative effects on the biotin-binding activity. It is interesting to note that biotin pockets for streptavidin which is one of the biotin-binding proteins have already been unraveled to some extent. While the streptavidin has only about 50% homology in amino acid sequence to tamavidin 2, the present inventors, with a view to obtaining findings about biotin pockets for tamavidin 2, compared the amino acid sequence of tamavidin 2 with that of streptavidin by placing them side by side. As it turned out, among the amino acids that formed the biotin pockets for streptavidin, the following residues in direct interaction with biotin, i.e. N23, S27, Y43, S45, N49, W79, S88, T90, W92, W108, W120, and D128 (Weber et al. (1989) Science 243: 85-88; and Livnah et al. (1993) Proc. Natl. Acad. Sci. U.S.A. 90: 5076-5080), corresponded to N14, S18, Y34, S36, D40, W69, S76, T78, W80, W96, W108, and D116, respectively, in TM2 and were conserved very well.

In particular, four tryptophan residues (W69, W80, W96, and W108) are considered to play an important role in the structure of biotin pockets, so they are desirably unmodified. In addition, other amino acids that are considered to participate in binding to biotin, namely, those amino acid residues in TM2 that are considered to interact directly with biotin (N14, S18, Y34, S36, S76, T78, and D116) are also desirably unmodified. Alternatively, if these amino acid residues are to be modified, they are desirably modified to amino acids having similar properties or structures so that binding to biotin can be maintained; in an exemplary case of asparagine (N14), a variant is desirably formed by modifying it to glutamine (Q) or aspartic acid (D), preferably to aspartic acid; in the case of aspartic acid (D40), a variant is desirably formed by modifying it to asparagine (N); in the case of serine (S18, S36, or S76), a variant is desirably formed by modifying it to threonine (T) or tyrosine (Y), preferably to threonine; in the case of tyrosine (Y34), a variant is desirably formed by modifying it to serine (S), threonine (T) or phenylalanine (F), preferably to phenylalanine; in the case of threonine (T78), a variant is desirably formed by modifying it to serine (S) or tyrosine (Y), preferably to serine; in the case of aspartic acid (D116), a variant is desirably formed by modifying it to glutamic acid (E) or asparagine (N), preferably to asparagine.

The variant of tamavidin 1 or 2 may also be a protein that is encoded by a nucleic acid comprising a base sequence that hybridizes with a strand complementary to the base sequence of SEQ ID NO:1 or SEQ ID NO: 3 under stringent conditions and which has the same biotin-binding activity as tamavidin 1 or 2 has.

The phrase "under stringent conditions" as used herein means hybridizing under conditions of moderate or high stringency. Specifically renditions of moderate stringency can be readily determined by those having ordinary skill in the art based on, for example, the length of DNA. The basic conditions are set forth in Sambrook et al. Molecular Cloning: A Laboratory Manual, 3rd ed. Chapter 6, Cold Spring Harbor Laboratory Press, 2001, and include use of: a pre-washing solution of 5×SSC, 0.5% SDS, and 1.0 mM EDTA (pH 8.0); hybridizing conditions of about 50% formamide, 2×SSC-6× SSC, preferably 5-6×SSC and 0.5% SDS, at about 42° C. (or other similar hybridization solutions, such as Stark's solution in about 50% fonnamide at about 42° C.); and washing conditions of about 50-68° C., 0.1-6×SSC, and 0.1% SDS. Preferably, conditions of moderate stringency include hybridizing conditions of about 50° C., 6×SSC, and 0.5% SDS. Conditions of high stringency can also be readily determined by the skilled artisan based on, for example, the length of DNA.

Generally, such conditions include hybridization at higher temperatures and/or at lower salt concentrations than the conditions of moderate stringency (e.g., hybridization in the presence of about 0.5% SDS at about 65° C. with 6×SSC to 0.2×SSC, preferably 6×SSC, more preferably 2×SSC, even more preferably 0.2×SSC, or 0.1×SSC) and/or washing, and may be defined as hybridizing conditions of the type described above, and involving washing at approximately 65-68° C. in 0.2-0.1×SSC and 0.1% SDS. In the buffer solution for use in hybridization and washing, SSC (1×SSC consists of 0.15 M NaCl and 15 mM sodium citrate) may be replaced by SSPE (1×SSPE consists of 0.15 M NaCl, 10 mM NaH$_2$PO$_4$, and 1.25 mM EDTA; pH 7.4), and washing is performed for approximately 15 minutes to one hour after hybridization is complete.

If desired, a commercial hybridization kit may be employed that does not use a radioactive substance as the probe. A specific example is hybridization that employs an ECL direct labeling & detection system (product of Amersham). Stringent hybridization may be performed at 42° C. for 4 hours after a blocking reagent and NaCl are added in respective amounts of 5% (w/v) and 0.5 M to the hybridization buffer in the kit; washing may be performed twice in 0.4% SDS and 0.5×SSC for 20 minutes each at 55° C., then once in 2×SSC for 5 minutes at room temperature.

The hintin-binding activity of the variants of tamavidin 1 or 2 can be measured by any one of the known techniques. For example, it may be determined by a fluorescent biotin-based method as described in Kada et al. (Biochim. Biophys. Acta., 1427: 33-43 (1999)). This method is an assay system that makes use of such a nature of fluorescent biotin that if it binds to a biotin-binding site in a biotin-bound protein, its fluorescence intensity becomes extinct. Alternatively, the biotin-binding activity of variant proteins can also be evaluated using a sensor capable of measuring the protein-biotin binding, such as a biosensor operating on the principle of surface plasmon resonance.

In a preferred mode of the present invention, tamavidins are selected from:

(a) a protein consisting of an amino acid sequence with deletion, substitution or addition of one or more amino acids in SEQ ID NO: 2 or SEQ ID NO: 4 and having biotin-binding activity; or (b) a protein consisting of an amino acid sequence sharing an identity of 60% or more with SEQ ID NO: 2 or SEQ ID NO: 4 and having biotin-binding activity; or (c) a protein consisting of the amino acid sequence of SEQ ID NO: 2 or SEQ ID NO: 4; or (d) a protein consisting of an amino acid sequence encoded by nucleic acids hybridizable under stringent conditions with a strand complementary to the base sequence of SEQ ID NO: 1 or SEQ ID NO: 3 and having biotin-binding activity.

Protein

The protein to be fused with tamavidins is not particularly limited and examples include antibodies, antigenic proteins, various enzymes, lectins, peptides, or protein A, protein G, protein L, etc. Antibodies include IgG as well as antibody fragments containing antigen-binding sites such as scFv and Fab; antigenic proteins include proteins derived from hepatitis B or C virus, HIV, influenza and other viruses, proteins derived from bacteria such as *Helicobacter pylori*, or tumor markers such as CEA and PSA, and sex hormones. Enzymes include: oxidoreductases such as peroxidase, glucose oxidase, pyranose oxidase, cytochrome P-450, and catalse; dephosphorylation enzymes such as alkali phosphatase; phosphorylated enzymes such as PPDK; glyrnsyl transferases such as sialyl transferase; sugar nucleotide synthetases such as CMP-sialyl synthetase; acyl trnasferase; amino transferase; proteolytic enzymes such as papain and thrombin; nucleases such as restriction enzymes; lipid decomposing enzymes such as PLD; carbohydrate decomposing enzymes such as amylase, lysozyme, and β-galactosidase; isomerases such as phosphoglycerate mutase and glucose-6-phosphate isomerase; luciferase; DNA/RNA polymerase; ATP synthesizing/hydrolyzing enzymes and the like. Lectins are sugar-binding proteins and include monosaccharide specific lectins and oligosaccharide specific lectins, as exemplified by mannose specific lectin, GalNAc specific lectin, GlcNAc specific lectin, fucose specific lectin, and sialic acid specific lectin, and the like. In addition, peptides include but are not limited to those composed of 2-100 amino acids, preferably those composed of 2-50 amino acids, and more preferably those composed of 2-30 amino acids.

Tamavidin-Fused Protein

The tamavidin-fused protein means fusion proteins of tamavidins and the proteins described above. The method of providing the tamavidin-fused protein is not particularly limited and may involve expressing using known genetic engineering techniques. For example, a gene coding for the fusion protein of a tamavidin and a desired protein may be expressed using an expression system such as *E. coli* to acquire the intended fusion protein.

In the tamavidin-fused protein, a tamavidin and a protein may be bound directly; alternatively, they may be bound via a linker, preferably via an amino acid linker. The length of this linker suffices to be at least one amino acid, preferably at least five amino acids, more preferably at least six amino acids. In order to further improve the force of binding between the tamavidin and the biotin as bound to the carrier, the linker preferably consists of at least 10 amino acids, more preferably at least 12 amino acids, or at least 15 amino acids or at least 18 amino acids, and even more preferably at least 25 amino acids. It is speculated that such linkers will also improve the activity of the tamavidin-fused protein. The amino acids that compose the linker are not particularly limited but they preferably consist of repeats of a neutral amino acid such as glycine, swine or alanine. Examples include but are not limited to GGGGS, GGSGG, GASAG, GSGAA, GSGAA, GGGGSG, GGGSGGS, GGSGGGGS, AAAAGSGAA, GGGGSGGGGSGGGGS, GGGGSGGGGSGGGGSGG-GGSGGGGS (SEQ IO NOs: 52-62).

The tamavidin may be bound to whichever side, N-terminus or C-terminus, of the desired protein. If the periplasmic space of *E coli* is more suitable than its cytoplasm for the purpose of expressing the desired protein, a leader sequence for targeting the periplasm may be employed. Examples of such leader sequence include but are not limited to PelB (Lei et al. (1987) J Bacteriol 169: 4379-4383), OmpA (Gentry-Weeks et al. (1992) J Bacteriol 174: 7729-7742).

If desired, a tag for purification and detection at later stages may be attached, for example, to the C-terminus of the fusion protein. Examples of such tag include a c-myc epitope tag (Munro and Pelham (1986) Cell 46: 291-300) and a histidine tag (Hochuli et al. (1988) Bio/Technol 6: 1321-1325, and Smith et al. (1988) J Biol Chem 263: 7211-7215).

If the tamavidin fusion protein is obtained from a soluble fraction, a crude protein extract may be brought into contact with the biotinylated carrier to be described later, so that the fusion protein is bound to the biotinylated carrier. By subsequently washing the carrier fully, the fusion protein can be purified and fixed to the carrier in one step. Alternatively, a column to which a biotin analog such as iminobiotin (Hofmann et al. (1980) Proc Natl Acad Sci USA 77: 4666-4668) may be used to purify the fusion protein, which is then bound to the biotinylated carrier.

If the fusion protein is obtained from an insoluble fraction, known techniques are adopted, in which a chaotropic salt such as urea or guanidine hydrochloride is used to solubilize the protein and, thereafter, dialysis or the like is employed to promote the refolding of the protein as the chaotropic salt is withdrawn gradually (Sano and Cantor (1991) Bio/Technology 9: 1378-1381, and Sano et al. (1992) Proc Natl Acad Sci USA 89: 1534-1538).

Alternatively, if the desired protein is to be expressed as an insoluble form in E. coli, a maltose-binding protein (Bach et al. (2001) J Mol Biol 312: 79-93), thioredoxin (Jurado et al. (2006) J Mol Biol 357: 49-61), glutathione S trasnferase (Tudyka and Skerra (1997) Protein Sci 6: 2180-2187) or chaperones as described in Ideno et al. (2004) Appl Microbiol Biotechnol 64: 99-105 may be co-expressed or a triplex fusion protein having a chaperone additionally fused to the fused protein may be prepared.

The fusion protein may be expressed in other known expression systems such as insect cells, plant cells, mammal cells, yeast cells, and cell-free expression systems. In particular, if the protein to which tamavidins are to be fused is of such a type that it is expressed in plant cells, the resulting fusion protein is also preferably expressed in the plant cell expression system. Skilled artisans can select the appropriate expression system by considering the nature of the protein to which tamavidins are to be fused.

Biotin-Bound Carriers

"Biotin" is the general name for D-[(+)-cis-hexahydro-2-oxo-1H-thieno-(3,4)-imidazole-4-pentanoic acid]. It is one of water-soluble vitamins classified in the vitamin B group and also called vitamin $B_7$, or sometimes referred to as vitamin H or coenzyme R. Biotin binds very strongly to avidin, one of glycoproteins contained in the white of an egg, and inhibits its absorption. Thus, mass intake of raw egg white is occasionally a cause of biotin deficiency.

"Biotin" as used herein includes not only the biotin defined above but also biotin analogs such as iminobiotin (Hofmann et al. (1980) Proc Natl Acad Sci USA 77: 4666-4668), desthiobiotin (Hirsch et al. (2002) Anal Biochem 308: 343-357), as well as biocytin and biotin sulfoxide.

Systems using the biotin-avidin complex are widely used in such fields as histoimmunology, DNA analysis, and clinical testing. The method of the present invention for binding proteins to carriers involves preparing a fusion protein having an intended protein bound to a tamavidin and binding that fusion protein to a carrier by making use of biotin-tamavidin binding. According to the method of the present invention, the protein can be allowed to act far more efficiently without impairing its functions than when the conventional biotin-avidin binding is utilized.

Materials that compose the solid carrier include but are not limited to cellulose, Teflon, nitrocellulose, agarose, dextran, chitosan, polystyrene, polyacrylamide, polyester, polycarbonate, polyamide, polypropylene, nylon, poly(divinylidene difluoride), latex, silica, glass, glass fiber, gold, platinum, silver, copper, iron, stainless steel, ferrite, silicon wafer, polyethylene, polyethyleneimine, poly(lactic acid), resins, polysaccharides, proteins (e.g. albumin), carbon, or combinations thereof. Preferred materials are those that have a certain strength, a stable composition, and a small extent of non-specific binding.

The solid carrier may assume various forms that include but are not limited to beads, magnetic beads, thin films, microtubes, filters, plates, microplates, carbon nanotubes, and sensor chips. Flat solid carriers such as thin films and plates may be provided with pits, grooves, filter bottoms or the like, as known in the technical field of interest.

In one mode of the present invention, beads can have a diameter of sphere in the range from about 25 nm to about 1 mm. In a preferred mode, the beads have a diameter in the range from aobut 50 nm to about 10 µm. The size of the beads is selectable according to a specific application. Some bacterial spores have a size on the order of about 1 µm, so the beads preferred for trapping such spores have a diameter greater than 1 µm.

Examples of the biotinylated microplate that can be utilized include but are not limited to Reacti-Bind™ Biotin Coated Polystyrene Plates (product of PIERCE). Examples of the biotinylated microbead that can be used include but are not limited to magnetic beads such as BioMag Biotin (product of Polysciences, Inc.), nano-magnetic beads such as nanomag (registered trademark)-D biotin and nanomag (registered trademark)-silica biotin, both being products of COREFRONT CORPORATION, polystyrene microbeads such as Beadlyte (registered trademark) Biotin Beads (product of Upstate), agaroses such as Biotin Agarose and 2-iminobiotin-Agarose, both being products of Sigma-Aldrich, and highly crosslinked agaroses such as Biotin-Sepharose (product of Bioscarch Technologies, Inc.).

Exemplary biotinylating reagents that can be utilized include but are not limited to the following products of PIERCE (the indications in parentheses are for linker length and reactive group in that order): EZ-Link (registered trademark) Sulfo-NHS-Biotin (13.5 Å, primary amine); EZ-Link (registered trademark) Sulfo-NHS-LC-Biotin (97.4 Å, primary amine); EZ-Link (registered trademark) Sulfo-NHS-LCLC-Biotin (30.5 Å, primary amine), EZ-Link (registered trademark) PFP-Biotin (9.6 Å, amine); EZ-Link (registered trademark) Maleimide-$PEO_2$-Biotin (29.1 Å, thiol group); EZ-Link (registered trademark) Biotin-$PEO_2$ Amine (20.4 Å, carboxyl group); EZ-Link (registered trademark) Biotin-$PEO_3$-LC Amine (22.9 Å, carboxyl group); EZ-Link (registered trademark) Biotin-Hydrazide (15.7 Å, aldehyde group); EZ-Link (registered trademark) Biotin-LC-Hydrazide (24.7 Å, aldehyde group); and EZ-Link (registered trademark) NHS-Iminobiotin (13.5 Å, primary amine).

With the aid of the biotinylating reagents mentioned above, biotin can be bound to desired carriers such as microplates, microbeads or sensor chips by using known methods. An exemplary method uses carriers (e.g. magnetic beads, Sepharose beads, agarose beads, latex beads, and microtiterplates) having various functional groups such as amino group, carboxyl group, thiol group, tosyl group, epoxy group, maleimide group, and activated esters. If a biotinylating reagent containing the NHS ester is used, it is dissolved in an organic solvent such as DMSO (dimethyl sulfoxide) or a phosphate buffer solution of pH 7-9 and then added to an immobilization carrier having amino groups so that biotin can be bound to it. If a biotinylating reagent containing the amino group is used, carboxyl groups on the immobilization carrier are first converted to an activated ester with the aid of a carbodiimide such as EDC (1-ethyl-3-(3-dimethylaminopropyl)carbodiimide hydrochloride) and, thereafter, the biotinylating reagent as dissolved in a buffer solution near pH 5 is added to the immobilization carrier so that biotin is bound to it. Note that the biotinylated immobilization carrier preferably gets the unreacted functional groups to be rendered inactive before it is blocked with BSA or the like.

In Example 3 to be described later, HEL scFv-TM2 was not bound at all to magnetic beads having a linker length of 13.5 Å but 72% of HEL scFv-TM2 was bound to magnetic beads having a linker length of 22.4 Å and 77% of HEL scFv-TM2 was hound to magnetic beads having a linker length of 30.5 Å. In Example 4, a fusion protein of tamavidin 2 and sialyl transferase showed specific binding to biotin when the linker length was 30.5 Å. Hence, the length of the linker for linking the carrier to biotin is preferably no smaller than 13.5 Å, more preferably at least 15 Å, at least 15.7 Å, at least 17 Å, at least 20 Å, at least 20.4 Å, at least 22.4 Å, at least 22.5 Å, and even more preferably at least 30.5 Å.

Method of Binding Proteins to the Carrier

The method of the invention comprises preparing a biotin-bound carrier and a tamavidin-fused protein, bringing the two into contact with each other, and causing the protein to bind to the carrier via tamavidin-biotin bonds.

Bound Carriers

The present invention also provides a carrier that has the tamavidin-fused protein bound thereto by the above-described method of the present invention for binding proteins to carriers. Briefly, the carrier provided by the present invention is a tamavidin-fused protein bound carrier characterized in that the fusion protein having a protein bound to a tamavidin is bound to the biotin-bound carrier via tamavidin-biotin bonds.

Expression Vectors

The expression vector for expressing the tamavidin-fused protein contains nucleic acids that code for the tamavidins of the present invention. The nucleic acids that code for the tamavidins of the present invention are not particularly limited as long as they code for the tamavidin proteins described above under the section "tamavidins". For example, they include a nucleic acid consisting of the base sequence of SEQ ID NO: 1 or 3, or nucleic acids that hybridize with the strands complementary to those base sequences under stringent conditions and which code for proteins having biotin-binding activity (hereinafter, all such nucleic acids are collectively referred to as "the tamavidin gene"). The tamavidin gene further has, at one or both ends thereof, a sequence for inserting a gene encoding a desired protein to be fused with tamavidins, say, a restriction enzyme recognition site, or alternatively, a sequence used in the Gateway system (Invitrogen) such as aatB1, aatB2 or aatB3, and it is further characterized in that a promoter that functions in a desired host is provided upstream of the unit consisting of the tamavidin gene and the sequence for inserting a gene encoding the desired protein (as exemplified by a unit in which the sequence of a restriction enzyme restriction site is present adjacent the tamavidin gene sequence) whereas a terminator is provided downstream of the same unit. While the type of the restriction enzyme restriction site is not particularly limited, it is preferably the sole recognition site in the expression vector. The number of recognition sites is not particularly limited, either, and it is one or more, but preferably not more than 10.

Note that a nucleic acid sequence coding for a linker amino acid sequence consisting of one or more amino acids, preferably five or more amino acids, more preferably 10 or more amino acids, even more preferably 25 or more amino acids, but not more than 50 amino acids (although not particularly limited, this may be a sequence commonly used by skilled artisans, such as a glycine- or serine-rich sequence) may be provided between the restriction enzyme site or the aatB sequence and the tamavidin gene sequence; in addition, although not particularly limited, a sequence such as Factor Xa that codes for a protease recognition site may also be provided. If, in the case where an antibody gene such as scFv or Fab is to be inserted into the expression vector under consideration, reducing conditions as within the cytoplasm are not suitable for the expression of the fusion protein, a nucleic acid sequence coding for the leader peptide, as exemplified by a signal peptide or a secretion signal, may be contained between the promoter and the unit consisting of the tamavidin gene and the sequence for inserting the desired protein gene.

In addition to the expression unit described above, the expression vector under consideration may have a unit for enabling replication in a desired host, say, a replication origin, as well as a drug resistance marker gene for selecting desired host cells. The host is not particularly limited but it is preferably *E. coli*. If desired, the expression vector under consideration may incorporate a suitable expression control system such as a lactose repressor system in *E. coli*.

Methods of Purifying Proteins

Proteins can be conveniently purified by using the expression vector described above. First, a gene coding for a desired protein is incorporated into the vector described above by the usual cloning technique and expressed in a desired host. The host is preferably one in which the desired protein is expressed. If the host is *E. coli*, an insect cell, a mammal cell, a plant cell or a yeast cell, expression may be performed by culture, and if the host is a plant, the fusion protein may be expressed and accumulated in the plant body.

Subsequently, the cells or living tissue in which the fusion protein has been expressed are disrupted in a suitable buffer solution and the protein is extracted. A biotinylated carrier is brought into contact with the protein extract obtained and, by making use of the strong binding between the tamavidin in the fusion protein and the biotin, a complex consisting of the carrier, biotin, tamavidin, and the desired protein is formed. Thereafter, depending on the nature of the carrier, if it is magnetic beads, a magnet is used, and otherwise, centrifugation may be applied, to recover the complex referred to above, and the fraction in the supernatant that has not bound to the biotinylated carrier is discarded. Further, the complex referred to above is washed several times with a suitable buffer solution (which may contain NaCl or the like at a concentration of approximately 0.5 M to 2 M). Finally, the biotin-tamavidin bonds are dissociated by a biotin solution, a low-pH (approximately pH 1.5-4) buffer solution, or heat treatment (preferably at about 85° C.-95° C.) to purify the desired protein.

As described above, by making use of the high-yield expression of tamavidins in a host such as *E. coli*, the fusion protein can be efficiently synthesized in the host cell and, at the same time, by making use of the strong binding between tamavidin and biotin, a washing operation can be performed under comparatively rigorous conditions to enable one-step purification of the tamavidin-fused protein. Note that if a protease recognition sequence is provided between a tamavidin and the desired protein, the fusion protein may be treated with the protease of interest, whereby the tamavidin is cut off to obtain only the desired protein. In this case, after washing the complex mentioned above, protease treatment may be performed, then the carrier is recovered, whereupon protein purification can be realized more efficiently. In addition, even a carrier having iminobiotin or other biotin analog bound thereto may be used to purify the tamavidin-fused protein in the same manner as described above.

Advantages of the Invention

As described above, the tamavidin-fused gene is constructed, a suitable expression system is used to express the fusion protein of interest, and the expressed protein is purified and immobilized simultaneously using a carrier having biotin bound to the surface, thereby producing a carrier having the tamavidin-containing fusion protein bound thereto. Alternatively, the expressed protein is purified using a biotin analog and, thereafter, it is immobilized on a carrier having biotin bound to the surface, thereby producing a carrier having the tamavidin-containing fusion protein bound thereto. These carriers can immobilize proteins with a stronger force than when they are immobilized by the conventional methods and, in addition, the carriers allow the proteins to act efficiently without impairing their functions.

EXAMPLES

Figure 1:
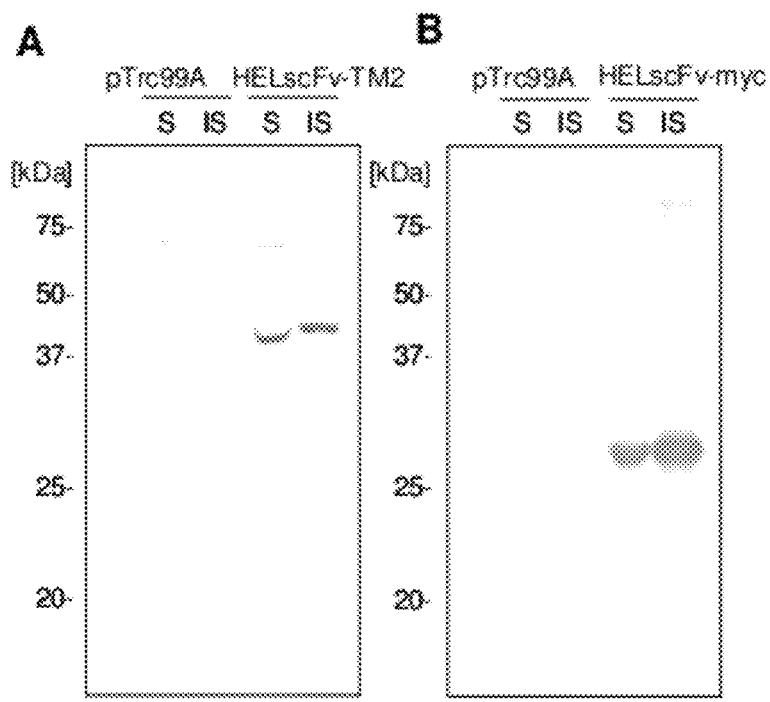
FIG. 1 shows the expression of a fusion protein of tamavidin 2 and an antibody scFv fragment; *E. coli* incorporating PelB-HELscFv-TM2/pTrc99A or PelB-HELscFv-myc/pTrc99A was induced for expression and a crude protein solution was prepared and subjected to western blot analysis. Panel A shows the result for HELscFv-TM2, and panel B for HELscFv-myc; S refers to the soluble fraction, and IS the insoluble fraction; as the primary antibody, an anti-TM2 antibody was used for HELscFv-TM2, and an anti-c-myc epitopic antibody was used for HELscFv-myc; as the secondary antibody, an alkali phosphatase labeled antibody was used; fractions similarly prepared from *E. coli* having only the expression vector pTrc99A were used as controls.

Hereinafter, the present invention is explained specifically by means of Examples, which are by no means intended to limit the technical scope of the present invention. Any skilled artisan can easily make modifications or changes to the present invention on the basis of the disclosures in the present specification and they are included within the technical scope of the present invention.

Example 1

Fusion Protein of Tamavidin and Antibody

In this Example, a fusion protein of tamavidin 2 and an antibody (HEL antibody's scFv fragment) was expressed in *E. coli* and immobilized on a carrier plate by tamavidin-biotin bonding. In addition, the antibody's activity for binding to an antigen was investigated. As a control, the antibody was directly immobilized on the plate by hydrophobic bonding. A concrete explanation is given below.

1-1. HEL Antibody's scFv Fragment

Using tamavidin 2 (TM2) and an scFv fragment of a mouse anti-hen egg-white lysozyme (HEL) antibody (D1.3), a tamavidin-antibody fused protein was prepared. The gene of the HEL (D1.3) antibody's scFv fragment (Iba et al. (1997) Gene 194: 35-46, and Ideno et al. (2004) Appl Microbiol Biotechnol 64: 99-105) was assigned from Mr. Akira Ideno of SEKISUI CHEMICAL CO., LTD.

Expression was performed in *E. coli* and an untagged vector pTrc99A (product of Pharmacia) was used as an expression vector. For the sole expression of HELscFv, a c-myc epitope tag (amino acid sequence: EQKLISEEDL (SEQ ID NO: 83); Munro and Pelham (1986) Cell 46: 291-300) was introduced at the C-terminus of HELscFv. The fusion protein was so designed that TM2 would be located at the C-terminus of HELscFv. On that occasion, the linker (amino acid sequence: GGGGSG (SEQ ID NO:57)) between TM2 and HELscFv was inserted. In addition, in order to target the HELscFv-myc fused protein and the HELscFv-TM2 fused protein to the periplasmic space, a PelB leader peptide (Lei et al. (1987) J Bacteriol 169: 4379-4383) was incorporated at the N-terminus of each of them.

1-1-1. Construction of a Vector for Expressing the Fusion Protein of Tamavidin 2 and HELscFv and a Vector for Expressing HELscFv The gene of the HEL antibody (D1.3) scFv fragment has such a structure that a $V_H$ gene fragment is provided on the 5' side and a $V_L$ gene fragment on the 3' side, the two being linked by DNA coding for a linker consisting of three repeats of Gly-Gly-Gly-Gly-Ser (SEQ ID NO: 521. By means of PCR, genes were constructed that coded for a fusion protein (Pe1B-HELscFv-TM2) (SEQ ID NO: 10) having the TM2 sequence connected to the C-terminus of the scFv antibody, as well as a protein (Pe1B-HELscFv-myc) (SEQ ID NO: 9) having the c-myc epitope tag connected to the C-terminus of the scFv antibody.

Designing Primers

To construct the Pe1B-HELscFv-TM2 fused gene, primers for joining the two genes HELscFv and TM2 via the linker (GGGGSG)(SEQ ID NO: 57) were first designed. Specifically, two primers were designed, one being HELscFvlinkTM2RV that consisted of the HELscFv portion on the 5' side, the linker in the center, and the TM2 portion on the 3' side, and the other being HELscFvlinkFW that consisted of the linker on the 5' side and a DNA sequence on the 3' side coding for the HELscFv portion in a reverse direction.

Subsequently, two additional primers were designed, one being PelB-HELscFv-VH-F that consisted of the 5' portion of the HELscFv gene and an upstream sequence coding for a restriction enzyme BspH I cleavage side (TCATGA) and the PelB leader peptide portion, and the other being TM2-3' Bam that consisted of the 3' portion of the TM2 gene and a downstream sequence coding for a restriction enzyme BamH I cleavage site (GGATCC). In addition, for constructing the PelB-HELscFv-myc gene, a primer HELscFv-VL-myc-R that consisted of the above-identified PelB-HELscFv-VH-F, the 3' portion of the HELscFv gene, and a downstream sequence coding for the c-myc epitope tag and the restriction enzyme BamH I cleavage side (GGATCC) was designed and used. The respective primers for constructing the fusion protein of tamavidin and HELscFv antibody are identified in Table 1.

TABLE 1

Table 1. Primers for constructing the fusion protein of tamavidin and HELscFv antibody

| Name | Sequence (5'-3') | Length |
|---|---|---|
| PeLB-HELscFv-VH-F | AAATCATGAAATACCTATTGCCTA CGGCAGCCGCTGGCTTGCTGCTGC TGGCAGCTCAGCCGGCCATGGCGC AGGTGCAGCTGCAGGAGTCA | 92 mer |
| HELscFv-VL-myc-R | TTTGGATCCTTATAGATCTTCTTC TGAGATCAGCTTTTGTTCTAGGGA AAGCTTGCATGCCT | 62 mer |
| HELscFvlinkFW | ACCGCTGCCACCGCCACCTAGGGA AAGCTTGCATGCC | 37 mer |
| HELscFvlinkTM2RV | GGCATGCAAGCTTTCCCTAGGTGG CGGTGGCAGCGGTTCAGACGTTCA ATCTTCACTC | 58 mer |
| TM2 3'Bm | TTTTTTGGATCCTTACTTCAACCT CGGTGCG | 31 mer |

The restriction enzyme recognition sites are underlined.
The individual sequences correspond to SEQ ID NOs: 11 to 15 as counted from the top.

PCR

Two-stage PCR was performed to construct the PelB-HELscFv-TM2 gene. In the firsts stage of PCR, the HELscFv portion was amplified using the primers Pc1B-HELscFv-VH-F and HELscFvlinkFW, with a plasmid incorporating the gene of the HEL (D1.3) scFv antibody fragment into the vector pT7 being used as a template, and the TM2 portion was amplified using the primers HELscFvlinkTM2RV and TM2 3' Barn, with a plasmid incorporating the TM2 gene into the vector pTrc99A (WO02/072817) being used as a template. The PCR reaction conditions were as follows: to a 50-µL reaction solution, 500 ng of the template DNA, 25 µL of 2×GC buffer II (Takara), 4 µL of 2.5 mM dNTP, and 25 pmoles of each of the primers, and 0.5 µL of 5 U/µL Pyrobest DNA polymerase (product of Takara) were added, and using a programmed template control system PC-500 (ASIEK), one cycle of 96° C.×3 min, 30 cycles of 96° C.×1 mM, 55° C.×1 min, and 72° C.×2 min, and one cycle of 72° C.×6 min were performed. As a result, a PCR product of 860 by was obtained in the HELscFv portion and another of 450 by was obtained in the TM2 portion. These PCR products were subjected to agarose electrophoresis in a TAE buffer solution using a low-melting point agarose (SeaPlaqueGTG). Each of the DNA fragments was excised together with the gel and after adding 200 mM NaCl in an amount equal to that of the gel, treatment was conducted at 70° C. for 10 min to melt the gel. The resulting sample was extracted with phenol, phenol/chloroform, and chloroform, each extraction performed once, and allowed to precipitate in ethanol to recover two DNA fragments, one for the HELscFv portion and the other for the TM2 portion.

With these two fragments used as templates, the second stage of PCR was performed using the primers PelB-HELscFv-VH-F and TM2 3'Bam. The reaction conditions were the same as in the first stage. As a result, about 1300 by of PCR product (PelB-HELscFv-TM2 gene fragment) (SEQ ID NO: 7) was obtained. Subsequently, to construct the PelB-HELscFv-myc gene, PCR was performed under the same conditions as described above, except that the template was a plasmid having the gene of the HEL(D1.3)scFv antibody fragment incorporated in the vector pT7 and that the primers PelB-HELscFv-VH-F and HELscFv-VL-myc-R were used. As a result, about 880 by of PCR product (PelB-HELscFv-myc gene fragment) (SEQ ID NO: 6) was obtained.

Cloning

The PelB-HELscFv-TM2 gene fragment and the PelB-HELscFv-myc gene fragment, both obtained by PCR, were cloned in the vector pCR4 Blunt TOPO (product of Invitrogen). The ligation reaction was in accordance with the instructions on the vector kit. DNA was transferred into *E. coli* TB1 by electroporation and plasmid DNA was extracted in accordance with the usual method (Sambrook et al. 1989, Molecular Cloning, A laboratory manual, $2^{nd}$ edition). The clones verified to have inserts were treated as follows: using the M13 primer (Takara), the base sequence of the PCR product was determined from both of its ends with an ABI PRISM fluorescence sequencer (Model 310 Genetic Analyzer, Perkin Elmer) to confirm that it had no mutation from the original gene. The plasmid incorporating the genes of interest was double digested with BspH I and BamH I and gel purification was performed by the aforementioned method to recover a DNA fragment. The recovered DNA fragment was ligated by a ligation kit (product of Takara) to the *E. coli* expression vector pTrc99A that had been preliminarily digested with NcoI and BamH I. The ligation product was transformed into *E. coli* TB1 and plasmid DNA was extracted and subjected to restriction enzyme analysis in accordance with the usual method to check for the presence of the inserted genes; this led to the completion of Pel-HELscFv-TM2/pTrc99A, or a vector for expressing the fusion protein of tamavidin 2 and HELscFv, as well as PelB-HELscFv-myc/pTrc99A, or a vector for expressing HELscFv.

1-1-2. Expression and Crude Purification of the Tamavidin 2-HELscFv Fused Protein and HELscFv To investigate the effect of immobilization of the scFv antibody on a substrate by means of fusion to tamavidin 2, the tamavidin 2-HELscFv fused protein and HELscFv were first expressed in *E. coli* and roughly purified.

Expression in *E. coli*

Two batches of *E. coli,* one transformed with PelB-HELscFv-TM2/pTrc99A and the other with PelB-HELscFv-myc/pTrc99A, were inoculated in 6 mL of an LB medium containing the antibiotic ampicillin (final concentration: 100 μg/mL) and shake cultured at 37° C. until the absorbance at $OD_{600}$ reached 0.5. Thereafter, 1 mM IPTG was added and further shake culture was performed overnight at 37° C. *E. coli* was harvested from 1 mL of the culture broth by centrifugation and suspended in 400 μL of a 20 mM phosphate buffer solution (pH 7); thereafter, the cells were disrupted by sonication. The solution containing the disrupted cells was centrifuged (15000 rpm) and the supernatant was collected as a soluble fraction. Further, the precipitate was suspended in 400 μL of a 20 mM phosphate buffer solution (pH 7) containing 8 M urea and disrupted again by sonication; the disrupted precipitate was collected as an insoluble fraction.

The soluble and insoluble fractions of each of HELscFv-TM2 and HELscFv-myc were subjected to analysis by western blotting. As the primary antibody, a rabbit anti-TM2-antibody (see "Purification of rabbit anti-TM2 antibodies" below) was used for HELscFv-TM2 and a rabbit anti-c-myc epitopic antibody (product of BETHYL) for HELscFv-myc. Further, an alkali phosphatase labeled anti-rabbit IgG antibody (product of BIO-RAD) was used as the secondary antibody. The results are shown in FIG. 1. From the HELscFv-TM2 expressing *E. coli,* a band was detected in the vicinity of 40 kDa, and from the HELscFv-myc expressing *E. coli,* a band was detected in the vicinity of 27 kDa. These sizes were in substantial agreement with the molecular masses predictable from the amine acid sequences of HELscFv-TM2 and HELscFv-myc (i.e., 43 kDa and 29 kDa, respectively). In addition, the solubilized protein accounted for approximately 40% of the HELscFv-TM2 and HELscFv-myc that were expressed in *E. coli* and the amount of the soluble protein that was expressed per liter of the culture broth was 120 μg for HELscFv-TM2 and 128 μg for HELscFv-myc. The amino acid sequences of HELscFv-TM2 and HELscFv-myc are depicted by SEQ ID NOs: 10 and 9, respectively.

Purification of Rabbit Anti-TM2 Antibodies

Tamavidin 2 (TM2) protein expressed in *E. coli* was purified on an iminobiotin column (tamavidin 2 was a tetramer) to make an antigen; to make another antigen, the purified TM2 was subjected to SDS-PAGE electrophoresis and thereafter excised from the gel and purified (tamavidin 2 was a monomer); rabbits were immunized with these antigens to prepare two kinds of antibody. The limit of detection of either kind of antigen by the western method using the alkali phosphatase labeled anti-IgG antibody was approximately 0.5 ng for a specimen of purified recombinant tamavidin 2. From this result, it was concluded that antibodies that were high in both specificity and titer had been completed. Note that the cross-reaction between the anti-tamavidin 2 antibody and tamavidin 1 was detected, although at low level (about 1/20 of the level for the inherent antigen).

The anti-TM2 antibody (as prepared from the antigen solely purified by means of the iminobiotin column) was further purified as described below. TM2 (40 μg) was separated by SDS-PAGE using two sheets of 15% acrylamide gel and the protein was transferred to two nitrocellulose membranes (BIO-RAD). Blocking was performed by shaking the membranes in a BSA-containing TBS buffer solution at room temperature for one hour. Subsequently, TM2 was reacted overnight at room temperature with the anti-TM2 antibody (as prepared from the antigen solely purified by means of the iminobiotin column; diluted 1000-fold) and, thereafter, the sites to which TM2 had been transferred were excised and shaken in an eluting buffer solution (0.2 M glycine, 1 mM EDTA, pH 2.8) at room temperature for 20 min to elute the antibodies out of the membranes. The purified antibodies were neutralized in a 1 M Tris solution whose volume was one tenth the volume of the eluting buffer solution; thereafter, the same amount of a 10×TBS buffer solution was added for storage at 4° C.

Antigen Binding Activity of the Expressed Proteins

The two proteins, HELscFv-TM2 and HELscFv-myc, which had been expressed in *E. coli* were verified for their antibody titers against a hen egg-white lysozyme (HEL) as described below. A hen egg-white lysozyme (50 μg/mL; product of SEIKAGAKU CORPORATION) was loaded on a microplate in 100-μl aliquots and left to stand still overnight at 4° C. until it turned into a solid phase. The wells were washed three times with 250 μl of a TBS buffer solution (10 mM Tris (pH 7.4) and 150 mM NaCl) containing 0.1% Tween 20 (TTBS) and, thereafter, 250 μl of 0.5% BSA containing TTBS was added and the mixture was left to stand still at room temperature for one hour to thereby effect blocking; another washing with 250 μl of TTBS was performed three times. In a separate step, an osmotic shock protocol (Ausubel et al., 1989) was followed to prepare a periplasm fraction from the cells of *E. coli* in which HELscFv-TM2 or HELscFv-myc had been expressed. A 10-fold dilution of the fraction was loaded on the aforementioned plate with immobilized HEL and reaction was carried out at room temperature for 3 hours. For use in a control test, a periplasm fraction was also prepared from *E. coli* into which only the vector pTrc99A had been incorporated.

After loading the respective periplasm fractions, the plates were washed three times with 250 μl of TTBS; thereafter, the rabbit anti-TM2 antibody (for HELscFv-TM2) and the rabbit anti-c-myc epitopic antibody (product of BETHYL; for HELscFv-myc) were diluted 1000-fold with 0.5% BSA containing TTBS and 100 μl of each dilution was loaded on the plates, which were left to stand still at room temperature for an hour to carry out the reaction. Following three additional washings with 250 μl of TTBS, 100 μl of an alkali phosphatase labeled anti-rabbit IgG antibody (product of BIO-RAD) that had been diluted 1000-fold with 0.5% BSA containing TTBS was loaded on the plates, which were subjected to reaction at room temperature for an hour. After three more washings with 250 μl of TTBS, 100 μL of 1-Step™ PNPP (product of PIERCE) was loaded on the plates for color formation that continued for 30 min at room temperature. The reaction was stopped by adding 100 μL of 2 N NaOH and the absorbance at 405 nm was measured by a plate reader Infinite M200 (product of TECAN).

As a result, the HELscFv-TM2 containing fraction and the HELscFv-myc containing fraction, each being diluted $10^3$-fold from $10^0$, saw marked increases in antibody titer over the extract of *E. coli* into which only the vector pTrc99A had been incorporated.

Crude Purification

In the next place, column chromatography was conducted to achieve crude purification of HELscFv-TM2 and HELscFv-myc from the soluble fractions each obtained from 300 mL of the culture broth. The cells obtained from 300 mL of the culture broth were suspended in 18 mL of a 50 mM Tris buffer solution (pH 8) containing 50 mM NaCl and thereafter disrupted by sonication. The solution containing the disrupted cells was centrifuged (9000 rpm) and 75% saturated ammonium sulfate was added to the supernatant; the resulting precipitate was dialyzed overnight in a 50 mM Tris buffer solution (pH 9) containing 50 mM NaCl to make a crude protein sample. The sample was loaded on an ion-exchange column MonoQ HR10/10 (product of Amersham-Pharmacia). After equilibrating the column with a 50 mM Tris buffer solution (pH 9) containing 50 mM NaCl, the sample was applied and elution was conducted with a 50 mM Tris buffer solution (pH 9) containing 50 mM NaCl. The flow rate was set at 3 mL/min and the protein was recovered in 1-mL aliquots. The purified proteins were verified by western blotting analysis in the same manner as described above. Six fractions in which the band of HELscFv-TM2 or HELscFv-myc was detected were recovered and 75% saturated ammonium sulfate was added to precipitate the protein of interest. The precipitate was re-suspended in 500 µL of a 20 mM phosphate buffer solution (pH 7) and dialyzed overnight in the same buffer solution. This series of operations allowed HELscFv-TM2 and HELscFv-myc to be recovered in respective amounts of 1.5 µg and 6.3 µg. The yield of recovery was 4% for HELscFv-TM2 and 16% for HELscFv-myc; the degree of purification was about 10% for both HELscFv-TM2 and HELscFv-myc.

As a control for ELISA analysis to be performed later, *E. coli* incorporating only the vector pTrc99A was subjected to induction of expression in the sane manner as described above to prepare a soluble fraction, which was purified by MonoQ; the fractions eluting at the same time as HELscFv-TM2 and HELscFv-myc (six fractions for each protein) were recovered; the fractions were precipitated by treatment with ammonium sulfate and dialyzed in the same manner as described above to prepare control samples.

1-1-3. Immobilization of the Tamavidin 2-HELscFv Fused Protein and HELscFv, and Comparative Analyses of Their Activities by ELISA To investigate the effect of immobilization of the scFv antibody on a substrate by means of fusion to tamavidin 2, the tamavidin 2-HELscFv fused protein (HELscFv-TM2) prepared in 1-1-2 and the control HELscFv-myc were immobilized on microplates and subjected to ELISA analysis, with the egg-white lysozyme detection sensitivity being used as an index.

Purification of Antibodies

Prior to ELISA analysis, the anti-lysozyme antibodies to be used in that analysis were first purified. An egg-white lysozyme (40 µg) was separated by SDS-PAGE using two sheets of 15% acrylamide gel and the protein was transferred to two nitrocellulose membranes (product of BIO-RAD). The membranes were subjected to blocking in a 3% BSA-containing TBS buffer solution (10 mM Tris (pH 7.4) and 150 mM Nacl) at room temperature for one hour. Subsequently, reaction was carried out overnight at room temperature with a rabbit anti-hen egg-white lysozyme antibody (product of Rockland) that had been diluted 1000-fold with a 3% BSA containing TBS buffer solution and, thereafter, the sites to which the egg-white lysozyme had been transferred were excised and shaken in an eluting buffer solution (0.2 M glycine, 1 mM EDTA, pH 2.8) at room temperature for 20 min to elute the antibodies. The eluted antibodies were neutralized with a 1 M Tris solution whose volume was one tenth the volume of the eluting buffer solution; thereafter, the same amount of a 10×TBS buffer solution was added for storage at 4° C.

ELISA Analysis

ELISA analysis was subsequently performed. The roughly purified HELscFv-TM2 and HELscFv-myc were each conditioned with a 20 mM phosphate buffer solution (pH 7) to give a concentration of 3 µg/mL and each preparation was loaded on a 96-well microplate in 50-µL aliquots. A biotinylated plate (Model No. 15151; product of PIERCE) was used for HELscFv-TM2 and a hydrophobic plate (Model No. 2592; product of Corning) was used for HELscFv-myc; the respective plates were left to stand still overnight at room temperature to effect protein immobilization by tamavidin-biotin bonding in the former case and by hydrophobic bonding in the latter case. Thereafter, the individual wells in each plate were washed three times with a 0.1% Tween 20 containing TBS buffer solution (TTBS); then, 0.5% BSA containing TTBS was added in an amount of 300 µL and the mixture was left to stand still at room temperature for an hour to effect blocking. After performing another washing with TTBS three times, lysozyme solutions serially diluted with TTBS from 50 ng/µL to 5 pg/µL were loaded in 50-µL aliquots. After leaving the plates to stand still at room temperature for an hour so as to carry out a reaction with the HELscFv-TM2 or HELscFv-myc immobilized on them, the plates were washed with TTBS three times.

Subsequently, for lysozyme detection, a solution prepared by adding 5040 µL of 0.5% BSA containing TTBS to 960 µL of the rabbit anti-hen egg-white lysozyme that had been purified as described before was loaded on the plates in an amount of 50 µl and reaction was performed at room temperature for an hour; thereafter, the plates were washed three times with TTBS and, subsequently, a reaction with an alkali phosphatase labeled anti-rabbit antibody (product of BIO-RAD) that had been diluted 1000-fold with 0.5% BSA containing TTBS was carried out at room temperature for an hour. After three more washings with TTBS, 50 pL of 1-Step™ PNPP (product of PIERCE) was loaded on the plates; when a color formation was recognized to have occurred, 50 µL of 2 N NaOH was added to stop the reaction and the absorbance at 405 nm was measured by a plate reader Infinite M200 (product of TECAN). The values of applicable data were obtained by the following procedure: in each of the concentration ranges of HELscFv-TM2 and HELscFv-myc, the relevant concentration of each control sample for HELscFv-TM2 and HELscFv-myc (the MonoQ fraction prepared from *E. coli* having an empty expression vector, as described above) was also measured and the absorbance value for that control was subtracted from the absorbance for each of the concentration ranges of HELscFv-TM2 and HELscFv-myc.

As a result, the plate having HELscFv-TM2 immobilized via tamavidin-biotin bonding had a higher lysozyme detection sensitivity than the plate having HELscFv-myc rendered into a solid phase by hydrophobic bonding. In other words, it turned out that preparing a fusion protein of the antibody scFv and tamavidin and then binding it to a biotinylated substrate allowed for a higher detection sensitivity to be achieved than when scFv was immobilized on a substrate by hydrophobic bonding.

Assay of the Biotin-Binding Activity of the Fusion Protein of Tamavidin 2 and HELscFv Biacore 3000 (product of BIACORE) was used to analyze the biotin-binding ability of the HELscFv-TM2 fused protein. HELscFv-TM2 secreted in the medium of a culture broth was roughly purified by column chromatography and the resulting fractions were used as the samples to be analyzed. To be more specific, *E. coli* strain TB1 was transformed with PelB-HELscFV-TM2/pTrc99A for protein expression and the protein contained in the medium was precipitated with 75% saturated ammonium sulfate.

The resulting precipitate was dialyzed overnight in a 50 mM Tris buffer solution (pH 9) containing 50 mM NaCl and loaded on an ion-exchange column MonoQ HRS/5 (product of Amersham-Pharmacia). The equilibrating buffer solution was a 50 mM Tris buffer solution (pH 9) containing 50 mM NaCl and the eluting buffer solution was a 50 mM Tris buffer solution (pH 9) containing 500 mM NaCl; using these solutions, the protein was recovered in 0.5 mL aliquots at a flow rate of 1 mL/min. The eluted fractions were subjected to SDS-PAGE and then to western blotting using the anti-TM2 antibody, to thereby detect fractions containing the fusion protein; further, from the signal level derived from the fusion protein, the amount of HELscFV-TM2 was computed and used in Biacore analysis. The degree of purification was approximately 20%. Onto a sensor chip CM5 (product of Biacore), a bovine serum albumin (BSA) biotinylated with EZ-Link (registered trademark) NHS-LCLC-Biotin (30.5 Å) (product of PIERCE; the parenthesized figure represents the length of the linker between biotin and NHS) was fixed by the amine coupling method. Using HBS-EP (product of Biacore) as the running buffer solution, HELscFV-TM2 was injected at a flow rate of 20 µl/min in 40-µl aliquots (2 min). From the resulting sensorgram, the binding rate constant (ka), the dissociation rate constant (kd) and the dissociation constant (KD) were computed with the aid of analysis software Biaevaluation version 4.1.

The result is shown in Table 2. As it turned out, HELscFv-TM2 interacted with biotin specifically and had a very low KD on the order of $10^{-8}$, indicating its strong bonding to biotin.

TABLE 2

| Sample name | Ka | Kd | KD |
|---|---|---|---|
| HELscFv-TM2 | $2.7 \times 10^4$ | $1.4 \times 10^{-3}$ | $5.3 \times 10^{-8}$ |

Example 2

Fusion Protein of Tamavidin and Enzyme

In this Example, a fusion protein of tamavidin 2 and an enzyme (α2,6 sialyl transferase) was expressed in *E. coli* and immobilized on carrier magnetic beads by tamavidin-biotin bonding. In addition, the enzymatic activity of the fusion protein was investigated. As a control, the enzyme was immobilized on the beads by covalent bonding. A concrete explanation is given below.

2-1. Glycosyl Transferase Fused Protein

As an example of the tamavidin-enzyme fused protein, tamavidin 2 (TM2) and a sialyl transferase, i.e., a kind of glycosyl transferase, were used. As the sialyl transferase, β-galactoside-α2,6-sialyl transferase derived from a bacterium of the genus *Photobacterium* (PCT/JP2006/304993) was used. Note that a gene coding for a type of protein that had the amino acids in the signal peptide portion deleted (ISH224-2,6ST N1C0, PCT/JP2006/304993) was used as the gene of the sialyl transferase.

2-1-1. Construction of Vectors for Expressing the Fusion Proteins of Tamavidin 2 and Sialyl Transferase Designing Primers To construct the following three nucleic acids by PCR, i.e., a nucleic acid (ISH224-2,6ST-linkTM2) coding for a protein consisting of tamavidin 2 fused to ISH224-2,6ST N1 C0 via a linker (GGGGSG)(SEQ ID NO: 57), a nucleic acid (ISH224-2,6ST-3XlinkTM2) coding for a protein with the joining effected by a linker of 15 amino acids consisting of three repeats of GGGGS (SEQ ID NO: 52), and a nucleic acid (ISH224-2,6ST-5XlinkTM2) coding for a protein with the joining effected by a linker of 25 amino acids consisting of five repeats of GGGGS (SEQ ID NO: 52), three primers were designed, i.e., a primer for joining the two genes ISH224-2,6ST and TM2 via GGGGSG (SEQ ID NO: 57), a primer for joining them via 15 amino acids consisting of three repeats of GGGGS (SEQ ID NO: 52), and a primer for joining them via 25 amino acids consisting of five repeats of GGGGS (SEQ ID NO: 52), were designed. Specifically, three primers were designed, i.e., 224-265T-linkTM2 RY, 224-26ST-3XlinkTM2 RV, and 224-26ST-5XlinkTM2 RV that each consisted of the ISH224-2,6ST portion on the 5' side, the linker in the center, and the TM2 portion on the 3' side; in addition, another primer 224-26ST-linkFW was designed that consisted of the linker on the 5' side and a DNA sequence on the 3' side coding for the IST224-2,6ST portion in a reverse direction. Note that for the cloning of the IST224-2,6ST portion, a primer 224-26ST-N1-PciI (PCT/JP2006/304993) having a portion coding for the N-terminus of the same gene, with the signal peptide excluded, and an upstream sequence coding for a restriction enzyme PciI recognition site was used. The respective primers for constructing the fusion protein of tamavidin and sialyl transferase are identified in Table 3.

TABLE 3

Table 3. Primers for constructing the fusion protein of tamavidin and sialyl transferase

| Name | Sequence 5'-3' | Length |
|---|---|---|
| 224-26ST-N1-PeiI | CTTGTA<u>ACATGT</u>CAGAAGAAAATACACAATC | 31 mer |
| 224-26ST-linkTM2RV | CAGGTGTTTGTATTGCAGTCGGTGGCGGTGG CAGCGGTTCAGACGTTCAATCTTCACTC | 59 mer |
| 224-26ST-3XlinkTM2FW | GGTGTTTGTATTGCAGTCGGTGGCGGTGGCA GCGGTGGCGGTGGCAGCGGTGGCGGTGGCAG CTCAGACGTTCAATCTTCA | 81 mer |
| 224-26ST-linkFW | ACCGCTGCCACCGCCACCGACTGCAATACAA ACACCTG | 38 mer |
| 224-26ST-5XlinkTM2RV | CAGGTGTTTGTATTGCAGTCGGTGGCGGTGG CAGCGGTGGCGGTGGCAGCGGTGGCGGTGGC AGCGGTGGCGGTGGCAGCGGTGGCGGTGGCA GCTCAGACGTTCAATCTTCACTC | 116 mer |
| TM2 3'Bam | TTTTTTGGATCCTTACTTCAACCTCGGTGCG | 31 mer |

The individual sequences correspond to SEQ ID NOs: 16-17, 23, 18, and 21-22 as counted from the top.

PCR

Two-stage PCR was performed to construct a nucleic acid coding for the ISH224-2,6ST-TM2 fused protein (the nucleic acid is hereinafter referred to as "1SH224-2,6ST-TM2 fused gene"). In the first stage of PCR, the ISH224-2,6ST portion was amplified using the primers 224-26ST-N1-PciI and 224-26ST-linkFW, with a plasmid incorporating the gene of ISH224-2,6ST N1C0 into the vector pTrc99A (see PCT/JP2006/304993) being used as a template, and the TM2 portion was amplified using the primers 224-26ST-linkTM2RV and TM2 3' Bam (as described above), or 224-26ST-3XlinkTM2FW and TM2 3' Bam, or even 224-26ST-5XlinkTM2RV and TM2 3' Bam, with a plasmid incorporating the TM2 gene into the vector pTrc99A (see WO 02/072817) being used as a template.

The PCR reaction conditions were as follows: to a 50-µL reaction solution, 500 ng of the template DNA, 5 µL of 10× Pyrobest buffer II (Takara), 4 µL of 2.5 mM dNTP, 50 pmoles of each of the primers, and 0.5 µL, of 5 U/µL Pyrobest DNA polymerase (product of Takara) were added, and using a programmed template control system PC-700 (ASTEK), one cycle of 96° C.×3 min, 10 cycles of 96° C.×1 min, 55° C.×1 min, and 72° C.×2 min, and one cycle of 72° C.×6 min were performed. As a result, a PCR product of 1530 by was obtained in the ISH224-2,6ST portion and another of 420 by was obtained in the TM2 portion. These PCR products were subjected to agarose electrophoresis in a TAE buffer solution using a low-melting point agarose (SeaPlaqueGTG).

Each of the DNA fragments was excised together with the gel and after adding 200 mM NaCl in an amount equal to that of the gel, treatment was conducted at 70° C. for 10 min to melt the gel. The resulting sample was extracted with phenol, phenol/chloroform, and chloroform, each extraction performed once, and allowed to precipitate in ethanol to recover two DNA fragments, one for the scFv portion and the other for the TM2 portion. With these two fragments used as templates, the second stage of PCR was performed using the primers 224-26ST-Nl-PciI and TM2 3'Bam. The reaction conditions were the same as in the first stage. As a result, about 1950 by of PCR product (ISH224-2,6ST-linkTM2) (SEQ ID NO: 5), about 1970 by of PCR product (ISH224-2, 6ST-3XlinkTM2) (SEQ ID NO: 24) and even about 1990 by of PCR product (ISH224-2,6ST-5XlinkTM2) (SEQ ID NO: 19) were obtained. The $1^{st}$ to $1494^{th}$ bases in SEQ ID NO: 5 correspond to ISH224-2,6ST whereas the $1513^{th}$ to $1935^{th}$ bases correspond to TM2. The $1^{st}$ to $1494^{th}$ bases in SEQ ID NO: 24 correspond to ISH224-2,6ST whereas the $1540^{th}$ to $1962^{nd}$ bases correspond to TM2. Further in addition, the $1^{st}$ to $1494^{th}$ bases in SEQ ID NO: 19 correspond to ISH224-2, 6ST whereas the $1570^{th}$ to $1992^{nd}$ bases correspond to TM2.

Cloning

The ISH224-2,6ST-TM2 fused gene obtained by PCR was cloned in the vector pCR4 Blunt TOPO (product of Invitrogen). The ligation reaction was in accordance with the instructions on the vector kit. DNA was transferred into E. coli TB1 by electroporation and plasmid DNA was extracted in accordance with the usual method (Sambrook et al. 1989, Molecular Cloning, A laboratory manual, $2^{nd}$ edition). The clones verified to have inserts were treated as follows: using the M13 primer (Takara), a sequencing primer (5'-TTT ITT GGA TCC CTA GAC TGC AAT ACA AAC ACC-3') (SEQ ID NO: 84), and another sequencing primer 2(5'-GCC CAT ACA GTC GTA CCT GTA A-3') (SEQ ID NO: 85), the base sequence of the PCR product was determined from both of its ends with an ABI PRISM fluorescence sequencer (Model 310 Genetic Analyzer, Perkin Elmer) to confirm that it had no mutation from the original gene. The plasmid incorporating the genes of interest was double digested with PciI and BamH I and gel purification was performed by the aforementioned method to recover a DNA fragment. The recovered DNA fragment was ligated by a ligation kit (product of Takara) to the E. coli expression vector pTrc99A that had been preliminarily digested with NcoI and BamH I. The ligation product was transformed into E. coliTB1 and plasmid DNA was extracted and subjected to restriction enzyme analysis in accordance with the usual method to check for the presence of the inserted genes; this led to the completion of ISH224-2,6ST-linkTM2 /pTrc99A, ISH224-2,6ST-3Xlink TM2 /pTrc99A, and ISH224-2,6ST-5XlinkTM2 /pTrc99A as vectors for expressing the fusion protein of tamavidin 2 and sialyl transferase.

2-1-2. Expression of the Tamavidin 2-Glycosyl Transferase Gused Protein in E. coli To investigate the increase in sensitivity on account of immobilization and orientation of the glycosyl transferase on a substrate by means of fusion to tamavidin 2, the tamavidin 2-glycosyl transferase fused protein was first expressed in E. coli.

Expression in E. coli

Three batches of E. coli strain TB1, one transformed with ISH224-2,6ST-linkTM2/pTrc99A, another with ISH224-2, 6ST-3XlinkTM2/pTrc99A, and the other with ISH224-2, 6ST-5XlinkTM2/pTrc99A, were inoculated in an Luria both (LB) medium containing the antibiotic ampicillin (final concentration: 100 µg/ml) and shake cultured at 30° C. until $A_{600}$=0.5 was reached. Further after that, 1 mM isopropyl-1-thio-b-D-galactopyranoside (IPTG) was added and shake culture was performed overnight at 30° C. E. coli was harvested from 1 ml of the culture broth by centrifugation and suspended in 400 µl of a 20 mM BisTris buffer solution (pH 6.0); thereafter, the cells were disrupted by sonication. The solution containing the disrupted cells was centrifuged (15000 rpm) and the resulting supernatant was collected as a crude extract.

Figure 2:
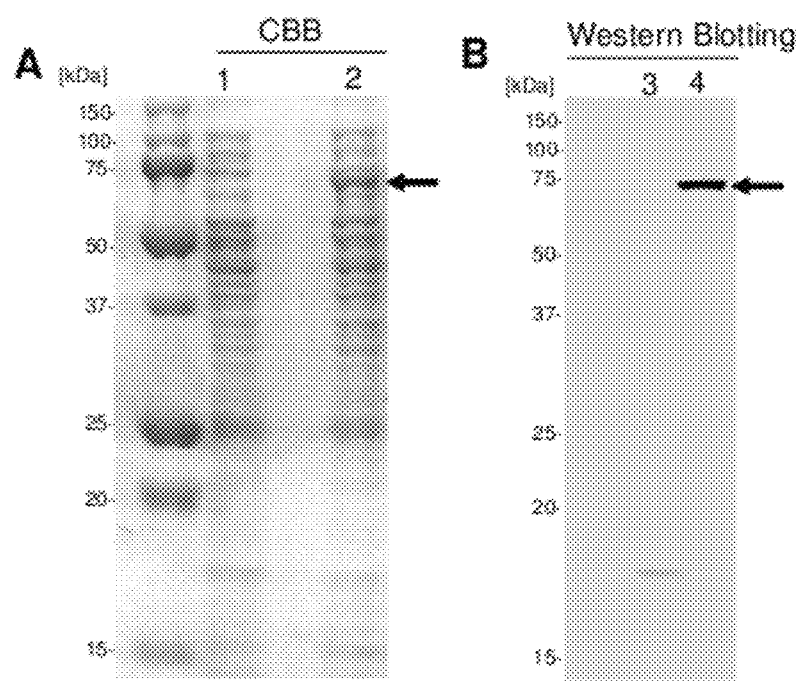
FIG. 2 shows the expression of a fusion protein of tamavidin 2 and a sialyl transferase; *E. coli* incorporating ISH224-2,6ST-linkTM2/pTrc99A was induced for expression and a crude protein solution was prepared and subjected to SDS-PAGE, followed by CBB staining (A) and western blot analysis (B) (lanes 2 and 4). An anti-TM2 antibody was used as the primary antibody, and an alkali phosphatase labeled antibody was used as the secondary antibody; fractions similarly prepared from *E. coli* having only the expression vector pTrc99A were used as controls (lanes 1 and 3). Bands of the expressed ISH224-2,6ST-linkTM2 protein are indicated by the arrows.

The crude extracts thus obtained were subjected to SDS-polyacrylamide electrophoresis (SDS-PAGE) and stained with Coomassie Brilliant Blue (CBB). As a result, in all crude extracts, a band that was not found in the E. coli transformed solely with pTrc99A was detected at a position of about 70 kDa. The results for ISH224-2,6ST-linkTM2 are shown in FIG. 2A. Since the molecular mass of ISH224-2,6ST N1C0 is about 55 kDa and that of tamavidin 2 is about 15 kDa, the molecular mass of the ISH224-2,6ST-TM2 fused protein is assumed to be about 70 kDa, so it is substantially of a size equal to the theoretical value; a verification was made by western blotting analysis and the band of interest was detected specifically for the anti-TM2 antibody (described above). The results for ISH224-2,6ST-linkTM2 are shown in FIG. 2B. The expression level of the fusion protein was estimated to be about 80 mg/L culture. From this was confirmed high-yield expression of the ISH224-2,6ST-TM2 fused protein in E. coli. The amino acid sequence of this protein is depicted in SEQ ID NO: 8.

The sialyl transfer activity of the above-described crude protein extract was measured in accordance with a modified version of the method described in Yamamoto et al. (1996) J. Biochem 120: 104-110; the specific activity of the ISH224-2,6ST-linkTM2 fused protein for sialyl transfer was computed to be 9.8 U/mg protein.

Speaking of the ISH224-2,6ST N1C0 protein to be used as a control, it was expressed and purified by the method described in a patent (PCT/JP2006/304993), provided that the purified enzyme was finally dialyzed overnight in 50 mM IVIES buffer solution (pH 5.0) at 4° C. The sialyl transferase activity was measured and the result was 9.3 U/mg protein.

Further, the fluorescent biotin binding activities of the crude protein extracts of ISH224-2,6ST-TM2, ISH224-2, 6ST-3XlinkTM2, and ISH224-2,6ST-5XlinkTM2 were measured by the following method to verify the biotin-binding activities of those fusion proteins.

Specifically, measurement of the biotin-binding activity was conducted in accordance with the method of Kada et al. (Biochim. Biophys. Acta., 1427: 33-43 (1999)). The crude protein extract of ISH224-2,6ST-TM2, ISH224-2,6ST-3XlinkTM2, or ISH224-2,6ST-5XlinkTM2 was so conditioned that it would be contained at serial concentrations in 200 µL of an assay buffer (50 mM $NaH_2PO_4$, 100 mM NaCl, and 1 mM EDTA (pH 7.5)). The resulting solution was mixed with a 20 pmol/µL fluorescent biotin solution (biotin-4-fluorescein: Molecular Probe) in an amount of 50 µL (1 nmol) and the mixture was left to stand at room temperature for 10 min, followed by measuring the fluorescent intensity by a plate reader Infinite M200 (product of TECAN). As a result, the crude protein extracts of ISH224-2,6ST-TM2, ISH224-2, 6ST-3Xlink TM2, and ISH224-2,6ST-5XlinkTM2 were found to have high fluorescent biotin binding activities.

On the other hand, no biotin-binding activity was detected in the crude protein extract prepared from E. coli having only pTrc99A and used as the control. From the foregoing, it became clear that ISH224-2,6ST-TM2 fused proteins had both the biotin-binding activity and the sialyl transferase activity.

2-1-3. Simplified Purification of the Fusion Protein of Tamavidin 2 and Glycosyl Transferase by Means of Biotin Solid-Phased Carrier and its Immobilization on the Carrier To investigate the effect of protein immobilization on a substrate by utilizing fusion to tamavidin 2, the fusion protein of tamavidin 2 and glycosyl transferase was subjected to simplified purification and immobilization by a biotin solid-phased carrier.

Binding of ISH224-2,6ST-TM2 Fused Protein to Magnetic Beads

Four hundred microliters of biotinylated magnetic beads (BioMag Biotin, product of Polysciences, Inc.; the length of the linker between biotin and a magnetic bead was 22.4 Å) were washed with 400 µl of a 20 mM BisTris buffer solution (pH 6.0). To the biotinylated magnetic beads, an extract of E. coli transformed with the ISH224-2,65T-linkTM2 fused gene (see above) was added and the mixture was incubated under shaking at 4° C. for 2 hours, whereby ISH224-2,6ST-linkTM2 was bound to the magnetic beads by tamavidin-biotin bonding. The magnetic beads were recovered by a magnet (Adem-Mag SV, product of Ademtech SA) and after removing the supernatant (unbound fraction), the magnetic beads were washed twice with 400 µl of a 20 mM Tris buffer solution (pH 6.0) containing 1 M sodium chloride. Thereafter, the magnetic beads were suspended in 400 µl of a 20 mM Tris buffer solution (pH 6.0) to complete ISH224-2,6ST-TM2 magnetic beads, or magnetic beads to which the fused protein was bound via tamavidin-biotin bonding.

Binding of ISH224-2,6ST N1C0 to Magnetic Beads

Two hundred microliters of magnetic beads coated with carboxyl groups on their surfaces (Dynabeads M-270 Carboxylic Acid, product of Dynal) were washed with 200 µl of 0.01 N sodium hydroxide for 10 minutes, then further washed with 200 µl of MilliQ water (product of Millipore) three times, each time for 10 min. To the as-washed magnetic beads, 1-ethyl-3-(3-dimethylaminopropyl)carbodiimide hydrochloride (EDC) (product of PIERCE) as dissolved in MilliQ water was added to give a final concentration of 0.2 M and the mixture was incubated under shaking at room temperature for 30 min. Thereafter, the magnetic beads were washed with 400 µl of cold MilliQ, then with 400 µl of a 50 mM MES buffer solution (pH 5.0). The purified ISH224-2,6ST N1C0 protein (PCT/JP2006/304993) was conditioned in a 50 mM MES buffer solution (pH 5.0) to have a concentration of 0.6 mg/ml. To 400 µl of the resulting protein solution (240 µg in terms of the purified enzyme), the aforementioned magnetic beads were added. The mixture was shaken at 4° C. for 2 hours so that ISH224 2,6ST N1C0 was bound to the magnetic beads by covalent bonding. The magnetic beads were recovered by a magnet and the supernatant (unbound fraction) was removed. Subsequently, 200 µl of a 50 mM Tris buffer solution (pH 7.0) was added to the beads to inactivate the unreacted carboxyl groups and thereafter the magnetic beads were blocked with 200 µl of a PBS buffer solution (10 mM sodium phosphate and 150 mM NaCl) containing 0.5% BSA and 0.1% Tween 20. The magnetic beads were re-suspended in 200 µl of a PBS buffer solution to complete ISH224-2,6ST magnetic beads to which the enzyme had been bound via the covalent bonding between the amino groups on the enzyme and the carboxyl groups on the magnetic beads.

Measurement of the Amounts of ISH224-2,6ST-linkTM2 and ISH224-2,6ST as Bound to the Magnetic Beads and the Degree of Their Purification The amounts of ISH224-2,6ST-linkTM2 and ISH224-2,6ST as bound to the magnetic beads were each calculated as the difference between the amount of the protein before it was bound to the magnetic beads and the amount of the unbound protein. The protein in the fraction before binding to the beads and the protein in the unbound fraction were fractionated by SDS-PAGE and detected by CBB staining. A band of ISH224-2,6ST-linkTM2 was detected in the vicinity of 70 kDa and a band of ISH224-2,6ST in the vicinity of 55 kDa. An image analyzer Las3000 (product of Fuji Film) was used to construct a calibration curve from the concentration of a band for a molecular weight marker (LMW marker kit; product of Pharmacia) with a preliminarily known protein mass and the bands of the yet-to-be bound and unbound fractions were quantified.

In the next place, the degree of purification of ISH224-2,6ST-linkTM2 was verified. To begin with, the protein bound to the magnetic beads was dissociated by heat. Specifically, the magnetic beads to which ISH224-2,6ST-linkTM2 had been bound were washed with PBS and thereafter suspended in an equal amount of 2×SDS sample buffer (100 mM Tris-HCl pH 6.8, 12% 2-mercaptoethanol, 2% SDS, and 20% glycerol) and heat treated at 95° C. for 40 min. The magnetic beads were recovered by a magnet and the resulting supernatant was subjected to SDS-PAGE, CBB staining, and western blotting analysis. An anti-TM2 antibody was used as the primary antibody and an alkali phosphatase labeled anti-rabbit IgG antibody was used as the secondary antibody.

Subsequently, a test was conducted to dissociate ISH224-2,6ST-linkTM2 from the magnetic beads by means of biotin. To 200 µL of the magnetic beads having ISH224-2,6ST-linkTM2 bund thereto, 16 nmoles D-biotin (product of Sigma) was added and mixed with inversion at room temperature for 2 hours. The amount of biotin was 500 times in excess of the number of biotin pockets as calculated from the expression level of the fusion protein. The magnetic beads were recovered by a magnet and the resulting supernatant was subjected to SDS-PAGE and CBB staining. Part of the supernatant was concentrated 5-fold by the trichloroacetic acid precipitation method. Specifically, 10 µL of 100% w/v trichloroacetic acid was added to 100 µL of the supernatant containing the protein as associated from the beads, and the mixture was left to stand still on ice for 20 min and thereafter centrifuged at 15000 rpm for 20 min at 4° C. The supernatant was removed and the precipitate was washed with 500 of acetone and thereafter re-centrifuged at 15000 rpm for 20 min at 4° C. The precipitate was dried and dissolved in 1×SDS sample buffer.

Figure 3:
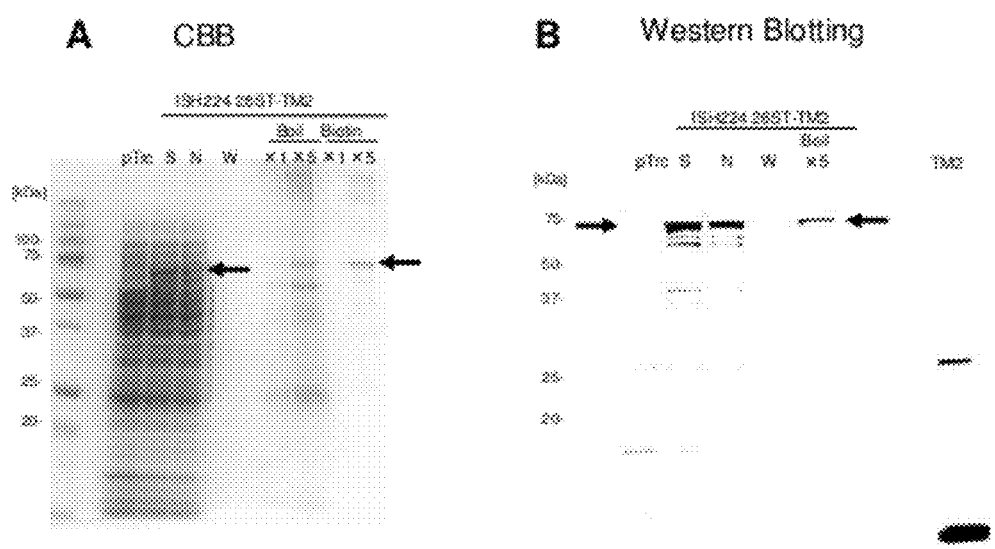
FIG. 3 shows simplified purification and immobilization of a sialyl transferase by fusion with tamavidin 2; an ISH224-2, 6ST-TM2 fused protein was reacted with biotinylated magnetic beads and purified and immobilized simultaneously; to examine the degree of purification, the fusion protein was heat treated (Boil) or biotin treated (Biotin) to be dissociated from the beads; panel A shows the result of CBB staining after SDS-PAGE, and panel B the result of western blot analysis; pTrc refers to the *E. coli* derived sample having only the expression vector, S the sample before binding ISH224-2, 6ST-linkTM2 to the beads, N the non-bound fraction, W the washed fraction, and TM2 the purified tamavidin 2; X1 and X5 indicate one- and five-fold concentrations, respectively; the position of the fusion protein is indicated by the arrows.

The fraction prior to binding ISH224-2,6ST-linkTM2 to the biotinylated magnetic beads, the unbound fraction, the washed fraction, and the dissociated fraction obtained by heat or biotin treatment were each subjected to SDS-PACE-CBB analysis or western blotting analysis, and the results are shown in FIG. 3. In CBB staining, the sample of crude protein extract from ISH224-2,6ST-linkTM2 expressing E. coli gave a thick band of ca. 70 kDa that was absent from pTrc99A expressing E. coli; since this band was detected specifically for the anti-TM2 antibody, it was shown to have derived from the ISH224-2,6ST-linkTM2 protein. Approximately 40% of this fusion protein bound to the biotinylated magnetic beads. In addition, the fusion protein, once bound to the biotinylated magnetic beads, exhibited a strong binding force and did not dissociate at all with 1 M sodium chloride and only about one tenth of it dissociated upon treatment at 95° C. for 40 min in the presence of 1% SDS or even when an excess of biotin was added. In CBB staining after heat treatment, not only the band of about 70 kDa but also bands in the vicinity of 60 kDa, 40 kDa and 25 kDa were observed; among these additional bands, those of 60 kDa and 40 kDa were recognized for the anti-TM2 antibody. Therefore, it was suggested that those bands were molecules resulting from the fusion protein. The origin of the band in the vicinity of 25 kDa is unknown but if assumption is made that it did not derive from the fusion protein, the degree of purification of the ISH224-2,6ST-linkTM2 protein bound to the biotinylated magnetic beads is approximately 50%. On the other hand, when an excess of biotin was added, no extra molecular species occurred unlike in the case of heat treatment and only the band of 70 kDa was detected.

From the foregoing, it was shown that the use of biotinylated magnetic beads successfully enabled the tamavidin fused protein to be purified and immobilized on the beads simultaneously.

2-1-4. Comparative Analysis of the Activities of the Fusion Protein of Tamavidin 2 and Glycosyl Transferase as Immobilized on the Biotin Solid-Phased Carrier and the Glycosyl Transferase as Immobilized on the Carrier by Covalent Bodning To investigate the effect of immobilizing the glycosyl transferase by making use of the fusion to tamavidin 2, the activity of the fusion protein of tamavidin 2 and glycosyl transferase as immobilized on the biotin fixed carrier was analyzed.

Comparative Analysis of the Activities of ISH224-2,6ST-linkTM2 Magnetic Beads and ISH224-2,6ST Magnetic Beads To compare the enzymatic activity of the magnetic beads having ISH224-2,6ST-linkTM2 bound via tamavidin 2-biotin with that of the magnetic beads having ISH224-2,6ST bound covalently via the amino acid residues on the ISH224-2,6ST itself, the yet-to-be-bound fraction (ISH224-2,6ST-linkTM2 or ISH224-2,6ST solution which was yet to be reacted with the magnetic beads) and the magnetic bead fraction (the magnetic beads to which ISH224-2,6ST-linkTM2 or ISH224-2,6ST was bound) were measured for the sialyl transferase.

The sialyl transfer activity was measured by the method described in Yamamoto et al. (1996) J Biochem 120: 104-110. An enzymatic reaction was performed using 30 µl of a reaction solution containing 70 nmol CMP-NeuAc (containing ca. 20000 cpm of CMP-NeuAc having NeuAc labeled with $^{14}C$; NeuAc represents N-acetylneuraminic acid) as a sugar donor substrate, 1.25 µmol lactose as a sugar receptor substrate, and the aforementioned fraction in 0.5 M NaCl. The enzymatic reaction was conducted at 30° C. for 5 min. After the end of the reaction, 1.9 mL of a 5 mM phosphate buffer solution (pH 6.8) was added to the reaction solution, which was then laoded on a Dowex 1×8 (PO 43-form, 0.2×2 cm; BIO-RAD). The radioactivity contained in sialyl lactose, or the reaction product contained in the eluate from the column, was measured to compute the enzymatic activity. One enzyme unit (1 U) is the amount of the enzyme that transfers 1 µmol of sialic acid in one minute. The enzymatic activities per milligram of the ISH224-2,6ST-linkTM2 and ISH224-2,6ST proteins as bound to the magnetic beads were computed to compare the strength of enzymatic activity depending on the mode of binding. The results are shown in Table 4.

TABLE 4

Activities of enzyme immobilized on substrate by making use of tamavidin fused protein

| Item | Protein ISH224-2, 6ST (A) | Protein ISH224-2, 6ST-linkTM2 (B) | B/A |
|---|---|---|---|
| Enzymatic activity before binding to beads (U/mg protein) | 9.3 | 9.8 | 1 |
| Enzymatic activity bound to beads (U/mg protein) | 0.9 | 10.7 | 12 |
| Protein mass per unit surface area of beads (mg/m²) | 48 | 48 | 1 |
| Enzymatic activity per unit surface area of beads (U/m²) | 43 | 519 | 12 |

When the sialyl transferase was bound to the magnetic beads by means of covalent bonding with the aid of the functional groups on the beads and those within the enzyme, the specific activity of the enzyme dropped to approximately one tenth of the initial value. On the other hand, when the sialyl transferase was fused to tamavidin and bound to the magnetic beads via tamavidin-biotin bonding, the enzymatic activity before the binding to the beads was maintained intact. In this connection, the magnetic beads that were used with ISH224-2,6ST-linkTM2 (which had an average particle size of 1 µm) were different from those used with ISH224-2,6ST (which had an average particle size of 2.8 µm), so their surface areas were determined from these average particle sizes and, in addition, the amounts of the proteins bound to the beads were divided by the obtained surface areas to determine the enzymatic activities per unit surface area of the beads. These results also show that the immobilization on the substrate via tamavidin-biotin exhibited an activity more than 10 times the value for the immobilization by covalent bonding. Also note that considering the fact that the ISH224-2,6ST protein has a molecular mass of ca. 55 kDa whereas the ISH224-2,6ST-TM2 fused protein (monomer) has a molecular mass of ca. 70 kDa, the activity difference per molecule of the actual protein is predicted to be even greater.

The magnetic beads on which the ISH224-2,6ST-TM2 fused protein was immobilized were stored at 4° C. for 3 weeks and their enzymatic activity was measured; as it turned out, there was hardly any drop in activity. Therefore, the binding of the fused protein to biotin was very strong and the activity of the immobilized enzyme was also stable.

Example 3

Binding of the HELscFv-TM2 Fused Protein to Magnetic Beads

In this Example, the HELscFv-TM2 prepared in Example 1 was bound to biotinylated magnetic beads and an investigation was made to see if the length of the linker between a magnetic head and biotin would cause any effect on binding to the bead.

Specifically, Ez-Link (registered trademark) NHS-Biotin (13.5 Å), Ez-Link (registered trademark) LC-Biotin (22.4 Å), and Ez-Link (registered trademark) NHS-LCLC-Biotin (30.5 Å), each being a product of PIERCE, were conditioned with DMSO (dimethyl sulfoxide) to 10 mM. These were added in an amount of 200 µL (2 µM) to 200 µL of Dynabeads M-270 Amine (product of PIERCE) and allowed to react at room temperature for 30 min, whereby each of the biotinylating reagents was bound to the magnetic beads.

Subsequently, the beads were washed twice simultaneously blocked with 400 µL of a PBS buffer solution (10 mM sodium phosphate and 150 mM NaCl, pH 7.4) containing 0.1% BSA and 0.01% Tween 20. Finally, the beads were suspended in 200 µL PBS buffer solution to prepare three lots of biotinylated magnetic beads having biotin-magnetic bead linker lengths of 13.5 Å, 22.4 Å, and 30.5 Å. The prepared biotinylated magnetic beads were measured for the biotinylation efficiency by the HABA:Avidin method and the magnetic beads modified with 200 pmol of biotin were used for binding to HELscFv-TM2.

A hundred micrograms of the HELscFv-TM2 secreted in an E. coli culture broth was reacted with the 200 pmol biotinylated magnetic beads at room temperature for an hour and, thereafter, the magnetic beads were collected by a magnet and the resulting supernatant, namely, the HELscFv-TM2 fraction not bound to biotin (unbound fraction) was recovered.

The fraction yet to be reacted with the beads and the unbound fraction were subjected to analysis by western blotting and the amount of HELscFv-TM2 in each fraction was measured to compute the amount of HELscFv-TM2 bound to the biotinylated magnetic beads. A mouse anti-TM2 antibody was used as the primary antibody and an alkali phosphatase labeled goat anti-mouse IgG antibody was used as the secondary antibody.

As a result, 72% of HELscFv-TM2 bound to the magnetic beads with a linker length of 22.4 Å and 77% of HELscFv-TM2 bound to the magnetic beads with a linker length of 30.5 Å. On the other hand, HELscFv-TM2 did not bind at all to the magnetic beads with a linker length of 13.5 Å. From these observations, it became clear that the binding between the HELscFv-TM2 fused protein and biotin would occasionally be affected by the length of the linker between the carrier and biotin and that its length must be longer than at least 13.5 Å.

Example 4

Assay of the Biotin Binding Activities of the Fusion Proteins of Tamavidin 2 and Sialyl Transferase In this Example, using Biacore 3000 (product of BIACORE), a test for the binding to biotin of the ISH224-2,6ST-TM2 fused proteins of Example 2 was carried out to see whether the length of the amino acid linker between tamavidin and protein (in this case, an enzyme) would affect the binding.

As ISH224-2,6ST fused TM2 proteins, ISH224-2,6ST-linkTM2, ISH224-2,6ST-3XlinkTM2, and ISH224-2,6ST-5XlinkTM2 were used. Expression vectors, 1SH224-2,6ST-linkTM2/pTrc99A, ISH224-2,6ST-3XlinkTM2/pTrc99A, and ISH224-2,6ST-5XlinkTM2/pTrc99A, were transformed into E. coli strain TB1 and protein expression was performed. The cells were suspended in a 50 mM Tris buffer solution (pH 8) containing 50 mM NaCl and thereafter they were disrupted by sonication to extract the protein. The solution containing the disrupted cells was centrifuged (150000 rpm) and the resulting supernatant was loaded on an ion-exchange column Q-Sepharose or MonoQ HRS/5 (product of Amersham-Pharmacia). The equilibrating buffer solution was a 50 mM Tris buffer solution (pH 8) containing 50 mM NaCl and the eluting buffer solution was a 50 mM Tris buffer solution (pH 8) containing 500 mM NaCl; using these buffer solutions, the protein was recovered in 0.5-mL aliquots at a flow rate of 1 mL/min. The eluted fractions were subjected to SDS-PAGE for detecting and quantifying the ISH224-2,6ST-TM2 fused proteins and thereafter used in Biacore analysis. The degree of purification of each protein was approximately 50%.

Onto a sensor chip CMS (product of Riarnre), a bovine albumin (RSA) biotinylated with Ez-Link (registered trademark) NHS-Biotin (13.5 Å) or Ez-Link (registered trademark) NHS-LCLC-Biotin (30.5 Å), each being a product of PIERCE and the parenthesized figures representing the length of the linker between biotin and NHS, was fixed by the amine coupling method. Using HBS-EP (product of Biacore) as the running buffer solution, ISH224-2,6ST-linkTM2, ISH224-2,6ST-3XlinkTM2, and ISH224-2,6ST-5XlinkTM2 were injected at a flow rate of 20 µl/min in 40-µl aliquots (for 2 min) at 25° C. From the resulting sensorgrams, the binding rate constant (ka), the dissociation rate constant (kd) and the dissociation constant (KD) were computed with the aid of analysis software BlAevaluation version 4.1. The results are shown in Tables 5-7. The figures in parentheses represent values that arc outside the range of measurement by Biacore 3000.

When the length of the linker between biotin and BSA was 13.5 Å, no binding between the fused protein and biotin was detected; however, when the linker length was 22.4 Å, each of the three types of fused protein showed a specific binding to biotin (Table 6). Their KD was low on the order of $10^{-8}$ to $10^{-9}$, the lowest value being exhibited by ISH224-2,6ST-5XlinkTM2. When the linker length was 30.5 Å, each of the three types of fused protein also showed a specific binding to biotin (Table 7). Even the KD of ISH224-2,6ST-linkTM2 was low on the order of $10^{-8}$, indicating the strong binding between the fused protein and biotin. ISH224-2,6ST-3XlinkTM2 and ISH224-2,6ST-5XlinkTM2, which had ISH224-2,6ST and TM2 fused together by longer linkers, exhibited an even stronger binding and, in particular, their dissociation rate constant kd decreased below the detection limit of Biacore 3000 ($>5\times10^{-6}$) to the order of $10^{-6}$ or $10^{-7}$. Thus, it was virtually shown that ISH224-2,6ST-3XlinkTM2 and ISH224-2,6ST-5XlinkTM2, once bound to biotin, would hardly be dissociated from it. They had extremely low values of dissociation constant KD which were on the orders of $10^{-10}$ and $10^{-11}$, respectively.

TABLE 5

| Sample name | ka | kd | KD |
| --- | --- | --- | --- |
| BSA-Biotin (13.5 Å) | | | |
| ISH224-2,6-ST-linkTM2 | Not bound | Not bound | Not bound |

TABLE 6

| Sample name | ka | kd | KD |
| --- | --- | --- | --- |
| BSA-LC-Biotin (22.4 Å) | | | |
| ISH224-2,6ST-TM2 | $2.3 \times 10^3$ | $6.6 \times 10^{-5}$ | $2.7 \times 10^{-8}$ |
| ISH224-2,6ST3XlinkTM2 | $2.5 \times 10^3$ | $2.0 \times 10^{-4}$ | $7.8 \times 10^{-8}$ |
| ISH224-2,6ST5XlinkTM2 | $2.3 \times 10^3$ | $1.6 \times 10^{-5}$ | $6.9 \times 10^{-9}$ |

TABLE 7

| Sample name | ka | kd | KD |
| --- | --- | --- | --- |
| BSA-LCLC-Biotin (30.5 Å) | | | |
| ISH224-2,6ST-linkTM2 | $1.0 \times 10^4$ | $1.9 \times 10^{-4}$ | $1.8 \times 10^{-8}$ |
| ISH224-2,6ST3XlinkTM2 | $2.7 \times 10^4$ | $(4.2 \times 10^{-6})$ | $1.6 \times 10^{-10}$ |
| ISH224-2,6ST-5XlinkTM2 | $4.8 \times 10^4$ | $(7.8 \times 10^{-7})$ | $(1.6 \times 10^{-11})$ |
| | $3.0 \times 10^4$ | $(9.3 \times 10^{-7})$ | $(3.1 \times 10^{-11})$ |

Example 5

Fusion Proteins of Tamavidin and Lectin

In this Example, the fusion proteins of tamavidin 2 and lectin were expressed in tobacco cultured cells BY2 and the lectin activities and biotin-binding activities of the fusion proteins were investigated. An immobilization experiment was also conducted.

Lectin Genes

As an example of the tamavidin-lectin fused protein, tamavidin 2 (hereinafter sometimes designated "TM2") and soybean lectin (SBA) or wheat germ lectin (WGA), each being a kind of lectin, were used. The gene coding for soybean agglutinin (NCBI:K00821) was used as SBA whereas each of the genes coding for wheat germ agglutinin isolectin A (WGA-A) (NCBI:M25536) and wheat germ agglutinin isolectin D (WGA-D) (NCBI:M25537) was used as WGA.

The fusion proteins were so designed that TM2 would be located at the C-terminus of lectin. On that occasion, a linker (amino acid sequence 1 xlink: GGGGSG (SEQ ID NO: 57), or 5xlink: GGGGSGGGGSGGGGSGGGGSGGGGS (SEQ ID NO: 62)) was inserted between lectin and TM2. The lectin's signal peptide for causing the lectin-TM2 fused proteins to be secreted into the medium was what was inherent in lectin. Expression was performed in tobacco cultured cells BY2 and pSB24 (Komari et al. 1996) was used as an expression vector.

5-1. Construction of vectors for expressing the fusion proteins of tamavidin 2 and lectin The following three nucleic acids were constructed: a nucleic acid (SBA-1xlink-TM2) coding for a protein consisting of tamavidin 2 fused to SBA via a linker (GGGGSG) (SEQ ID NO: 57), as well as nucleic acids (WGA-A-5xlink-TM2 and WGA-D-5xlink-TM2) each coding for a protein consisting of tamavidin 2 fused to WGA via a 5xlinker (GGGGSGGGGSGGGGSGGGGSGGGGS) (SEQ ID NO: 62) (the respective base sequences: SEQ ID NOs: 63, 65, and 67; the amino acid sequences encoded by the respective base sequences: SEQ ID NOs: 64, 66, and 68).

Designing primers

To construct lectin-TM2 fused genes, primers for joining the lectin and TM2 genes via a linker (1xlink: GGGGSG (SEQ ID NO: 57), or 5xlink: GGGGSGGGGSGGGG-SGGGGSGGGGS (SEQ ID NO: 62)) were designed. Specifically, three primers (SBA-link-TM2 -FW, WGA-A-5xlink-TM2 -F, and WGA-D-5xlink-TM2 -F) were designed, each consisting of the C-terminal site of lectin on the 5' side, the linker in the center, and the TM2 portion on the 3' side; three additional primers (SBA-link-TM2 -RV, WGA-A-5xlink-TM2 -R, and WGA-D-Sxlink-TM2 -R) were also designed, each consisting of the N-terminal site of TM2 on the 5' side, the linker, and a DNA sequence on the 3' side coding for the C-terminal site of lectin in a reverse direction.

Subsequently, three more primers (SBA5' XbaI, WGA-A5' XbaI, and WGA-D5' XbaI) were designed, each consisting of the 5' portion including the signal sequence site of lectin and an upstream sequence coding for a restriction enzyme Xba I cleavage site (TCTAGA); in addition, there was designed a primer (TM2 CtermSacI) consisting of the 3' portion of the TM2 gene and a downstream sequence coding for a restriction enzyme Sac I cleavage site (GAGCTC). The respective primers for constructing the fusion proteins of tamavidin and lectin are identified in Table 8.

TABLE 8

Table 8 Primers for constructing the fusion proteins of tamavidin and lectin

| Name | Sequence (5'-3') | Length |
|---|---|---|
| SBA5'XbaI | AAA<u>TCTAGA</u>ATGGCTACTTCAAAGTT GAAAAC | 32 mer |
| SBA-link-TM2-RV | TGAAGATTGAACGTCTGAaccgctgc caccgccaccGATGGCCTCATG-CAAC AC | 54 mer |
| SBA-link-TM2-FW | GTGTTGCATGAGGCCATCggtggcgg tggcagcggtTCAGACGT-TCAATCTT CA | 54 mer |

TABLE 8-continued

Table 8 Primers for constructing the fusion proteins of tamavidin and lectin

| Name | Sequence (5'-3') | Length |
|---|---|---|
| TM2CtermSac | AAA<u>GAGCTC</u>TTACTTCAACCTCGGTG CG | 28 mer |
| WGA-A5'XbaI | AAA<u>TCTAGA</u>ATGAAGATGATGAGCAC CAG | 29 mer |
| WGA-A-5xlink-TM2-R | TGAAGATTGAACGTCTGAgctgccac cgccaccgctgccaccgccaccgctg ccaccgccaccgctgccaccgccacc gctgccaccgccaccTTCTTGGAGAA GAGTGGA | 111 mer |
| WGA-A-5xlink-TM2-F | TCCACTCTTCTCCAAGAAggtggcgg tggcagcggtggcggtggcagcggtg gcggtggcagcggtggcggtggcagc ggtggcggtggcagcTCAGACGTTCA ATCTTCA | 111 mer |
| WGA-D5'XbaI | AAA<u>TCTAGA</u>ATGAGAAAGATGATGAG CAC | 29 mer |
| WGA-D-5xlink-TM2-R | TGAAGATTGAACGTCTGAgctgccac cgccaccgctgccaccgccaccgctg ccaccgccaccgctgccaccgccacc gctgccaccgccaccTTCTGCGAGAA GAGTGGA | 111 mer |
| WGA-D-5xlink-TM2-F | TCCACTCTTCTCGCAGAAggtggcgg tggcagcggtggcggtggcagcggtg gcggtggcagcggtggcggtggcagc ggtggcggtggcagcTCAGACGTTCA ATCTTCA | 111 mer |

The restriction enzyme recognition sites are underlined.
The linker sequences are written in lower case.
The individual sequences correspond to SEQ ID NOs: 26-35 as counted from the top.

PCR

Two-stage PCR was performed to construct the lectin-TM2 genes. In the firsts stage of PCR, the lectin site was amplified using the primers SBA5' XbaI and SBA-link-TM2-RV, or the primers WGA-A5' XbaI and WGA-A-5xlink-TM2-R, or the primers WGA-D5' XbaI and WGA-D-5xlink-TM2-R, with the soybean or wheat genomic DNA being used as a template, and the TM2 site was amplified using the primers SBA-link-TM2-FW and TM2CtermSac, or the primers WGA-A-5xlink-TM2-F and TM2CtermSac, or the primers WGA-D-5xlink-TM2-F and TM2CtermSac, with a plasmid incorporating the TM2 gene into the vector pTrc99A (see WO02/072817) being used as a template.

The PCR reaction conditions were as follows: to a 20-µl reaction solution, 500 ng of the template DNA, 2 µl of 10×Ex-Taq buffer II (TaKaRa) in the case of 1xlink or 10 µl of 2×GC buffer (TaKaRa) in the case of 5xlink, 1.6 µl of 2.5 mM dNTP, 10 pmoles of each of the primers, and 5 U/µl Ex Taq in 0.1 µl (XX U) were added, and using GeneAmp PCR System 9600 (PERKIN ELMER), one cycle of 96° C.×3 min, 25 cycles of 95° C.×1 min, 60° C.×1 min, and 72° C.×2 min, and one cycle of 72° C.×6 min were performed. As a result, three PCR products were obtained in the lectin portion, with respective sizes of 900 by in the case of SBA-1xlink-TM2, 663 by in the case of WGA-A-5xlink-TM2, and 666 by in the case of WGA-D-5xlink-TM2. In the TM2 portion, three PCR products were also obtained, with respective sizes of 468 by in the case of SBA-1xlink-TM2 and 525 by in each of the cases of WGA-A-5xlink-TM2 and WGA-D-5xlink-TM2.

These PCR products were fractionated by agarose gel electrophoresis in a TAE buffer solution. Each of the DNA fragments was excised together with the gel and recovered using a QIAEX II gel extraction kit (QIAGEN). The extraction method was in accordance with the instructions on the kit.

With those fragments used as templates, the second stage of PCR was performed using the primers SBA5' XbaI and TM2CtermSac in the case of SBA-1xlink-TM2 (the templates were the SBA and TM2 portions of the above-mentioned SBA-1xlink-TM2), or the primers WGA-A5' XbaI and TM2CtermSac in the case of WGA-A-5xlink-TM2 (the templates were the WGA-A and TM2 portions of the above-mentioned WGA-A-5xlink-TM2), or the primers WGA-D5' XbaI and TM2CtermSac in the case of WGA-D-5xlink-TM2 (the templates were the WGA-D and TM2 portions of the above-mentioned WGA-D-5xlink-TM2). The reaction conditions were the same as in the first stage. As a result, three PCR products were obtained, with respective sizes of 1314 by in the case of SBA-1xlink-TM2, 1152 by in the case of WGA-A-5xlink-TM2, and 1155 by in the case of WGA-D-5xlink-TM2.

Cloning

The lectin-TM2 gene fragments obtained by PCR were cloned in the vector pCR4 TOPO (product of Invitrogen). The ligation reaction was in accordance with the instructions on the vector kit. DNA was transferred into *E. coli* TB1 by electroporation and plasmid DNA was extracted in accordance with the usual method (Sambrook et al. 1989, Molecular Cloning, A laboratory manual, $2^{nd}$ edition).

The clones verified to have inserts were treated as follows: using the M13 primer (TaKaRa), the base sequence of each PCR product was determined from both of its ends with an ABI PRISM fluorescence sequencer (Model 310 Genetic Analyzer, Perkin Elmer) to confirm that it had no mutation from the original gene. The plasmid incorporating the genes of interest was double digested with XbaI and Sac I and gel purification was performed by the aforementioned method to recover a DNA fragment.

The recovered DNA fragment was ligated by a ligation kit (product of TaKaRa) to the vector for plants pSB24 (Komari et al. 1996 Plant J) that had been preliminarily digested with Xba I and Sac I to remove the GUS gene. The ligation product was transformed into *E. coli* TB1 and the resulting *E. coli* colonies were subjected to amplification analysis of the inserted gene sites by PCR under the aforementioned conditions using the primers SBA5' XbaI and TM2CtermSac in the case of using SBA-1xlink-TM2 as a template, or the primers WGA-A5' XbaI and TM2CtermSac in the case of using WGA-A-5xlink-TM2 as a template, or the primers WGA-D5' XbaI and TM2CtermSac in the case of using WGA-D-5xlink-TM2 as a template; by checking for the presence of the inserted genes, the vectors for expressing the fusion proteins of tamavidin 2 and lectin, i.e., SBA-link-TM2/pSB24, WGA-A-5xlink-TM2/pSB24, and WGA-D-5xlink-TM2/pSR24, were completed. Using the thus constructed vectors, the lectin-TM2 fused protein genes were transferred into tobacco cultured cells BY2 using the method of Horsch et al. (1985) Science 227: 1229-1231.

5-2. Expression and Functional Analysis of the Fusion Proteins of Tamavidin 2 and Lectin To investigate the activity of lectin as fused to tamavidin 2, the fusion protein of tamavidin 2 and lectin was first expressed in tobacco cultured cells BY2 and purified roughly.

Expression in Tobacco Cultured Cells BY2

Tobacco cultured cells BY2, transformed with SBA-1xlink-TM2, were cultured for 7 days and thereafter a cell fraction was separated from a medium fraction by suction filtration. To 3 g of the recovered cells, 4 ml of 50 mM HEPES/KOH (pH 7.4) was added and after the mixture was ground in a mortar, the cells were disrupted by sonication. The solution containing the disrupted cells was centrifuged (15,000 rpm) and the resulting supernatant was collected as a soluble fraction. As for the medium fraction, ammonium sulfate was added to give 70% saturation; an incubation overnight at 4° C. was followed by centrifugation (14,500 rpm) to precipitate the protein contained in the medium. The resulting precipitate was re-suspended in 1 mL of 50 mM HEPES/KOH (PH 7.4) and dialyzed in 100 mL of 0.1 M HEPES/KOH (PH 7.4); the resulting fraction was used as an enriched medium fraction.

The soluble fraction and the enriched medium fraction of SBA-1xlink-TM2 were subjected to analysis by western blotting. For detection, a rabbit anti-TM2 antibody was used as the primary antibody and an alkali phosphatase labeled anti-rabbit IgG antibody (product of BIO-RAD) was used as the secondary antibody. As a result, a band was detected from SBA-1xlink-TM2 transferred BY2 cells only in the soluble fraction in the vicinity of 45 kDa. This size was in substantial agreement with the molecular mass (43 kDa) obtained after cleavage of the signal peptide from SBA-1xlink-TM2.

Measurement of the Lection Activity of the Fusion Protein (Erythrocyte Agglutination Reaction)

To investigate the lectin activity of the tamavidin 2-SBA fused protein, the erythrocyte agglutination activity was investigated using roughly purified SBA-1xlink-TM2.

Ten milliliters of PBS was added to 2 ml of a stored rabbit blood sample (COSMO BIO) and after centrifugation, the supernatant was removed to yield an erythrocyte fraction. The resulting erythrocyte fraction was washed three times with 10 ml of PBS and thereafter a 5% trypsin solution was added in an amount equal to that of the erythrocyte fraction, followed by incubation under gentle shaking at 37° C. for an hour. The trypsinized erythrocyte fraction was re-washed three times with 10 ml of PBS and thereafter diluted with PBS to prepare a 2% (v/v) erythrocyte suspension.

The protein was extracted from the tobacco cultured cells expressing SBA-1xlink-TM2 and roughly purified on an iminobiotin column The column binding buffer consisted of 50 mM CAPS pH 11 and 50 mM NaCl; the washing buffer consisted of 50 mM CAPS pH 11 and 500 mM NaCl; and the eluting buffer was 50 mM $NH_4OAc$ pH 4. As a control, the protein was extracted from tobacco cultured cells having pSB24 and roughly purified on an iminobiotin column in a similar way.

Then, for activity measurement, SBA (J-OIL MILLS) solution diluted to 1 µg/µl, 10 ng/µl and 0.1 ng/µl, the TM2 solution, and the roughly purified SBA-1xlink-TM2 solution were loaded on a 96-well plate; as a control, a solution of roughly purified proteins from BY2 cells into which the vector pSB24 (expressing the GUS gene) had been introduced was also loaded on the plate; each sample was serially diluted by a factor of 2. To each dilution, a 2% (v/v) erythrocyte suspension was added in an equal amount and after incubation at room temperature for an hour, the samples were tested for the occurrence of erythrocyte agglutination.

Figure 4:
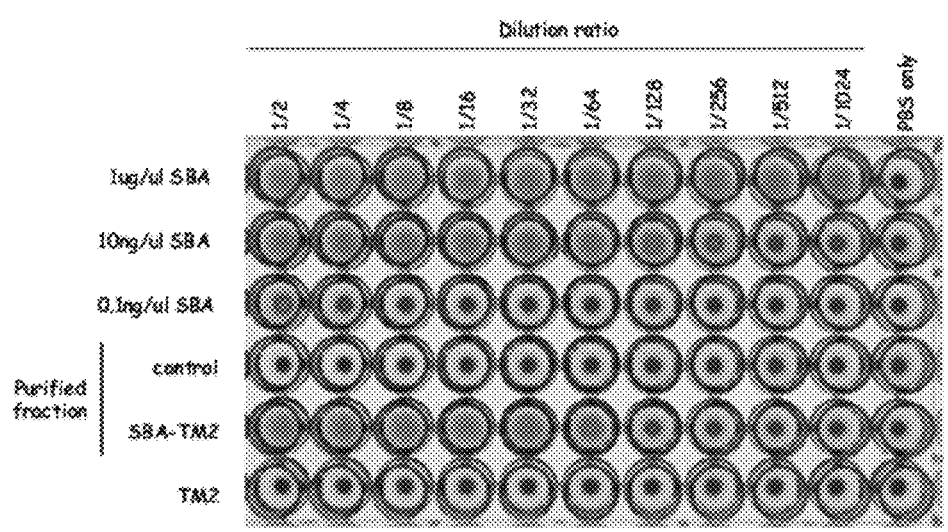
FIG. 4 shows the SBA activity of a fusion protein of tamavidin 2 and lectin (SBA); a crude protein solution was prepared from cultured tobacco cells BY2 into which SBA-1xlink-TM2 had been introduced and roughly purified fractions were measured for their erythrocyte agglutinating activity; a roughly purified fraction of BY2 cells into which pSB24 had been introduced was used as a control.

As a result, an erythrocyte agglutination reaction was also observed in the roughly purified SBA-1xlink-TM2, indicating that the tamavidin 2 fused SBA retained the lectin (SBA) activity (FIG. 4).

Partial Purification and the Sugar Binding Activity of the Expressed Protein

In the next step, a 7-day culture batch of tobacco cultured cells BY2 transformed with SBA-1xlink-TM2 was subjected to column chromatography for crude purification. Soluble fractions prepared from 15 g cells of the 7-day culture $^{batch}$ by the same method as described above were directly used as crude protein samples. These samples were mixed with D-GalNAc agarose (product of SIGMA) equilibrated with 50 mM HEPES/KOH (pH 7.4) and incubated at room temperature for an hour before preparing an open column. For elution, an eluting buffer (50 mM HEPES/KOH (pH 7.4), 0.1% Nonidet P40, and 20 mM GalNAc) was used.

Figure 5:
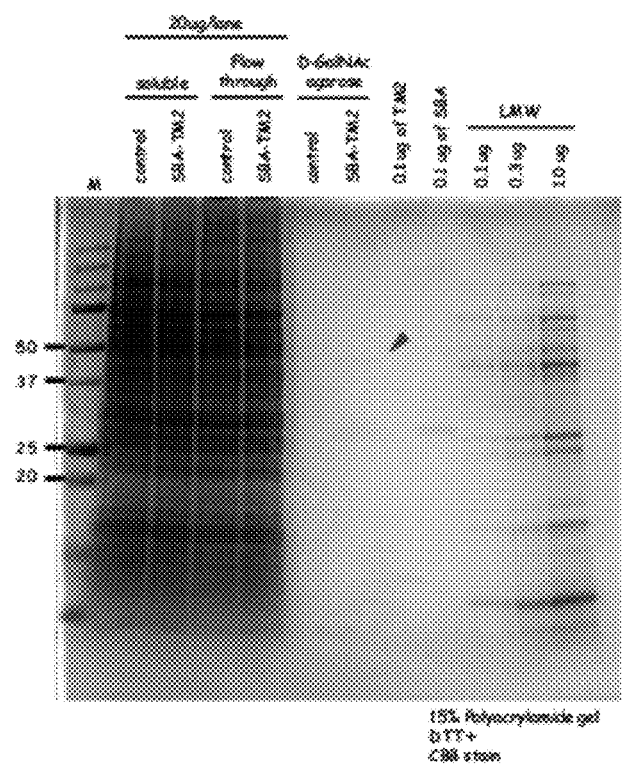
FIG. 5 shows simplified purification of a fusion protein of tamavidin 2 and lectin (SBA); the lectin-TM2 fused protein was reacted with D-GalNAc agarose and purified; panel A shows the result of CBB staining after SDS-PAGE, and panel B the result of western blot analysis; Control refers to a sample of BY2 cells transformed with the pSB24 vector; the position of the fusion protein is indicated by the arrows.
Figure 5:
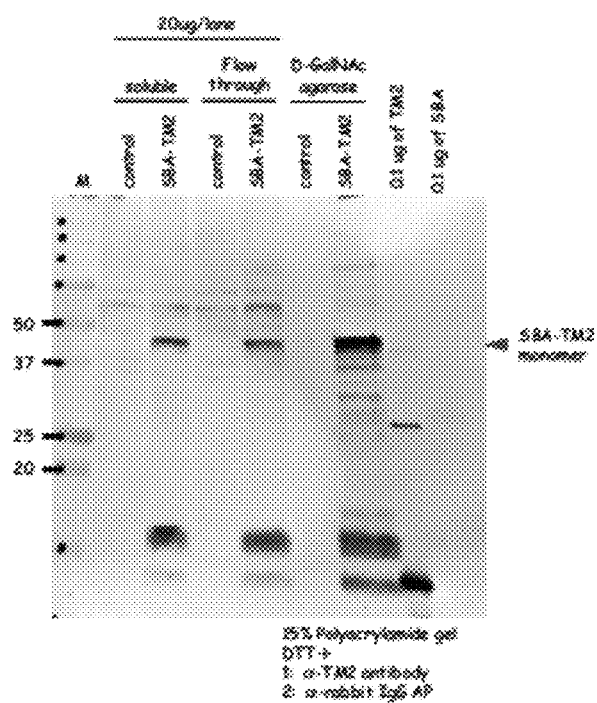

The purified protein was detected by CBB staining that followed SDS-PAGE (FIG. 5A), as well as by western blotting analysis in which, as described above, a rabbit anti-TM2 antibody was used as the primary antibody and an alkali phosphatase labeled anti-rabbit IgG antibody (product of BIO-RAD) was used as the secondary antibody (FIG. 5B). As a result, SBA-1xlink-TM2 was detected in an eluted fraction (indicated by arrows in FIGS. 5A and 5B). Thus, SBA-1xlink-TM2 was found to bind to D-GalNAc agarose, indicating that the tamavidin 2 fused SBA retained the sugar chain binding activity. Subsequently, the purified protein solution from which the band of SBA-1xlink-TM2 was detected was dialyzed in 50 mM HEPES/KOH (pH 7.4). By this operation, 7.5 µg of SBA-1xlink-TM2 was recovered. The degree of purification was 26%.

Assay of the Biotin Binding Activity of the Fusion Protein of Tamavidin 2 and Lectin The biotin binding ability of the SBA-1xlink-TM2 fused protein was analyzed by using Biacore 3000 (product of BIACORE). Fractions roughly purified from a 7-day culture batch of tobacco cultured cells BY2 transformed with SBA-1xlink-TM2 by the aforementioned method were used as samples to be analyzed.

Onto a sensor chip CM5 (product of BIACORE), a bovine serum albumin (BSA) biotinylated with EZ-Link™ NHS-LCLC-Biotin (30.5 Å) (product of PIERCE and the parenthesized figure represents the length of the linker between biotin and NHS) was fixed by the amine coupling method. Using HBS-EP (product of BIACORE) as the running buffer solution, SBA-1xlink-TM2 was injected at a flow rate of 20 µl/min in 40-µl aliquots (for 2 min) at a temperature of 25° C. From the resulting sensorgram, the binding rate constant (ka), the dissociation rate constant (kd) and the dissociation constant (KD) were computed with the aid of analysis software Biaevaluation version 4.1. The result is shown in Table 9. SBA-1xlink-TM2 interacted specifically with biotin and its KD was low on the order of $10^{-9}$, indicating the strong binding to biotin.

From the foregoing, it can be said that the fusion protein of lectin and tamavidin 2 was successfully expressed in plant cells while retaining both the sugar binding activity of lectin and the biotin binding activity of tamavidin 2.

TABLE 9

| Result of Biacore analysis | | | |
|---|---|---|---|
| Sample name | ka | kd | KD |
| SBA-1xlink-TM2 | $3.8 \times 10^4$ | $5.9 \times 10^{-5}$ | $1.5 \times 10^{-9}$ |

Example 6

Fusion Proteins of Tamavidin and Protein A

In this Example, fusion proteins of tamavidin 2 and protein A were expressed in *E. coli* and the fusion proteins as purified were immobilized on biotinylated plates by tamavidin-biotin bonding. The thus prepared protein A plates were reacted with a polyclonal antibody, which was immobilized by making use of its affinity for protein A and its antigen binding activity was investigated. As a control, the polyclonal antibody directly immobilized on the plate by hydrophobic bonding was used. Details are given below.

The structures of the protein A gene and the fusion proteins

Protein A derived from *Staphylococcus aureus* was used. The *Staphylococcus aureus* protein A (spa) gene was assigned from the Biological Resource Center of the National Institute of Technological Evaluation (NBRC), Incorporated Administrative Agency. NBRC distributes genomic DNA clones derived from two strains of Staphylococcus aureus, N315 and MW2, and the spa genes of these two strains, NBRC G04-000-249 (ORF ID: SA0107) and NBRC G05-000-311 (ORF ID: MW0084), were used.

The fusion proteins were so designed that tamavidin 2 (which is hereinafter sometimes written as "TM2") would be located at the C-terminus of spa. On that occasion, a linker (amino acid sequence 1xlink: GGGGSG (SEC, ID NO: 57), or 5xlink: GGGGSGGGGSGGGGSGGGGSGGGGS (SEQ ID NO: 62)) was inserted between spa and TM2. To cause the spa-TM2 fused proteins to be secreted into the medium, the signal peptide of spa was used as such. Further, the cell wall binding domain present at the C-terminus of spa (Uhlen et al. (1984) J. Biol. Chem. 259: 1695-1702) was removed. Expression was performed in *E. coli* and an untagged pTrc99A (product of Pharmacia) was used as an expression vector.

6-1. Construction of Vectors for Expressing the Fusion Proteins of Tamavidin 2 and Protein A The spa gene has such a structured that it consists of, in order from the N-terminus, the signal peptide, five IgG binding domains, and the cell wall binding domain. Using PCR, four genes were constructed that coded for fused proteins having the sequence of TM2 joined to the C-terminus of the IgG binding domains in spa.

1. spa(SA)ΔC-1xlink-TM2 (base sequence 69, amino acid sequence 70)
2. spa(MW)ΔC-1xlink-TM2 (base sequence 71, amino acid sequence 72)
3. spa(SA)ΔC-5xlink-TM2 (base sequence 73, amino acid sequence 74)
4. spa(MW)ΔC-5xlink-TM2 (base sequence 75, amino acid sequence 76)

Designing primers

To construct spa-TM2 fused genes, primers for joining the spa and TM2 genes via a linker (1xlink: GGGGSG (SEQ ID NO: 57), or 5xlink: GGGGSGGGGSGGGGSGGGGSGGGGS (SEQ ID NO: 62)) were designed. Specifically, two primers (spaΔC-1xlink-TM2 -F and spaΔC-5xlink-TM2 -F) were designed, each consisting of the spa IgG binding site on the 5' side, the linker in the center, and the TM2 portion on the 3' side; and two additional primers (spaΔC-1xlink-TM2 R and spaΔC-5xlink-TM2 -R) were also designed, each consisting of the TM2 N-terminal site on the 5' side, the linker, and a DNA sequence on the 3' side coding for the spa IgG binding site in a reverse direction.

Subsequently, two more primers (sp-spa 5' NcoI-F and TM2CtermBam) were designed, the first consisting of the 5' portion including the signal sequence site of spa and an upstream sequence coding for a restriction enzyme Nco I cleavage site (CCATGG) and the second consisting of the 3' portion of the TM2 gene and a downstream sequence coding for a restriction enzyme BamH I cleavage site (GGATCC). The respective primers for constructing the fusion proteins of tamavidin and spa are identified in Table 10.

TABLE 10

Table 10 Primers for constructing the fusion proteins of tamavidin and protein A

| Name | Sequence (5'-3') | Length |
|---|---|---|
| sp-spa 5'NcoI-F | AAA<u>CCATGG</u>CCATGAAAAAGAAA AACATTTAT | 32 mer |
| spaΔC-1xlink-TM2-R | TGAAGATTGAACGTCTGAaccgc tgccaccgccaccTTTTGGTGCT TGTGCATC | 54 mer |
| spaΔC-5xlink-TM2-R | TGAAGATTGAACGTCTGAgctgc caccgccaccgctgccaccgcca ccgctgccaccgccaccgctgcc accgccaccgctgccaccgccac cTTTTGGTGCTTGTGCATC | 111 mer |
| spaΔC-1xlink-TM2-F | GATGCACAAGCACCAAAAggtgg cggtggcagcggtTCAGACGTTC AATCTTCA | 54 mer |
| spaΔC-5xlink-TM2-F | GATGCACAAGCACCAAAAggtgg cggtggcagcggtggcggtggca gcggtggcggtggcagcggtggc ggtggcagcggtggcggtggcag cTCAGACGTTCAATCTTCA | 111 mer |
| TM2CtermBam | TTT<u>GGATCC</u>TTACTTCAACCTC GGTGCG | 28 mer |

The restriction enzyme recognition sites are underlined.
The linker sequences are written in lower case.
The individual sequences correspond to SEQ ID NOs: 36-41 as counted from the top.

PCR

Two-stage PCR was performed to construct the spa-TM2 genes. In the first stage of PCR, the spa IgG binding site was amplified using the primers sp-spa 5' NcoI-F and spaΔC-1xlink-TM2-R or spaΔC-5xlink-TM2-R, with a plasmid incorporating a spa-encoding genomic DNA into a vector pUC18 being used as a template, and the TM2 site was amplified using the primers spaΔC-1xlink-TM2-F or spaΔC-5xlink-TM2-F and TM2CtermBam, with a plasmid incorporating the TM2 gene into the vector pTrc99A (see WO02/072817) being used as a template.

The PCR reaction conditions were as follows: to a 20-μl reaction solution, 500 ng of the template DNA, 2 μl of 10×Ex-Taq buffer II (TaKaRa) in the case of 1xlink or 10 μl of 2×GC buffer (TaKaRa) in the case of 5xlink, 1.6 μl of 2.5 mM dNTP, 10 pmoles of each of the primers, and 0.1 μl of 5 U/μL Ex Taq were added, and using GeneAmp PCR System 9600 (PERKIN ELMER), one cycle of 96° C.×3 min, 25 cycles of 95° C.×1 min, 60° C.×1 min, and 72° C.×2 min, and one cycle of 72° C.×6 min were performed. As a result, two PCR products were obtained in the spa portion, with sizes of 854 by and 912 by in the respective cases of 1xlink and 5xlink-TM2; in the TM2 portion, two PCR products were also obtained, with sizes of 468 by and 525 by in the respective cases of 1xlink and 5xlink.

These PCR products were fractionated by agarose gel electrophoresis in a TAE buffer solution. Each of the DNA fragments was excised together with the gel and recovered using a QIAEX II gel extraction kit (QIAGEN). The extraction method was in accordance with the instructions on the kit.

With those fragments used as templates, the second stage of PCR was performed using the primers sp-spa 5' NcoI-F and TM2CtermBam. The reaction conditions were the same as in the first stage. As a result, two PCR products were obtained, with respective sizes of 1268 by and 1325 by in the respective cases of 1xlink and 5xlink.

Cloning

The spa-TM2 gene fragments obtained by PCR were cloned in the vector pCR4 TOPO (product of Invitrogen). The ligation reaction was in accordance with the instructions on the vector kit. DNA was transferred into *E. coli* TB1 by electroporation and plasmid DNA was extracted in accordance with the usual method (Sambrook et al. 1989, Molecular Cloning, A laboratory manual, $2^{nd}$ edition). The clones verified to have inserts were treated as follows: using the M13 primer (TaKaRa), the base sequence of each PCR product was determined from both of its ends with an ABI PRISM fluorescence sequencer (Model 310 Genetic Analyzer, Perkin Elmer) to confirm that it had no mutation from the original rule. The plasmid incorporating the genes of interest was double digested with Nco I and BamH I and gel purification was performed by the aforementioned method to recover a DNA fragment. This fragment was ligated by a ligation kit (product of TaKaRa) to the vector pTrc99A for expression in *E. coli* that had been preliminarily digested with Nco I and BamH I.

The ligation product was transformed into *E. coli* BL21 and the resulting *E. coli* colonies were subjected to amplification analysis of the inserted gene sites by PCR under the aforementioned conditions using sp-spa 5' NcoI-F and TM2CtermBam as templates; by checking for the presence of the inserted genes, the vectors for expressing the fusion proteins of tamavidin 2 and spa, i.e., spa(SA)ΔC-1xlink-TM2/pTrc99A, spa(MW)ΔC-1xlink-TM2/pTrc99A, spa(SA)ΔC-5xlink-TM2/pTrc99A, and spa(MW)ΔC-5xlink-TM2/pTrc99A, were completed.

6-2. Expression and Partial Purification of the Fusion Proteins of Tamavidin 2 and Spa To investigate the effect of immobilization of protein A on the substrate by means of fusion to tamavidin 2, the fusion proteins of tamavidin 2 and spa were first expressed in *E. coli* and purified roughly.

Expression in *E. coli* and the IgG Binding Activity of the Expressed Proteins

Two batches of *E. coli* BL21, one transformed with spa (SA)ΔC-1xlink-TM2/pTrc99A and the other with spa(MW)ΔC-1xlink-TM2/pTrc99A, were inoculated in 50 mL of an LB medium containing the antibiotic ampicillin (final concentration: 100 μg/mL) and cultured under shaking at 30° C. until the absorbance at $OD_{600}$ reached 0.5. Thereafter, 1 mM IPTG was added and shake culture was performed for another 5 hours at 30° C. The culture broth (50 mL) was separated into an *E. coli* fraction and a medium fraction by centrifugation. The *E. coli* fraction was suspended in 3 mL of 0.1 M HEPES/KOH (pH 7.4) and the cells were disrupted by sonication. The solution containing the disrupted cells was centrifuged (15,000 rpm) and the resulting supernatant was collected as a soluble fraction. The precipitate was suspended in 3 mL of 0.1 M HEPES/KOH (pH 7.4) containing 8 M urea and thereafter subjected to another disruption by sonication to collect an insoluble fraction. As for the medium fraction, ammonium sulfate was added to give 70% saturation; an incubation overnight at 4° C. was followed by centrifugation (14,500 rpm) to precipitate the protein contained in the medium. The resulting precipitate was re-suspended in 1 mL of 0.1 M HEPES/KOH (PH 7.4) and dialyzed in 100 mL of 0.1 M HEPES/KOH (PH 7.4); the resulting fraction was used as an enriched medium fraction.

The soluble fraction and the enriched medium fraction of each of spa(SA)ΔC-1xlink-TM2 and spa(MW)ΔC-1xlink-TM2 were subjected to analysis by western blotting. For detection, an alkali phosphatase labeled rabbit IgG antibody (product of BIO-RAD) was used. As a result, a band was detected from the spa(SA)ΔC-1xlink-TM2 and spa(MW)ΔC-1xlink-TM2 expressing *E. coli* in both the soluble fraction and the enriched medium fraction in the vicinity of 40 kDa. This size was in substantial agreement with the molecular mass (42 kDa) obtained after cleavage of the signal peptide from spa(SA)ΔC-1xlink-TM2 and spa(MW)ΔC-1xlink-TM2. What is more, since the detection was possible by using the alkali phosphatase labeled rabbit IgG antibody alone (this antibody is usually employed as the secondary antibody), the tamavidin 2 fused spa was shown to retain the IgG binding activity.

Partial Purification

In the next step, 50 mL each of the culture broths of *E. coli* transformed with spa(SA)ΔC-1xlink-TM2/pTrc99A and spa(MW)ΔC-1xlink-TM2/pTrc99A was subjected to column chromatography for partial purification of spa(SA)ΔC-1xlink-TM2 and spa(MW)ΔC-1xlink-TM2. The medium fractions of *E. coli* induced for expression by the same method as described above were directly used as crude protein samples. These samples were mixed with IgG sepharose™ 6 Fast Flow (product of GE Healthcare) equilibrated with a TST solution (50 mM Tris buffer solution, 150 mM NaCl, and 0.05% Tween 20; pH 7.6) and incubated at room temperature for an hour before preparing an open column. For elution, a 0.5 M acetic acid solution (pH 3.4) was used.

Figure 6:
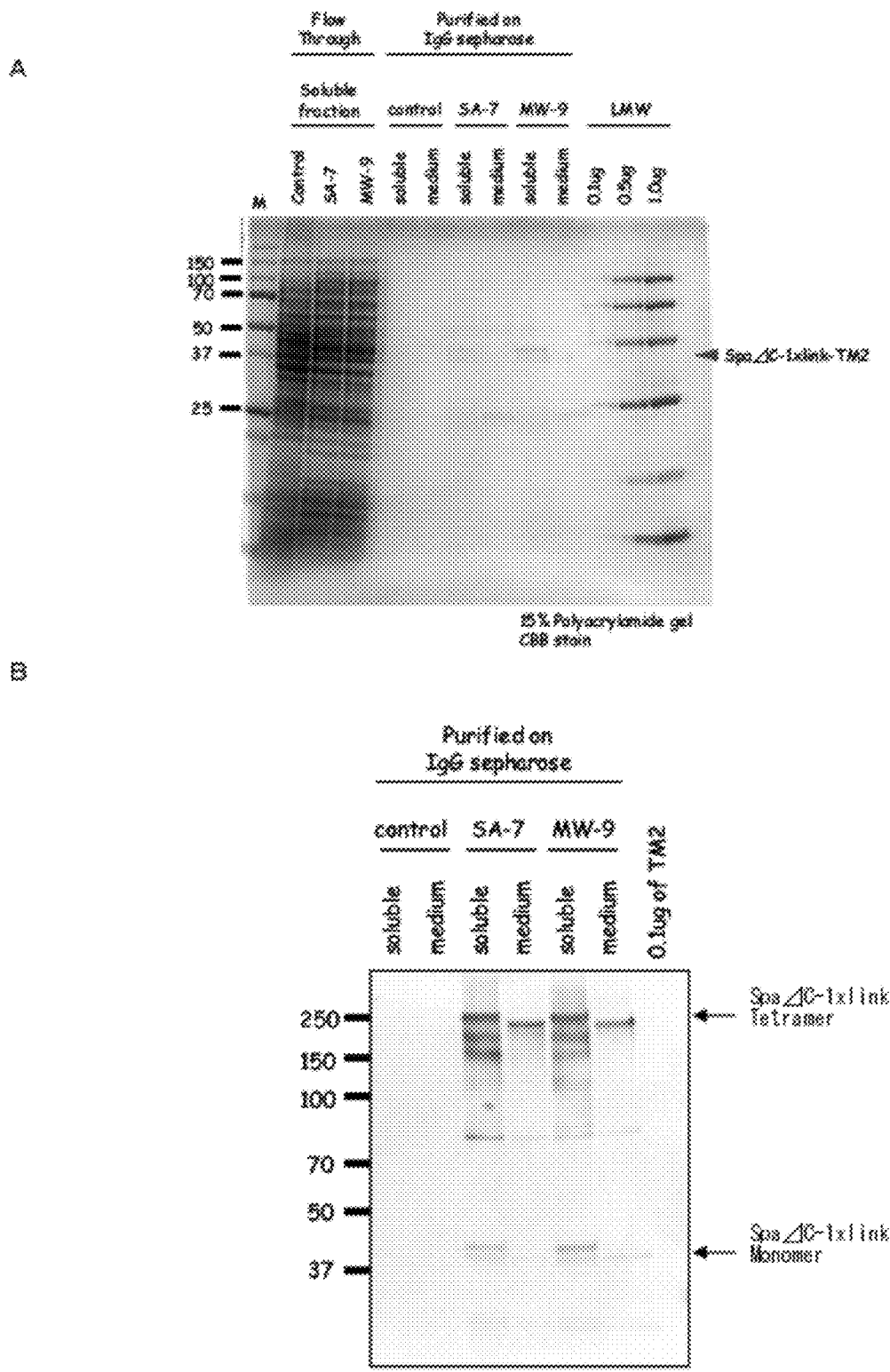
FIG. 6 shows simplified purification of a fusion protein of tamavidin 2 and protein A; the spa-TM2 fused protein was reacted with IgG sepharose™ 6 Fast Flow (product of GE Healthcare) and purified; panel A shows the result of CBB staining after SDS-PAGE, and panel B the result of western blot analysis using an alkali phosphatase labeled rabbit IgG antibody; Control refers to an *E. coli* derived sample having only the expression vector, SA-7 refers to spa(SA)ΔC-1xlink-TM2, and MW-9 refers to spa(MW)ΔC-1xlink-TM2; the position of the fusion protein is indicated by the arrows.

In the same manner as described above, the purified proteins were verified by SDS-PAGE-CBB staining (FIG. 6A), as well as by western blotting analysis using an alkali phosphatase labeled rabbit IgG antibody (FIG. 6B). Note that in the latter case, in order to examine the state of protein association, the protein samples were added to a reducer free SDS sample buffer and subjected to SDS-PAGE without heating. As a result, both fusion proteins were purified by IgG sepharose, indicating that the tamavidin 2 fused spa retained the IgG binding activity. Specifically, in the SDS-PAGE-CBB staining experiment, two bands were detected in the soluble fractions in the vicinity of 40 kDa (as indicated by an arrow in FIG. 6A). These bands were considered to be the fusion proteins in view of their molecular mass. In western analysis, the fusion proteins were detected in the soluble fractions both as a monomer (in two bands) and as a tetramer (in several bands) (FIG. 6B). The monomer bands were of the same size as detected in the aforementioned SDS-PAGE. From the medium enriched fractions, a single band was detected at each of the monomer and tetramer sizes (FIG. 6B). Also note that in the western analysis under consideration, the detection was possible by using the alkali phosphatase labeled rabbit IgG antibody alone as in the case described above, so the tamavidin 2 fused spa was shown to retain the IgG binding activity.

The purified protein solutions from which the bands of spa(SA)ΔC-1xlink-TM2 and spa(MW)ΔC-1xlink-TM2 were detected (medium fractions of SA-7 and MW-9 in FIG. 6B) were freeze-dried. The series of operations described above allowed spa(SA)ΔC-1xlink-TM2 and spa(MW)ΔC-1xlink-TM2 to be recovered in respective amounts of 10.8 μg and 12.6 μg.

6-3. Immobilization of the Tamavidin 2-Spa Fused Proteins and Spa, and Comparative Analyses of Their Activities by ELISA To investigate the effect of immobilization of spa protein A on a substrate by means of fusion to tamavidin 2, roughly purified spa(SA)ΔC-1xlink-TM2 and spa(MW)ΔC-1xlink-TM2 were immobilized on microplates, followed by immobilization of a soybean lectin antibody, and subjected to ELISA analysis, with the soybean lectin detection sensitivity being used as an index.

ELISA Analysis

The roughly purified spa(SA)ΔC-1xlink-TM2 and spa(MW)ΔC-1xlink-TM2 were each conditioned with PBS (137 mM NaCl, 2.68 mM KCl, 8.1 mM $Na_2HPO_4$, and 1.47 mM $KH_2PO_4$) to give a concentration of 20 ng/μL and each preparation was loaded in 100-μL aliquots on a biotinylated 96-well microplate (Model No. 15151; product of PIERCE). The respective plates were left to stand still for 30 minutes at room temperature to immobilize the fusion proteins by tamavidin-biotin bonding. Thereafter, the individual wells in each plate were washed three times with a TBS buffer solution containing 0.1% Tween 20 (TTBS). Then, antibody immobilization was performed as follows: a rabbit anti-SBA antibody (product of EY LABORATORIES) was conditioned with PBS to give a concentration of 50 ng/μl and loaded in 100-μl aliquots on the plates to which the fusion proteins were preliminarily fixed, as well as on control plates, i.e., hydrophobic plates (Model No. 15031; product of PIERCE) and protein A coated plates [as prepared by diluting protein A (nacalai tesque) with PBS to give a concentration of 5 ng/μl, then loading it in 50-μl aliquots on hydrophobic plates (Model No. 15031; product of PIERCE), leaving the plates to stand still overnight at room temperature, and thereafter washing the individual wells in each plate three times with a TBS buffer solution containing 0.1% Tween 20 (TTBS)]; the respective plates were then left to stand still overnight at room temperature. The biotinylated plates and the protein A coated plates each had the rabbit anti-SBA antibody immobilized by protein A-IgG bonding, whereas the hydrophobic plates achieved the same effect by hydrophobic bonding.

Subsequently, those plates were washed with TTBS three times and after adding 300 μl of TTBS containing 0.5% BSA, the plates were left to stand still at room temperature for an hour to effect blocking. After performing another washing with TTBS three times, horseradish peroxidase labeled SBA (J-OIL MILLS) solutions serially diluted with TTBS from 100 ng/μl to 0.1 pg/μl were loaded in 100-μL aliquots. As controls, similarly diluted horseradish peroxidase labeled SBA solutions were also loaded on biotinylated plates to which the rabbit anti-SBA antibody was not fixed and on hydrophobic plates. After the addition of horseradish peroxidase labeled SBA, the respective plates were left to stand still at room temperature for an hour so as to carry out a reaction with the rabbit anti-SBA antibody immobilized on them. After three more washings with TTBS, 100 μl of 1-Step™ Ultra TMB-ELISA was added in order to detect the horseradish peroxidase labeled SBA bound to the individual wells; when a color formation was recognized to have occurred, 100 μl of 2 M sulfuric acid was added to stop the reaction and the absorbance at 450 nm was measured by a plate reader Infinite M200 (product of TECAN).

The values of applicable data were obtained by the following procedure: in each of the concentration ranges of horseradish peroxidase labeled SBA, the relevant absorbances of the control samples in each plate (which were not immobilized but to which only the horseradish peroxidase labeled SBA was added) were also measured and the absorbance values for those controls were subtracted from the absorbance for each of the concentration ranges in which the rabbit anti-SBA antibody was immobilized. Further, the amount of antibodies immobilized via spa-TM2 fused protein, the amount of antibodies directly immobilized by hydrophobic bonding, and the amount of antibodies immobilized via protein A immobilized by hydrophobic bonding were quantified to compute the amount of horseradish peroxidase labeled SBA as detected per unit amount of antibodies immobilized.

In the next step, the sensitivity of rabbit anti-SBA antibody detection using horseradish peroxidase labeled SBA (SBA-HRP) was measured. The amount of SBA-HRP bound to 1 ng of the rabbit anti-SBA antibody was calculated and as it turned out, compared to the case where the antibody was bound to the plate by hydrophobic bonding, the antigen SBA-HRP was bound in 2.3 to 4.5 times greater amounts when the antibody was bound after the tamavidin-protein A (spa) fused protein was bound to the biotinylated plate (Table 11). From this fact, it was shown that when the polyclonal antibody (IgG antibody) was immobilized on the substrate via the protein A-tamavidin fused protein, the detection sensitivity was approximately 2-4 times higher than when it was immobilized by hydrophobic bonding. It was also found that sensitivity was about 2 to 3 times higher than when the antibody was immobilized on the plate to which protein A was directly fixed by hydrophobic bonding (see the data for 10 pg/µl and 1 pg/µl as the concentration of added SBA-HRP in Table 11).

TABLE 11

Amount of SBA-HRP bound to 1 ng of rabbit anti-SBA antibody

| Concentration of added SBA-HRP (pg/µl) | Hydrophobic bonding | spa(SA)ΔC-1xlink-TM2 | spa(SA)ΔC-1xlink-TM2 | Protein A |
|---|---|---|---|---|
| 100 | 1 | 4.3 | 4.5 | 3.9 |
| 10 | 1 | 3.1 | 2.3 | 1.2 |
| 1 | 1 | 2.9 | 3.0 | 0.9 |

At respective concentrations of SBA-HRP, data are shown as relative values, with the amount of binding by hydrophobic bonding being taken as unity.

6-4. Assay of the Biotin-Binding Activities of the Fusion Proteins of Tamavidin 2 and Spa Biacore 3000 (product of BIACORE) was used to analyze the biotin-binding ability of the spa-TM2 fused proteins. The fusion protein, spa-TM2, secreted in the medium of a culture broth was roughly purified by the method described above and the resulting fractions were used as the samples to be analyzed.

Onto a sensor chip CM5 (product of BIACORE), a bovine serum albumin (BSA) biotinylated with EZ-Link™ NHS-LCLC-Biotin (30.5 Å) (product of PIERCE and the parenthesized figure represents the length of the linker between biotin and NHS) was fixed by the amine coupling method. Using HBS-EP (product of BIACORE) as the running buffer solution, spa(SA)ΔC-1xlink-TM2 and spa(MW)ΔC-1xlink-TM2 were injected at a flow rate of 20 µl/min in 40-µl aliquots (for 2 min) at a temperature of 25° C. From the resulting sensorgram, the binding rate constant (ka), the dissociation rate constant (kd) and the dissociation constant (KD) were computed with the aid of analysis software Biaevaluation version 4.1. The results are shown in Table 12. The fusion proteins, spa(SA)ΔC-1xlink-TM2 and spa(MW)ΔC-1xlink-TM2, interacted specifically with biotin and their KD values were low on the order of $10^{-8}$, indicating the strong binding to biotin.

TABLE 12

Results of Biacore analysis

| Sample name | ka | kd | KD |
|---|---|---|---|
| spa (SA) ΔC-1xlink-TM2 | $7.6 \times 10^3$ | $2.0 \times 10^{-4}$ | $2.7 \times 10^{-8}$ |
| spa (MW) ΔC-1xlink-TM2 | $1.6 \times 10^4$ | $1.8 \times 10^{-4}$ | $1.2 \times 10^{-8}$ |

Example 7

Tamavidin Fused Protein Expressing Vectors

In this Example, expression vectors for expressing tamavidin 2 fused proteins in *E. coli* were constructed. Two expression vectors were constructed, one for allowing tamavidin 2 to be fused to the N-terminus of a desired protein, and the other for allowing tamavidin 2 to be fused to the C-terminus. A specific explanation is given below.

7-1. Construction of Vectors for Expressing Tamavidin 2 Fused Proteins

The vectors for expressing tamavidin 2 (hereinafter sometimes written as "TM2") fused proteins have such a structure that it comprises pTrc99A (product of Pharmacia) as a backbone and that between two sites of recognition by restriction enzymes Nco I and Hind III, TM2, a linker site for fusing TM2 to a desired protein, a multiple cloning site (hereunder "MCS") for incorporating the gene coding for the desired protein, a sequence for the site of recognition by an enterokinase (hereunder "EK") that removes the TM2 sequence after the desired proein has been expressed, and a His tag sequence were incorporated in the orders indicated below.

Figure 7:
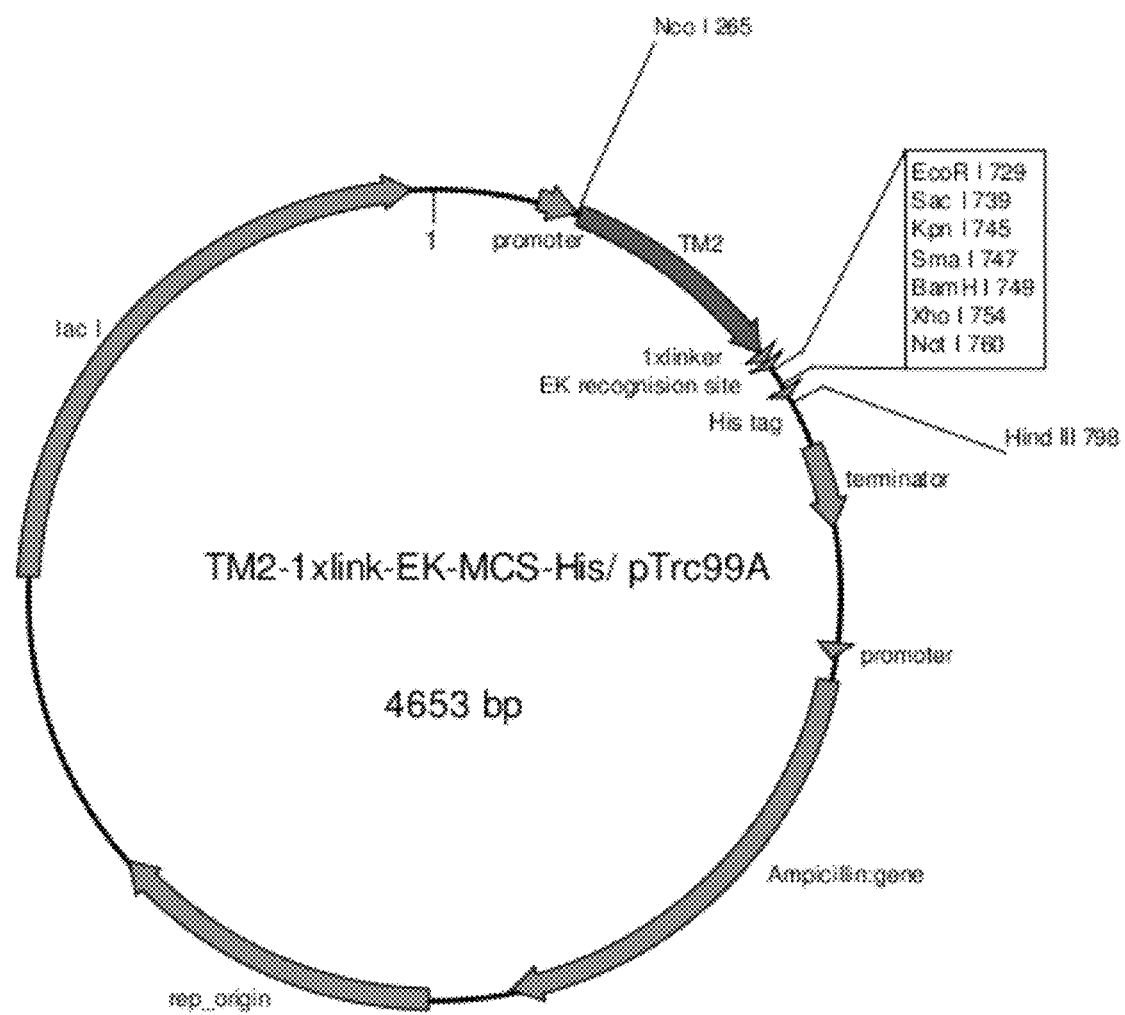
FIG. 7 shows a plasmid map of TM2-1xlink-EK-MCS-His/pTrc99A.
Figure 8:
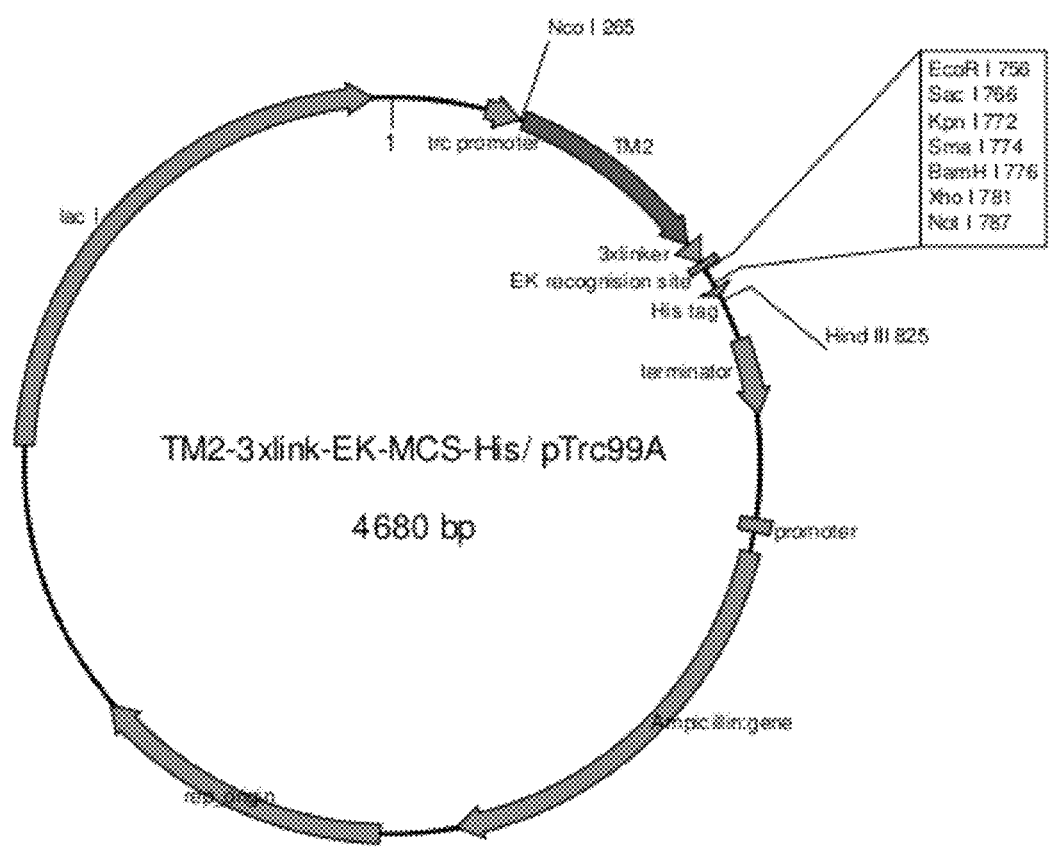
FIG. 8 shows a plasmid map of TM2-3xlink-EM-MCS-His/pTrc99A.
Figure 9:
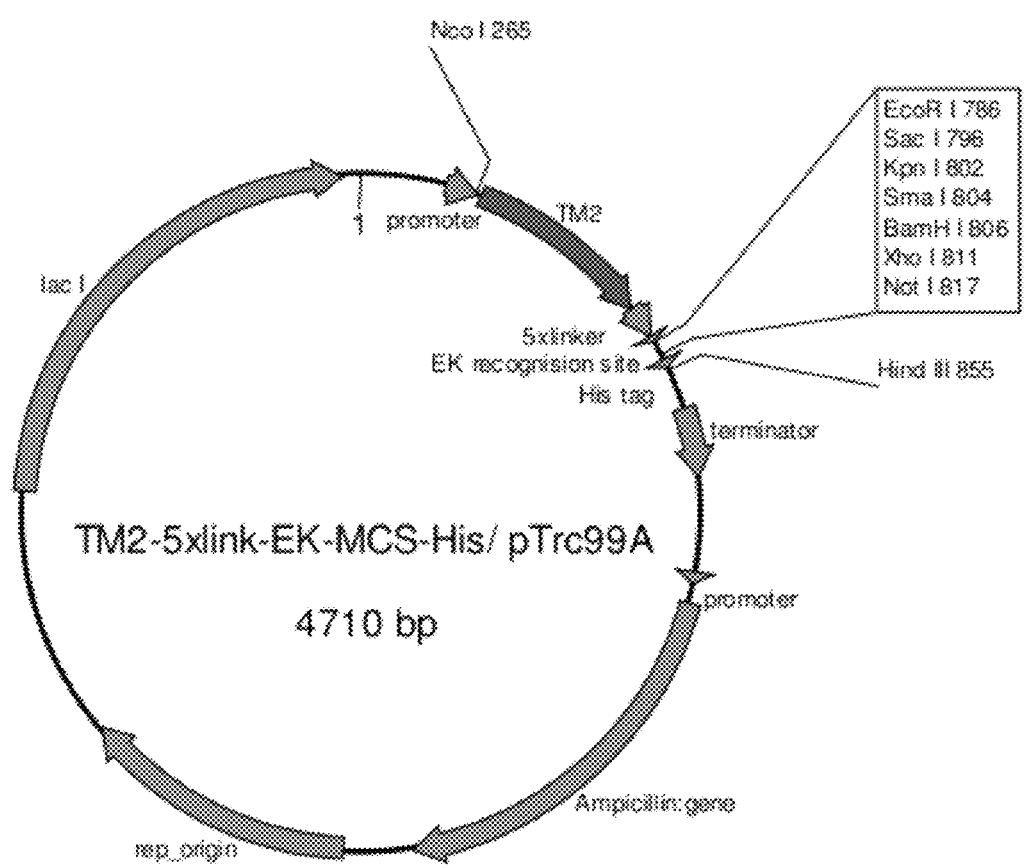
FIG. 9 shows a plasmid map of TM2-5xlink-EM-MCS-His/pTrc99A.
Figure 10:
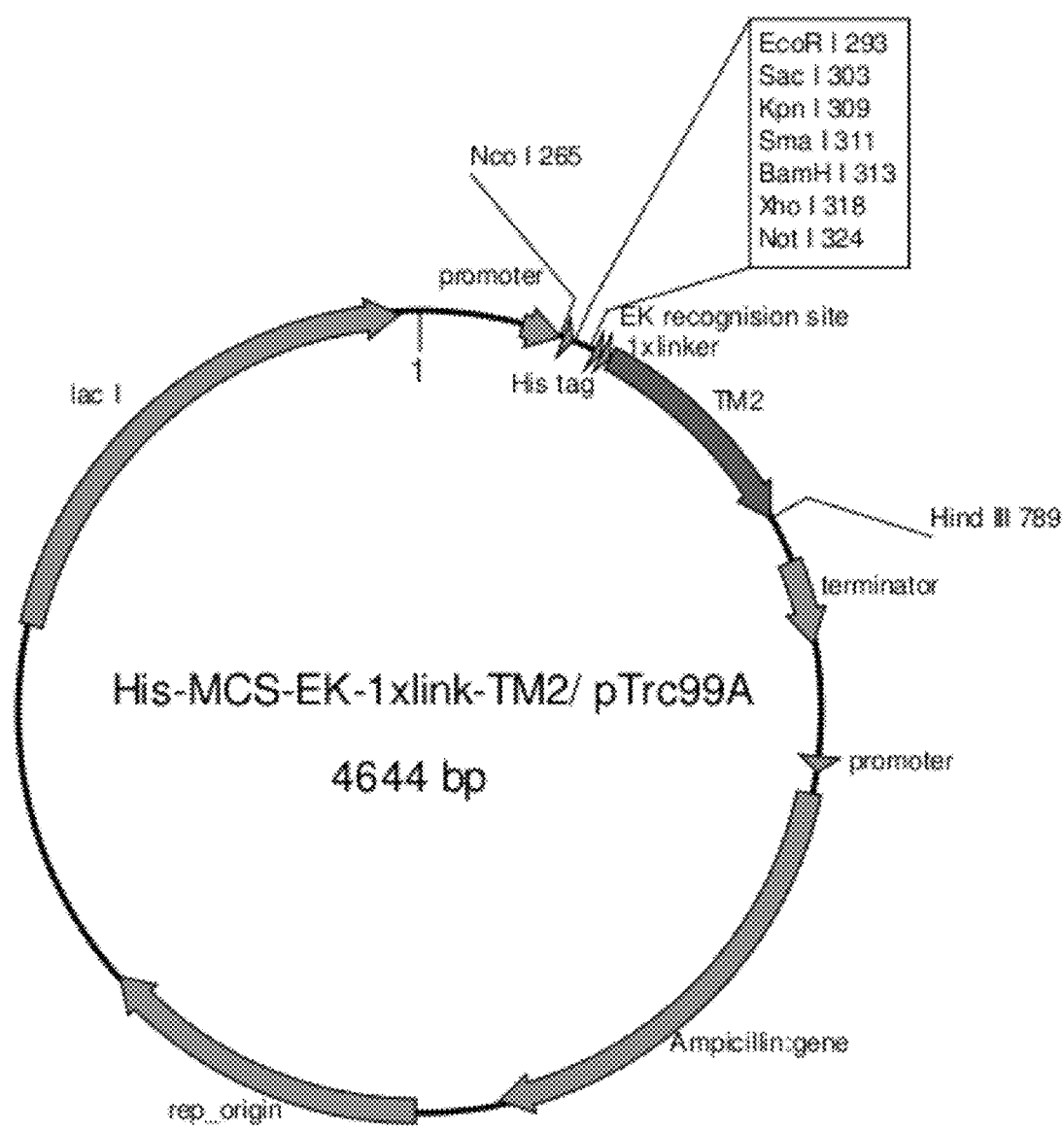
FIG. 10 shows a plasmid map of His-MCS-EK-1xlink-TM2/pTrc99A.
Figure 11:
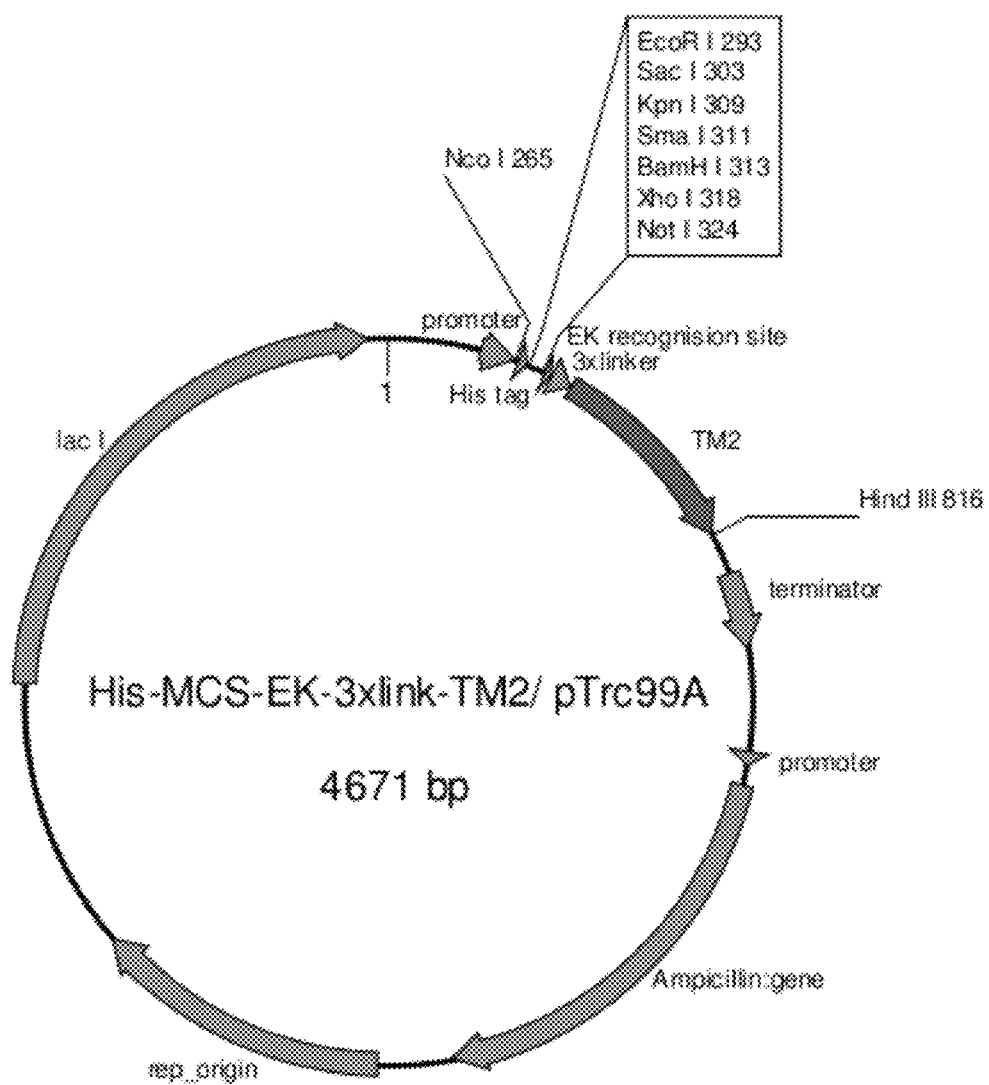
FIG. 11 shows a plasmid map of His-MCS-EK-3xlink-TM2/pTrc99A.
Figure 12:
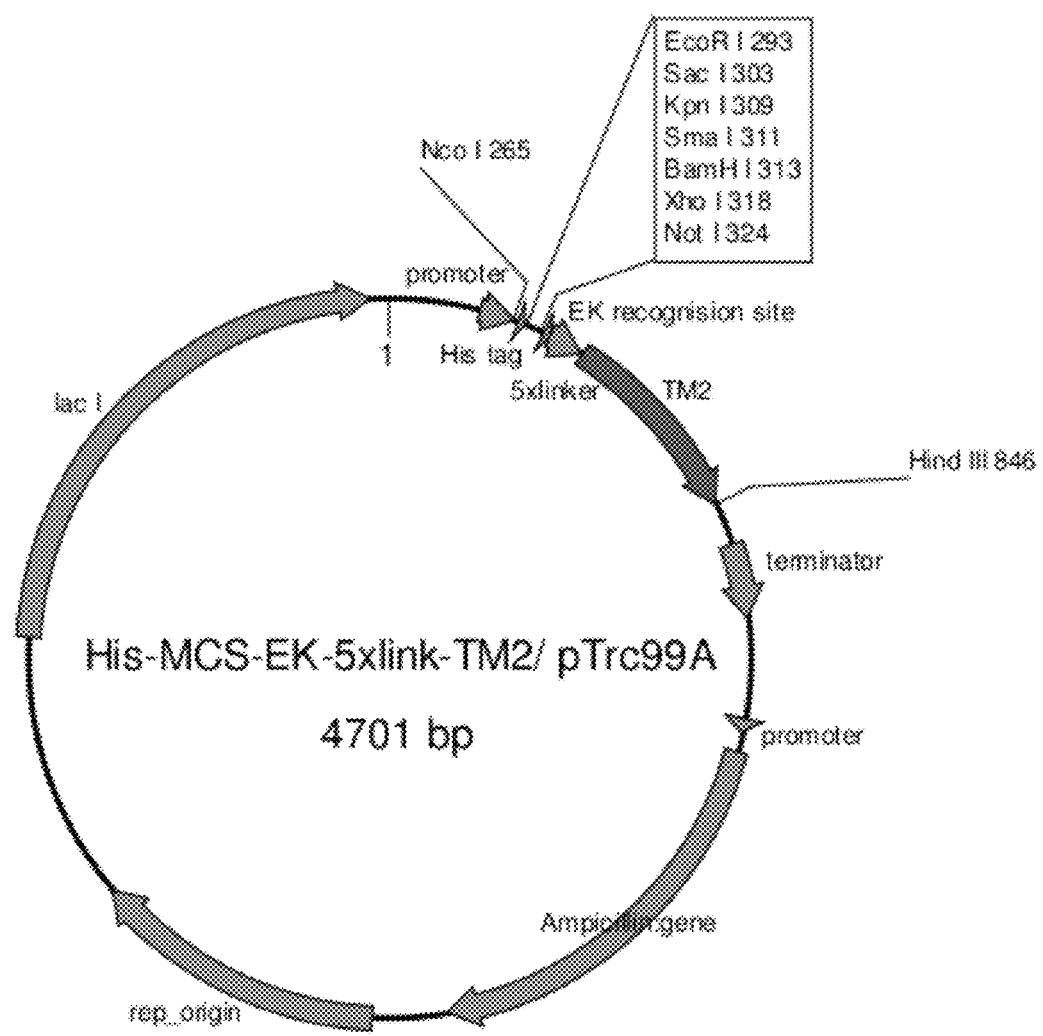
FIG. 12 shows a plasmid map of His-MCS-EK-5xlink-TM2/pTrc99A.

In the case of the vector for fusing tamavidin 2 to the N-terminus of the desired protein, the TM2 gene, a linker (1 xlink: GGGGSG (SEQ ID NO: 57); 3xlink: GGGGSGGGGSGGGGS (SEQ ID NO: 61); or 5xlink: GGGGSGGGGSGGGGSGGGGSGGGGS ISM) ID NO: 62)), the sequence of EK recognition site, MCS with the arrangement of restriction enzyme recognition sites in the order of EcoR I, Sac I, Kpn I, Sma I, BamH I, Xho I and Not I, and a His tag sequence consisting of six histidines were inserted downstream of the restriction enzyme Nco I recognition site in pTrc99A. Detailed vector maps are shown in FIGS. 7-9. In the case of the vector for fusing tamavidin 2 to the C-terminus of the desired protein, a His tag sequence consisting of six histidines, MCS with the arrangement of restriction enzyme recognition sites in the order of EcoR I, Sac I, Kpn I, Sma I, BamH I, Xho I and Not I, the sequence of EK recognition site, a linker (1xlink: GGGGSG (SEQ ID NO: 57); 3xlink: GGGGSGGGGSGGGGS (SEQ ID NO: 61); or 5xlink: GGGGSGGGGSGGGGSGGGGSGGGGS (SEQ ID NO: 62)), and the TM2 gene were inserted downstream of the restriction enzyme Nco I recognition site in pTrc99A. Detailed vector maps are shown in FIGS. 10-12.

Designing Primers

To construct TM-2 fused protein expressing vectors, primers for causing a linker, EK recognition site, MCS site, His tag sequence, and a sequence coding for the restriction enzyme Nco I cleavage site (CCATGG) or the restriction enzyme Hind III cleavage site (AAGCTT) to be joined either upstream or downstream of the TM2 gene were designed. Specifically, two primers (His-MCS-EK-1xlink-TM2-F and His-MCS-EK-3xlink-TM2-F) were designed, each consisting of the restriction enzyme Nco I cleavage site, His tag sequence, MCS site, EK recognition site, and linker on the 5' side and the N-terminal site of TM2 on the 3' side; two additional primers (TM2-1xlink-EK-MCS-His-R and TM2-3xlink-EK-MCS-His-R) were also designed, each consisting of the restriction enzyme Hind III cleavage site, His tag sequence, MCS site, EK recognition site, and linker on the 5' side and a DNA sequence on the 3' side coding for the C-terminal site of TM2 in a reverse direction. Note that in the case where the linker sequence was 5xlink, the primer length was so great as 180mer that two primers were designed, one being a 5'-side 110mer and the other a 3'-side 110mer, as identified by His-MCS-EK-5xlink-TM2-F1, His-MCS-EK-5xlink-TM2-F2, TM2-5xlink-EK-MCS-His-R1 and TM2-5xlink-EK-MCS-His-R2.

Subsequently, two more primers were designed, one being TM2NtermNcoI-F and consisting of the 5' portion of TM2 and an upstream sequence coding for the restriction enzyme Nco I cleavage site, and the other being TM2CtermHindIII-R and consisting of the 3' portion of TM2 and a downstream sequence coding for the restriction enzyme Hind III cleavage site in a reverse direction. The respective primers for constructing the tamavidin-fused protein expressing vectors are identified in Table 13.

3xlink, a sequence comprising a linker, EK recognition sequence, MCS site, and His tag sequence either upstream or downstream of the TM2 gene was amplified using the primers TM2NtermNotI-F and TM2-1xlink-EK-MCS-His-R or TM2-3xlink-EK-MCS-His-R, or the primers His-MCS-EK-1xlink-TM2-F or His-MCS-EK-3xlink-TM2-F and TM2CtermHindIII-R, with a plasmid incorporating the TM2 gene into the vector pTrc99A (see WO02/072817) being used as a template. When the linker length was 5xlink, a sequence comprising a linker, EK recognition sequence, and part of the MCS site either upstream or downstream of the TM2 gene was amplified using the primers TM2NtermNotI-F and TM2-5xlink-EK-MCS-His-R1 or the primers His-MCS-EK-5xlink-TM2-F1 and TM2CtermHindIII-R, with a plasmid incorporating the TM2 gene into the vector pTrc99A (see WO02/072817) being used as a template.

The PCR reaction conditions were as follows: to a 20-μl reaction solution, 500 ng of the template DNA, 10 μl of 2×GC

TABLE 13

Table 13 Primers for constructing the tamavidin fused protein expressing vectors

| Name | Sequence (5'-3') | Length |
|---|---|---|
| TM2NtermNotI-F | AAACCATGGGCTCAGACGTTCAATCTTCA | 29 mer |
| TM2-1xlink-EK-MCS-His-R | GTTTAAGCTTTCATCAGCCGTGGTGATGGTGATGGTGGCCCGCGGCCGCTCGAGGATCCC GGGTACCGAGCTCGAATTCCGGCTTATCGTCATCGTCaccgctgccaccgccaccCTTCA ACCTCGGTGCGCG | 133 mer |
| TM2-3xlink-EK-MCS-His-R | GTTTAAGCTTTCATCAGCCATGGTGATGGTGATGGTGGCCCGCGGCCGCTCGAGGATCCC GGGTACCGAGCTCGAATTCCGGCTTATCGTCATCGTCgctgccaccgccaccgctgccac cgccaccgctgccaccgccaccCTTCAACCTCGGTGCGCG | 160 mer |
| TM2-5xlink-EK-MCS-His-R1 | GGCTTATCGTCATCGTCgctgccaccgccaccgctgccaccgccaccgctgccaccgcca ccgctgccaccgccaccgctgccaccgccaccCTTCAACCTCGGTGCGCG | 110 mer |
| TM2-5xlink-EK-MCS-His-R2 | GTTTAAGCTTTCATCAGCCATGGTGATGGTGATGGTGgcccgcggccgctcgaggatccc gggtaccgagctcgaattccggCTTATCGTCATCGTCgctgccaccgcca | 110 mer |
| His-MCS-EK-1xlink-TM2-F | CAAACCATGGCCCACCATCACCATCACCATGCGAATTCGAGCTCGGTACCCGGGATCCTC GAGCGGCCGCGGGACGATGACGACGATAAGggtggcggtggcagcggtTCAGACGTTCAA TCTTCA | 123 mer |
| His-MCS-EK-3xlink-TM2-F | CAAACCATGGCCCACCATCACCATCACCATTGCGAATTCGAGCTCGGTACCCGGGATCCTC GAGCGGCCGCGGGACGATGACGATAAGggtggcggtggcagcggtggcggtggcagcggt ggcggtggcagcTCAGACGTTCAATCTTCA | 150 mer |
| His-MCS-EK-5xlink-TM2-F1 | GGGACGATGACGATAAGggtggcggtggcagcggtggcggtggcagcggtggcggtggca gcggtggcggtggcagcggtggcggtggcagcTCAGACGTTCAATCTTCA | 110 mer |
| His-MCS-EK-5xlink-TM2-F2 | CAAACCATGGCCCACCATCACCATCACCATGCGAATTCGAGCTCGGTACCCGGGATCCTC GAGCGGCCGCGGGACGATGACGATAAGggtggcggtggcagcggtggcgg | 110 mer |
| TM2CtermHindIII-R | GTTTAAGCTTTTACTTCAACCTCGGTGCGCG | 31 mer |

The restriction enzyme recognition sites are underlined by solid lines.
The His tag sequences are underlined by dotted lines.
The sites coding for the EK recognition sequence are underlined by wavy lines.
The linker sequences are written in lower case.
The individual sequences correspond to SEQ ID NOs: 42-51 as counted from the top.

PCR

To construct the TM2 fused protein expressing vectors, one-stage PCR was performed when the linker length was 1xlink or 3xlink, whereas two-stage PCR was performed in the case of 5xlink. When the linker length was 1xlink or buffer II (TaKaRa), 1.6 μl of 2.5 mM dNTP, 10 pmoles of each of the primers, and 0.1 μl of 5 U/μl Pyrobest were added, and using GeneAmp PCR System 9600 (PERKIN ELMER), one cycle of 96° C.×3 min, 25 cycles of 95° C.×1 min, 60° C.×1 min, and 72° C.×2 min, and one cycle of 72° C.×6 min were performed. As a result, three PCR products were obtained for the sequence to which TM2 was fused to the N-terminus, with respective sizes of 546 by in the case of 1xlink, 573 by in the case of 3xlink, and 523 by in the case of 5xlink; three additional PCR products were obtained for the sequence to which TM2 was fused to the C-terminus, with respective sizes of 538 by in the case of 1xlink, 565 by in the case of 3xlink, and 525 by in the case of 5xlink. The PCR products obtained in the case of 5xlink were subjected to agarose electrophoresis in a TAE buffer solution using agarose (Agarose Type II: SIGMA).

Each of the DNA fragments was excised together with the gel and recovered using a QIAEX II gel extraction kit (QIAGEN). The extraction method was in accordance with the instructions on the kit. With the fragments of 5xlink used as templates, the second stage of PCR was performed using the primers TM2NtermNotI-F and TM2-5xlink-EK-MCS-His-R2 in the case of the sequence to which TM2 was fused to the N-terminus, and the primers His-MCS-EK-5xlink-TM2-F2 and TM2CtermHindIII-R in the case of the sequence to which TM2 was fused to the C-terminus. The reaction conditions were the same as in the first stage. As a result, two PCR products were obtained, with respective sizes of 603 by in the case of the sequence to which TM2 was fused to the N-terminus and 595 by in the case of the sequence to which TM2 was fused to the C-terminus.

Clonin

The fragments obtained by PCR which contained the linker, EK recognition sequence, MCS site, and His tag sequence either upstream or downstream of the TM2 gene were cloned in the vector pCR4 blunt TOPO (product of Invitrogen). The ligation reaction was in accordance with the instructions on the vector kit. DNA was transferred into *E. coli* TB1 by electroporation and plasmid DNA was extracted in accordance with the usual method (Sambrook et al. 1989, Molecular Cloning, A laboratory manual, $2^{nd}$ edition). The clones verified to have inserts were treated as follows: using the M13 primer (TaKaRa), the base sequence of each PCR product was determined from both of its ends with an ABI PRISM fluorescence sequencer (Model 310 Genetic Analyzer, Perkin Elmer) to confirm that it had no mutation from the original gene. The plasmid incorporating the genes of interest was $d_{ou}bl_e$ digested with Nco I and Hind III and gel purification was performed by the aforementioned method to recover a DNA fragment. The recovered DNA fragment was ligated by a ligation kit (product of TaKaRa) to the *E. coli* expression vector pTrc99A that had been preliminarily digested with Nco I and Hind III.

The ligation product was transformed into *E. coli* TB1 and plasmid DNA was extracted and analyzed by restriction enzymes in accordance with the usual method to check for the presence of the inserted genes, whereby the following vectors for expressing the tamavidin 2 fused proteins were completed: TM2-1xlink-EK-MCS-His/pTrc99A (FIG. 7), TM2-3xlink-EK-MCS-His/pTrc99A (FIG. 8), TM2-5xlink-EK-MCS-His/pTrc99A (FIG. 9), His-MCS-EK-1xlink-TM2/pTrc99A (FIG. 10), His-MCS-EK-3xlink-TM2/pTrc99A (FIG. 11), and His-MCS-EK-5xlink-TM2/pTrc99A (FIG. 12), which are respectively depicted in SEQ ID NOs: 77-82.

The invention claimed is:

1. A method of binding a protein to a carrier, which comprises:
   providing a biotin-bound carrier;
   preparing a fusion protein having the protein bound to a tamavidin; and
   binding the protein to the carrier via tamavidin-biotin bonds, wherein the tamavidin is selected from:
   (a) a protein consisting of an amino acid sequence sharing an identity of 90% or more with SEQ ID NO: 2 or SEQ ID NO: 4 and having biotin-binding activity; or
   (b) a protein consisting of the amino acid sequence of SEQ ID NO: 2 or SEQ ID NO: 4; or
   (c) a protein consisting of an amino acid sequence encoded by a nucleic acid hybridizable under stringent conditions (0.5% SDS, 65° C., 0.2×SSC) with a strand complementary to the base sequence of SEQ ID NO: 1 or SEQ ID NO: 3 and having biotin-binding activity.

2. The method according to claim 1, wherein the protein is selected from the group consisting of antibodies or fragments thereof, antigenic proteins, enzymes, lectins, peptides, protein A, protein G, and protein L.

3. The method according to claim 1, wherein the carrier is selected from the group consisting of beads, magnetic beads, thin films, microtubes, filters, plates, microplates, carbon nanotubes, and sensor chips.

4. The method according to claim 1, wherein the tamavidin and the protein are bound via a linker to constitute the fusion protein.

5. The method according to claim 1, wherein the tamavidin and the protein are bound via a linker consisting of six or more amino acids to constitute the fusion protein.

6. The method according to claim 1, wherein the fusion protein further has a leader sequence bound thereto.

7. The method according to claim 1, wherein biotin and the carrier are bound via a linker greater than 13.5 Å in length.

8. A tamavidin fused protein-bound carrier in which a fusion protein having a protein bound to a tamavidin is bound to a biotin-bound carrier via tamavidin-biotin bonds, wherein the tamavidin is selected from:
   (a) a protein consisting of an amino acid sequence sharing an identity of 90% or more with SEQ ID NO: 2 or SEQ ID NO: 4 and having biotin-binding activity; or
   (b) a protein consisting of the amino acid sequence of SEQ ID NO: 2 or SEQ ID NO: 4; or
   (c) a protein consisting of an amino acid sequence encoded by a nucleic acid hybridizable under stringent conditions (0.5% SDS, 65° C., 0.2×SSC) with a strand complementary to the base sequence of SEQ ID NO: 1 or SEQ ID NO: 3 and having biotin-binding activity, wherein the tamavidin fused protein-bound carrier is prepared by the method of claim 1 for binding a protein to a carrier.

* * * * *